US012599680B1

(12) United States Patent
Burns et al.

(10) Patent No.: US 12,599,680 B1
(45) Date of Patent: *Apr. 14, 2026

(54) TREATMENTS FOR OCULAR NEOVASCULARIZATION

(71) Applicant: 4D MOLECULAR THERAPEUTICS INC., Emeryville, CA (US)

(72) Inventors: Christian Burns, Emeryville, CA (US); Melissa Calton, Emeryville, CA (US); Meredith Leong, Emeryville, CA (US); Paul Szymanski, Emeryville, CA (US)

(73) Assignee: 4D Molecular Therapeutics Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/300,498

(22) Filed: Aug. 14, 2025

Related U.S. Application Data

(63) Continuation of application No. 18/767,370, filed on Jul. 9, 2024, which is a continuation of application No. 18/482,628, filed on Oct. 6, 2023, now abandoned, which is a continuation of application No. PCT/US22/26395, filed on Apr. 26, 2022.

(60) Provisional application No. 63/180,247, filed on Apr. 27, 2021.

(51) Int. Cl.
| | |
|---|---|
| *A61K 48/00* | (2006.01) |
| *A61K 9/00* | (2006.01) |
| *A61K 38/00* | (2006.01) |
| *A61P 27/02* | (2006.01) |
| *C07K 14/005* | (2006.01) |
| *C07K 14/71* | (2006.01) |
| *C12N 15/113* | (2010.01) |
| *C12N 15/62* | (2006.01) |
| *C12N 15/86* | (2006.01) |

(52) U.S. Cl.
CPC .......... *A61K 48/005* (2013.01); *A61K 9/0048* (2013.01); *A61K 48/0075* (2013.01); *A61K 48/0083* (2013.01); *A61P 27/02* (2018.01); *C07K 14/005* (2013.01); *C07K 14/71* (2013.01); *C12N 15/113* (2013.01); *C12N 15/62* (2013.01); *C12N 15/86* (2013.01); *A61K 38/00* (2013.01); *C07K 2319/30* (2013.01);

*C12N 2310/11* (2013.01); *C12N 2310/141* (2013.01); *C12N 2750/14122* (2013.01); *C12N 2750/14143* (2013.01); *C12N 2830/42* (2013.01)

(58) Field of Classification Search
CPC .................. C12N 15/86; C12N 15/113; C12N 2310/141; C12N 2830/42; A61P 27/02; A61K 48/005
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 2011/0054005 A1 | 3/2011 | Naito et al. | |
| 2011/0293625 A1 | 12/2011 | Murali | |
| 2019/0345573 A1 | 11/2019 | Khvorova et al. | |
| 2024/0226336 A9* | 7/2024 | Burns ................. | A61K 48/005 |

FOREIGN PATENT DOCUMENTS

| | | |
|---|---|---|
| CN | 102533763 | 7/2012 |
| WO | 2006/110813 A2 | 10/2006 |
| WO | 2008/154482 A2 | 12/2008 |
| WO | 2014/182635 A1 | 11/2014 |
| WO | 2019/104279 A1 | 5/2019 |

OTHER PUBLICATIONS

U.S. Appl. No. 19/300,466, filed 2025.*
U.S. Appl. No. 18/482,628, filed 2023.*
U.S. Appl. No. 18/767,370, filed 2024.*
CN 102533763A English language translation.
Gu Xi-Ling et al "Inhibition effect of shRNA on VEGF-C in breast cancer cells", Chinese Journal of Cancer Research, vol. 21, Aug. 11, 2009 (Aug. 11, 2009), pp. 202-206.
JP Appl. No. 2023-565505 notice of allowance and granted claims.
EP Appl. No. 22796576.1 notice of allowance and allowed claims.
AU Appl. No. 2022266774 notice of acceptance and granted claims.
CN102533763A Chinese Publication.

* cited by examiner

*Primary Examiner* — Jane J Zara

(74) *Attorney, Agent, or Firm* — Much Shelist PC; Christopher M. Cabral

(57) ABSTRACT

Provided herein are compositions and methods for the treatment of ocular neovascular diseases such as wet age-related macular degeneration.

24 Claims, 36 Drawing Sheets

Specification includes a Sequence Listing.

VEGFR3-Fc
6 I kDa
Afliberecept
49 kDa

1:50 dilution

FIG. 5B
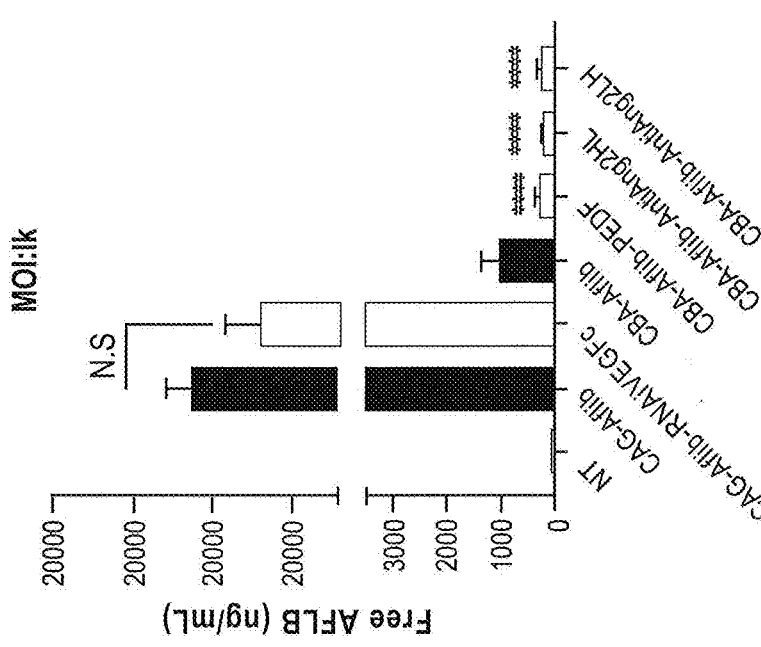
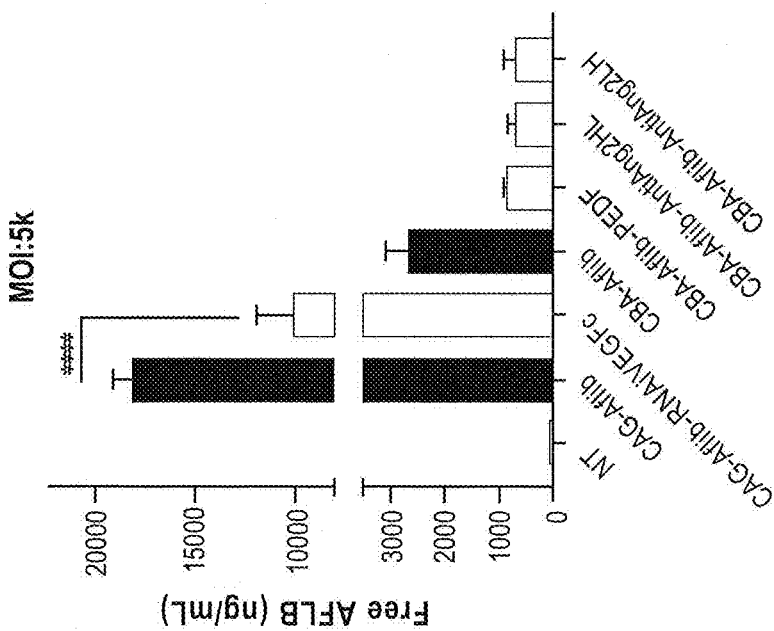

FIG. 6B
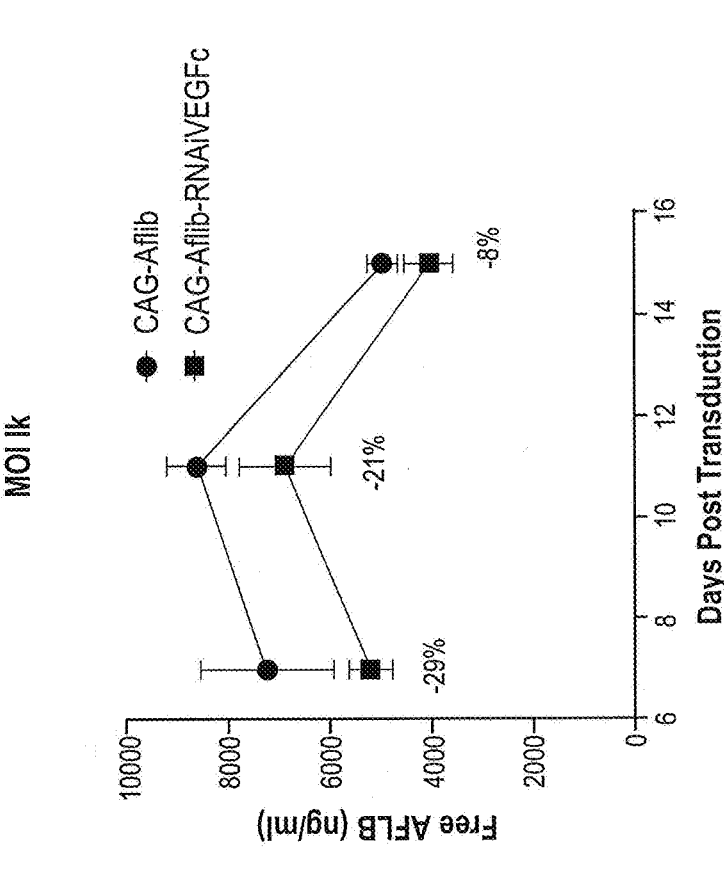
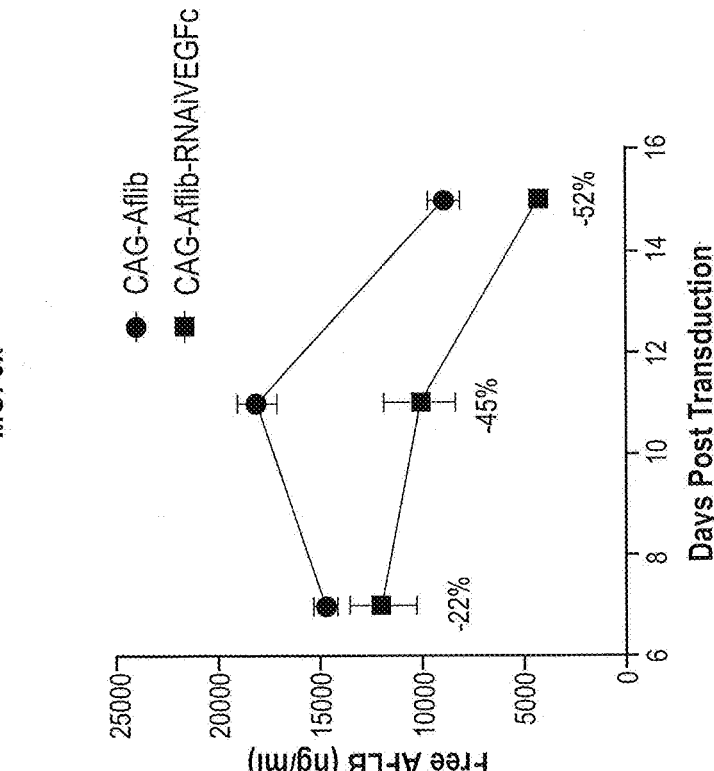

VEGF-A vs MOI

- ● CAG-AFLB
- ▢ CAG-AFLB-VEGFC-RNAi
- ▲ CAG-AFLB-ANG2-RNAi
- ▽ CAG-GFP

VEGF-A vs MOI

- ● CAG-AFLB
- ▢ CAG-AFLB-VEGFC-RNAi
- ▲ CAG-AFLB-ANG2-RNAi
- ▽ CAG-GFP

FIG. 8D
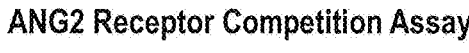
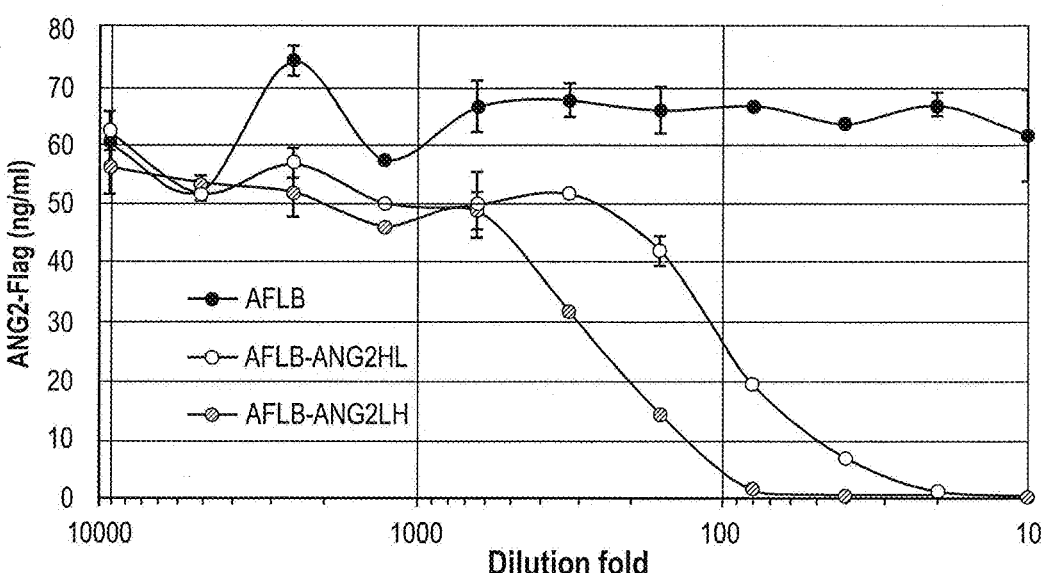
FIG. 9
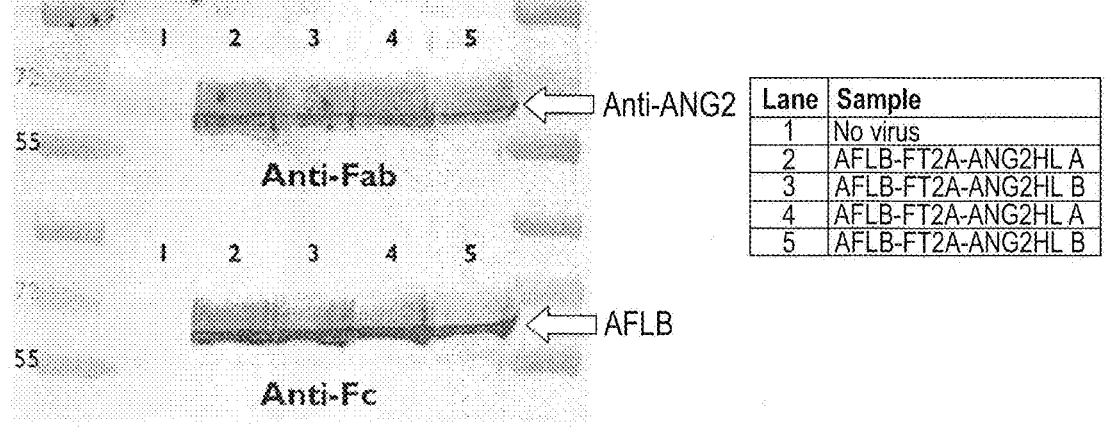
| Lane | Sample |
|------|--------|
| 1 | No virus |
| 2 | AFLB-FT2A-ANG2HL A |
| 3 | AFLB-FT2A-ANG2HL B |
| 4 | AFLB-FT2A-ANG2HL A |
| 5 | AFLB-FT2A-ANG2HL B |

FIG. 10A
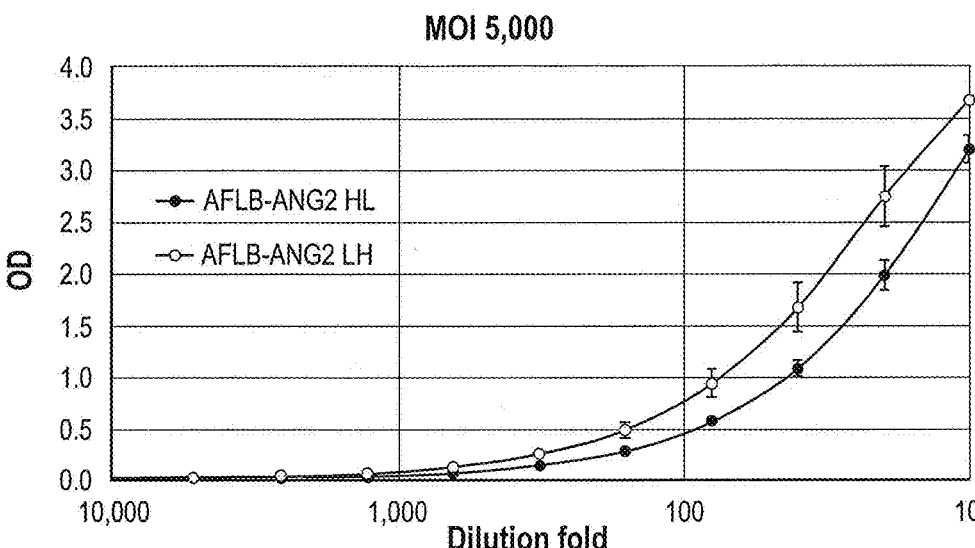
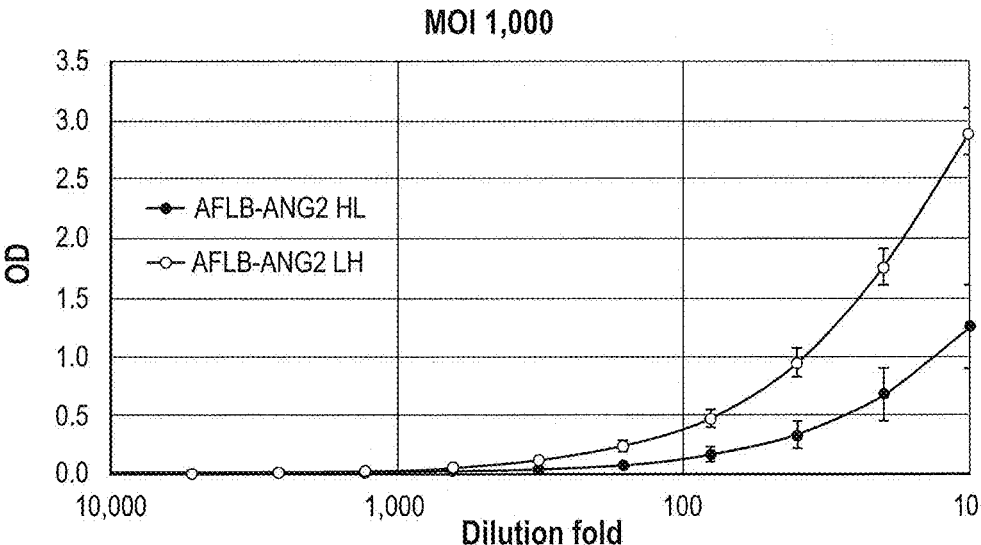

FIG. 10B
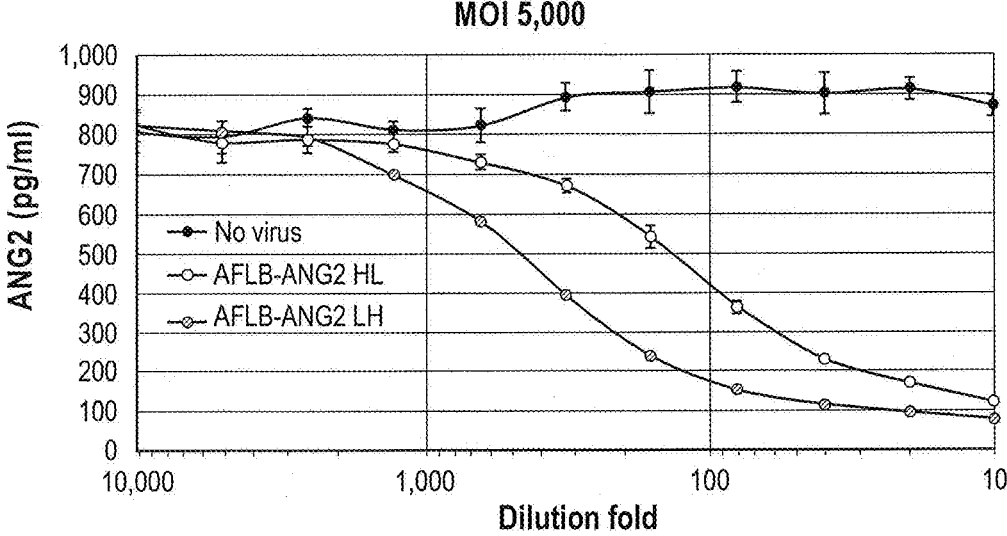
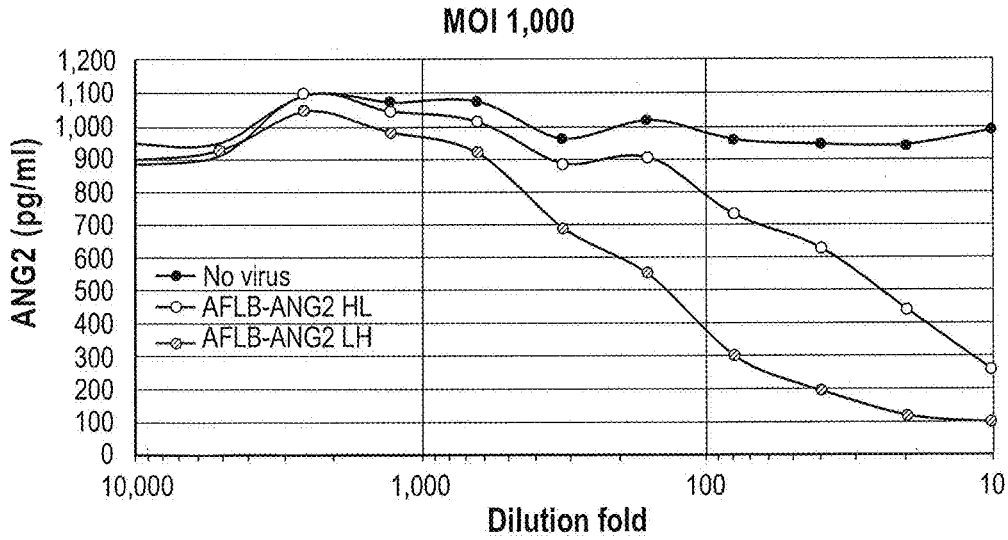

| Protein | V2 # | ka ( l /Ms) | kd ( l /s) | KD (kd/ka, M) | V2.3/V2.2 ka | V2.3/V2.2 kd | V2.3/V2.2 KD |
|---------|------|-------------|-----------|---------------|--------------|--------------|--------------|
| Anti-ANG2 HL | V2.2 | 1.15E+06 | 1.68E-03 | 1.46 nM | 5.6 | 91.1 | 16.3 |
| Anti-ANG2 LH | V2.3 | 6.44E+06 | 1.53E-01 | 23.8 nM | | | |

CBA-AFLB-PEDF

Secreted ANG2                    Cellular ANG2

- ● CAG-AFLB
- □ CAG-AFLB-VEGFC-RNAi
- ▲ CAG-AFLB-ANG2-RNAi
- ▽ CAG-GFP

FIG. 23

201LTI ≤ 25% CD3l+/GFP+    205LTI ≤ 25% CD3l+/GFP+    305LTI ≤ 25% CD3l+/GFP+    305LTI OF ≤ 25% CD3l+/GFP+

Purple - GFP
Teal - CD3l
Blue - nuclei

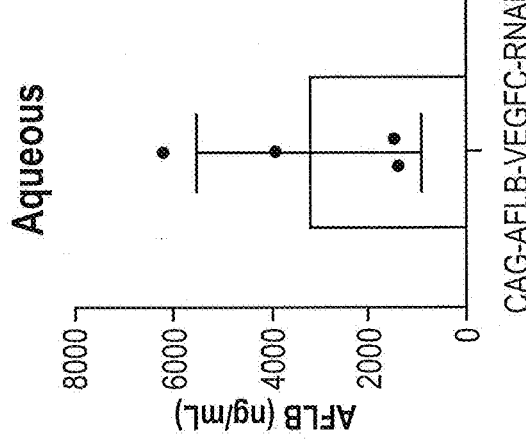
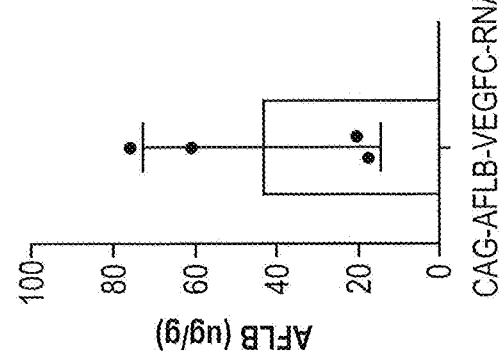
FIG. 24

FIG. 25
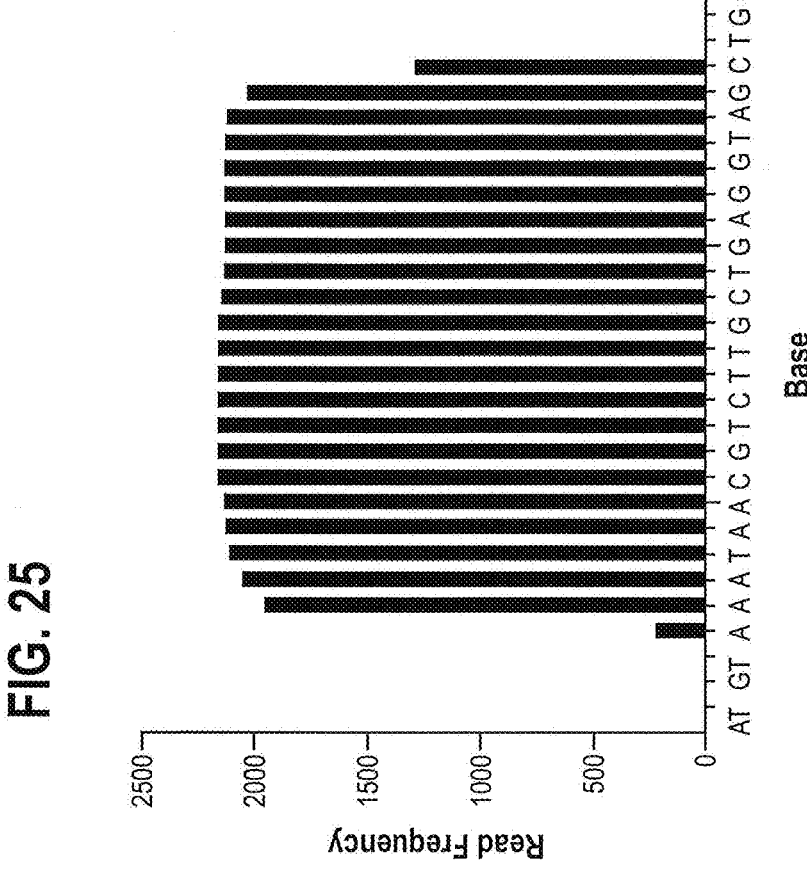
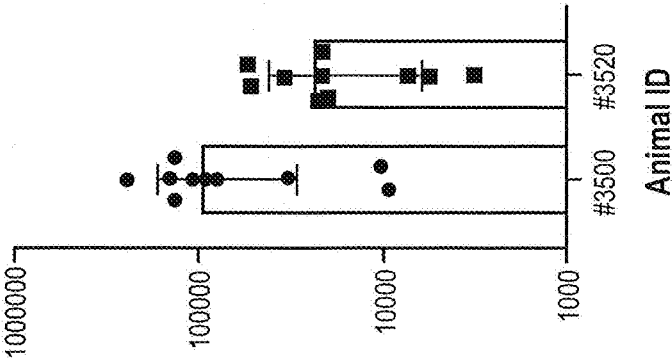

FIG. 26

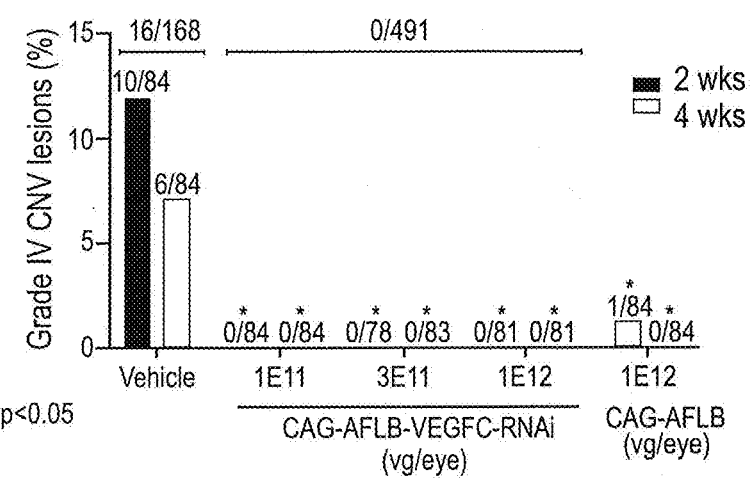

| TREATMENT | CNV GRADE | DAY 56 | | DAY 70 | | DAY 84 | |
|---|---|---|---|---|---|---|---|
| | | LESION COUNT | INCIDENCE | LESION COUNT | INCIDENCE | LESION COUNT | INCIDENCE |
| VEHICLE | IV | 10 | 11.9% | 6 | 7.1% | 6 | 7.1% |
| | III | 16 | 19.0% | 16 | 19.0% | 13 | 15.5% |
| | II | 56 | 66.7% | 62 | 73.8% | 65 | 77.4% |
| | I | 2 | 2.4% | 0 | 0% | 0 | 0% |
| | Total | 84 | 100% | 84 | 100% | 84 | 100% |
| CAG-AFLB $1 \times 10^{12}$ vg | IV | 10 | 11.9% | 6 | 7.1% | 6 | 7.1% |
| | III | 17 | 20.2% | 12 | 19.0% | 13 | 15.5% |
| | II | 63 | 75.0% | 72 | 85.7% | 71 | 84.5% |
| | I | 3 | 3.6% | 0 | 0% | 0 | 0% |
| | Total | 84 | 100% | 84 | 100% | 84 | 100% |
| CAG-AFLB-VEGFC-RNAi $1 \times 10^{12}$ vg | IV | 10 | 11.9% | 6 | 7.1% | 6 | 7.1% |
| | III | 11 | 13.6% | 8 | 9.9% | 12 | 14.8% |
| | II | 69 | 85.2% | 73 | 90.1% | 69 | 8.52% |
| | I | 1 | 1.2% | 0 | 0% | 0 | 0% |
| | Total | 84 | 100% | 84 | 100% | 84 | 100% |
| CAG-AFLB-VEGFC-RNAi $3 \times 10^{11}$ vg | IV | 10 | 11.9% | 6 | 7.1% | 6 | 7.1% |
| | III | 16 | 19.0% | 16 | 19.0% | 13 | 15.5% |
| | II | 56 | 66.7% | 62 | 73.8% | 65 | 77.4% |
| | I | 2 | 2.4% | 0 | 0% | 0 | 0% |
| | Total | 84 | 100% | 84 | 100% | 84 | 100% |
| CAG-AFLB-VEGFC-RNAi | IV | 0 | 0% | 0 | 0% | 0 | 0% |
| | III | 16 | 19.0% | 13 | 15.5% | 14 | 16.7% |
| | II | 67 | 79.8% | 70 | 83.3% | 70 | 83.3% |
| | I | 1 | 1.2% | 1 | 1.2% | 0 | 0% |
| | Total | 84 | 100% | 84 | 100% | 84 | 100% |

SEQUENCE LISTING

```
Sequence total quantity: 75
SEQ ID NO: 1              moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 1
gccgcagcct ataacaactt t                                          21

SEQ ID NO: 2              moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 2
aaagttgtta taggctgcgg c                                          21

SEQ ID NO: 3              moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 3
gccgcagcct ataacaactt t                                          21

SEQ ID NO: 4              moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 4
ccctaattct acagaagaga t                                          21

SEQ ID NO: 5              moltype = DNA  length = 21
```

-continued

```
FEATURE                    Location/Qualifiers
misc_feature               1..21
                           note = Synthetic Polynucleotide
source                     1..21
                           mol_type = other DNA
                           organism = synthetic construct
SEQUENCE: 5
atctcttctg tagaattagg g                                                21

SEQ ID NO: 6               moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 6
ccctaattct acagaagaga t                                                21

SEQ ID NO: 7               moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 7
gatgatagaa atagggacaa a                                                21

SEQ ID NO: 8               moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 8
tttgtcccta tttctatcat c                                                21

SEQ ID NO: 9               moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 9
gatgatagaa atagggacaa a                                                21

SEQ ID NO: 10              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 10
gccacggtga ataattcagt t                                                21

SEQ ID NO: 11              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 11
aactgaatta ttcaccgtgg c                                                21

SEQ ID NO: 12              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 12
gccacggtga ataattcagt t                                                21
```

```
SEQ ID NO: 13              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 13
gcttactcat tgtatgaaca t                                          21

SEQ ID NO: 14              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 14
atgttcatac aatgagtaag c                                          21

SEQ ID NO: 15              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 15
gcttactcat tgtatgaaca t                                          21

SEQ ID NO: 16              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 16
cgcgacaaac accttcttta a                                          21

SEQ ID NO: 17              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 17
ttaaagaagg tgtttgtcgc g                                          21

SEQ ID NO: 18              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 18
cgcgacaaac accttcttta a                                          21

SEQ ID NO: 19              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 19
ctacctcagc aagacgttat t                                          21

SEQ ID NO: 20              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 20
aataacgtct tgctgaggta g                                          21
```

```
SEQ ID NO: 21             moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 21
ctacctcagc aagacgttat t                                              21

SEQ ID NO: 22             moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 22
accaattaca tgtggaataa t                                              21

SEQ ID NO: 23             moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 23
attattccac atgtaattgg                                                20

SEQ ID NO: 24             moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 24
accaattaca tgtggaataa t                                              21

SEQ ID NO: 25             moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 25
atgaccaaac agccaagatt t                                              21

SEQ ID NO: 26             moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 26
aaatcttggc tgtttggtca                                                20

SEQ ID NO: 27             moltype = DNA  length = 22
FEATURE                   Location/Qualifiers
misc_feature              1..22
                          note = Synthetic Polynucleotide
source                    1..22
                          mol_type = other DNA
                          organism = synthetic construct
SEQUENCE: 27
aatgaccaaa cagccaagat tt                                             22

SEQ ID NO: 28             moltype = DNA  length = 21
FEATURE                   Location/Qualifiers
misc_feature              1..21
                          note = Synthetic Polynucleotide
source                    1..21
                          mol_type = other DNA
                          organism = synthetic construct
SEQUENCE: 28
```

-continued

```
gtcgttgtgt cccttcatat t                                                    21

SEQ ID NO: 29         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 29
aatatgaagg gacacaacga c                                                    21

SEQ ID NO: 30         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 30
gtcgttgtgt cccttcatat t                                                    21

SEQ ID NO: 31         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 31
acaacggcat ccagcgattt c                                                    21

SEQ ID NO: 32         moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 32
gaaatcgctg gatgccgttg                                                      20

SEQ ID NO: 33         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 33
acaacggcat ccagcgattt c                                                    21

SEQ ID NO: 34         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 34
ggcaccctg caagatgttt g                                                     21

SEQ ID NO: 35         moltype = DNA   length = 21
FEATURE               Location/Qualifiers
misc_feature          1..21
                      note = Synthetic Polynucleotide
source                1..21
                      mol_type = other DNA
                      organism = synthetic construct
SEQUENCE: 35
caaacatctt gcagggtgtc c                                                    21

SEQ ID NO: 36         moltype = DNA   length = 21
FEATURE               Location/Qualifiers
misc_feature          1..21
                      note = Synthetic Polynucleotide
source                1..21
                      mol_type = other DNA
                      organism = synthetic construct
```

-continued

```
SEQUENCE: 36
ggacaccctg caagatgttt g                                                    21

SEQ ID NO: 37          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 37
caccgtgtgg gctgagttta a                                                    21

SEQ ID NO: 38          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 38
ttaaactcag cccacacggt g                                                    21

SEQ ID NO: 39          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 39
caccgtgtgg gctgagttta a                                                    21

SEQ ID NO: 40          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 40
ctttaagact ttcgctattt c                                                    21

SEQ ID NO: 41          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 41
gaaatagcga aagtcttaaa g                                                    21

SEQ ID NO: 42          moltype = DNA  length = 22
FEATURE                Location/Qualifiers
misc_feature           1..22
                       note = Synthetic Polynucleotide
source                 1..22
                       mol_type = other DNA
                       organism = synthetic construct
SEQUENCE: 42
ctttaagact ttcgctattt cg                                                   22

SEQ ID NO: 43          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 43
tcacaggcaa cgagctctat g                                                    21

SEQ ID NO: 44          moltype = DNA  length = 21
FEATURE                Location/Qualifiers
misc_feature           1..21
                       note = Synthetic Polynucleotide
source                 1..21
                       mol_type = other DNA
```

-continued

```
                          organism = synthetic construct
SEQUENCE: 44
catagagctc gttgcctgtg a                                                21

SEQ ID NO: 45            moltype = DNA   length = 21
FEATURE                  Location/Qualifiers
misc_feature             1..21
                         note = Synthetic Polynucleotide
source                   1..21
                         mol_type = other DNA
                         organism = synthetic construct
SEQUENCE: 45
tcacaggcaa cgagctctat g                                                21

SEQ ID NO: 46            moltype = RNA   length = 155
FEATURE                  Location/Qualifiers
misc_feature             1..155
                         note = Synthetic Polynucleotide
misc_difference          57..78
                         note = n is a, c, g, u, or absent
misc_difference          98..119
                         note = n is a, c, g, u, or absent
source                   1..155
                         mol_type = other RNA
                         organism = synthetic construct
SEQUENCE: 46
cttcaggtta acccaacaga aggctaaaga aggtatattg ctgttgacag tgagcgnnnn      60
nnnnnnnnnn nnnnnnnnct gtgaagccac agatgggnnn nnnnnnnnnn nnnnnnnnnt     120
gcctactgcc tcggacttca aggggctact ttagg                               155

SEQ ID NO: 47            moltype = RNA   length = 153
FEATURE                  Location/Qualifiers
misc_feature             1..153
                         note = Synthetic Polynucleotide
misc_difference          56..77
                         note = n is a, c, g, or u
misc_difference          97..118
                         note = note = n is a, c, g, or u
source                   1..153
                         mol_type = other RNA
                         organism = synthetic construct
SEQUENCE: 47
gacttcttaa cccaacagaa ggctcgagaa ggtatattgc tgttgacagt gagcgnnnnn      60
nnnnnnnnnn nnnnnnntag tgaagccaca gatgtannnn nnnnnnnnnn nnnnnnnntg     120
cctactgcct cggacttcaa ggggctagaa ttc                                 153

SEQ ID NO: 48            moltype = AA   length = 745
FEATURE                  Location/Qualifiers
REGION                   1..745
                         note = Synthetic Polypeptide
source                   1..745
                         mol_type = protein
                         organism = synthetic construct
SEQUENCE: 48
MAADGYLPDW LEDTLSEGIR QWWKLKPGPP PPKAAERHKD DSRGLVLPGY KYLGPFNGLD      60
KGEPVNEADA AALEHDKAYD RQLDSGDNPY LKYNHADAEF QERLKEDTSF GGNLGRAVFQ     120
AKKRVLEPLG LVEEPVKTAP GKKRPVEHSP VEPDSSSGTG KAGQQPARKR LNFGQTGDAD     180
SVPDPQPLGQ PPAAPSGLGT NTMATGSGAP MADNNEGADG VGNSSGNWHC DSTWMGDRVI     240
TTSTRTWALP TYNNHLYKQI SSQSGASNDN HYFGYSTPWG YFDFNRFHCH FSPRDWQRLI     300
NNNWGFRPKR LNFKLFNIQV KEVTQNDGTT TIANNLTSTV QVFTDSEYQL PYVLGSAHQG     360
CLPPFPADVF MVPQYGYLTL NNGSQAVGRS SFYCLEYFPS QMLRTGNNFT FSYTFEDVPF     420
HSSYAHSQSL DRLMNPLIDQ YLYYLSRTNT PSGTTTQSRL QFSQAGASDI RDQSRNWLPG     480
PCYRQQRVSK TSADNNNSEY SWTGATKYHL NGRDSLVNPG PAMASHKDDE EKFFPQSGVL     540
IFGKQGSEKT NVDIEKVMIT DEEEIRTTNP VATEQYGSVS TNLQRGNLAI SDQTKHARQA     600
ATADVNTQGV LPGMVWQDRD VYLQGPIWAK IPHTDGHFHP SPLMGGFGLK HPPPQILIKN     660
TPVPANPSTT FSAAKFASFI TQYSTGQVSV EIEWELQKEN SKRWNPEIQY TSNYNKSVNV     720
DFTVDTNGVY SEPRPIGTRY LTRNL                                          745

SEQ ID NO: 49            moltype = AA   length = 10
FEATURE                  Location/Qualifiers
REGION                   1..10
                         note = Synthetic Polypeptide
source                   1..10
                         mol_type = protein
                         organism = synthetic construct
SEQUENCE: 49
LAISDQTKHA                                                            10

SEQ ID NO: 50            moltype = DNA   length = 1374
```

```
FEATURE                    Location/Qualifiers
misc_feature               1..1374
                           note = Synthetic Polynucleotide
source                     1..1374
                           mol_type = other DNA
                           organism = synthetic construct
SEQUENCE: 50
atggtttctt actgggacac cggcgtgctg ctgtgtgccc tgctttcttg tctgctgctg   60
accggctcta gcagcggctc tgataccggc agacccttcg tggaaatgta cagcgagatc   120
cccgagatca tccacatgac cgagggcaga gagctggtca tcccttgcag agtgacaagc   180
cccaacatca ccgtgactct gaagaagttc cctctggaca cactgatccc cgacggcaag   240
agaatcatct gggacagccg gaagggcttc atcatcagca acgccaccta caaagagatc   300
ggcctgctga cctgtgaagc caccgtgaat ggccaccgt acaagaccaa ctacctgaca   360
cacagacaga ccaacaccat catcgacgtg gtgctgagcc ctagccacgg cattgaactg   420
tctgtgggcg agaagctggt gctgaactgt accgccagaa ccgagctgaa cgtgggcatc   480
gacttcaact gggagtaccc cagcagcaag caccagcaca agaaactggt caaccgggac   540
ctgaaaaccc agagcggcag cgagatgaag aaattcctga gcaccctgac catcgacggc   600
gtgaccagaa gtgaccaggg cctgtacaca tgtgccgcca gctctggcct gatgaccaag   660
aaaaacagca ccttcgtgcg ggtgcacgag aaggacaaga cccacacctg tcctccatgt   720
cctgctccag aactgctcgg cggaccttcc gtgttcctgt ttcctccaaa gcctaaggac   780
accctgatga tcagcagaac ccctgaagtg acctgcgtgg tggtggatgt gtcccacgag   840
gatcccgaag tgaagttcaa ttggtacgtg gacggcgtgg aagtgcacaa cgccaagacc   900
aagcctagag aggaacagta caatagcacc tacagagtgg tgtccgtgct gaccgtgctg   960
caccaggatt ggctgaacgg caaagagtac aagtgcaagg tgtccaacaa ggccctgcct  1020
gctcctatcg agaaaaccat ctccaaggcc aagggccagc ctaggggaacc ccaggtttac  1080
acactgcctc caagcaggga cgagctgaca aagaaccagg tgtccctgac ctgcctggtc  1140
aagggcttct acccttccga tatcgccgtg gaatgggaga gcaatggcca gcctgagaac  1200
aactacaaga caacccctcc tgtgctggac agcgacggct cattcttcct gtacagcaag  1260
ctgacagtgg acaagagcag atggcagcag ggcaacgtgt tcagctgctc cgtgatgcac  1320
gaggccctgc acaaccacta cacccagaag tccctgagcc tgtctcctgg caaa         1374

SEQ ID NO: 51             moltype = AA  length = 458
FEATURE                   Location/Qualifiers
REGION                    1..458
                          note = Synthetic Polypeptide
source                    1..458
                          mol_type = protein
                          organism = synthetic construct
SEQUENCE: 51
MVSYWDTGVL LCALLSCLLL TGSSSGSDTG RPFVEMYSEI PEIIHMTEGR ELVIPCRVTS   60
PNITVTLKKF PLDTLIPDGK RIIWDSRKGF IISNATYKEI GLLTCEATVN GHLYKTNYLT   120
HRQTNTIIDV VLSPSHGIEL SVGEKLVLNC TARTELNVGI DFNWEYPSSK HQHKKLVNRD   180
LKTQSGSEMK KFLSTLTIDG VTRSDQGLYT CAASSGLMTK KNSTFVRVHE KDKTHTCPPC   240
PAPELLGGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPREPQVY   360
TLPPSRDELT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                            458

SEQ ID NO: 52             moltype = AA  length = 5
FEATURE                   Location/Qualifiers
REGION                    1..5
                          note = Synthetic Polypeptide
source                    1..5
                          mol_type = protein
                          organism = synthetic construct
SEQUENCE: 52
GYYMH                                                                 5

SEQ ID NO: 53             moltype = AA  length = 17
FEATURE                   Location/Qualifiers
REGION                    1..17
                          note = Synthetic Polypeptide
source                    1..17
                          mol_type = protein
                          organism = synthetic construct
SEQUENCE: 53
WINPNSGGTN YAQKFQG                                                   17

SEQ ID NO: 54             moltype = AA  length = 20
FEATURE                   Location/Qualifiers
REGION                    1..20
                          note = Synthetic Polypeptide
source                    1..20
                          mol_type = protein
                          organism = synthetic construct
SEQUENCE: 54
SPNPYYYDSS GYYYPGAFDI                                                20

SEQ ID NO: 55             moltype = AA  length = 11
```

```
FEATURE            Location/Qualifiers
REGION             1..11
                   note = Synthetic Polypeptide
source             1..11
                   mol_type = protein
                   organism = synthetic construct
SEQUENCE: 55
GGNNIGSKSV H                                                                        11

SEQ ID NO: 56      moltype = AA  length = 7
FEATURE            Location/Qualifiers
REGION             1..7
                   note = Synthetic Polypeptide
source             1..7
                   mol_type = protein
                   organism = synthetic construct
SEQUENCE: 56
DDSDRPS                                                                             7

SEQ ID NO: 57      moltype = AA  length = 11
FEATURE            Location/Qualifiers
REGION             1..11
                   note = Synthetic Polypeptide
source             1..11
                   mol_type = protein
                   organism = synthetic construct
SEQUENCE: 57
QVWDSSSDHW V                                                                        11

SEQ ID NO: 58      moltype = DNA  length = 1686
FEATURE            Location/Qualifiers
misc_feature       1..1686
                   note = Synthetic Polynucleotide
source             1..1686
                   mol_type = other DNA
                   organism = synthetic construct
SEQUENCE: 58
atgcaaagag gcgccgctct ctgtctgaga ctgtggctgt gtctgggcct gctggatgga   60
ctggtgtctg gctacagcat gacccctcca acactgaaca tcaccgagga atcccacgtg   120
atcgacaccg gcgatagcct gagcatcagc tgcagaggac agcaccctct ggaatgggct   180
tggcctggtg ctcaagaagc tcctgccaca ggcgacaagg acagcgagga tacaggcgtt   240
gtgcgggatt gcgagggcac agatgccaga ccttactgca aggtgctgct gctgcacgaa   300
gtgcacgccc aggataccgg cagctacgtg tgctactaca agtacatcaa ggcccggatc   360
gagggcacca cagccgcaag ctcttatgtg ttcgtgcggg acttcgagca gcccttcatc   420
aacaagcccg acacactgct ggtcaaccgg aaggacgcta tgtgggtgcc ctgtctggtg   480
tctatccccg gcctgaatgt gaccctgaga agccagagtt ccgtgctgtg gcctgatggc   540
caagaggtcg tgtgggacga tagaaggggc atgctggtgt ccacacctct gctgcatgat   600
gccctgtacc tgcagtgcga gacaacctgg ggcgaccagg acttcctgag caaccctttc   660
ctggtgcaca tcaccggcaa cgagctgtac gacatccagc tgctgcctcg caagagcctg   720
gaactgctcg tgggagagaa gctggtgctg aactgtaccg tgtgggccga gttcaatagc   780
ggcgtgacct tcgactggga ctaccctgga aagcaggccg agcgtggaaa atgggtgccc   840
gagagaagaa gccagcagac ccacacagag ctgagcagca tcctgaccat ccacaacgtg   900
tcccagcacg atctgggctc ttacgtgtgc aaggccaaca acggcatcca gcggttccgg   960
gaaagcaccg aagtgatcgt gcatgaggaa cccaagagct gcgacaagac acacacctgt   1020
cctccatgtc ctgctccaga gcttctcggc ggaccttccg tgttcctgtt tcctccaaag   1080
cctaaggaca ccctgatgat cagcagaacc cctgaagtga cctgcgtggt ggtggatgtg   1140
tcccacgagg atcccgaagt gaagttcaat tggtacgtgg acggcgtgga agtgcacaat   1200
gccaagacca agcctagaga ggaacagtac aacagcacct acagagtggt gtccgtgctg   1260
accgtgctgc atcaggattg gctgaacggc aaagagtaca agtgcaaggt gtccaacaag   1320
gccctgcctg ctcctatcga gaaaaccatc tccaaggcca agggccagcc tcgggaacct   1380
caagtgtata ccctgcctcc tagccgcgac gaactcacca agaatcaagt gtctctgaca   1440
tgtctcgtga aggggtttta ccccagcgac attgccgtcg agtgggagtc caatggacaa   1500
cccgagaaca attataagac cacgccacca gtcctggact ccgacggctc atttttttctc   1560
tactccaaac tgaccgtgga taagtcccgg tggcagcaag ggaatgtgtt ttcctgtagc   1620
gtgatgcatg aagctctcca caatcattac acccaaaaat ctctgtctct gagccccggc   1680
aaatga                                                                             1686

SEQ ID NO: 59      moltype = AA  length = 1674
FEATURE            Location/Qualifiers
REGION             1..1674
                   note = Synthetic Polypeptide
source             1..1674
                   mol_type = protein
                   organism = synthetic construct
SEQUENCE: 59
ATGCAGAGGG GAGCCGCCCT GTGCCTGAGG CTGTGGCTGT GCCTGGGCCT GCTGGACGGC   60
CTGGTGTCTG GCTACAGCAT GACCCCCCCT ACACTGAACA TCACCGAGGA GAGCCACGTG   120
ATCGACACAG GCGATAGCCT GTCCATCTCT TGCAGGGGCC AGCACCCCCT GGAGTGGGCA   180
TGGCCTGGAG CACAGGAGGC ACCAGCCACC GGCGACAAGG ATAGCGAGGA CACAGGAGTG   240
```

```
GTGCGGGACT GCGAGGGAAC CGATGCCAGA CCTTACTGTA AGGTGCTGCT GCTGCACGAG   300
GTGCACGCCC AGGATACAGG CTCCTACGTG TGCTACTATA AGTATATCAA GGCAAGGATC   360
GAGGGAACCA CAGCAGCCAG CTCCTACGTG TTCGTGCGGG ATTTTGAGCA GCCTTTCATC   420
AACAAGCCAG ACACCCTGCT GGTGAATCGG AAGGATGCCA TGTGGGTGCC CTGTCTGGTG   480
TCTATCCCTG GCCTGAATGT GACACTGAGA AGCCAGTCTA GCGTGCTGTG GCCAGACGGA   540
CAGGAGGTGG TGTGGGACGA TCGGAGAGGC ATGCTGGTGA GCACCCCTCT GCTGCACGAT   600
GCCCTGTACC TGCAGTGCGA GACAACATGG GGCGACCAGG ATTTTCTGTC CAACCCTTTC   660
CTGGTGCACA TCACAGGCAA TGAGCTGTAT GACATCCAGC TGCTGCCACG GAAGTCCCTG   720
GAGCTGCTGG TGGGCGAGAA GCTGGTGCTG AACTGTACCG TGTGGGCCGA GTTTAATTCT   780
GGCGTGACAT TCGACTGGGA TTACCCCGGC AAGCAGGCCG AGAGGGGCAA GTGGGTGCCT   840
GAGAGGCGCA GCCAGCAGAC CCACACAGAG CTGTCCTCTA TCCTGACCAT CCACAACGTG   900
AGCCAGCACG ATCTGGGCTC CTACGTGTGC AAGGCCAACA ATGGCATCCA GCGGTTTAGA   960
GAGTCTACAG AAGTGATCGT GCACGAGGAG AGGAAGTGCT GCGTGGAGTG CCCACCATGT   1020
CCAGCACCTC CAGTGGCAGG ACCATCCGTG TTCCTGTTTC CACCTAAGCC TAAGGACACC   1080
CTGATGATCA GCCGCACCCC AGAGGTGACA TGCGTGGTGG TGGACGTGTC CCACGAGGAT   1140
CCAGAGGTGC AGTTCAACTG GTACGTGGAT GGCGTGGAGG TGCACAATGC CAAGACCAAG   1200
CCCAGGGAGG AGCAGTTTAA TTCTACCTTC CGCGTGGTGA GCGTGCTGAC AGTGGTGCAC   1260
CAGGACTGGC TGAACGGCAA GGAGTATAAG TGCAAGGTGT CTAATAAGGG CCTGCCCGCC   1320
CCTATCGAGA AGACCATCAG CAAGACAAAG GGACAGCCAC GGGAGCCACA GGTGTACACC   1380
CTGCCACCAT CCAGAGAGGA GATGACCAAG AACCAGGTGT CTCTGACATG TCTGGTGAAG   1440
GGCTTTTATC CAAGCGACAT CGCCGTGGAG TGGGAGTCCA ATGGCCAGCC CGAGAACAAT   1500
TACAAGACCA CACCTCCAAT GCTGGACTCC GATGGCTCTT TCTTTCTGTA TTCCAAGCTG   1560
ACCGTGGATA AGTCTCGGTG GCAGCAGGGC AACGTGTTCA GCTGTTCCGT GATGCACGAG   1620
GCCCTGCACA ATCACTACAC ACAGAAGTCT CTGAGCCTGT CCCCCGGCAA GTGA          1674
```

```
SEQ ID NO: 60          moltype = DNA  length = 1257
FEATURE                Location/Qualifiers
misc_feature           1..1257
                       note = Synthetic Polynucleotide
source                 1..1257
                       mol_type = other DNA
                       organism = synthetic construct
SEQUENCE: 60
atgcaagctc tggtgctgct gctgtgtatc ggagccctgc tgggccacag ctcctgtcaa   60
aatcctgcct ctccacctga ggaaggcagc cccgatccag attctacagg cgccctggtg   120
gaagaagagg acccattctt caaggtgccc gtgaacaaac tggccgctgc cgtgtccaac   180
ttcggctacg acctgtacag agtgcggagc agcacaagcc caccaccaa tgttctgctg    240
agccctctgt ctgtggccac cgctctttct gctctgtctc tgggagccga gcagagaacc   300
gagagcatca ttcacagagc cctgtactac gatctgatca gcagccctga catccacggc   360
acctacaaag aactgctgga caccgtgaca gcccctcaga agaatctgaa gtccgccagc   420
cggatcgtgt tcgagaagaa gctgcggatc aagagcagct cgtggcccc tctggaaaag    480
agctacggca ccagacctag agtgctgacc ggcaatccca gactggacct gcaagagatc   540
aacaactggg tgcaagccca gatgaagggc aagctggcca gaagcaccaa agagatcccc   600
gacgagatca gcatcctgct gctgggcgtc gcccacttta aaggccagtg ggtcaccaag   660
ttcgactcca gaaagaccag cctcgaggac ttctacctgg acgaggaacg gaccgtcaga   720
gtgcccatga tgagcgatcc taaggccgtg ctgagatacg gcctggatag cgacctgagc   780
tgcaagattg ctcagctgcc tctgaccggc tctatgaacc tcatattctt tctgcccctg   840
aaagtgacc  agaatctgac cctgatcgag gaaagcctga ccagcgagtt catccacgac   900
atcgaccgcg agctgaaaac cgtgcaggct gtgctgactg tgcccaagct gaagctgagc   960
tacgagggcg aagtgaccaa gagcctgcaa gaaatgaagc tgcagagcct gttcgacagc   1020
cccgacttca gcaagatcac cggcaagccc atcaagctga cccaggtgga acacagagcc   1080
ggcttcgagt ggaatgaaga tggcgccgga accacacctt ctccaggact gcaacctgct   1140
cacctgacct ttccactgga ctaccacctg aaccagcctt tcatcttcgt gctgcgggac   1200
acagatactg gcgccctgct gttcatcggc aagatcctgg atcctagagg cccctga      1257
```

```
SEQ ID NO: 61          moltype = DNA  length = 145
FEATURE                Location/Qualifiers
source                 1..145
                       mol_type = other DNA
                       organism = Adeno-associated virus 2
SEQUENCE: 61
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg   120
gccaactcca tcactagggg ttcct                                          145
```

```
SEQ ID NO: 62          moltype = DNA  length = 145
FEATURE                Location/Qualifiers
source                 1..145
                       mol_type = other DNA
                       organism = Adeno-associated virus 2
SEQUENCE: 62
aggaacccct agtgatggag ttggccactc cctctctgcg cgctcgctcg ctcactgagg   60
ccgcccgggc aaagcccggg cgtcgggcga cctttggtcg cccggcctca gtgagcgagc   120
gagcgcgcag agagggagtg gccaa                                          145
```

```
SEQ ID NO: 63          moltype = DNA  length = 245
FEATURE                Location/Qualifiers
misc_feature           1..245
                       note = Synthetic Polynucleotide
```

```
source                    1..245
                          mol_type = other DNA
                          organism = synthetic construct
SEQUENCE: 63
ggggatccag acatgataag atacattgat gagtttggac aaaccacaac tagaatgcag   60
tgaaaaaaat gctttatttg tgaaatttgt gatgctattg cttttatttg aaccattata  120
agctgcaata aacaagttaa caacaacaat tgcattcatt ttatgtttca ggttcagggg  180
gaggtgtggg aggttttta aagcaagtaa aacctctaca aatgtggtat ggctgattat  240
gatca                                                             245

SEQ ID NO: 64            moltype = DNA   length = 4297
FEATURE                  Location/Qualifiers
misc_feature             1..4297
                         note = Synthetic Polynucleotide
source                   1..4297
                         mol_type = other DNA
                         organism = synthetic construct
SEQUENCE: 64
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcctatcga ttgaattcca ggcgcgccat cctgcaggta  180
ttgacgtcaa taatgacgta tgttcccata gtaacgccaa tagggacttt ccattgacgt  240
caatgggtgg agtatttacg gtaaactgcc cacttggcag tacatcaagt gtatcatatg  300
ccaagtacgc cccctattga cgtcaatgac ggtaaatggc ccgcctggca ttatgcccag  360
tacatgacct tatgggactt tcctacttgg cagtacatct acgtattagt catcgctatt  420
accatggtcg aggtgagccc cacgttctgc ttcactctcc ccatctcccc ccctcccca   480
cccccaattt tgtatttatt tattttttaa ttatttgtg cagcgatggg ggcgggggg   540
gggggggggc gcgcgccagg cggggcgggg cggggcgagg ggcggggcgg ggcgaggcgg   600
agaggtgcgg cggcagccaa tcagagcggc gcgctccgaa agtttccttt tatggcgagg   660
cggcggcggc ggcggcccta taaaaagcga agcgcgcggc gggcgggagt cgctgcgcgc   720
tgccttcgcc ccgtgccccg ctccgccgcc gcctcgcgcc gcccgccccg gctctgactg   780
accgcgttac tcccacaggt gagcgggcgg gacggccctt ctcctccggg ctgtaattag   840
cgcttggttt aatgacggct tgtttctttt ctgtggctgc gtgaaagcct tgagggctc   900
cgggagggcc ctttgtgcgg ggggagcggc tcggggctgt ccgacggggg acggctgcct   960
tcgggggga cggggcaggg cggggttcgg cttctggcgt gtgaccggcg gctctagagc  1020
ctctgctaac catgttcatg ccttcttctt tttcctacag ctcctgggca acgtgctggt  1080
tattgtgctg tctcatcatt ttggcaaaga attgtacagg atatcttgct agcacgccac  1140
catggtttct tactgggaca ccggcgtgct gctgtgtgcc ctgctttctt gtctgctgct  1200
gaccggctct agcagcggct ctgataccgg cagacccttc gtggaaatgt acagcgagat  1260
ccccgagatc atccacatga ccgagggcag agagctggtc atcccttgca gagtgacaag  1320
ccccaacatc accgtgactc tgaagaagtt ccctctggac acactgatcc ccgacggcaa  1380
gagaatcatc tgggacagcc ggaagggctt catcatcagc aacgccacct acaaagagat  1440
cggcctgctg acctgtgaag ccaccgtgaa tggccacctg tacaagacca actacctgac  1500
acacagacag accaacacca tcatcgacgt ggtgctgagc cctagccacg gcattgaact  1560
gtctgtgggc gagaagctgg tgctgaactg taccgccaga accgagctga acgtgggcat  1620
cgacttcaac tgggagtacc ccagcagcaa gcaccagcac aagaaactgg tcaaccggga  1680
cctgaaaacc cagagcggca gcgagatgaa gaaattcctg agcacccctga ccatcgacgg  1740
cgtgaccaga agtgaccagg gcctgtacac atgtgccgcc agctctggcc tgatgaccaa  1800
gaaaaacagc accttcgtgc gggtgcacga gaaggacaag acccacacct gtcctccatg  1860
tcctgctcca gaactgctcg gcggaccttc cgtgttcctg tttcctccaa agcctaagga  1920
caccctgatg atcagcagaa cccctgaagt gacctgcgtg gtggtggatg tgtcccacga  1980
ggatcccgaa gtgaagttca attggtacgt ggacggcgtg gaagtgcaca cgccaagac  2040
caagcctaga gaggaacagt acaatagcac ctacagagtg gtgtccgtgc tgaccgtgct  2100
gcaccaggat tggctgaacg gcaaagagta caagtgcaag gtgtccaaca aggccctgcc  2160
tgctcctatc gagaaaacca tctccaaggc caagggccag cctagggaac cccaggttta  2220
cacactgcct ccaagcaggg acgagctgac aaagaaccag gtgtccctga cctgcctggt  2280
caagggcttc taccttccg atatcgccgt ggaatgggag agcaatggc agcctgagaa  2340
caactacaag acaacccctc ctgtgctgga cagcgacggc tcattcttcc tgtacagcaa  2400
gctgacagtg gacaagagca gatggcagca gggcaacgtg ttcagctgct ccgtgatgca  2460
cgaggccctg cacaaccact acacccagaa gtccctgagc ctgtctcctg gcaaacggaa  2520
gagaagaggc agcggcgaag gcagaggatc cctgcttaca tgtggcgacg tggaagagaa  2580
ccccggacct atgcaagctc tggtgctgct gctgtgtatc ggagcctgc tgggccacgc  2640
ctcctgtcaa aatcctgcct ctccacctga ggaaggcagc cccgatccag attctacagg  2700
cgccctggtg gaagaagagg acccattctt caaggtcgcc gtgaacaaac tggcccgcct  2760
cgtgtccaac ttcggctacg acctgtacag agtgcggagc agcacaagcc ccaccaccaa  2820
tgttctgctg agcctctgt ctgtggccac cgctctttct gctctgtctc tgggagccga  2880
gcagagaacc gagagcatca ttcacagagc cctgtactac gatctgatca gcagccctga  2940
catccacggc acctacaaag aactgctgga caccgtgaca gcccctcaga agaatctgaa  3000
gtccgacaac cggatcgtgt tcgagaagaa gctgcggatc aagagcagct tcgtggcccc  3060
tctggaaaag agctacggca ccagacctag agtgctgacc ggcaatccca gactggacct  3120
gcaagagatc aacaactggg tgcaagccca gatgaagggc aagctggcca gaagcaccaa  3180
agagatcccc gacgagatca gcatcctgct gctgggcgtc gcccacttta aaggccagtg  3240
ggtcaccaag ttcgactcca gaaagaccag cctcgaggac ttctacctgg acgaggaacg  3300
gaccgtcaga gtgcccatga tgagcgatcc taaggccgtg ctgagatacg gcctggatag  3360
cgacctgagc tgcaagattg ctcagctgcc tctgaccggc tctatgagca tcatattctt  3420
tctgcccctg aaagtgaccc agaatctgac cctgatcgag gaaagcctga ccagcgagtt  3480
catccacgac atcgaccgcg agctgaaaac cgtgcaggct gtgctgactg tgcccaagct  3540
gaagctgagc tacgagggcg aagtgaccaa gagcctgcaa gaaatgaagc tgcagagcct  3600
gttcgacagc cccgacttca gcaagatcac cggcaagccc atcaagctga cccaggtgga  3660
```

```
acacagagcc ggcttcgagt ggaatgaaga tggcgccgga accacacctt ctccaggact  3720
gcaacctgct cacctgacct ttccactgga ctaccacctg aaccagcctt tcatcttcgt  3780
gctgcgggac acagatactg cgcgcctgct gttcatcggc aagatcctgg atcctagagg  3840
cccctgagcc acgcgtaaca cgtgcatgcg agagatctgc ggccgcgagc tcggggatcc  3900
agacatgata agatacattg atgagtttgg acaaaccaca actagaatgc agtgaaaaaa  3960
atgctttatt tgtgaaattt gtgatgctat tgctttattt gtaaccatta taagctgcaa  4020
taaacaagtt aacaacaaca attgcattca ttttatgttt caggttcagg gggaggtgtg  4080
ggaggttttt taaagcaagt aaaacctcta caaatgtggt atggctgatt atgatcaatg  4140
catcctagcc ggaggaaccc ctagtgatgg agttggccac tccctctctg cgcgctcgct  4200
cgctcactga ggccgcccgg gcaaagcccg ggcgtcgggc gacctttggt cgcccggcct  4260
cagtgagcga gcgagcgcgc agagagggag tggccaa                            4297

SEQ ID NO: 65            moltype = DNA  length = 4726
FEATURE                  Location/Qualifiers
misc_feature            1..4726
                        note = Synthetic Polynucleotide
source                  1..4726
                        mol_type = other DNA
                        organism = synthetic construct
SEQUENCE: 65
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg  120
gccaactcca tcactagggg ttcctatcga ttgaattcca ggcgcgccat cctgcaggta  180
ttgacgtcaa taatgacgta tgttcccata gtaacgccaa tagggacttt ccattgacgt  240
caatgggtgg agtatttacg gtaaactgcc cacttggcag tacatcaagt gtatcatatg  300
ccaagtacgc cccctattga cgtcaatgac ggtaaatggc ccgcctggca ttatgcccag  360
tacatgacct tatgggactt tcctacttgg cagtacatct acgtattagt catcgctatt  420
accatggtcg aggtgagccc cacgttctgc ttcactctcc ccatctcccc ccctccccca  480
cccccaattt tgtatttatt tattttttaa ttattttgtg cagcgatggg ggcgggggg  540
ggggggggc gcgcgccagg cggggcgggg cggggcggga ggcggggcgg ggcgaggcgg  600
agaggtgcgg cggcagccaa tcagagcggc gcgctccgaa agtttccttt tatggcgagg  660
cggcggcggc ggcggcccta taaaaagcga agcgcgcggc gggcgggagt cgctgcgcgc  720
tgccttcgcc ccgtgccccg ctccgccgcc gcctcgcgcc gcccgccccg gctctgactg  780
accgcgttac tcccacaggt gagcgggcgg gacggccctt ctcctccggg ctgtaattag  840
cgcttggttt aatgacggct tgtttctttt ctgtggctgc gtgaaagcct tgaggggctc  900
cgggagggcc ctttgtgcgg ggggagcggc tcggggctgt ccgaggggg acggctgcct  960
tcgggggga cggggcaggg cggggttcgg cttctggcgt gtgaccggcg gctctagagc  1020
ctctgctaac catgttcatg ccttcttctt tttcctacag ctcctgggca acgtgctggt  1080
tattgtgctg tctcatcatt ttggcaaaga attgtacagg atatcttgct agcacgccaa  1140
catggtttct tactgggaca ccggcgtgct gctgtgtgcc ctgctttctt gtctgctgct  1200
gaccggctct agcagcggct ctgataccgg cagacccttc gtggaaatgt acagcgagat  1260
ccccgagatc atccacatga ccgagggcag agagctggtc atcccttgca gagtgacaag  1320
ccccaacatc accgtgactc tgaagaagtt ccctctggac ctgctggct ccgacggcaa  1380
gagaatcatc tgggacagcc ggaagggctt catcatcagc aacgccacct acaaagagat  1440
cggcctgctg acctgtgaag ccaccgtgaa tggccacctg tacaagacca actacctgac  1500
acacagacag accaacacca tcatcgacgt ggtgctgagc cctagccacg gcattgaact  1560
gtctgtgggc gagaagctgg tgctgaactg taccgccaga accgagctga acgtgggcat  1620
cgacttcaac tgggagtacc ccagcagcaa gcaccagcac aagaaactgg tcaaccggga  1680
cctgaaaacc cagagcggca gcgagatgaa gaaattcctg agcaccctga ccatcgacgg  1740
cgtgaccaga agtgaccagg gcctgtacac atgtgccgcc agctctggcc tgatgaccaa  1800
gaaaaacagc accttcgtgc gggtgcacga gaaggacaag acccacacct gtcctccatg  1860
tcctgctcca gaactgctcg gcggaccttc cgtgttcctg tttcctccaa agcctaagga  1920
caccctgatg atcagcagaa cccctgaagt gacctgcgtg gtggtggatg tgtcccacga  1980
ggatcccgaa gtgaagttca attggtacgt ggacggcgtg gaagtgcaca cgccaagac  2040
caagcctaga gaggaacagt acaatagcac ctacagagtg gtgtccgtgc tgaccgtgct  2100
gcaccaggat tggctgaacg gcaaagagta caagtgcaag gtgtccaaca ggccctgcc  2160
tgctcctatc gagaaaacca tctccaaggc caagggccag cctagggaac cccaggttta  2220
cacactgcct ccaagcaggg acgagctgac aaagaaccag gtgtccctga cctgcctggt  2280
caagggcttc tacccttccg atatcgccgt ggaatgggag agcaatggcc agcctgagaa  2340
caactacaag acaaccccctc ctgtgctgga cagcgacggc tcattcttcc tgtacagcaa  2400
gctgacagtg gacaagagca gatggcagca gggcaacgtg ttcagctgct ccgtgatgca  2460
cgaggccctg cacaaccact acacccagaa gtccctgagc ctgtctcctg gcaaacggaa  2520
gagaagaggc agcggcgaag gcagaggatc cctgcttaca tgtggcgacg tggaagagaa  2580
ccccgacct atgcaaagag gcgccgctct ctgtctgaga ctggtgctgt gtctggggcct  2640
gctggatgga ctggtgtctg ctacagcat gaccctcca acactgaaca tcaccgagga  2700
atcccacgtg atcgacaccg gcgatagcct gagcatcagc tgcagaggac agcacccct  2760
ggaatgggct tggcctggtg ctcaagaagc tcctgccaca ggcgacaagg acagcgagga  2820
tacaggcgtt gtgcgggatt gcgagggcac agatgccaga ccttactgca aggtgctgct  2880
gctgcacgaa gtgcacgccc aggataccgg cagctacgtg tgctactaca gtacatcaa  2940
ggccccggatc gagggcacca cagccgctag ctcttatgtg ttcgtgcggg acttcgagca  3000
gcccttcatc aacaagcccg cacacactgct ggtcaaccgg aaggacgcta tgtgggtgcc  3060
ctgtctggtc tctatcccg gcctgaatgt gaccctgaga agccagagtt ccgtgctgtg  3120
gcctgatggc caagaggtcg tgtgggacga tagaagggc atgctggtgt ccacacctct  3180
gctgcatgat gccctgtacc tgcagtgcga gacaacctgg ggcgaccagg acttcctgag  3240
caaccctttc ctggtgcaca tcaccggcaa cgagctgtac gacatccagc tgctgcctcg  3300
caagagcctg gaactgctcg tgggagagaa gctggtgctg aactgtaccg tgtgggcga  3360
gttcaatagc ggcgtgacct tcgactggga ctaccctgga aagcaggccg agcgtggaaa  3420
atgggtgccc gagagaagaa gccagcagac ccacacagag ctgagcagca tcctgaccat  3480
ccacaacgtg tcccagcacg atctgggctc ttacgtgtgc aaggccaaca acggcatcca  3540
```

-continued

```
gcggttccgg gaaagcaccg aagtgatcgt gcatgaggaa cccaagagct gcgacaagac   3600
acacacctgt cctccatgtc ctgctccaga gcttctcggc ggaccttccg tgttcctgtt   3660
tcctccaaag cctaaggaca ccctgatgat cagcagaacc cctgaagtga cctgcgtggt   3720
ggtggatgtg tcccacgagg atcccgaagt gaagttcaat tggtacgtgg acggcgtgga   3780
agtgcacaat gccaagacca agcctagaga ggaacagtac aacagcacct acagagtggt   3840
gtccgtgctg accgtgctgc atcaggattg gctgaacggc aaagagtaca agtgcaaggt   3900
gtccaacaag gccctgcctg ctcctatcga gaaaaccatc tccaaggcca agggccagcc   3960
tcgggaacct caagtgtata ccctgcctcc tagccgcgac gaactcacca agaatcaagt   4020
gtctctgaca tgtctcgtga aggggtttta ccccagcgac attgccgtcg agtgggagtc   4080
caatggacaa cccgagaaca attataagac cacgcccacca gtcctggact ccgacggctc   4140
attttttctc tactccaaac tgaccgtgga taagtcccgg tggcagcaag ggaatgtgtt   4200
ttcctgtagc gtgatgcatg aagctctcca caatcattac acccaaaaat ctctgtctct   4260
gagccccggc aaatgagcca cgcgtaacac gtgcatgcga gagatctgcg gccgcgagct   4320
cggggatcca gacatgataa gatacattga tgagtttgga caaaccacaa ctagaatgca   4380
gtgaaaaaaa tgctttattt gtgaaatttg tgatgctatt gctttatttg taaccattat   4440
aagctgcaat aaacaagtta acaacaacaa ttgcattcat tttatgtttc aggttcaggg   4500
ggaggtgtgg gaggtttttt aaagcaagta aaacctctac aaatgtggta tggctgatta   4560
tgatcaatgc atcctagccg gaggaacccc tagtgatgga gttggccact ccctctctgc   4620
gcgctcgctc gctcactgag gccgcccggg caaagcccgg gcgtcgggcg acctttggtc   4680
gcccggcctc agtgagcgag cgagcgcgca gagagggagt ggccaa            4726
```

SEQ ID NO: 66              moltype = DNA   length = 4642
FEATURE                   Location/Qualifiers
misc_feature              1..4642
                          note = Synthetic Polynucleotide
source                    1..4642
                          mol_type = other DNA
                          organism = synthetic construct SEQUENCE: 66
```
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg   120
gccaactcca tcactagggg ttcctatcga ttgaattcca ggcgcgccat cctgcaggta   180
ttgacgtcaa taatgacgta tgttcccata gtaacgccaa tagggacttt ccattgacgt   240
caatgggtgg agtatttacg gtaaactgcc cacttggcag tacatcaagt gtatcatatg   300
ccaagtacgc cccctattga cgtcaatgac ggtaaatggc ccgcctggca ttatgcccag   360
tacatgacct tatgggactt tcctacttgg cagtacatct acgtattagt catcgctatt   420
accatggtcg aggtgagccc cacgttctgc ttcactctcc ccatctcccc ccctcccca   480
cccccaattt tgtatttatt tattttttaa ttattttgtg cagcgatggg ggcggggggg   540
ggggggggc gcgcgccagg cggggcgggg cggggcgagg ggcggggcgg ggcgaggcgg   600
agaggtgcgg cggcagccaa tcagagcggc gcgctccgaa agtttccttt tatggcgagg   660
cggcggcggc ggcggcccta taaaaagcga agcgcgcggc gggcgggagt cgctgcgcgc   720
tgccttcgcc ccgtgcccgc ctccgccgcc gcctcgcgcc gcccgccccg gctctgactg   780
accgcgttac tcccacaggt gagcgggcgg gacggcccct ctcctccggg ctgtaattag   840
cgcttggttt aatgacggct tgtttctttt ctgtggctgc gtgaaagcct tgaggggctc   900
cgggagggc ctttgtgcgg ggggagcggc tcggggctgt ccgcgggggg acggctgcct   960
tcggggggga cggggcaggg cggggttcgg cttctggcgt gtgaccggcg gctctagagc   1020
ctctgctaac catgttcatg ccttcttctt tttcctacag ctcctgggca acgtgctggt   1080
tattgtgctg tctcatcatt ttggcaaaga attgtacagg atatcttgct agcacgccac   1140
catggtttct tactgggaca ccggcgtgct gctgtgtgcc ctgctttctt gtctgctgct   1200
gaccggctct agcagcggct ctgataccgg cagaccttc gtggaaatgt acagcgagat   1260
ccccgagatc atccacatga ccgagggcag agagctgatc atcccttgca gagtgaccaa   1320
ccccaacatc accgtgactc tgaagaagtt ccctctggac acactgatcc ccgacggcaa   1380
gagaatcatc tgggacagcc ggaagggctt catcatcagc aacgccacct acaaagagat   1440
cggcctgctg acctgtgaag ccaccgtgaa tggccacctg tacaagacca actacctgac   1500
acacagacag accaacacca tcatcgacgt ggtgctgagc cctagccacg gcattgaact   1560
gtctgtgggc gagaagctgg tgctgaactg taccgccaga accgagctga acgtgggcat   1620
cgacttcaac tgggagtacc ccagcagcaa gcaccagcac aagaaactgg tcaaccggga   1680
cctgaaaacc cagagcggca gcgagatgaa gaaattcctg agcaccctga ccatcgacgg   1740
cgtgaccaga agtgaccagg gcctgtacac atgtgccgcc agctctggcc tgatgaccaa   1800
gaaaaacagc accttcgtgc gggtgcacga gaaggacaag acccacacct gtcctccatg   1860
tcctgctcca gaactgctcg gcggaccttc cgtgttcctg tttcctccaa agcctaagga   1920
caccctgatg atcagcagaa ccctgaagt gacctgcgtg gtggtggatg tgtcccacga   1980
ggatcccgaa gtgaagttca attggtacgt ggacggcgtg gaagtgcaca acgccaagac   2040
caagcctaga gaggaacagt acaatagcac ctacagagtg gtctccgtgc tgaccgtgct   2100
gcaccaggat tggctgaacg gcaaagagta caagtgcaag gtgtccaaca aggccctgcc   2160
tgctcctatc gagaaaacca tctccaaggc caagggccag cctagggaac cccaggttta   2220
cacactgcct ccaagcaggg acgagctgac aaagaaccag gtgtccctga cctgcctggt   2280
caagggcttc tacccttccg atatcgccgt ggaatggag agcaatggcc agcctgaaaa   2340
caactacaag acaaccccctc ctgtgctgga cagcgacggc tcattcttcc tgtacagcaa   2400
gctgacagtg gacaagagca gatggcagca gggcaacgtg ttcagctgct ccgtgatgca   2460
cgaggccctg cacaaccact acacccagaa gtccctgagc ctgtctcctg gcaaacggaa   2520
gagaagaggc agcggcgaag gcagaggatc cctgcttaca tgtggcgacg tggaagagaa   2580
ccccggacct atggattgga cctggtccat cctgtttctg gtggccgctg ccacaggcac   2640
atactctcag gttcagctgg tgcagtctgg cgccgaagtg aaaaaacctg gcgcctccgt   2700
gaaggtgtcc tgcaaggcta gcggctacac ctttaccggc tactacatgc actgggtccg   2760
acaggctcca ggacagggac ttgaatggat gggctggatc aacccccata gcggcggcac   2820
caattacgcc cagaaattcc agggcagagt gaccatgacc agagacacca gcatcagcac   2880
cgcctacatg gaactgagcc ggctgagatc cgatgacacc gccgtgtact actgcgccag   2940
atctcccaat cccttactact acgacagcag cgggtactac tacccaggcg cctttgatat   3000
```

```
ctggggccag ggcacaatgg tcaccgtgtc atctgcatct gtggccgctc ctagcgtgtt   3060
catcttccca ccttccgacg aacagctgaa gtctggcaca gccagcgtcg tgtgcctgct   3120
gaacaacttc taccccagag aagccaaggt gcagtggaag gtggacaacg ctctgcagtc   3180
cggcaacagc caagagagcg tgacagagca ggacagcaag gactccacct acagcctgag   3240
cagcaccctg acactgagca aggccgacta cgagaagcac aaagtgtacg cctgcgaagt   3300
gacccaccag ggcctttcta gccctgtgac caagagcttc aaccggggcg agtgcgataa   3360
gacacacaca ggcggaagca gcggcagcgg atctggatct accggcacat ctagctctgg   3420
caccggaaca tctgccggca caactggcac aagcgcctct acatctggaa gcggttctgg   3480
cggaggcgga ggatctggtg gtggtggatc tgctggcgga acagctacag ctggcgcttc   3540
tagcggcagc agctatgtgc tgacacagcc tccatccgtg tctgtggcac ctggacagac   3600
cgccagaatt acctgtggcg gcaacaacat cggcagcaag agcgtgcact ggtatcagca   3660
gaagcctgga caggcaccag tgctggtggt gtacgacgac agcgatagac ctagcggcat   3720
ccccgagaga ttcagcggct ctaacagcgg caataccgcc acactgacca tcagcagagt   3780
ggaagctggc gacgaggccg attactactg ccaagtgtgg gacagcagca ggcaccactg   3840
ggttttcggc ggaggcacca aactgacagt gctgtctagc gccagcacaa agggcccatc   3900
tgtgttccct ctggctccca gcagcaagtc tacaagcgga ggaacagccg ctctgggctg   3960
cctcgtgaag gattactttc ccgagcctgt gaccgtgtcc tggaatagcg gagcactgac   4020
aagcggcgtg cacacctttc cagctgtgct gcaaagctcc ggcctgtact ctctgagcag   4080
cgtggtcaca gtgccagct ctagcctggg cacccagacc tacatctgca atgtgaacca   4140
caagcctagc aacaccaagg tcgacaagaa ggtggaaccc aagagctgct gagccacgcg   4200
taacacgtgc atgcgagaga tctgcggccg cgagctcggg gatccagaca tgataagata   4260
cattgatgag tttggacaaa ccacaactag aatgcagtga aaaaaatgct ttatttgtga   4320
aatttgtgat gctattgctt tatttgtaac cattataagc tgcaataaac aagttaacaa   4380
caacaattgc attcatttta tgtttcaggt tcaggggggag gtgtgggagg tttttttaaag   4440
caagtaaaac ctctacaaat gtggtatggc tgattatgat caatgcatcc tagccggagg   4500
aacccctagt gatggagttg gccactccct ctctgcgcgc tcgctcgctc actgaggccg   4560
cccgggcaaa gcccgggcgt cgggcgacct ttggtcgccc ggcctcagtg agcgagcgag   4620
cgcgcagaga gggagtggcc aa                                             4642
```

```
SEQ ID NO: 67          moltype = DNA   length = 4645
FEATURE                Location/Qualifiers
misc_feature           1..4645
                       note = Synthetic Polynucleotide
source                 1..4645
                       mol_type = other DNA
                       organism = synthetic construct
SEQUENCE: 67
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg   120
gccaactcca tcactagggg ttcctatcga ttgaattcca ggcgcgccat cctgcaggta   180
ttgacgtcaa taatgacgta tgttcccata gtaacgccaa tagggacttt ccattgacgt   240
caatgggtgg agtatttacg gtaaactgcc cacttggcag tacatcaagt gtatcatatg   300
ccaagtacgc ccctattga cgtcaatgac ggtaaatggc ccgcctggca ttatgcccag   360
tacatgacct tatgggactt tcctacttgg cagtacatct acgtattagt catcgctatt   420
accatggtcg aggtgagccc cacgttctgc ttcactctcc ccatctcccc ccctcccca   480
cccccaattt tgtatttatt tattttttaa ttattttgtg cagcgatggg ggcggggggg   540
gggggggggc gcgcgccagg cggggcgggg cggggcgagg ggcgggggcg gtgcgaggcgg   600
agaggtgcgg cggcagccaa tcagagcggc gcgctccgaa agtttccttt tatggcgagg   660
cggcggcggc ggcggcccta taaaaagcga agcgcgcggc gggcgggagt cgctgcgcgc   720
tgccttcgcc ccgtgcccg ctccgccgcc gcctcgcgcc gcccgcccg gctctgactg   780
accgcgttac tcccacaggt gagcgggcgg gacggccctt ctcctccggg ctgtaattag   840
cgcttggttt aatgacggct tgtttctttt ctgtggctgc gtgaaagcct tgaggggctc   900
cgggagggcc ctttgtgcgg ggggagcggc tcggggctgt ccgcgggggg acggctgcct   960
tcggggggga cggggcaggg cggggttcgg cttctggcgt gtgaccggcg gctctagagc   1020
ctctgctaac catgttcatg ccttcttctt tttcctacag ctcctgggca acgtgctggt   1080
tattgtgctg tctcatcatt ttggcaaaga attgtacagg atatcttgct agcacgccac   1140
catggtttct tactgggaca ccggcgtgct gctgtgtgcc ctgctttctt gtctgctgct   1200
gaccggctct agcagcggct ctgataccgg cagacccttc gtgaaatgt acagcgagat   1260
ccccgagatc atccacatga ccgagggcag agagctggtc atcccttgca gagtgacaag   1320
ccccaacatc accgtgactc tgaagaagtt ccctctggac acactgatcc ccgacggcaa   1380
gagaatcatc tgggacagcc ggaagggctt catcatcagc aacgccacct acaaagagat   1440
cggcctgctg acctgtgaag ccaccgtgaa tggccacctg tacaagacca actacctgac   1500
acacagacag accaacacca tcatcgacgt ggtgctgagc cctagccacg gcattgaact   1560
gtctgtggc gagaagctgg tgctgaactg taccgcccaga accgagctga acgtgggcat   1620
cgacttcaac tgggagtacc ccagcagcaa gcaccagcac aagaaactgg tcaacccgga   1680
cctgaaaacc cagagcggca gcgagatgaa gaaattcctg agcaccctga ccatcgacgt   1740
cgtgaccaga agtgaccagg gcctgtacac atgtgccgcc agctctggcc tgatgaccaa   1800
gaaaaacagc accttcgtgc gggtgcacga aaggacaaag acccacacct gtcctccatg   1860
tcctgctcca gaactgctcg gcggaccttc cgtgttcctg tttcctccaa gccctaagga   1920
caccctgatg atcagcagaa cccctgaagt gacctgcgtg gtggtggatg tgtcccacga   1980
ggatcccgaa gtgaagttca attggtacgt ggacggcgtg gaagtgcaca acgccaagac   2040
caagcctaga gaggaacagt acaatagcac ctacagagtg gtgtccgtgc tgaccgtgct   2100
gcaccaggat tggctgaacg gcaaagagta caagtgcaag gtgtccaaca ggccctgcc   2160
tgctcctatc gagaaaacca tctccaaggc caagggacag cccagagaac cccaggttta   2220
cacactgcct ccaagcaggg acgagctgac aaagaaccag gtgtccctga cctgcctggt   2280
caagggcttc taccttccg atatcgccgt ggaatgggag agcaatggcc agcctgagaa   2340
caactacaag acaaccccctc ctgtgctgga cagcgacggc tcattcttcc tgtacagcaa   2400
gctgacagtg gacaagagca gatggcagca gggcaacgtg ttcagctgct ccgtgatgca   2460
cgaggccctg cacaaccact acacccagaa gtccctgagc ctgtctcctg gcaaacggaa   2520
```

```
gagaagaggc agcggcgaag gcagaggatc cctgcttaca tgtggcgacg tggaagagaa   2580
ccccggacct atggttctgc agacccaggt gttcatcagc ctgctgctgt ggatctctgg   2640
cgcctacggc agctatgtgc tgacacagcc tccatccgtg tctgtggctc caggacagac   2700
cgccagaatt acctgcggcg gcaacaacat cggcagcaag agcgtgcact ggtatcagca   2760
gaagcctgga caggctccag tgctggtggt gtacgacgac agcgatagac ctagcggcat   2820
ccccgagaga ttcagcggca gcaattccgg caataccgcc acactgacca tcagcagagt   2880
ggaagctggc gacgaggccg actactactg ccaagtgtgg gatagcagca gcgaccactg   2940
ggttttcggc ggaggcacca aactgacagt gctgagcagc gcctctacaa agggccctag   3000
tgtgttccct ctggctccca gcagcaagtc tacatctggc ggaacagccg ctctgggctg   3060
cctcgtgaag gattactttc ccgagcctgt gaccgtgtcc tggaatagcg gagcactgac   3120
aagcggcgtg cacacctttc cagctgtgct gcaaagcagc ggcctgtact ctctgtccag   3180
cgtggtcaca gtgccaagct ctagcctggg cacccagacc tacatctgca atgtgaacca   3240
caagcctagc aacaccaagg tcgacaagaa ggtggaaccc aagagctgtg gcggcagctc   3300
tggttctgga tctggcagca caggcacatc tagctctggc accggaacaa gcgctggcac   3360
aactggcaca tctgccagca caagcggatc tggaagtggc ggaggcggag gatctggtgg   3420
cggtggatct gcaggcggaa ctgctacagc tggcgcttct agtggaagcc aggtgcagct   3480
ggttcagtct ggcgccgaag tgaaaaagcc tggcgcctct gtgaaggtgt cctgcaaggc   3540
cagcggctac acctttaccg gctactacat gcactgggtc cgacaggcac caggacaggg   3600
acttgaatgg atgggctgga tcaaccccaa tagcggcggc accaattacg cccagaaatt   3660
ccagggcaga gtgaccatga ccagagacac cagcatcagc accgcctaca tggaactgag   3720
ccggctgaga tccgatgaca ccgccgtgta ctactgcgcc agatctccca atccttacta   3780
ctacgacagc agcgggtact actacccagg cgcctttgat atctggggcc agggcaccat   3840
ggtcaccgtg tcatctgcat ctgtggccgc tcctagcgtg ttcatcttcc caccttccga   3900
cgaacagctg aagtccggca cagcctctgt cgtgtgcctg ctgaacaact tctaccccag   3960
agaagccaaa gtgcagtgga aggtggacaa cgccctgcag agcggcaata gccaagagag   4020
cgtgaccgag caggacagca aggactctac ctacagcctg agcagcaccc tgacactgag   4080
caaggccgat tacgagaagc acaaggtgta cgcctgcgaa gtgacacacc agggcctgtc   4140
tagccctgtg accaagagct tcaatcgggg cgagtcgac aagacccaca cctaagccac   4200
gcgtaacacg tgcatgcgag agatctgcgg ccgcgagctc ggggatccag acatgataag   4260
atacattgat gagtttggac aaaccacaac tagaatgcag tgaaaaaaat gctttatttg   4320
tgaaatttgt gatgctattg ctttattttgt aaccattata agctgcaata aacaagttaa   4380
caacaacaat tgcattcatt ttatgtttca ggttcagggg gaggtgtggg aggttttttta   4440
aagcaagtaa aacctctaca aatgtggtat ggctgattat gatcaatgca tcctagccgg   4500
aggaacccct agtgatggag ttggccactc cctctctgcg cgctcgctcg ctcactgagg   4560
ccgcccgggc aaagcccggg cgtcgggcga cctttggtcg cccggcctca gtgagcgagc   4620
gagcgcgcag agagggagtg gccaa                                        4645
```

SEQ ID NO: 68            moltype = DNA   length = 3834
FEATURE                  Location/Qualifiers
misc_feature             1..3834
                         note = Synthetic Polynucleotide
source                   1..3834
                         mol_type = other DNA
                         organism = synthetic construct
SEQUENCE: 68

```
ttggccactc cctctctgcg cgctcgctcg ctcactgagg ccgggcgacc aaaggtcgcc   60
cgacgcccgg gctttgcccg ggcggcctca gtgagcgagc gagcgcgcag agagggagtg   120
gccaactcca tcactagggg ttcctatcga ttgaattccc cggggatcca ctagttatta   180
atagtaatca attacggggt cattagttca tagcccatat atggagttcc gcgttacata   240
acttacggta aatggcccgc ctggctgacc gcccaacgac ccccgcccat tgacgtcaat   300
aatgacgtat gttcccatag taacgccaat agggactttc cattgacgtc aatgggtgga   360
gtatttacgg taaactgccc acttggcagt acatcaagtg tatcatatgc caagtacgcc   420
ccctattgac gtcaatgacg gtaaatggcc cgcctggcat tatgcccagt acatgacctt   480
atgggacttt cctacttggc agtacatcta cgtattagtc atcgctatta ccatggtcga   540
ggtgagcccc acgttctgct tcactctccc catctccccc cctccccac cccaattttg   600
gtatttattt attttttaat tattttgtgc agcgatgggg gcggggggg gggggggggc   660
cgcgccaggc ggggcggggc ggggcgaggg gcggggcggg gcgaggcgga gaggtgcggc   720
ggcagccaat cagagcggcg cgctccgaaa gtttcctttt atggcgaggc ggcggcggcg   780
gcggccctat aaaaagcgaa gcgcgcggcg ggcggggagt cgctgcgacg ctgccttcgc   840
cccgtgcccc gctccgccgc cgcctcgcgc cgcccgcccc ggctctgact gaccgcgtta   900
ctcccacagg tgagcgggcg ggacggccct tctcctccgg gctgtaatta gcgcttggtt   960
taatgacggc ttgtttcttt tctgtggctg cgtgaaagcc ttgaggggct ccgggagggc   1020
cctttgtgcg ggggagcgg ctcggggggt gcgtgcgtgt gtgtgtgcgt ggggagcgcc   1080
gcgtgcggct ccgcgctgcc cggcggctgt gagcgctgcg ggcgcggcgc gggcctttgt   1140
gcgctccgca gtgtgcgcga ggggagcgcg gccgggggcg gtgccccgcg gtgcgggggg   1200
ggctgcgagg ggaacaaagg ctgcgtgcgg ggtgtgtgcg tggggggtg agcagggggt   1260
gtgggcgcgt cggtcgggct gcaacccccc ctgcaccccc ctccccgagt tgctgagcac   1320
ggcccggctt cgggtgcggg gctccgtacg gggcgtggcg cggggctcgc cgtgccgggc   1380
ggggggtggc ggcaggtggg ggtgccgggc gggcggggc cgcctcgggc cggggagggc   1440
tcggggggag ggcgcggcgg cccccggagc gccggcgcga cttcttaacc caacagaagg   1500
ctcgagaagg tatattgctg ttgacagtga gcggcttact cattgtatga acatttagtg   1560
aagccacaga tgtaaatgtt catacaatga gtaagctgcc tactgcctcg gacttcaagg   1620
ggctagaatt cgcggctgtc gaggcgcggc gagccgcagc cattgccttt tatggtaatc   1680
gtgcgagagg cgcagggac ttcctttgtc ccaaatctgt gcggagccga aatctgggag   1740
gcgccgccgc accccctcta gcgggcgcgg ggcgaagcgg tgcggcgccg gcaggaagga   1800
aatgggcggg gagggccttc gtgcgtcgcc gcgccgccgt cccttctcc ctctccagcc   1860
tcggggctgt ccgcggggg acggctgcct tcggggggga cggggcaggg cggggttcgg   1920
cttctggcgt gtgaccggcg gctctagagc ctctgctaac catgttcatg ccttcttctt   1980
tttcctacag tctagagtcg acctgcaggt ggatatcttg gctagcacgc caccatggtt   2040
```

```
tcttactggg acaccggcgt gctgctgtgt gccctgcttt cttgtctgct gctgaccggc  2100
tctagcagcg gctctgatac cggcagaccc ttcgtggaaa tgtacagcga gatccccgag  2160
atcatccaca tgaccgaggg cagagagctg gtcatccctt gcagagtgac aagccccaac  2220
atcaccgtga ctctgaagaa gttccctctg gacacactga tccccgacgg caagagaatc  2280
atctgggaca gccggaaggg cttcatcatc agcaacgcca cctacaaaga gatcggcctg  2340
ctgacctgtg aagccaccgt gaatggccac ctgtacaaga ccaactacct gacacacaga  2400
cagaccaaca ccatcatcga cgtggtgctg agccctagcc acggcattga actgtctgtg  2460
ggcgagaagc tggtgctgaa ctgtaccgcc agaaccgagc tgaacgtggg catcgacttc  2520
aactgggagt accccagcag caagcaccag cacaagaaac tggtcaaccg ggacctgaaa  2580
acccagagcg gcagcgagat gaagaaattc ctgagcaccc tgaccatcga cggcgtgacc  2640
agaagtgacc agggcctgta cacatgtgcc gccagctctg gcctgatgac caagaaaaac  2700
agcaccttcg tgcgggtgca cgagaaggac aagacccaca cctgtcctcc atgtcctgct  2760
ccagaactgc tcggcggacc ttccgtgttc ctgtttcctc caaagcctaa ggacaccctg  2820
atgatcagca gaacccctga agtgacctgc gtggtggtga tgtgtcccca cgaggatccc  2880
gaagtgaagt tcaattggta cgtggacggc gtggaagtgc acaacgccaa gaccaagcct  2940
agagaggaac agtacaatag cacctacaga gtggtgtccg tgctgaccgt gctgcaccag  3000
gattggctga acggcaaaga gtacaagtgc aaggtgtcca acaaggccct gcctgctcct  3060
atcgagaaaa ccatctccaa ggccaagggc cagcctaggg aaccccaggt ttacacactg  3120
cctccaagca gggacgagct gacaaagaac caggtgtccc tgacctgcct ggtcaagggc  3180
ttctacccct tccgatatcgc cgtggaatgg gagagcaatg gccagcctga gaacaactac  3240
aagacaaccc ctcctgtgct ggacagcgac ggctcattct tcctgtacag caagctgaca  3300
gtggacaaga gcagatggca gcagggcaac gtgttcagct gctccgtgat gcacgaggcc  3360
ctgcacaacc actacaccca gaagtccctg agcctgtctc ctggcaaatg agccacgcgt  3420
aacacgtggg ggatccagac atgataagat acattgatga gtttggacaa accacaacta  3480
gaatgcagtg aaaaaaatgc tttatttgtg aaatttgtga tgctattgct ttatttgtaa  3540
ccattataag ctgcaataaa caagttaaca acaacaattg cattcatttt atgtttcagg  3600
ttcagggggg ggtgtgggag gttttttaaa gcaagtaaaa cctctacaaa tgtggtatgg  3660
ctgattatga tcaatgcatg gccggccgga ggaacccta gtgatggagt tggccactcc  3720
ctctctgcgc gctcgctcgc tcactgaggc cgcccgggca aagcccgggc gtcgggcgac  3780
ctttggtcgc ccggcctcag tgagcgagcg agcgcgcaga gagggagtgg ccaa  3834
```

```
SEQ ID NO: 69            moltype = DNA   length = 3834
FEATURE                  Location/Qualifiers
misc_feature             1..3834
                         note = Synthetic Polynucleotide
source                   1..3834
                         mol_type = other DNA
                         organism = synthetic construct
SEQUENCE: 69
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctatcga ttgaattccc cggggatcca ctagttatta  180
atagtaatca attacggggt cattagttca tagcccatat atggagttcc gcgttacata  240
acttacggta aatggcccgc ctggctgacc gcccaacgac ccccgcccat tgacgtcaat  300
aatgacgtat gttcccatag taacgccaat agggactttc cattgacgtc aatgggtgga  360
gtatttacgg taaactgccc acttggcagt acatcaagtg tatcatatgc caagtacgcc  420
ccctattgac gtcaatgacg gtaaatggcc cgcctggcat tatgcccagt acatgacctt  480
atgggacttt cctacttggc agtacatcta cgtattagtc atcgctatta ccatggtcga  540
ggtgagcccc acgttctgct tcactctccc catctccccc cctccccac ccccaatttt  600
gtatttattt attttttaat tattttgtgc agcgatgggg gcggggggg ggggggggcg  660
cgcgccaggc ggggcgggc ggggcgaggg gcggggcgga gaggtgcggc  720
ggcagccaat cagagcggcg cgctccgaaa gtttcctttt atggcgaggc ggcggcggcg  780
gcggccctat aaaaagcgaa gcgcgcggcg ggcggggagt cgctgcgacg ctgccttcgc  840
cccgtgcccc gctccgccgc cgcctcgcgc cgcccgcccc ggctctgact gaccgcgtta  900
ctcccacagg tgagcgggcg ggacggcccct tctcctccgg gctgtaatta gcgcttggtt  960
taatgacggc ttgtttcttt tctgtggctg cgtgaaagcc ttgaggggct ccgggagggc  1020
cctttgtgcg gggggagcgg ctcgggggggt gcgtgcgtgt gtgtgtgcgt ggggagcgcc  1080
gcgtgcggct ccgcgctgcc cggcggctgt gagcgctgcg ggcgcggcgc ggggctttgt  1140
gcgctccgca gtgtgcgcga ggggagcgcg gccgggggcg gtgcccgcg gtgcgggggg  1200
ggctgcgagg ggaacaaagg ctgcgtgcgg ggtgtgtgcg tgggggggtg agcaggggt  1260
gtgggcgcgt cggtcgggct gcaacccccc ctgcaccccc ctccccgagt tgctgagcac  1320
ggcccggctt cgggtgcggg gctccgtacg gggcgtggcg cggggctcgc cgtgccgggc  1380
gggggtggc ggcaggtggg ggtgccgggc ggggcggggc cgcctcgggc cggggagggc  1440
tcggggggag ggcgcggcgc ccccgggagc gccggcgca cttcttaacc caacagaagg  1500
ctcgagaagg tatattgctg ttgacagtga gcggctacct cagcaagacg ttatttagtg  1560
aagccacaga tgtaaataac gtcttgctga ggtagctgcc tactgcctcg gacttcaagg  1620
ggctagaatt cgcggctgtc gaggcgcggc gagccgcagc cattgccttt tatggtaatc  1680
gtgcgagagg gcgcaggggac ttcctttgtc ccaaatctgt gcggagccga aatctgggag  1740
gcgccgcgc accccctcta tcgggggcgcg ggcgaagcgg tgcggcgcg gcggaagga  1800
aatgggcggg gagggccttc gtgcgtcgcc gcgccgccct ccccttctcc ctctccagcc  1860
tcggggctgt ccgcggggg acggctgcct tcgggggggga cggggcaggg cggggttcgg  1920
cttctgcgt gtgaccggcg gctctagagc ctctgctaac catgttcatg ccttcttctt  1980
tttcctacag tctagagtcg acctgcaggt ggatatcttg gctagcacgc caccatggtt  2040
tcttactggg acaccggcgt gctgctgtgt gccctgcttt cttgtctgct gctgaccggc  2100
tctagcagcg gctctgatac cggcagaccc ttcgtggaaa tgtacagcga gatccccgag  2160
atcatccaca tgaccgaggg cagagagctg gtcatccctt gcagagtgac aagccccaac  2220
atcaccgtga ctctgaagaa gttccctctg gacacactga tccccgacgg caagagaatc  2280
atctgggaca gccggaaggg cttcatcatc agcaacgcca cctacaaaga gatcggcctg  2340
ctgacctgtg aagccaccgt gaatggccac ctgtacaaga ccaactacct gacacacaga  2400
```

-continued

```
cagaccaaca ccatcatcga cgtggtgctg agccctagcc acggcattga actgtctgtg  2460
ggcgagaagc tggtgctgaa ctgtaccgcc agaaccgagc tgaacgtggg catcgacttc  2520
aactgggagt accccagcag caagcaccag cacaagaaac tggtcaaccg ggacctgaaa  2580
acccagagcg gcagcgagat gaagaaattc ctgagcaccc tgaccatcga cggcgtgacc  2640
agaagtgacc agggcctgta cacatgtgcc gccagctctg gcctgatgac caagaaaaac  2700
agcaccttcg tgcgggtgca cgagaaggac aagacccaca cctgtcctcc atgtcctgct  2760
ccagaactgc tcggcggacc ttccgtgttc ctgtttcctc caaagcctaa ggacaccctg  2820
atgatcagca gaacccctga agtgacctgc gtggtggtgg atgtgtccca cgaggatccc  2880
gaagtgaagt tcaattggta cgtggacggc gtggaagtgc acaacgccaa gaccaagcct  2940
agagaggaac agtacaatag cacctacaga gtggtgtccg tgctgaccgt gctgcaccag  3000
gattggctga acggcaaaga gtacaagtgc aaggtgtcca acaaggccct gcctgctcct  3060
atcgagaaaa ccatctccaa ggccaagggc cagcctaggg aaccccaggt ttacacactg  3120
cctccaagca gggacgagct gacaaagaac caggtgtccc tgacctgcct ggtcaagggc  3180
ttctaccctt ccgatatcgc cgtggaatgg gagagcaatg gccagcctga gaacaactac  3240
aagacaaccc ctcctgtgct ggacagcgac ggctcattct tcctgtacag caagctgaca  3300
gtggacaaga gcagatggca gcagggcaac gtgttcagct gctccgtgat gcacgaggcc  3360
ctgcacaacc actacaccca gaagtccctg agcctgtctc ctggcaaatg agccacgcgt  3420
aacacgtggg ggatccgac atgataagat acattgatga gtttggacaa accacaacta  3480
gaatgcagtg aaaaaaatgc tttatttgtg aaatttgtga tgctattgct ttatttgtaa  3540
ccattataag ctgcaataaa caagttaaca acaacaattg cattcatttt atgtttcagg  3600
ttcaggggga ggtgtgggag gttttttaaa gcaagtaaaa cctctacaaa tgtggtatgg  3660
ctgattatga tcaatgcatg gccggccgga ggaaccccta gtgatggagt tggccactcc  3720
ctctctcgcgc gctcgctcgc tcactgaggc cgcccgggca aagcccgggc gtcgggcgac  3780
ctttggtcgc ccggcctcag tgagcgagcg agcgcgcaga gagggagtgg ccaa  3834
```

SEQ ID NO: 70           moltype = DNA   length = 3834
FEATURE                Location/Qualifiers
misc_feature         1..3834
                     note = Synthetic Polynucleotide
source                  1..3834
                     mol_type = other DNA
                     organism = synthetic construct SEQUENCE: 70
```
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctatcga ttgaattccc cggggatcca ctagttatta  180
atagtaatca attacggggt cattagttca tagcccatat atggagttcc gcgttacata  240
acttacggta aatggcccgc ctggctgacc gcccaacgac ccccgcccat tgacgtcaat  300
aatgacgtat gttcccatag taacgccaat agggactttc cattgacgtc aatgggtgga  360
gtatttacgg taaactgccc acttggcagt acatcaagtg tatcatatgc caagtacgcc  420
ccctattgac gtcaatgacg gtaaatggcc cgcctggcat tatgcccagt acatgacctt  480
atgggacttt cctacttggc agtacatcta cgtattagtc atcgctatta ccatggtcga  540
ggtgagcccc acgttctgct tcactctccc catctcccac cccaattttg  600
gtatttattt attttttaat tattttgtgc agcgatgggg gcggggggg gggggggcg  660
cgcgccaggc ggggcggggc ggggcgaggg gcgggcgggg gcgaggcgga gaggtgcggc  720
ggcagccaat cagagcggcg cgctccgaaa gtttcctttt atggcgaggc ggcggcggcg  780
gcggccctat aaaaagcgaa gcgcgcggcg ggcggggagt ggccttcgac ctgccttcgc  840
cccgtgcccc gctccgccgc cgcctcgcgc cgcccgcccc ggctctgact gaccgcgtta  900
ctcccacagg tgagcgggcg ggacggccct tctcctccgg gctgtaatta gcgcttggtt  960
taatgacggc ttgtttcttt tctgtggctg cgtgaaagcc ttgagggct ccgggagggc  1020
cctttgtgcg ggggagcgg ctcggggggt gcgtgcgtgt gtgtgtgcgt ggggagcgcc  1080
gcgtgcggct ccgcgctgcc cggcggctgt gagcgctgcg ggcgcggcgc ggggctttgt  1140
gcgctccgca gtgtgcgcga ggggagcgcg gccggggggcg gtgccccgcg gtgcgggggg  1200
ggctgcgagg ggaacaaagg ctgcgtgcgg ggtgtgtgcg tggggggggtg agcagggggt  1260
gtgggcgcgt cggtcgggct gcaaccccc ctgcaccccc ctccccgagt tgctgagcac  1320
ggcccggctt cgggtcgcgg gctccgtacg gggcgtggcg cggggctcgc cgtgccggac  1380
ggggggtggc ggcaggtggg ggtgccgggc ggggcggggc cgcctcgggc cggggagggc  1440
tcgggggagg ggcgcggcgg ccccccggagc gccggcgcga cttcttaacc caacagaagg  1500
ctcgagaagg tatattgctg ttgacagtga gcgcaccgtg tgggctgagt ttaactagtg  1560
aagccacaga tgtagttaaa ctcagcccac acggtgtgcc tactgcctcg gacttcaagg  1620
ggctagaatt cgcggctgtc gaggcgcggc gagccgcagc cattgccttt tatggtaatc  1680
gtgcgagagg gcgcaggga ttcctttgtc ccaaatctgt gcggagccga aatctgggag  1740
gcgccgccgc accccctcta gcgggcgcgg ggcgaagcgg tgcggcgccg gcaggaagga  1800
aatggggcgg gagggccttc gtgcgtcgcc gcgccgccac cccttctcc ctctccagcc  1860
tcggggctgt ccgcgggggg acggctgcct tcgggggggga cggggcaggg cggggttcgg  1920
cttctggcgt gtgaccggcg gctctagagc ctctgctaac catgttcatg ccttcttctt  1980
tttcctacag tctagagtcg acctgcaggt ggatatcttg gctagcacgc caccatggtt  2040
tcttactggg acaccggcgt gctgctgtgt gccctgcttt cttgtctgct gctgaccggc  2100
tctagcagcg gctctgatac cggcagacct ttcgtgaaca tgtacagcga tatccccgag  2160
atcatccaca tgaccgaggg cagagagctg gtcatccctt gcagagtgac aagccccaac  2220
atcaccgtga ctctgaagaa gttccctctg gacacactga tccccgacgg caagagaatc  2280
atctgggaca gccggaaggg cttcatcatc agcaacgcca cctacaaaga gatcggcctg  2340
ctgacctgtg aagccaccgt gaatggccac ctgtacaaga ccaactacct gacacacaga  2400
cagaccaaca ccatcatcga cgtggtgctg agccctagcc acggcattga actgtctgtg  2460
ggcgagaagc tggtgctgaa ctgtaccgcc agaaccgagc tgaacgtggg catcgacttc  2520
aactgggagt accccagcag caagcaccag cacaagaaac tggtcaaccg ggacctgaaa  2580
acccagagcg gcagcgagat gaagaaattc ctgagcaccc tgaccatcga cggcgtgacc  2640
agaagtgacc agggcctgta cacatgtgcc gccagctctg gcctgatgac caagaaaaac  2700
agcaccttcg tgcgggtgca cgagaaggac aagacccaca cctgtcctcc atgtcctgct  2760
```

-continued

```
ccagaactgc tcggcggacc ttccgtgttc ctgtttcctc caaagcctaa ggacaccctg    2820
atgatcagca gaacccctga agtgacctgc gtggtggtgg atgtgtccca cgaggatccc    2880
gaagtgaagt tcaattggta cgtggacggc gtggaagtgc acaacgccaa gaccaagcct    2940
agagaggaac agtacaatag cacctacaga gtggtgtccg tgctgaccgt gctgcaccag    3000
gattggctga acggcaaaga gtacaagtgc aaggtgtcca acaaggccct gcctgctcct    3060
atcgagaaaa ccatctccaa ggccaagggc cagcctaggg aaccccaggt ttacacactg    3120
cctccaagca gggacgagct gacaaagaac caggtgtccc tgacctgcct ggtcaagggc    3180
ttctacccct tccgatatcgc cgtggaatgg gagagcaatg gccagcctga gaacaactac    3240
aagacaaccc ctcctgtgct ggacagcgac ggctcattct tcctgtacag caagctgaca    3300
gtggacaaga gcagatggca gcagggcaac gtgttcagct gctccgtgat gcacgaggcc    3360
ctgcacaacc actacaccca gaagtccctg agcctgtctc ctggcaaatg agccacgcgt    3420
aacacgtggg ggatccagac atgataagat acattgatga gtttggacaa accacaacta    3480
gaatgcagtg aaaaaaatgc tttatttgtg aaatttgtga tgctattgct ttatttgtaa    3540
ccattataag ctgcaataaa caagttaaca acaacaattg cattcatttt atgtttcagg    3600
ttcaggggga ggtgtgggag gttttttaaa gcaagtaaaa cctctacaaa tgtggtatg    3660
ctgattatga tcaatgcatg gccggccgga ggaacccta gtgatggagt tggccactcc    3720
ctctctgcgc gctcgctcgc tcactgaggc cgcccgggca aagcccgggc gtcgggcgac    3780
ctttggtcgc ccggcctcag tgagcgagcg agcgcgcaga gagggagtgg ccaa          3834
```

```
SEQ ID NO: 71             moltype = AA   length = 8
FEATURE                   Location/Qualifiers
REGION                    1..8
                          note = Synthetic Polypeptide
source                    1..8
                          mol_type = protein
                          organism = synthetic construct
SEQUENCE: 71
DYKDDDDK                                                                8

SEQ ID NO: 72             moltype = RNA   length = 22
FEATURE                   Location/Qualifiers
misc_feature              1..22
                          note = Reverse Transcriptase PCR primer
source                    1..22
                          mol_type = other RNA
                          organism = synthetic construct
SEQUENCE: 72
aatgttcata caatgagtaa gc                                               22

SEQ ID NO: 73             moltype = RNA   length = 22
FEATURE                   Location/Qualifiers
misc_feature              1..22
                          note = Reverse Transcriptase PCR Primer
source                    1..22
                          mol_type = other RNA
                          organism = synthetic construct
SEQUENCE: 73
aataacgtct tgctgaggta gc                                               22

SEQ ID NO: 74             moltype = AA   length = 7
FEATURE                   Location/Qualifiers
REGION                    1..7
                          note = Synthetic Polypeptide
source                    1..7
                          mol_type = protein
                          organism = synthetic construct
SEQUENCE: 74
ISDQTKH                                                                 7

SEQ ID NO: 75             moltype = AA   length = 10
FEATURE                   Location/Qualifiers
REGION                    1..10
                          note = Synthetic Polypeptide
VAR_SEQ                   1..2
                          note = Xaa is A, L, G, S, T, P, or absent
VAR_SEQ                   10
                          note = Xaa is A, L, G, S, T, P, or absent
source                    1..10
                          mol_type = protein
                          organism = synthetic construct
SEQUENCE: 75
XXISDQTKHX                                                              10
```

TREATMENTS FOR OCULAR NEOVASCULARIZATION

SEQUENCE LISTING SUBMISSION VIA EFS-WEB

A computer readable XML file, entitled "090400-5036-US-Sequence-Listing" created on Aug. 19, 2025, with a file size of about 132,000 bytes, contains the sequence listing for this application and is hereby incorporated by reference in its entirety

BACKGROUND OF THE INVENTION

The vascular endothelial growth factor (VEGF) proteins and their receptors (VEGFRs) play important roles in vasculogenesis, the development of the embryonic vasculature from early differentiating endothelial cells, angiogenesis, the process of forming new blood vessels from pre-existing ones, and lymphangiogenesis, the process of forming new lymph vessels.

Ocular vascular diseases such as age-related macular degeneration and diabetic retinopathy are due to abnormal choroidal or retinal neovascularization respectively. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa, are also associated with vascular abnormalities, such as arteriolar narrowing and vascular atrophy.

Strategies have been employed to block the function of VEGF. Current standard-of-care treatments include intravitreal (IVT) injections of protein therapies, such as aflibercept, ranibizumab, and brolucizumab that bind to vascular endothelial growth factor A (VEGF-A, VEGF) to prevent binding to its receptors. Regimens of anti-VEGF therapies shown to be safe and effective require repeated monthly-to-bimonthly IVT administrations to maintain vision and many patients fail to maintain initial visual acuity benefit due to undertreatment. The need for repeated injections can become a substantial burden for patients and caregivers with some patients requiring regular anti-VEGF injections despite treatment for a decade. Recent studies have shown that in real-world use, many patients receive fewer than recommended injections and do not receive or maintain the same benefits shown in clinical trial settings with vision gains during the first 2 years not maintained at 5 years.

Thus, there remains a need for new or improved compounds and therapies for the treatment of angiogenic ocular diseases such as wetAMD.

SUMMARY OF THE INVENTION

Disclosed are compositions and methods for the treatment of an ocular disease associated with ocular angiogenesis including but not limited to wet (neovascular, exudative) age-related macular degeneration; macular edema following retinal vein occlusion; retinal neovascularization resulting from retinal vein occlusion; diabetic macular edema, diabetic retinopathy (including all stages of non-proliferative diabetic retinopathy and proliferative diabetic retinopathy); myopic macular degeneration; branch retinal vein occlusion, hemi-retinal vein occlusion, and central retinal vein occlusion; retinopathy of prematurity; idiopathic choroidal neovascularization; myopia macular degeneration and secondary retinal and choroidal neovascularization; retinal telangiectasia; neovascular glaucoma; vitreous hemorrhage; retinal and choroidal neovascularization secondary to retinal diseases, including but not limited to uveitis, trauma, retinal degenerative disorders, genetic retinal and/or choroidal disease, tumors of the eye, corneal and iris neovascularization. In some embodiments, the angiogenic ocular disease is selected from wet (neovascular, exudative) age-related macular degeneration; diabetic macular edema; macular edema following retinal vein occlusion; diabetic retinopathy; and myopic choroidal neovascularization.

In some embodiments, a nucleic acid is provided comprising (i) a nucleotide sequence encoding a first anti-angiogenic polypeptide (e.g., aflibercept) and (ii) a nucleotide sequence encoding one or more interfering RNA molecule(s) that reduce expression of one or more pro-angiogenic target genes. In some aspects, the RNA molecule is a short hairpin RNA (shRNA). In other aspects, the RNA molecule is a primary miRNA molecule. In some aspects, the nucleic acid comprises an expression cassette comprising (i) a nucleotide sequence encoding a first anti-angiogenic polypeptide, operably linked to an expression control sequence and (ii) a nucleotide sequence encoding an interfering RNA molecule that reduces expression of one or more pro-angiogenic target genes, operably linked to an expression control sequence. In some embodiments, the nucleotide sequence encoding the anti-angiogenic polypeptide and the nucleotide sequence encoding the interfering RNA molecule are operably linked to distinct expression control sequences. In preferred embodiments, expression of the anti-angiogenic polypeptide and the interfering RNA molecule are driven by a common (i.e., the same) expression control sequence. In some aspects, the expression control sequence(s) comprise(s) a constitutive promoter such as a CAG or CBA promoter. In other aspects, the expression control sequence(s) comprise(s) a cell-specific promoter.

In some embodiments, the nucleic acid comprises nucleotide sequence encoding an interfering RNA molecule that targets angiopoietin-2 (aka Ang2 or Ang-2). Representative human Ang2 sequences can be found at e.g., NCBI Accession No. 015123 and SEQ ID Nos: 517 and 518 of U.S. Pat. No. 8,987,420, the contents of which are incorporated herein by reference. In preferred embodiments, the interfering RNA molecule targets Ang-2 and comprises a sense strand and an antisense strand comprising, consisting essentially of, or consisting of a sequence selected from those listed in Table 1 below:

TABLE 1

Interfering RNAs targeting human Ang-2

| Sense Strand Sequence | Antisense Strand Sequence | Reference Sequence Target Region (NCBI Accession Number; NM_001118887.2) |
|---|---|---|
| GCCGCAGCCTATAAC AACTTT (SEQ ID NO: 1) | AAAGTTGTTATAGGC TGCGGC (SEQ ID NO: 2) | GCCGCAGCCTATAAC AACTTT (SEQ ID NO: 3) |
| CCCTAATTCTACAGA AGAGAT (SEQ ID NO: 4) | ATCTCTTCTGTAGAA TTAGGG (SEQ ID NO: 5) | CCCTAATTCTACAGA AGAGAT (SEQ ID NO: 6) |
| GATGATAGAAATAGG GACAAA (SEQ ID NO: 7) | TTTGTCCCTATTTCT ATCATC (SEQ ID NO: 8) | GATGATAGAAATAGG GACAAA (SEQ ID NO: 9) |

TABLE 1-continued

Interfering RNAs targeting human Ang-2

| Sense Strand Sequence | Antisense Strand Sequence | Reference Sequence Target Region (NCBI Accession Number; NM_001118887.2) |
|---|---|---|
| GCCACGGTGAATAAT TCAGTT (SEQ ID NO: 10) | AACTGAATTATTCAC CGTGGC (SEQ ID NO: 11) | GCCACGGTGAATAAT TCAGTT (SEQ ID NO: 12) |
| GCTTACTCATTGTAT GAACAT (SEQ ID NO: 13) | ATGTTCATACAATGA GTAAGC (SEQ ID NO: 14) | GCTTACTCATTGTATG AACAT (SEQ ID NO: 15) |

In some embodiments, the interfering RNA molecule comprises a sense strand and an antisense strand, one or both of which comprises, consists essentially of, or consists of a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a sequence selected from those listed in Table 1. In some particularly preferred embodiments, the nucleic acid comprises nucleotide sequence encoding a first anti-angiogenic polypeptide that is aflibercept and nucleotide sequence encoding an interfering RNA molecule targets human angiopoietin-2.

In some preferred embodiments, the nucleic acid comprises nucleotide sequence encoding an interfering RNA molecule that targets VEGF-C. Representative human VEGF-C sequences can be found at e.g., GenBank Accession numbers NM-005429 and X94216. In preferred embodiments, the interfering RNA molecule targets VEGF-C and comprises a sense strand and an antisense strand comprising, consisting essentially of, or consisting of a sequence selected from those listed in Table 2 below:

TABLE 2

Interfering RNAs targeting human VEGF-C

| Sense Strand Sequence | Antisense Strand Sequence | Reference Sequence Target Region (NCBI Accession Number: NM_005429.5) |
|---|---|---|
| CGCGACAAACACCTT CTTTAA (SEQ ID NO: 16) | TTAAAGAAGGTGTTT GTCGCG (SEQ ID NO: 17) | CGCGACAAACACCTT CTTTAA (SEQ ID NO: 18) |
| CTACCTCAGCAAGAC GTTATT (SEQ ID NO: 19) | AATAACGTCTTGCTG AGGTAG (SEQ ID NO: 20) | CTACCTCAGCAAGAC GTTATT (SEQ ID NO: 21) |
| ACCAATTACATGTGG AATAAT (SEQ ID NO: 22) | ATTATTCCACATGTA ATTGG (SEQ ID NO: 23) | ACCAATTACATGTGG AATAAT (SEQ ID NO: 24) |

TABLE 2-continued

Interfering RNAs targeting human VEGF-C

| Sense Strand Sequence | Antisense Strand Sequence | Reference Sequence Target Region (NCBI Accession Number: NM_005429.5) |
|---|---|---|
| ATGACCAAACAGCCA AGATTT (SEQ ID NO: 25) | AAATCTTGGCTGTTT GGTCA (SEQ ID NO: 26) | AATGACCAAACAGCC AAGATTT (SEQ ID NO: 27) |
| GTCGTTGTGTCCCTT CATATT SEQ ID NO: 28) | AATATGAAGGGACAC AACGAC (SEQ ID NO: 29) | GTCGTTGTGTCCCTT CATATT (SEQ ID NO: 30) |

In some embodiments, the interfering RNA molecule comprises a sense strand and an antisense strand, one or both of which comprises, consists essentially of, or consists of a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a sequence selected from those listed in Table 2. Additional interfering RNA molecules targeting VEGF-C include those listed at Table 1 of US Patent Application Publication No. 2011/0293625A1, the contents of which are incorporated herein by reference. In some particularly preferred embodiments, the nucleic acid comprises nucleotide sequence encoding a first anti-angiogenic polypeptide that is aflibercept and nucleotide sequence encoding an interfering RNA molecule targets human VEGF-C.

In related embodiments, the nucleic acid comprises nucleotide sequence encoding a first anti-angiogenic protein (e.g., aflibercept) and further comprises an interfering RNA molecule that targets human VEGF-C and an interfering RNA molecule that targets human Ang-2.

In other embodiments, the nucleic acid comprises a nucleotide sequence encoding an interfering RNA molecule that targets VEGFR-3. Representative human VEGFR-3 sequences can be found e.g., at GenBank Accession Number X68203. In preferred embodiments, the interfering RNA molecule targets VEGFR-3 and comprises a sense strand and an antisense strand comprising, consisting essentially of, or consisting of a sequence selected from those listed in Table 3 below:

TABLE 3

Interfering RNAs targeting human VEGFR-3

| Sense Strand Sequence | Antisense Strand Sequence | Reference Sequence Target Region (NCBI Accession Number: NM_001354989.2) |
|---|---|---|
| ACAACGGCATCCAGC GATTTC (SEQ ID NO: 31) | GAAATCGCTGGATGC CGTTG (SEQ ID NO: 32) | ACAACGGCATCCAGC GATTTC (SEQ ID NO: 33) |

TABLE 3-continued

Interfering RNAs targeting human VEGFR-3

| Sense Strand Sequence | Antisense Strand Sequence | Reference Sequence Target Region (NCBI Accession Number: NM_001354989.2) |
|---|---|---|
| GGACACCCTGCAAGA TGTTTG (SEQ ID NO: 34) | CAAACATCTTGCAGG GTGTCC (SEQ ID NO: 35) | GGACACCCTGCAAGA TGTTTG (SEQ ID NO: 36) |
| CACCGTGTGGGCTGA GTTTAA (SEQ ID NO: 37) | TTAAACTCAGCCCAC ACGGTG SEQ ID NO: 38) | CACCGTGTGGGCTGA GTTTAA (SEQ ID NO: 39) |
| CTTTAAGACTTTCGC TATTTC SEQ ID NO: 40) | GAAATAGCGAAAGTC TTAAAG (SEQ ID NO: 41) | CTTTAAGACTTTCGC TATTTCG (SEQ ID NO: 42) |
| TCACAGGCAACGAGC TCTATG (SEQ ID NO: 43) | CATAGAGCTCGTTGC CTGTGA (SEQ ID NO: 44) | TCACAGGCAACGAGC TCTATG (SEQ ID NO: 45) |

In some embodiments, the interfering RNA molecule comprises a sense strand and an antisense strand, one or both of which comprises, consists essentially of, or consists of a sequence at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a sequence selected from those listed in Table 3. Additional interfering RNA molecules targeting VEGFR-3 include those listed at Table 2 of U.S. Pat. No. 7,517,864, the contents of which are incorporated herein by reference. In some particularly preferred embodiments, the nucleic acid comprises nucleotide sequence encoding a first anti-angiogenic polypeptide that is aflibercept and nucleotide sequence encoding an interfering RNA molecule targets human VEGFR-3.

In some embodiments, the synthetic RNA molecule is a small interfering RNA (siRNA). In some embodiments, the interfering RNA is a small hairpin RNA (shRNA). In some aspects, the shRNA has a loop comprising (5' to 3') the sequence CTCGAG or a sequence at least 70% or at least 80% identical thereto.

In some preferred embodiments, the synthetic RNA molecule is an artificial micro RNA (miRNA). In some embodiments, the artificial miRNA comprises a sense strand and antisense strand as herein described embedded into an miRNA "scaffold" derived from miR-30, miR-22, miR-15, miR-16, miR-103 or miR-107. In some preferred aspects, the artificial miRNA comprises a sense and antisense strand as herein described embedded into mir-30:

(SEQ ID NO: 46)
CUUCAGGUUAACCCAACAGAAGGCUAAAGAAGGUAUAUUGCUGUUGAC

AGUGAGCG(X)$_n$CUGUGAAGCCACAGAUGGG(Y)$_n$

UGCCUACUGCCUCGGACUUCAAGGGGCUACUUUAGG, $(X)_n$ comprises a sense strand and $(Y)_n$ comprises a sense strand from any one of Tables 1-3.

In particularly preferred aspects, the artificial miRNA comprises a sense and antisense strand as herein described embedded into mir-E:

(SEQ ID NO: 47)
GACUUCUUAACCCAACAGAAGGCUCGAGAAGGUAUAUUGCUGUUGACA

GUGAGCG(X)$_n$UAGUGAAGCCACAGAUGUA(Y)$_n$

UGCCUACUGCCUCGGACUUCAAGGGGCUAGAAUUC, wherein $(X)_n$ comprises a sense strand and $(Y)_n$ comprises a sense strand from any one of Tables 1-3.

In some embodiments, a nucleic acid is provided comprising (i) nucleotide sequence encoding a first anti-angiogenic polypeptide (e.g., aflibercept) and (ii) nucleotide sequence encoding a second anti-angiogenic polypeptide. In some aspects, the nucleic acid comprises an expression cassette comprising (i) nucleotide sequence encoding a first anti-angiogenic polypeptide, operably linked to an expression control sequence and (ii) nucleotide sequence encoding a second anti-angiogenic polypeptide, operably linked to an expression control sequence. In some embodiments, the nucleotide sequence encoding the first anti-angiogenic polypeptide and the nucleotide sequence encoding the second anti-angiogenic polypeptide are operably linked to distinct expression control sequences. In preferred embodiments, expression of the first and second anti-angiogenic polypeptides are driven by a common (i.e. the same) expression control sequence. In some aspects, the expression control sequence(s) comprise(s) a constitutive promoter such as a CAG or CBA promoter. In other aspects, the expression control sequence(s) comprise(s) a cell-specific promoter.

In some aspects, the first and/or second anti-angiogenic polypeptide (i.e., a polypeptide that inhibits angiogenesis) is selected from endostatin; tumstatin; angiostatin; pigment epithelium-derived factor (PEDF). In some aspects, the first and/or second anti-angiogenic polypeptide is a "decoy" fusion protein (e.g., a soluble receptor fusion protein) that binds to and inhibits the activity of a VEGF (VEGF-A (see e.g., GenBank Acc. No. Q16889), VEGF-B (see e.g., GenBank Ace. No. U48801), VEGF-C(see e.g., GenBank Acc. No. X94216), VEGF-D (see e.g., GenBank Ace. No. AJOOO185) and/or placenta growth factor (PIGF; see e.g., GenBank Ace. No. X54936)), representative examples of which include soluble VEGFR-1 (aka Flt-1; see e.g., GenBank Ace. No. X51602) receptor fusion proteins, soluble VEGFR-2 (aka Flk-1; see e.g., GenBank Acc. No. X59397) receptor fusion proteins, soluble VEGFR-3 (aka Flt-4; see e.g., GenBank Acc. Nos. X68203 and 566407) receptor fusion proteins and chimeric soluble receptor fusion proteins comprising binding regions from at least two of VEGFR-1, VEGFR-2 and VEGFR-3. VEGF-A binds to VEGFR-1 and VEGFR-2; VEGF-B and PIGF bind to VEGFR-2; VEGF-C and VEGF-D bind to VEGFR-3.

In some preferred aspects, the first anti-angiogenic polypeptide is a soluble fusion protein comprising VEGF-binding portions from the extracellular domains of VEGFR-1 and VEGFR-2, optionally fused to a human IgG1 Fc portion. In particularly preferred aspects, the first anti-angiogenic polypeptide is aflibercept. Aflibercept is a recombinant fusion protein consisting of VEGF-binding portions from the extracellular domains of human VEGFR-1 and VEGFR-2 fused to a human IgG1 Fe portion. Aflibercept is indicated for the treatment of neovascular (wet) age-related macular degeneration, macular edema following retinal vein occlusion, diabetic macular edema and diabetic retinopathy.

In other preferred aspects, the first and/or second anti-angiogenic polypeptide is a soluble fusion protein comprising one or more VEGF-binding portions from the extracellular domain of VEGFR-3.

In other aspects, the first and/or second anti-angiogenic polypeptide is an antibody or antigen-binding fragment thereof that binds to and inhibits the activity of a pro-angiogenic protein such as a VEGF and/or an angiopoietin (angiopoietin-1/Ang1/Ang-1, angiopoietin-2/Ang2/Ang-2). In some aspects, the first and/or second anti-angiogenic polypeptide is an antibody against Ang1 and/or Ang2. In other aspects the first and/or second anti-angiogenic polypeptide is an antibody against VEGF-A (e.g., bevacizumab), VEGF-B, VEGF-C, VEGF-D, or PIGF (e.g., TB-403, 16D3) that blocks binding of the VEGF to its cognate receptor. In other aspects, the first and/or second anti-angiogenic polypeptide is an antibody against VEGFR-1 (e.g., icrucumab, D16F7, KM1730/KM1732), VEGFR-2 (e.g., ramucirumab), or VEGFR-3 that blocks binding of the receptor to a VEGF. In some aspects, the antibody is a bifunctional antibody. In some preferred embodiments, the first and/or second anti-angiogenic polypeptide is an antibody or antigen binding fragment thereof that binds to Ang-2.

In some embodiments, the nucleic acid comprises nucleotide sequence encoding a first anti-angiogenic polypeptide and nucleotide sequence encoding a second anti-angiogenic polypeptide, wherein the second anti-angiogenic polypeptide is pigment epithelium-derived factor (PEDF).

In some embodiments, provided herein is a vector (e.g., an adeno-associated virus (AAV) plasmid vector) comprising a nucleic acid as herein described (e.g., comprising nucleotide sequence encoding a first and/or second anti-angiogenic polypeptide and/or an interfering RNA interfering RNA molecule that reduces expression of one or more pro-angiogenic target genes). In preferred embodiments, the vector is a recombinant adeno-associated (rAAV):expression vector. In some embodiments, the rAAV vector comprises a native capsid (e.g., a capsid of AAV serotype 2 or AAV serotype 5 or AAV serotype 8). In other embodiments-, the rAAV vector comprises a capsid that is modified (e.g., comprises one or more peptide insertions and/or one or more amino acid substitutions (e.g., tyrosine to phenylalanine) and/or amino acid insertions or amino acid deletions) relative to a native AAV capsid (e.g., comprising one or more modifications relative to an AAV capsid of serotype 2, 5 or 8).

In preferred embodiments, the rAAV vector comprises a capsid with a variant capsid protein comprising the following amino acid sequence or a sequence at least 80%, 90%, 95% or 99% identical thereto:

```
                                    (SEQ ID NO: 48)
MAADGYLPDWLEDTLSEGIRQWWKLKPGPPPPKAAERHKDDSRGLVLPG

YKYLGPFNGLDKGEPVNEADAAALEHDKAYDRQLDSGDNPYLKYNHADA

EFQERLKEDTSFGGNLGRAVFQAKKRVLEPLGLVEEPVKTAPGKKRPVE

HSPVEPDSSSGTGKAGQQPARKRLNFGQTGDADSVPDPQPLGQPPAAPS

GLGTNTMATGSGAPMADNNEGADGVGNSSGNWHCDSTWMGDRVITTSTR

TWALPTYNNHLYKQISSQSGASNDNHYFGYSTPWGYFDFNRFHCHFSPR

DWQRLINNNWGFRPKRLNFKLFNIQVKEVTQNDGTTTIANNLTSTVQVF

TDSEYQLPYVLGSAHQGCLPPFPADVFMVPQYGYLTLNNGSQAVGRSSF
```

```
-continued
YCLEYFPSQMLRTGNNFTFSYTFEDVPFHSSYAHSQSLDRLMNPLIDQY

LYYLSRTNTPSGTTTQSRLQFSQAGASDIRDQSRNWLPGPCYRQQRVSK

TSADNNNSEYSWTGATKYHLNGRDSLVNPGPAMASHKDDEEKFFPQSGV

LIFGKQGSEKTNVDIEKVMITDEEEIRTTNPVATEQYGSVSTNLQRGNL

AISDQTKHARQAATADVNTQGVLPGMVWQDRDVYLQGPIWAKIPHTDGH

FHPSPLMGGFGLKHPPPQILIKNTPVPANPSTTFSAAKFASFITQYSTG

QVSVEIEWELQKENSKRWNPEIQYTSNYNKSVNVDFTVDTNGVYSEPRP

IGTRYLTRNL
```

The variant AAV capsid protein of SEQ ID NO:48 contains the following modifications relative to native AAV2 capsid: (i) a proline (P) to alanine (A) mutation at amino acid position 34, which is located inside the assembled capsid (VP1 protein only), and (ii) an insertion of 10 amino acids (leucine-alanine-isoleucine-serine-aspartic acid-glutamine-threonine-lysine-histidine-alanine/LAISDQTKHA (SEQ ID NO:49)) at amino acid position 588, which is present in VP1, VP2, and VP3. In some embodiments, the capsid comprises a variant capsid protein comprising a sequence at least 90%, at least 95%, at least 98%, at least 99% identical to SEQ ID NO:48 and comprising a P34A substitution and an LAISDQTKHA (SEQ ID NO:49) peptide insertion in the GH loop of the capsid, e.g., between two adjacent amino acids at a position between amino acids 570 and 611 of VP1, preferably between amino acids 588 and 589 of VP1 (numbering is relative to native AAV2 VP1 capsid).

In another embodiment, provided herein is a host cell comprising a nucleic acid as herein described. In some aspects, the host cell is a mammalian cell, including without limitation, a CHO cell, an HEK293 cell, a HeLa cell, a BHK21 cell, a Vero cell or a V27 cell. In other aspects, the host cell is a photoreceptor cell (e.g., rods; cones), a retinal ganglion cell (RGC), a glial cell (e.g., a Miller glial cell, a microglial cell); a bipolar cell, an amacrine cell, a horizontal cell, or a retinal pigmented epithelium (RPE) cell.

In some embodiments, the disclosure provides a method of treating an ocular disease associated with ocular angiogenesis in a subject (e.g. a human subject) comprising administering to the subject a nucleic acid molecule or vector as described herein.

DESCRIPTION OF THE DRAWINGS

FIGS. 1A-B Dual transgene construction. Approaches to building multi-mechanistic anti-angiogenic gene therapy are shown. FIG. 1A: this construct is a representative embodiment of a nucleic acid encoding aflibercept and a second anti-angiogenic protein. FIG. 1B: this construct is a representative embodiment of a nucleic acid encoding aflibercept and an interfering RNA targeting a pro-angiogenic gene. A ubiquitous promoter (CBA) is employed in both constructs.

FIG. 3B is a graph illustrating expression of aflibercept in HEK293T media following transfection with AAV plasmid encoding aflibercept and a second polypeptide (PEDF, anti-Ang2 scFab) or encoding aflibercept and an interfering RNA under control of the indicated promoter. Results are normalized to expression of aflibercept in HEK293T media following transfection with AAV plasmid encoding aflibercept alone under the control of a CBA promoter. Error represents S.E.M. N=6 Biological replicates. Analyzed by one-way ANOVA. ****: P<0.0001. Constructs only weighed statistically against their appropriate control. % Shows mean difference compared to CBA-AFLB.

FIGS. 5A-C FIGS. 5A and 5B illustrate free and active aflibercept (AFLB) in the media seven (FIG. 5A) and eleven (FIG. 5B) days after transduction of RPE cells with rAAV comprising a capsid of SEQ ID NO:48 and heterologous nucleic acid encoding the indicated transgenes at MOI of 5K and 1K. FIG. 5C compares AFLB following transduction of RPE cells with a rAAV comprising a construct encoding AFLB only with rAAV comprising a construct encoding AFLB+ RNAi against VEGF-C.

FIGS. 6A-B illustrate time course comparisons of free and active AFLB in media of RPE cells following transduction with a rAAV comprising a construct encoding AFLB only with rAAV comprising a construct encoding AFLB+ RNAi against VEGF-C.

FIGS. 8A-D illustrate expression of functional anti-Ang2 scFab from dual protein constructs (plasmid encoding AFLB+anti-Ang2 scFab in LH or HL configuration) following transfection of HEK293T cells (assessed by competition ELISA and Tie2 receptor competition assays.

FIG. 9 illustrates anti-Ang2 scFab (and anti-AFLB) Western blot results from media of RPE cells following transduction with rAAV comprising capsid protein of SEQ ID NO:48 and heterologous nucleic acid encoding AFLB+anti-Ang2 scFab (HL and LH conformations) at MOI 5000 and 1000, with similar expression levels of LH and HL forms observed.

FIGS. 10A-B illustrate the results of anti-Ang2 functional ELISA (ANG2-coated plates) (FIG. 10A) and competition ELISA (FIG. 10B) on media from RPE cells eleven days after transduction with rAAV as described in FIG. 9 at MOI of 5000 and 1000.

FIG. 16B illustrates a significant decrease in Ang2 secretion from RMVEC assessed by Ang2 qPCR.

FIG. 17A) and protein levels (ELISA; FIG. 17B) in human RPE cells eight days after transduction with rAAV as described in FIG. 16 at the specified MOIs (rAAV encoding AFLB only or GFP served as controls).

FIG. 21A) and VEGF-C mRNA (by qPCR; FIG. 21B) following transduction of human RPE cells at the specified MOI with rAAV comprising a capsid protein of SEQ ID NO:48 and the specified nucleic acid constructs. FIG. 21C illustrates a dose-dependent increase in expression of miRNA targeting VEGF-C in the cells.

Figure 23:
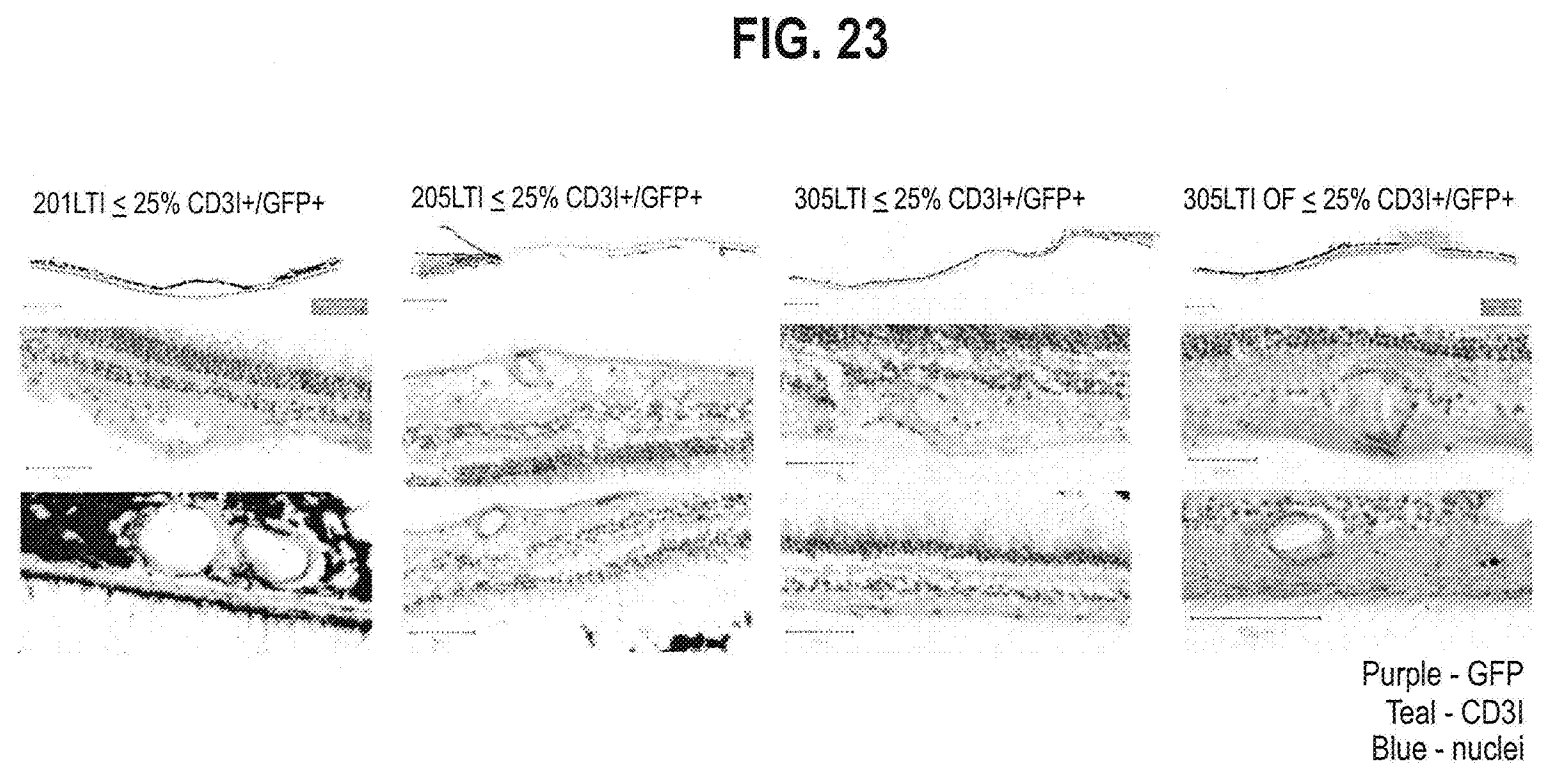

FIG. 23 illustrates histopathological staining for GFP and CD31 colocalization in retinal endothelial cells from NHP eyes following intravitreal injection with $1.2\times 10^{12}$ vg of rAAV comprising a capsid protein of SEQ ID NO:48 (R100) and nucleic acid encoding GFP.

FIG. 24 illustrates aflibercept (AFLB) expression in the aqueous, vitreous and retina+ choroid of NHPs following intravitreal administration of rAAV comprising a capsid protein of SEQ ID NO:48 and a nucleic acid encoding aflibercept and an miRNA targeting VEGF-C.

FIG. 25 illustrates miRNA copies in the retina of NHPs (as described in FIG. 24, left panel) and MiSeq data confirming miRNA targeting VEGF-C as the predominant miRNA species in the NHP retinas.

FIG. 26 illustrates the protective effect of rAAV comprising a capsid protein of SEQ ID NO:48 and a nucleic acid encoding aflibercept and an miRNA targeting VEGF-C, administered at the specified doses, compared to vehicle control in an NHP model of choroidal neovascularization.

DETAILED DESCRIPTION OF THE INVENTION

Definitions

Figure 2:
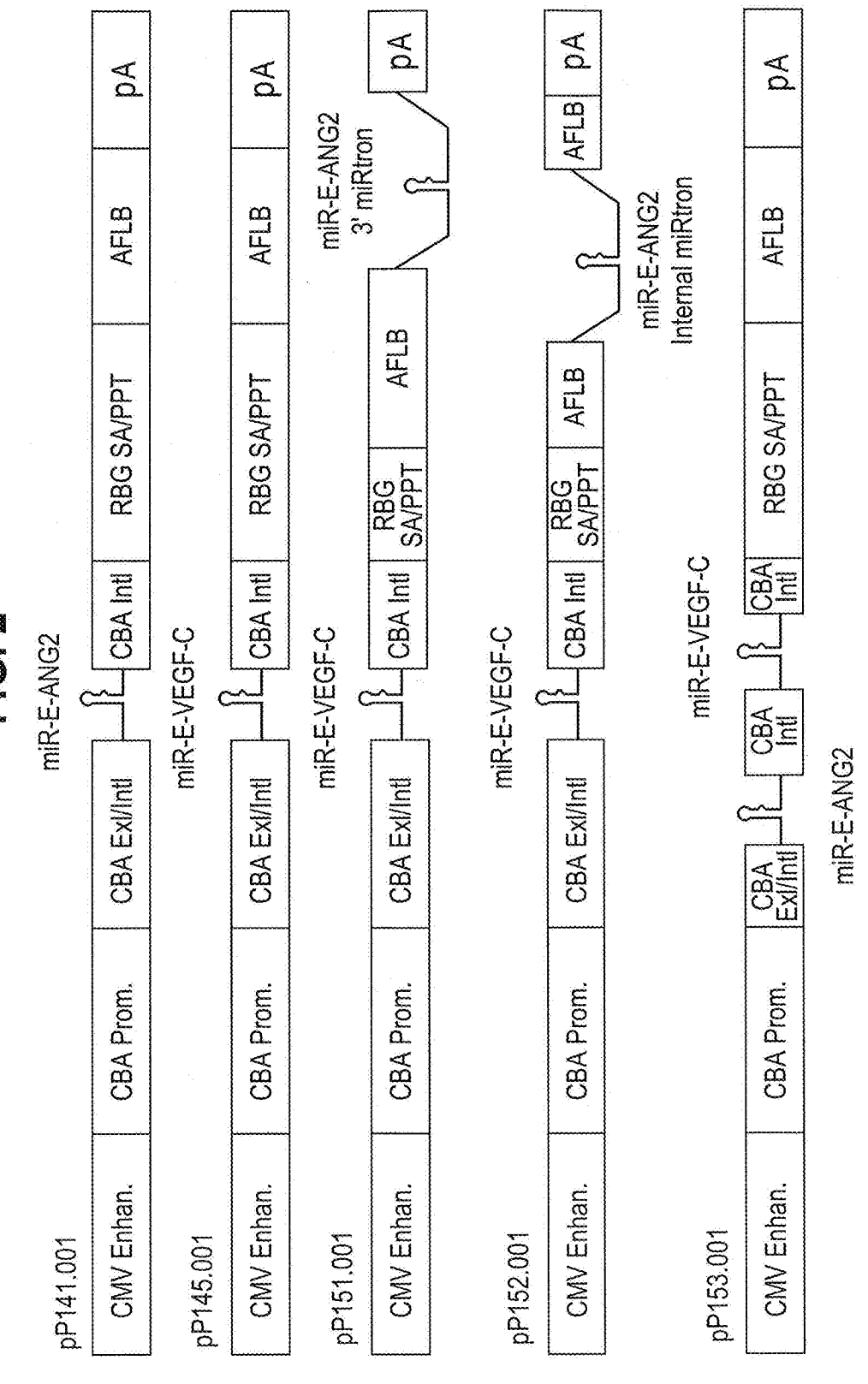
FIG. 2 Depiction of Representative Constructs. pP141.001 comprises a CAG promoter with a miR-E-Ang2 sequence placed within the CAG intron (well after the splice donor site) followed by codon-optimized sequence encoding aflibercept. pP145.001 is identical to pP141.001 except that a mir-E-VEGF-C sequence is placed within the CAG intron. pP151.001 is identical to pP145.001 except that a miR-E-Ang2 sequence is placed within the 3' UTR of the aflibercept gene. pP151.002 is identical to pP145.001 except that a miR-E-Ang2 sequence is placed within the aflibercept coding sequence. pP153.001 comprises a CAG promoter with miR-E-Ang2 and miR-E-VEGF-C sequences placed within the CAG intron (followed by codon-optimized sequence encoding aflibercept). CBA Prom.: ubiquitous chicken b-actin promoter, CBA Ex1/Intl: chicken b-actin exon 1/hybrid chicken b-actin and rabbit beta globulin intron, RGB SA/PPT: rabbit beta globulin exon 3 fragment (splice acceptor)/polypyrimidine tract, T2A: self cleaving peptide, AFLB: aflibercept.

A "codon adaptation index," as used herein, refers to a measure of codon usage bias. A codon adaptation index (CAI) measures the deviation of a given protein coding gene sequence with respect to a reference set of genes (Sharp P M and Li W H, Nucleic Acids Res. 15(3):1281-95 (1987)). CAI is calculated by determining the geometric mean of the weight associated to each codon over the length of the gene sequence (measured in codons):

$$CAI = \exp\left(1/L\sum_{l=1}^{L}\ln(w_1(l))\right)$$ (I)

For each amino acid, the weight of each of its codons, in CAI, is computed as the ratio between the observed frequency of the codon (fi) and the frequency of the synonymous codon (fj) for that amino acid:

$$w_i = \frac{f_i}{\max(f_j)}ij \in [\text{synonymous codons for amino acid}]$$ (II)

The term "isolated" designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then that a single vector can contain just a single coding region or can comprise two or more coding regions.

A "2A peptide" refers to "self-cleaving" peptides of about 20 amino acids that produce equimolar levels of multiple genes from the same mRNA and may be used in place of IRES elements in multicistronic vectors. Non-limiting examples include T2A, P2A, E2A and F2A peptides sequences. In embodiments wherein a heterologous nucleic acid comprises nucleotide sequence encoding multiple gene products, expression of the multiple (e.g. 2) gene products can be mediated by multiple (e.g. 2) independent promoters or may be mediated by a single promoter, with the multiple transgenes separated by an internal ribosome entry site (IRES) or a 2A peptide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

As used herein, the term "nucleic acid" is interchangeable with "polynucleotide" or "nucleic acid molecule" and a polymer of nucleotides is intended.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

"Transcriptional control sequences" or "expression control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit beta-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

A "CAG promoter" is composed of (C) the cytomegalovirus (CMV) early enhancer element, (A) the promoter, the first exon and the first intron of chicken beta-actin gene, (G) the splice acceptor of the rabbit beta-globin gene. See Miyazaki, J., Takaki, S., Araki, K., Tashiro, F., Tominaga, A., Takatsu, K., & Yamamura, K. (1989). Expression vector system based on the chicken β-actin promoter directs efficient production of interleukin-5. Gene, 79(2), 269-277, the contents of which are incorporated herein by reference.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), primary miRNA, small hairpin RNA (shRNA), small interfering RNA (siRNA), or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses, Insertion, of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers can also be considered to be reporters.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Nucleic acids encoding a first anti-angiogenic polypeptide and an antibody or antigen-binding fragment thereof In some embodiments, a nucleic acid is provided comprising a nucleotide sequence encoding a first and second anti-angiogenic polypeptide, wherein the first anti-angiogenic polypeptide is aflibercept and the second anti-angiogenic polypeptide is an antibody or antigen-binding fragment thereof that binds to and inhibits the activity of a pro-angiogenic protein.

A preferred nucleotide sequence encoding aflibercept, codon-optimized for expression in humans, is provided below:

```
                                    (SEQ ID NO: 50)
ATGGTTTCTTACTGGGACACCGGCGTGCTGCTGTGTGCCCTGCTTTCTT

GTCTGCTGCTGACCGGCTCTAGCAGCGGCTCTGATACCGGCAGACCCTT

CGTGGAAATGTACAGCGAGATCCCCGAGATCATCCACATGACCGAGGGC

AGAGAGCTGGTCATCCCTTGCAGAGTGACAAGCCCCAACATCACCGTGA

CTCTGAAGAAGTTCCCTCTGGACACACTGATCCCCGACGGCAAGAGAAT
```

-continued
```
CATCTGGGACAGCCGGAAGGGCTTCATCATCAGCAACGCCACCTACAAA

GAGATCGGCCTGCTGACCTGTGAAGCCACCGTGAATGGCCACCTGTACA

AGACCAACTACCTGACACACAGACAGACCAACACCATCATCGACGTGGT

GCTGAGCCCTAGCCACGGCATTGAACTGTCTGTGGGCGAGAAGCTGGTG

CTGAACTGTACCGCCAGAACCGAGCTGAACGTGGGCATCGACTTCAACT

GGGAGTACCCCAGCAGCAAGCACCAGCACAAGAAACTGGTCAACCGGGA

CCTGAAAACCCAGAGCGGCAGCGAGATGAAGAAATTCCTGAGCACCCTG

ACCATCGACGGCGTGACCAGAAGTGACCAGGGCCTGTACACATGTGCCG

CCAGCTCTGGCCTGATGACCAAGAAAAACAGCACCTTCGTGCGGGTGCA

CGAGAAGGACAAGACCCACACCTGTCCTCCATGTCCTGCTCCAGAACTG

CTCGGGGGACCTTCCGTGTTCCTGTTTCCTCCAAAGCCTAAGGACACCC

TGATGATCAGCAGAACCCCTGAAGTGACCTGCGTGGTGGTGGATGTGTC

CCACGAGGATCCCGAAGTGAAGTTCAATTGGTACGTGGACGGCGTGGAA

GTGCACAACGCCAAGACCAAGCCTAGAGAGGAACAGTACAATAGCACCT

ACAGAGTGGTGTCCGTGCTGACCGTGCTGCACCAGGATTGGCTGAACGG

CAAAGAGTACAAGTGCAAGGTGTCCAACAAGGCCCTGCCTGCTCCTATC

GAGAAAACCATCTCCAAGGCCAAGGGCCAGCCTAGGGAACCCCAGGTTT

ACACACTGCCTCCAAGCAGGGACGAGCTGACAAAGAACCAGGTGTCCCT

GACCTGCCTGGTCAAGGGCTTCTACCCTTCCGATATCGCCGTGGAATGG

GAGAGCAATGGCCAGCCTGAGAACAACTACAAGACAACCCCTCCTGTGC

TGGACAGCGACGGCTCATTCTTCCTGTACAGCAAGCTGACAGTGGACAA

GAGCAGATGGCAGCAGGGCAACGTGTTCAGCTGCTCCGTGATGCACGAG

GCCCTGCACAACCACTACACCCAGAAGTCCCTGAGCCTGTCTCCTGGCA

AA
```

In some embodiments, the sequence is at least 80%, at least 90%, at least 95% or at least 99% identical to the nucleotide sequence of SEQ ID NO:50 and/or comprises a stop codon (e.g. TGA) at the end of the sequence. In some embodiments, the aflibercept gene product comprises the following amino acid sequence or a sequence at least 90%, 95%, 97%, 98%, or at least 99% identical thereto:

```
                                    (SEQ ID NO: 51)
MVSYWDTGVLLCALLSCLLLTGSSSGSDTGRPFVEMYSEIPEIIHMTEG

RELVIPCRVTSPNITVTLKKFPLDTLIPDGKRIIWDSRKGFIISNATYK

EIGLLTCEATVNGHLYKTNYLTHRQTNTIIDVVLSPSHGIELSVGEKLV

LNCTARTELNVGIDFNWEYPSSKHQHKKLVNRDLKTQSGSEMKKFLSTL

TIDGVTRSDQGLYTCAASSGLMTKKNSTFVRVHEKDKTHTCPPCPAPEL

LGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGK
```

In some preferred embodiments, the second anti-angiogenic polypeptide is an antibody or antigen-binding fragment that binds to and inhibits the activity of an angiopoietin (angiopoietin-1/Ang1/Ang-1, angiopoietin-2/Ang2/Ang-2). In some aspects, the second anti-angiogenic polypeptide is an antibody against Ang1 and/or Ang2. In some preferred embodiments, the second anti-angiogenic polypeptide is an antibody or antigen binding fragment thereof that binds to Ang-2. In a particularly preferred embodiment, the antibody or antigen-binding fragment thereof comprises a heavy chain variable region (HCVR) comprising heavy chain complementarity determining regions (HCDRs) of HCDR1=GYYMH (SEQ ID NO:52); HCDR2= WINPNSGGTNYAQKFQG (SEQ ID NO:53) and HCDR3=SPNPYYYDSSGYYYPGAFDI (SEQ ID NO:54) and a light chain variable region (LCVR) comprising light chain complementarity determining regions (LCDRs) of LCDR1=GGNNIGSKSVH (SEQ ID NO:55) LCDR2= DDSDRPS (SEQ ID NO:56) and LCDR3=QVWD-SSSDHWV (SEQ ID NO:57) or comprising HCDRs and LCDRs at least 90%, at least 95%, at least 98% or at least 99% identical thereto. In a related embodiment, the antibody is a single chain Fab (scFab) fragment in LH or HL orientation. In some particularly preferred embodiments, the first anti-angiogenic polypeptide is aflibercept and the second anti-angiogenic polypeptide is an antibody or antigen-binding fragment thereof that binds to human Ang-2 (e.g., an scFab fragment).

Ang-2 promotes angiogenesis and vascular permeability. Ang-2 expression is increased, inter alia, in vitreous of diabetic macular edema (DME), wet age-related macular degeneration (wAMD) and retinal vein occlusion (RVO) patients. High Ang-2 expression is correlated with decreased BVCA (best-corrected visual acuity) and high central macular thickness (CMT) in wAMD patients.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment," as used herein, refers to one or more fragments of an antibody that retain the ability to specifically bind to an antigen. An antibody fragment may include a Fab fragment, a F(ab')2 fragment, a Fv fragment, a dAb fragment, a fragment containing a CDR, or an isolated CDR. In certain embodiments, the term "antigen-binding fragment" refers to a polypeptide fragment of a multi-specific antigen-binding molecule. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments (e.g., single chain Fab (scFab) fragments); (ii) F(ab')2 fragments; (iii) Fd fragments; (iv) Fv fragments; (v) single-chain Fv (scFv) molecules; (vi) dAb fragments (single domain antibody, i.e., nanobody or VHH domain); and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, mini-bodies, nanobodies (e.g., monovalent nanobodies, bivalent nanobodies, etc.), small modular immunopharnaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments comprising a VH domain associated with a VL domain, the VH and VL domains may be situated relative to one another in any suitable arrangement. For example, the variable region may be dimeric and contain VH—VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH—CH1; (ii) VH—CH2; (iii) VH—CH3; (iv) VH-CH1-CH2; (v) VH-CH1-CH2-CH3, (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3, and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

In some preferred embodiments, an expression cassette is provided comprising nucleotide sequence encoding (i) aflibercept+anti-Ang2 HL scFab (ii) aflibercept+anti-Ang2 LH scFab (iii) aflibercept+anti-Ang2 HL scFv or (iv) aflibercept+anti-Ang2 LH scFv, preferably wherein the scFab or scFV comprises HCDR1, HCDR2 and HCDR3 of SEQ ID Nos: 52-54 and LCDR1, LCDR2 and LCDR3 of SEQ ID Nos: 55-57. Nucleic acids encoding a first anti-angiogenic polypeptide and a soluble fusion protein In some embodiments, a nucleic acid is provided comprising nucleotide sequence encoding a first and second anti-angiogenic polypeptide, wherein the first anti-angiogenic polypeptide is aflibercept and the second anti-angiogenic polypeptide a soluble fusion protein that inhibits the activity of a pro-angiogenic polypeptide.

In some preferred embodiments, the first anti-angiogenic polypeptide is aflibercept and the second anti-angiogenic polypeptide is a soluble form of a VEGF receptor (e.g., comprises one or more VEGF-binding domains of VEGFR-1, VEGFR-2 and/or VEGFR-3).

In some preferred embodiments, the first anti-angiogenic polypeptide is aflibercept and the second anti-angiogenic polypeptide is a soluble fusion protein comprising one or more VEGF-binding portions from the extracellular domain of VEGFR-3, representative examples of which include soluble fusion proteins as described in U.S. Pat. Nos. 7,034,105, 5,952,199, and 7,422,741, the contents of each of which is incorporated herein by reference.

VEGF-C promotes angiogenesis and lymphangiogenesis and increases vascular permeability and leakage. VEGF-C is elevated in the eyes of wAMD patients after anti-VEGF treatment. Delivery of VEGFR-3-FC, which binds VEGF-C and VEGF-D, in combination with aflibercept (which binds VEGF-A, VEGF-B and PIGF) provides an improved therapy for ocular disease such as wAMD and DME.

A combination of targeting VEGF-A with a blockade of VEGFR3 is effective in preclinical models of choroidal neovascularization (CNV) and is being evaluated in clinical trials. In a phase 2b clinical trial in subjects with neovascular AMD, the combination of intravitreal ranibizumab and VEGF C/D antagonist OPT-302 resulted in a benefit of 3.4 letters (p=0.0107) in mean best-corrected visual acuity at 24 weeks compared with treatment with ranibizumab alone.

In particularly preferred aspects, the second anti-angiogenic polypeptide is Opt-302, a soluble form of VEGFR-3 comprising the extracellular domains 1-3 of human VEGFR-3 and the Fe fragment of human IgG1 that binds and inhibits the activity of VEGF-C and VEGF-D on endogenous VEGFR-2 and VEGFR-3, described in U.S. Pat. No. 9,745,558, the contents of which are incorporated herein by reference.

A preferred nucleotide sequence encoding OPT-302, codon-optimized for expression in humans, is provided below:

(SEQ ID NO: 58)
ATGCAAAGAGGCGCCGCTCTCTGTCTGAGACTGTGGCTGTGTCTGGGCC

TGCTGGATGGACTGGTGTCTGGCTACAGCATGACCCCTCCAACACTGAA

CATCACCGAGGAATCCCACGTGATCGACACCGGCGATAGCCTGAGCATC

AGCTGCAGAGGACAGCACCCTCTGGAATGGGCTTGGCCTGGTGCTCAAG

AAGCTCCTGCCACAGGCGACAAGGACAGCGAGGATACAGGCGTTGTGCG

GGATTGCGAGGGCACAGATGCCAGACCTTACTGCAAGGTGCTGCTGCTG

CACGAAGTGCACGCCCAGGATACCGGCAGCTACGTGTGCTACTACAAGT

ACATCAAGGCCCGGATCGAGGGCACCACAGCCGCAAGCTCTTATGTGTT

-continued
CGTGCGGGACTTCGAGCAGCCCTTCATCAACAAGCCCGACACACTGCTG

GTCAACCGGAAGGACGCTATGTGGGTGCCCTGTCTGGTGTCTATCCCCG

GCCTGAATGTGACCCTGAGAAGCCAGAGTTCCGTGCTGTGGCCTGATGG

CCAAGAGGTCGTGTGGGACGATAGAAGGGGCATGCTGGTGTCCACACCT

CTGCTGCATGATGCCCTGTACCTGCAGTGCGAGACAACCTGGGGCGACC

AGGACTTCCTGAGCAACCCTTTCCTGGTGCACATCACCGGCAACGAGCT

GTACGACATCCAGCTGCTGCCTCGCAAGAGCCTGGAACTGCTCGTGGGA

GAGAAGCTGGTGCTGAACTGTACCGTGTGGGCCGAGTTCAATAGCGGCG

TGACCTTCGACTGGGACTACCCTGGAAAGCAGGCCGAGCGTGGAAAATG

GGTGCCCGAGAGAAGAAGCCAGCAGACCCACACAGAGCTGAGCAGCATC

CTGACCATCCACAACGTGTCCCAGCACGATCTGGGCTCTTACGTGTGCA

AGGCCAACAACGGCATCCAGCGGTTCCGGGAAAGCACCGAAGTGATCGT

GCATGAGGAACCCAAGAGCTGCGACAAGACACACACCTGTCCTCCATGT

CCTGCTCCAGAGCTTCTCGGCGGACCTTCCGTGTTCCTGTTTCCTCCAA

AGCCTAAGGACACCCTGATGATCAGCAGAACCCCTGAAGTGACCTGCGT

GGTGGTGGATGTGTCCCACGAGGATCCCGAAGTGAAGTTCAATTGGTAC

GTGGACGGCGTGGAAGTGCACAATGCCAAGACCAAGCCTAGAGAGGAAC

AGTACAACAGCACCTACGAGTGGTGTCCGTGCTGACCGTGCTGCATCA

GGATTGGCTGAACGGCAAAGAGTACAAGTGCAAGGTGTCCAACAAGGCC

CTGCCTGCTCCTATCGAGAAAACCATCTCCAAGGCCAAGGGCCAGCCTC

GGGAACCTCAAGTGTATACCCTGCCTCCTAGCCGCGACGAACTCACCAA

GAATCAAGTGTCTCTGACATGTCTCGTGAAGGGGTTTTACCCCAGCGAC

ATTGCCGTCGAGTGGGAGTCCAATGGACAACCCGAGAACAATTATAAGA

CCACGCCACCAGTCCTGGACTCCGACGGCTCATTTTTTCTCTACTCCAA

ACTGACCGTGGATAAGTCCCGGTGGCAGCAAGGGAATGTGTTTTCCTGT

AGCGTGATGCATGAAGCTCTCCACAATCATTACACCCAAAAATCTCTGT

CTCTGAGCCCCGGCAAATGA

A preferred nucleotide sequence encoding a soluble VEGFR-3 containing an alternative IgG2 Fc domain, codon-optimized for expression in humans, is provided below:

(SEQ ID NO: 59)
ATGCAGAGGGGAGCCGCCCTGTGCCTGAGGCTGTGGCTGTGCCTGGGCC

TGCTGGACGGCCTGGTGTCTGGCTACAGCATGACCCCCCCTACACTGAA

CATCACCGAGGAGAGCCACGTGATCGACACAGGCGATAGCCTGTCCATC

TCTTGCAGGGGCCAGCACCCCCTGGAGTGGGCATGGCCTGGAGCACAGG

AGGCACCAGCCACCGGCGACAAGGATAGCGAGGACACAGGAGTGGTGCG

GGACTGCGAGGGAACCGATGCCAGACCTTACTGTAAGGTGCTGCTGCTG

CACGAGGTGCACGCCCAGGATACAGGCTCCTACGTGTGCTACTATAAGT

ATATCAAGGCAAGGATCGAGGGAACCACAGCAGCCAGCTCCTACGTGTT

CGTGCGGGATTTTGAGCAGCCTTTCATCAACAAGCCAGACACCCTGCTG

GTGAATCGGAAGGATGCCATGTGGGTGCCCTGTCTGGTGTCTATCCCTG

-continued

GCCTGAATGTGACACTGAGAAGCCAGTCTAGCGTGCTGTGGCCAGACGG

ACAGGAGGTGGTGTGGGACGATCGGAGAGGCATGCTGGTGAGCACCCCT

CTGCTGCACGATGCCCTGTACCTGCAGTGCGAGACAACATGGGGCGACC

AGGATTTTCTGTCCAACCCTTTCCTGGTGCACATCACAGGCAATGAGCT

GTATGACATCCAGCTGCTGCCACGGAAGTCCCTGGAGCTGCTGGTGGGC

GAGAAGCTGGTGCTGAACTGTACCGTGTGGGCCGAGTTTAATTCTGGCG

TGACATTCGACTGGGATTACCCCGGCAAGCAGGCCGAGAGGGGCAAGTG

GGTGCCTGAGAGGCGCAGCCAGCAGACCCACACAGAGCTGTCCTCTATC

CTGACCATCCACAACGTGAGCCAGCACGATCTGGGCTCCTACGTGTGCA

AGGCCAACAATGGCATCCAGCGGTTTAGAGAGTCTACAGAAGTGATCGT

GCACGAGGAGAGGAAGTGCTGCGTGGAGTGCCCACCATGTCCAGCACCT

CCAGTGGCAGGACCATCCGTGTTCCTGTTTCCACCTAAGCCTAAGGACA

CCCTGATGATCAGCCGCACCCCAGAGGTGACATGCGTGGTGGTGGACGT

GTCCCACGAGGATCCAGAGGTGCAGTTCAACTGGTACGTGGATGGCGTG

GAGGTGCACAATGCCAAGACCAAGCCCAGGGAGGAGCAGTTTAATTCTA

CCTTCCGCGTGGTGAGCGTGCTGACAGTGGTGCACCAGGACTGGCTGAA

CGGCAAGGAGTATAAGTGCAAGGTGTCTAATAAGGGCCTGCCCGCCCCT

ATCGAGAAGACCATCAGCAAGACAAAGGGACAGCCACGGGAGCCACAGG

TGTACACCCTGCCACCATCCAGAGAGGAGATGACCAAGAACCAGGTGTC

TCTGACATGTCTGGTGAAGGGCTTTTATCCAAGCGACATCGCCGTGGAG

TGGGAGTCCAATGGCCAGCCCGAGAACAATTACAAGACCACACCTCCAA

TGCTGGACTCCGATGGCTCTTTCTTTCTGTATTCCAAGCTGACCGTGGA

TAAGTCTCGGTGGCAGCAGGGCAACGTGTTCAGCTGTTCCGTGATGCAC

GAGGCCCTGCACAATCACTACACACAGAAGTCTCTGAGCCTGTCCCCCG

GCAAGTGA

In some preferred embodiments, an expression cassette is provided comprising nucleotide sequence encoding (i) aflibercept+VEGFR3-Fc or (ii) aflibercept+ VEGFR3-Fc-IgG2. Preferably, the nucleotide sequence encoding aflibercept comprises the sequence of SEQ ID NO:50 or a sequence at least 90%, identical thereto and/or the nucleotide sequence encoding VEGFR3-Fc comprises the sequence of SEQ ID NO:58 and/or the nucleotide sequence encoding VEGFR3-Fc-IgG2 comprises the sequences of SEQ ID NO:59.

Nucleic acids encoding a first and second anti-angiogenic polypeptide

In some embodiments, a nucleic acid is provided comprising nucleotide sequence encoding a first and second anti-angiogenic polypeptide, wherein the first anti-angiogenic polypeptide is aflibercept and the second anti-angiogenic polypeptide is selected from endostatin; tumstatin; angiostatin; pigment epithelium-derived factor (PEDF).

In some preferred embodiments, the nucleic acid comprises nucleotide sequence encoding aflibercept and nucleotide sequence encoding PEDF (see e.g., Dawson et al., Science 285:245, 1999; U.S. Pat. No. 5,840,686, and International Patent Applications WO93/24529 and WO99/04806, the contents of each of which is incorporated herein by reference). PEDF is a secreted protein with homology to members of the serpin family of serine protease inhibitors. PEDF is predominantly produced by retinal pigment epithelial cells, is expressed in most human tissues, and has anti-angiogenic and neuroprotectant qualities (see e.g., Dawson D W et al., Science. 1999 Jul. 9; 285(5425):245-8). PEDF prevents photoreceptor degeneration and deficiency of PEDF is associated with angiogenic diseases such as wAMD. Preclinical data points to an inhibitory role of VEGF and FGF in mouse and pig models of choroidal neovascularization (CNV) (see e.g., Lei X L, Oxid Med Cell Longev.; Vol. 2020, Art. ID 8941057).

A representative human PEDF sequence is found at GenBank Accession P36955 (e.g., P36955.4). In some aspects, a preferred nucleotide sequence encoding human PEDF that has been codon-optimized for expression in humans has the following sequence or a sequence at least 90%, at least 95%, at least 98% or at least 99% identical thereto:

(SEQ ID NO: 60)
ATGCAAGCTCTGGTGCTGCTGCTGTGTATCGGAGCCCTGCTGGGCCACA

GCTCCTGTCAAAATCCTGCCTCTCCACCTGAGGAAGGCAGCCCCGATCC

AGATTCTACAGGCGCCCTGGTGGAAGAAGAGGACCCATTCTTCAAGGTG

CCCGTGAACAAACTGGCCGCTGCCGTGTCCAACTTCGGCTACGACCTGT

ACAGAGTGCGGAGCAGCACAAGCCCCACCACCAATGTTCTGCTGAGCCC

TCTGTCTGTGGCCACCGCTCTTTCTGCTCTGTCTCTGGGAGCCGAGCAG

AGAACCGAGAGCATCATTCACAGAGCCCTGTACTACGATCTGATCAGCA

GCCCTGACATCCACGGCACCTACAAAGAACTGCTGGACACCGTGACAGC

CCCTCAGAAGAATCTGAAGTCCGCCAGCCGGATCGTGTTCGAGAAGAAG

CTGCGGATCAAGAGCAGCTTCGTGGCCCCTCTGGAAAAGAGCTACGGCA

CCAGACCTAGAGTGCTGACCGGCAATCCCAGACTGGACCTGCAAGAGAT

CAACAACTGGGTGCAAGCCCAGATGAAGGGCAAGCTGGCCAGAAGCACC

AAAGAGATCCCCGACGAGATCAGCATCCTGCTGCTGGGCGTCGCCCACT

TTAAAGGCCAGTGGGTCACCAAGTTCGACTCCAGAAAGACCAGCCTCGA

GGACTTCTACCTGGACGAGGAACGGACCGTCAGAGTGCCCATGATGAGC

GATCCTAAGGCCGTGCTGAGATACGGCCTGGATAGCGACCTGAGCTGCA

AGATTGCTCAGCTGCCTCTGACCGGCTCTATGAGCATCATATTCTTTCT

GCCCCTGAAAGTGACCCAGAATCTGACCCTGATCGAGGAAAGCCTGACC

AGCGAGTTCATCCACGACATCGACCGCGAGCTGAAAACCGTGCAGGCTG

TGCTGACTGTGCCCAAGCTGAAGCTGAGCTACGAGGGCGAAGTGACCAA

GAGCCTGCAAGAAATGAAGCTGCAGAGCCTGTTCGACAGCCCCGACTTC

AGCAAGATCACCGGCAAGCCCATCAAGCTGACCCAGGTGGAACACAGAG

CCGGCTTCGAGTGGAATGAAGATGGCGCCGGAACCACACCTTCTCCAGG

ACTGCAACCTGCTCACCTGACCTTTCCACTGGACTACCACCTGAACCAG

CCTTTCATCTTCGTGCTGCGGGACACAGATACTGGCGCCCTGCTGTTCA

TCGGCAAGATCCTGGATCCTAGAGGCCCCTGA

In some preferred embodiments, an expression cassette is provided comprising nucleotide sequence encoding aflibercept+ PEDF, preferably wherein the nucleotide sequence encoding aflibercept comprises the sequence of SEQ ID NO:50 and/or the nucleotide sequence encoding PEDF comprises the sequence of SEQ ID NO:60.

Nucleic acids encoding a first anti-angiogenic polypeptide and an interfering RNA molecule that reduces expression of an angiopoietin In some embodiments, a nucleic acid is provided that comprises nucleotide sequence encoding a first anti-angiogenic polypeptide and an interfering RNA molecule that targets an angiopoietin, wherein the first anti-angiogenic polypeptide is aflibercept.

In preferred aspects, the interfering RNA molecule targets human angiopoietin-1 (aka Ang1 or Ang-1) and/or targets human angiopoietin-2 (aka Ang2 or Ang-2). Representative human Ang2 sequences can be found at e.g., NCBI Accession No. 015123 and SEQ ID Nos: 517 and 518 of U.S. Pat. No. 8,987,420, the contents of which are incorporated herein by reference. Suitable target sequences within the human Ang-2 gene as well as representative interfering RNA molecules targeting human Ang-2 include those in U.S. Pat. No. 7,994,305 (e.g., SEQ ID Nos:228-427 of U.S. Pat. No. 7,994,305) and 8,829,179 (e.g., SEQ ID Nos:2-69 and 73-104 of U.S. Pat. No. 8,829,179), the contents of each of which are incorporated herein by reference. In particularly preferred embodiments, the interfering RNA molecule targets human Ang-2 and comprises a sense strand and antisense strand according to Table 1.

In preferred embodiments, an expression cassette is provided comprising nucleotide sequence encoding aflibercept and one or more interfering RNAs set forth in Table 1. Preferably, the nucleotide sequence encoding aflibercept comprises the sequence of SEQ ID NO:50.

Nucleic acids encoding a first anti-angiogenic polypeptide and an interfering RNA molecule that reduces expression of VEGF-C and/or VEGF-D In some preferred embodiments, a nucleic acid is provided comprising nucleotide sequence encoding a first anti-angiogenic polypeptide and an interfering RNA molecule that targets VEGF-C and/or VEGF-D, wherein the first anti-angiogenic polypeptide is aflibercept.

In particularly preferred aspects, the interfering RNA molecule targets human VEGF-C and/or human VEGF-D. Representative human VEGF-C sequences can be found at e.g., GenBank Accession numbers NM_005429 and X94216. Representative human VEGF-D sequences can be found e.g., at GenBank Accession number AJ000185.1. Suitable target sequences within the human VEGF-C gene as well as representative interfering RNA molecules targeting human VEGF-C include those in U.S. Pat. No. 7,517,864 (e.g., Table II) and US Patent Application Publication No. US2011/0293625 (e.g., SEQ ID Nos:1-3 and 7-12), the contents of each of which are incorporated-herein by reference. In particularly preferred embodiments, the interfering RNA molecule targets human VEGF-C and comprises a sense strand and antisense strand according to Table 2.

VEGF-C target sequence(s) were selected based on in silico determination of specificity, homology to human and non-human primate (NHP) sequences and knockdown of VEGF-C in vitro (see working examples). The region of VEGF-C targeted by the RNAi molecule(s) has 100% homology between human and NHP sequences, whereas mouse VEGF-C has 2 point mutations that would likely influence the ability of this target sequence to be effective in mice. A sequence alignment of the VEGF-C target region is provided below:

```
VEGF-C miRNA Target Sequence
Homo sapiens
...CTACCTCAGCAAGACGTTATTT...

Macaca fascicularis
...CTACCTCAGCAAGACGTTATTT...

Chlorocebus aethiops
...CTACCTCAGCAAGACGTTATTT...

Mus musculus
...TTACCTCAGCAAGACGTTGTTT...
```

Wet AMD (wAMD) is a retinal condition characterized by growth of abnormal, leaky blood vessels from the choroidal layer through Bruch's membrane and into the retina which can lead to a rapid loss of central vision. Current approved treatments include injections of anti-angiogenic protein therapies, such as aflibercept, ranibizumab, or brolucizumab, or the aptamer pegaptinib sodium that block signaling through VEGF-A. However, these injected therapies require repeated intravitreal (IVT) administrations to maintain vision. Many patients fail to maintain initial visual benefit due to undertreatment related to burdensome frequency of required treatment visits. Nucleic acids described herein comprising an anti-angiogenic polypeptide targeting VEGF-A (e.g., aflibercept) and an RNAi molecule targeting VEG-C provides an improved efficacy for wetAMD patients by reducing expression of additional angiogenic factors such as VEGF-C that are upregulated following administration of current anti-VEGF therapies.

In preferred embodiments, an expression cassette is provided comprising nucleotide sequence encoding aflibercept and one or more interfering RNAs set forth in Table 2. Preferably, the nucleotide sequence encoding aflibercept comprises the sequence of SEQ ID NO:50.

Nucleic acids encoding a first anti-angiogenic polypeptide and an interfering RNA molecule that reduces expression of VEGFR-3

In some embodiments, a nucleic acid is provided comprising nucleotide sequence encoding a first anti-angiogenic polypeptide and an interfering RNA molecule that targets VEGFR-3, wherein the first anti-angiogenic polypeptide is aflibercept.

In preferred aspects, the interfering RNA molecule targets human VEGFR-3. Representative human VEGFR-3 sequences can be found e.g., at GenBank Accession number X68203. Suitable target sequences within the human VEGFR-3 gene as well as representative interfering RNA molecules targeting human VEGFR-3 include those listed in Table II of U.S. Pat. No. 7,517,864, the contents of each of which are incorporated herein by reference. In particularly preferred embodiments, the interfering RNA molecule targets human VEGFR-3 and comprises a sense strand and antisense strand according to Table 3.

In preferred embodiments, an expression cassette is provided comprising nucleotide sequence encoding aflibercept and one or more interfering RNAs set forth in Table 3. Preferably, the nucleotide sequence encoding aflibercept comprises the sequence of SEQ ID NO:50.

In embodiments where the nucleic acid encodes a first anti-angiogenic polypeptide and one or more interfering RNAs, the sequence encoding the interfering RNA(s) may be placed within a natural or artificial intron (e.g., an artificial intron, within a transcription control sequence, within a 5' UTR region of a gene, within the coding sequence of a gene or within the 3' UTR region of a gene). In some aspects, the interfering RNA is placed within a synthetic U2 or U12 based intron or within an interferon regulating factor 7 intron 4 (IRF7int4; 93 bp).

In some preferred aspects, the interfering RNA is placed within an artificial intron in a transcription control sequence. In some preferred aspects, the intron is located within the hybrid chicken D-actin and rabbit P-globin intron of the CAG promoter, whereby the intron is co-transcribed within a pre-mRNA by Pol-II and cleaved out of the pre-mRNA by RNA splicing. The spliced intron containing the pre-miRNA structure is further processed into mature miRNA capable of silencing a pro-angiogenic target gene.

In other aspects, the interfering RNA is placed within an artificial intron that is located within the coding sequence of a gene (e.g., encoding aflibercept), whereby the intron is co-transcribed within a pre-mRNA by Pol-II and cleaved out of the pre-mRNA by RNA splicing. The spliced intron containing the pre-miRNA structure is further processed into mature miRNA capable of silencing a pro-angiogenic target gene.

In other aspects, the sequence encoding the interfering RNA is placed within the 5' UTR or 3' UTR region of a gene but is not within an intron, in which case some portion (e.g., 50%) of the transcribed pre-mRNA is translated into the encoded protein and some portion (e.g., 50%) of the transcribed pre-mRNA is processed into active shRNA or miRNA. In some preferred aspects, the interfering RNA is placed within a 3' UTR region of a gene.

Codon Optimized Nucleic Acid Sequences

In some embodiments, the present invention provides a nucleic acid molecule comprising a nucleotide sequence that is codon optimized for expression in humans. In some embodiments, the nucleotide sequence encodes PEDF and comprises or consists of the nucleotide sequence set forth as SEQ ID NO:60 or a sequence at least 90%, at least 95%, at least 98% or at least 99% identical thereto. In another embodiment, the nucleotide sequence encodes OPT-302 and comprises or consists of the nucleotide sequence set forth as SEQ ID NO:58 or a sequence at least 90%, at least 95%, at least 98% or at least 99% identical thereto. In another embodiment, the nucleotide sequence encodes VEGFR3-Fc-IgG2 and comprises or consists of the nucleotide sequence set forth as SEQ ID NO:59 or a sequence at least 90%, at least 95%, at least 98% or at least 99% identical thereto.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprises the codons encoding the amino acids of, any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 4

| The Standard Genetic Code | | | | |
|---|---|---|---|---|
| | T | C | A | G |
| T | TTT Phe (F) | TCT Ser (S) | TAT Tyr (Y) | TGT Cys (C) |
| | TTC | TCC | TAC" | TGC |
| | TTA Leu (L) | TCA | TAA Stop | TGA Stop |
| | TTG | TGG | TAG Stop | TGG Trp (W) |
| C | CTT Leu (L) | CCT Pro (P) | CAT His (H) | CGT Arg (R) |
| | CTC | CCC | CAC | CGC |
| | CTA | CCA | CAA Gln (Q) | CGA |
| | CTG | CCG | CAG | CGG |
| A | ATT Ile (I) | ACT Thr (T) | AAT Asn (N) | AGT Ser (S) |
| | ATC | ACC | AAC | AGC |
| | ATA | ACA | AAA Lys (K) | AGA Arg (R) |
| | ATG Met (M) | ACG | AAG | AGG |
| G | GTT (Val) V | GCT Ala (A) | GAT Asp (D) | GGT Gly (G) |
| | GTC | GCC | GAC | GGC |
| | GTA | GCA | GAA Glu (E) | GGA |
| | GTG | GCG | GAG | GGG |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, the relative frequencies of codon usage have been calculated. Codon usage tables are available, for example, at the "Codon Usage Database" available at www.kazusa.or.jp/codon/(visited Jun. 18, 2012). See Nakamura, Y., et al. Nucl. Acids Res. 28:292 (2000).

Randomly assigning codons at an optimized frequency to encode a given polypeptide sequence can be done manually by calculating codon frequencies for each amino acid, and then assigning the codons to the polypeptide sequence randomly. Additionally, various algorithms and computer software programs can be used to calculate an optimal sequence.

Non-Viral Vectors

In some embodiments, a non-viral vector (e.g., an expression plasmid) is provided comprising any nucleotide sequence as herein described. In some embodiments, the non-viral vector comprises a nucleotide sequence encoding a first anti-angiogenic polypeptide (e.g., aflibercept) as herein described and one or more interfering RNA(s) as herein described and/or a second anti-angiogenic polypeptide as herein described. Preferably, the non-viral vector is a plasmid comprising an expression cassette comprising a nucleotide sequence as herein described.

Viral Vectors

In some embodiments, a viral vector comprising a modified (codon optimized) nucleic acid as herein described is provided. In preferred embodiments, the viral vector comprises a nucleic acid comprising nucleotide encoding a first anti-angiogenic polypeptide (e.g., aflibercept) and nucleotide sequence encoding one or more interfering RNA(s) as herein described and/or comprising nucleotide sequence encoding a first and second anti-angiogenic polypeptide. Examples of suitable viral vectors include but are not limited to adenoviral, retroviral, lentiviral, herpesvirus and adeno-associated virus (AAV) vectors.

In a preferred embodiment, the viral vector includes a portion of a parvovirus genome, such as an AAV genome with the rep and cap genes deleted and/or replaced by an expression cassette comprising sequence encoding a first anti-angiogenic polypeptide (e.g., aflibercept) and nucleotide sequence encoding one or more interfering RNA(s) as herein described and/or comprising nucleotide sequence encoding a first and second anti-angiogenic polypeptide and their associated expression control sequences. The expression cassette is typically inserted adjacent to one or two (i.e., is flanked by) AAV TRs or TR elements adequate for viral replication (Xiao et al., 1997, J. Virol. 71(2): 941-948), in place of the nucleic acid encoding viral rep and cap proteins. Other regulatory sequences suitable for use in facilitating tissue-specific expression in the target cell may also be included.

In some embodiments, the AAV viral vector comprises a nucleic acid comprising: (a) an AAV2 terminal repeat (b) a transcription control sequence (c) nucleotide sequence encoding a first anti-angiogenic polypeptide (d) nucleotide sequence(s) encoding an RNAi molecule as herein described (d) a polyadenylation sequence and (e) an AAV2 terminal repeat.

In other embodiments, the AAV viral vector comprises a nucleic acid comprising: (a) an AAV2 terminal repeat (b) a transcription control sequence (c) nucleotide sequence encoding a first anti-angiogenic polypeptide (d) a 2A sequence (e) nucleotide sequence encoding a second anti-angiogenic polypeptide (f) a polyadenylation sequence and (g) an AAV2 terminal repeat.

In particularly preferred embodiments, the AAV viral vector comprises a nucleic acid (transgene cassette) comprising the sequence of any of SEQ ID NOs:64-70, more preferably comprising the sequence of any of SEQ ID Nos: 68-70, or a sequence at least 90%, at least 95%, at least 98% or at least 99% identical thereto.

In some embodiments, the 5' ITR has the following sequence:

TTGGCCACTCCCTCTCTGCGCGCTCGCTCGCTCAC-TGAGGCCGGGCGACCAAAGGTCGCCCGACGCC-CG-GGCTTTGCCCGGGCGGCCTCAGTGAGCGAGC-GAGCGCGCA GAGAGGGAGTGGCCAACTCCATCA-CTAGGGGTTCCT (SEQ ID NO:61)

In some embodiments, the 3' ITR has the following sequence:

```
                                    (SEQ ID NO: 62)
AGGAACCCCTAGTGATGGAGTTGGCCACTCCCTCTCTGCGCGCTCGCTC

GCTCACTGAGGCCGCCCGGGCAAAGCCCGGGCGTCGGGCGACCTTTGGT

CGCCCGGCCTCAGTGAGCGAGCGAGCGCGCAGAGAGGGAGTGGCCAA
```

In some embodiments, the SV40 polyadenylation sequence has the following sequence:

```
                                    (SEQ ID NO: 63)
GGGGATCCAGACATGATAAGATACATTGATGAGTTTGGACAAACCACAA

CTAGAATGCAGTGAAAAAAATGCTTTATTTGTGAAATTTGTGATGCTAT

TGCTTTATTTGTAACCATTATAAGCTGCAATAAACAAGTTAACAACAAC

AATTGCATTCATTTTATGTTTCAGGTTCAGGGGGAGGTGTGGGAGGTTT

TTTAAAGCAAGTAAAACCTCTACAAATGTGGTATGGCTGATTATGATCA
```

Those skilled in the art will appreciate that an AAV vector comprising a transgene and lacking virus proteins needed for viral replication (e.g., cap and rep), cannot replicate since such proteins are necessary for virus replication and packaging. Helper viruses include, typically, adenovirus or herpes simplex virus. Alternatively, as discussed below, the helper functions (E1a, E1b, E2a, E4, and VA RNA) can be provided to a packaging cell including by transfecting the cell with one or more nucleic acids encoding the various helper elements and/or the cell can comprise the nucleic acid encoding the helper protein. For instance, HEK 293 were generated by transforming human cells with adenovirus 5 DNA and now express a number of adenoviral genes, including, but not limited to E1 and E3 (see, e.g., Graham et al., 1977, J. Gen. Virol. 36:59-72). Thus, those helper functions can be provided by the HEK 293 packaging cell without the need of supplying them to the cell by, e.g., a plasmid encoding them.

The viral vector may be any suitable nucleic acid construct, such as a DNA or RNA construct and may be single stranded, double stranded, or duplexed (i.e., self-complementary as described in WO 2001/92551).

The viral capsid component of the packaged viral vectors may be a parvovirus capsid. AAV Cap and chimeric capsids are preferred. For example, the viral capsid may be an AAV capsid (e.g., AAV1, AAV2, AAV3, AAV4, AAV5, AAV6, AAV7 AAV8, AAV9, AAV10, AAV11, AAV12, AAV1.1, AAV2.5, AAV6.1, AAV6.3.1, AAV9.45, AAVrh10, AAVrh74, RHM4-1, AAV2-TT, AAV2-TT-S312N, AAV3B-S312N, AAV-LK03, snake AAV, avian AAV, bovine AAV, canine AAV, equine AAV, ovine AAV, goat AAV, shrimp AAV, and any other AAV now known or later discovered. see, e.g., Fields et al., VIROLOGY, volume 2, chapter 69 (4.sup.th ed., Lippincott-Raven Publishers).

In some embodiments, the viral capsid component of the packaged viral vector is a variant of a native AAV capsid (i.e., comprises one or more modifications relative to a native AAV capsid). In some embodiments, the capsid is a variant of an AAV2, AAV5 or AAV8 capsid. In preferred embodiments, the capsid is a variant of an AAV2 capsid, such as those described in U.S. Patent Application Publication Number 2019/0255192A1 (e.g., comprising the amino acid sequence of any of SEQ ID NOs: 42-59), the entire contents of which are incorporated herein by reference. In a particularly preferred embodiment, the capsid comprises a VP1 capsid protein comprising, consisting essentially of, or consisting of the amino acid sequence of SEQ ID NO:48. In certain embodiments, the capsid protein comprises a peptide insertion in the GH-loop of the capsid protein relative to a corresponding parental AAV capsid protein, wherein the peptide insertion comprises the amino acid sequence ISDQTKH (SEQ ID NO:74), preferably wherein the peptide insertion comprises the amino acid sequence. $Y_1Y_2$ISDQTKH$Y_3$ (SEQ ID NO:75), wherein each of $Y_1$-$Y_3$ is independently selected from Ala, Leu, Gly, Ser, Thr, and Pro. In specific embodiments, the peptide insertion comprises the amino acid sequence LAISDQTKHA (SEQ ID NO:49), preferably wherein the insertion site is between amino acids corresponding to amino acids 587 and 588 of VP1 of AAV2 or the corresponding position in the capsid protein of another AAV serotype. In some embodiments, the capsid protein comprises one or more amino acid substitutions relative to VP1 capsid of AAV2 or one or more corresponding substitutions in another AAV serotype, preferably wherein the capsid protein comprises a P34A amino acid substitution relative to VP1 capsid of AAV2 or the corresponding substitution in another AAV serotype.

A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

In yet another embodiment the present invention provides for the use of ancestral AAV vectors for use in therapeutic in vivo gene therapy. Specifically, in silico-derived sequences were synthesized de novo and characterized for biological activities. This effort led to the generation of nine functional putative ancestral AAVs and the identification of Anc80, the predicted ancestor of AAV serotypes 1, 2, 8 and 9 (Zinn et al., 2015, Cell Reports 12:1056-1068). Predicting and synthesis of such ancestral sequences in addition to assembling into a virus particle may be accomplished by using the methods described in WO 2015/054653, the contents of which are incorporated by reference herein. Notably, the use of the virus particles assembled from ancestral viral sequences may exhibit reduced susceptibility to pre-existing immunity in current day human population than do contemporary viruses or portions thereof.

The invention includes packaging cells, which are encompassed by "host cells," which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Initially, the vectors can be made by several methods known to skilled artisans (see, e.g., WO 2013/063379). A preferred method is described in Grieger, et al. 2015, Molecular Therapy 24(2):287-297, the contents of which are incorporated by reference herein for all purposes. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV production. Using the triple transfection method (e.g., WO 96/40240), the suspension HEK293 cell line generates greater than 10' vector genome containing particles (vg)/cell or greater than $10^{14}$ vg/L of cell culture when harvested 48 hours post-transfection. More specifically, triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the transgene and its various control elements (e.g., modified RPGRorfl5 gene and hGRK promoter).

To achieve the desired yields, a number of variables are optimized such as selection of a compatible serum-free suspension media that supports both growth and transfection, selection of a transfection reagent, transfection conditions and cell density. A universal purification strategy, based on ion exchange chromatography methods, was also developed that resulted in high purity vector preps of AAV serotypes 1-6, 8, 9 and various chimeric capsids. This user-friendly process can be completed within one week, results in high full to empty particle ratios (>90% full particles), provides post-purification yields (>1× $10^{13}$ vg/L) and purity suitable for clinical applications and is universal with respect to all serotypes and chimeric particles. This scalable manufacturing technology has been utilized to manufacture GMP Phase I clinical AAV vectors for retinal neovascularization (AAV2), Hemophilia B (scAAV8), Giant Axonal Neuropathy (scAAV9) and Retinitis Pigmentosa (AAV2), which have been administered into patients. In addition, a minimum of a 5-fold increase in overall vector production by implementing a perfusion method that entails harvesting rAAV from the culture media at numerous timepoints post-transfection.

The packaging cells include viral vector functions, along with packaging and vector functions. The viral vector functions typically include a portion of a parvovirus genome, such as an AAV genome, with rep and cap deleted and replaced by the first anti-angiogenic polypeptide sequence that inhibits the activity of VEGF-A and at least one synthetic RNA molecule or a second anti-angiogenic polypeptide sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide.

The terminal repeats (TR(s)) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2.

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1, AAV2, AAV3, AAV4, AAV5, AAV6, AAV7, AAV8, AAV9, AAV10, AAV11, AAV12, AAVrh10, AAVrh74, RHM4-1, RHM15-1, RHM15-2, RHM15-3/RHM15-5, RHM15-4, RHM15-6, AAV Hu.26, AAV1.1, AAV2.5, AAV6.1, AAV6.3.1, AAV9.45, AAV2i8, AAV2G9, AAV2i8G9, AAV2-TT, AAV2-TT-S312N, AAV3B-S312N, and AAV-LK03, and other novel capsids as yet unidentified or from non-human primate sources. Capsid components may include components from two or more AAV capsids.

The packaged viral vector generally includes sequence encoding one or more anti-angiogenic polypeptides and/or interfering RNAs as herein described and corresponding expression control sequence(s) flanked by TR elements, referred to herein as the "transgene" or "transgene expression cassette," sufficient to result in packaging of the vector DNA and subsequent expression of the interfering RNA and/or gene sequence in the transduced cell (e.g., a photoreceptor). The viral vector functions may, for example, be supplied to the cell as a component of a plasmid or an amplicon. The viral vector functions may exist extrachromosomally within the cell line and/or may be integrated into the cell's chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but are preferably integrated into the cell's chromosomal DNA. Examples include genes encoding AAV Rep and Cap proteins.

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but are preferably integrated into the cell's chromosomal DNA (e.g., E1 or E3 in HEK 293 cells).

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, more preferably, the cell is capable of growing in serum-free culture. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV packaging cell lines are known in the art, including, but not limited to, those disclosed in WO 2002/46359. In another aspect, the packaging cell is cultured in the form of a cell stack (e.g., 10-layer cell stack seeded with HEK293 cells).

Cell lines for use as packaging cells include insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, N J (1995); O'Reilly et al., Baculovirus Expression Vectors: A Laboratory Manual, Oxford Univ. Press (1994); Samulski et al., 1989, J. Virol. 63:3822-3828; Kajigaya et al., 1991, Proc. Nat'l. Acad. Sci. USA 88: 4646-4650; Ruffing et al., 1992, J. Virol. 66:6922-6930; Kimbauer et al., 1996, Virol. 219: 37-44; Zhao et al., 2000, Virol. 272:382-393; and Samulski et al., U.S. Pat. No. 6,204,059.

Virus capsids according to the invention can be produced using any method known in the art, e.g., by expression from a baculovirus (Brown et al., (1994) Virology 198:477-488). As a further alternative, the virus vectors of the invention can be produced in insect cells using baculovirus vectors to deliver the rep/cap genes and rAAV template as described, for example, by Urabe et al., 2002, Human Gene Therapy 13:1935-1943.

In another aspect, the present invention provides for a method of rAAV production in insect cells wherein a baculovirus packaging system or vectors may be constructed to carry the AAV Rep and Cap coding region by engineering these genes into the polyhedrin coding region of a baculovirus vector and producing viral recombinants by transfection into a host cell. Notably when using Baculovirus production for AAV, preferably the AAV DNA vector product is a self-complementary AAV like molecule without using mutation to the AAV ITR. This appears to be a by-product of inefficient AAV rep nicking in insect cells which results in a self-complementary DNA molecule by virtue of lack of functional Rep enzyme activity. The host cell is a baculovirus-infected cell or has introduced therein additional nucleic acid encoding baculovirus helper functions or includes these baculovirus helper functions therein.

These baculovirus viruses can express the AAV components and subsequently facilitate the production of the capsids.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA The rAAV vector may be purified by methods standard in the art such as by column chromatography or cesium chloride gradients. Methods for purifying rAAV vectors are known in the art and include methods described in Clark et al., 1999, Human Gene Therapy 10(6):1031-1039; Schenpp and Clark, 2002, Methods Mol. Med. 69:427-443; U.S. Pat. No. 6,566,118 and WO 98/09657.

Treatment Methods

In some embodiments, a nucleic acid as herein described—or a pharmaceutical composition comprising such a nucleic acid and a pharmaceutically acceptable excipient—is administered to a subject (e.g., a human) intraocularly, preferably by subretinal, suprachoroidal, or intravitreal injection. In some preferred embodiments, the nucleic acid or pharmaceutical composition is administered via intravitreal and/or subretinal injection, more preferably by a single intravitreal injection, to treat a VEGF-associated ocular disease. In some embodiments, the VEGF-associated ocular disease is a VEGF-A-associated ocular disease. In other embodiments, the nucleic acid or pharmaceutical composition is administered topically or intracamerally. In some embodiments, the VEGF-associated ocular disease is selected from wet (neovascular, exudative) age-related macular degeneration; macular edema following retinal vein occlusion; retinal neovascularization resulting from retinal vein occlusion; diabetic macular edema, diabetic retinopathy (including all stages of non-proliferative diabetic retinopathy and proliferative diabetic retinopathy), myopic macular degeneration, branch retinal vein occlusion, hemi-retinal vein occlusion, and central retinal vein occlusion; retinopathy of prematurity; idiopathic choroidal neovascularization; myopia macular degeneration and secondary retinal and choroidal neovascularization; retinal telangiectasia; neovascular glaucoma; vitreous hemorrhage; retinal and choroidal neovascularization secondary to retinal diseases, including but not limited to uveitis, trauma, retinal degenerative disorders, genetic retinal and/or choroidal disease, tumors of the eye, corneal and iris neovascularization. In preferred embodiments, the nucleic acid is delivered to the subject in a vector, preferably a recombinant AAV (rAAV) vector as herein described, preferably wherein the rAAV vector comprises a capsid protein of SEQ ID NO:48 or sequence comprising at least 90% identity thereto, or a pharmaceutical composition comprising such a vector and a pharmaceutically acceptable excipient.

In related aspects, a nucleic acid as herein described for use in the treatment of a VEGF-associated ocular disease (e.g., a VEGF-A-associated ocular disease) or for the manufacture of a medicament for the treatment of a VEGF-associated ocular disease is provided. In other related aspects, an rAAV comprising a nucleic acid as herein described for use in the treatment of a VEGF-associated ocular disease or for the manufacture of a medicament for the treatment of a VEGF-associated ocular disease is provided. In preferred embodiments, the rAAV comprises a capsid sequence of SEQ ID NO:48 or sequence comprising at least 90% identity thereto, and is intravitreally administered to a subject to treat a VEGF-associated ocular disease, preferably by a single intravitreal injection.

In certain preferred embodiments, a method is provided for the treatment and/or prevention of wet (neovascular, exudative) age-related macular degeneration; diabetic macular edema; macular edema following retinal vein occlusion; diabetic retinopathy; or myopic choroidal neovascularization and all other forms of abnormal ocular and retinal angiogenesis, including but not limited to idiopathic retinal neovascularization, neovascular glaucoma, retinopathy of prematurity, radiation retinopathy, central serous retinopathy, diabetic vitreous hemorrhage, pseudoxanthoma elasticum, Coat's and other forms of peripheral retinal neovasculation in a subject (e.g., human subject) by administering to the subject an effective amount of an rAAV comprising a nucleic acid as herein described or a pharmaceutical composition comprising such an rAAV and a pharmaceutically acceptable excipient. Preferably the rAAV comprises a capsid protein of SEQ ID NO:48 or sequence comprising at least 90% identity thereto. In particularly preferred embodiments, a method is provided for the treatment of wet age-related macular degeneration.

In some aspects, the nucleic acid comprises a nucleotide sequence encoding aflibercept and a nucleotide sequence encoding a second anti-angiogenic polypeptide. In related aspects, the second anti-angiogenic polypeptide is selected from endostatin; tumstatin; angiostatin; and pigment epithelium-derived factor (PEDF). In some preferred embodiments, the second anti-angiogenic polypeptide is PEDF. In particularly preferred embodiments, provided herein is an rAAV vector comprising a capsid protein of SEQ ID NO:48 and a nucleic acid comprising the following sequence (aflibercept+ PEDF dual construct) or a sequence at least 80%, at least 85%, at least 90%, at least 95%; at least 98% or at least 99% identical thereto:

(SEQ ID NO: 64)

```
TTGGCCACTCCCTCTCTGCGCGCTCGCTCGCTCACTGAGGCCGGGCGACCAAAGGTC

GCCCGACCCCCGGGCTTTGCCCGGGCGGCCTCAGTGAGCGAGCGAGCGCGCAGAGA

GGGAGTGGCCAACTCCATCACTAGGGGTTCCTATCGATTGAATTCCAGGCGCGCCAT

CCTGCAGGTATTGACGTCAATAATGACGTATGTTCCCATAGTAACGCCAATAGGGAC

TTTCCATTGACGTCAATGGGTGGAGTATTTACGGTAAACTGCCCACTTGGCAGTACA
```

-continued

```
TCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACT

CTCCCCATCTCCCCCCCCTCCCCACCCCCAATTTTGTATTTATTTATTTTTTAATTATT

TTGTGCAGCGATGGGGGGGGGGGGGGGGGGGGGGGGGCGCGCCAGGCGGGGGGGGG

CGGGGCGAGGGGCGGGGGGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTAT

AAAAAGCGAAGCGCGCGGGGGGCGGGAGTCGCTGCGCGCTGCCTTCGCCCCGTGCC

CCGCTCCGCCGCCGCCTCGCGCCGCCCGCCCCGGCTCTGACTGACCGCGTTACTCCC

ACAGGTGAGCGGGCGGGACGGCCCTTCTCCTCCGGGCTGTAATTAGCGCTTGGTTTA

ATGACGGCTTGTTTCTTTTCTGTGGCTGCGTGAAAGCCTTGAGGGGCTCCGGGAGGG

CCCTTTGTGCGGGGGGAGCGGCTCGGGGCTGTCCGCGGGGGGACGGCTGCCTTCGG

GGGGGACGGGGCAGGGGGGGGTTCGGCTTCTGGCGTGTGACCGGCGGCTCTAGAGC

CTCTGCTAACCATGTTCATGCCTTCTTCTTTTTCCTACAGCTCCTGGGCAACGTGCTG

GTTATTGTGCTGTCTCATCATTTTGGCAAAGAATTGTACAGGATATCTTGCTAGCACG

CCACCATGGTTTCTTACTGGGACACCGGCGTGCTGCTGTGTGCCCTGCTTTCTTGTCT

GCTGCTGACCGGCTCTAGCAGCGGCTCTGATACCGGCAGACCCTTCGTGGAAATGTA

CAGCGAGATCCCCGAGATCATCCACATGACCGAGGGCAGAGAGCTGGTCATCCCTT

GCAGAGTGACAAGCCCCAACATCACCGTGACTCTGAAGAAGTTCCCTCTGGACACA

CTGATCCCCGACGGCAAGAGAATCATCTGGGACAGCCGGAAGGGCTTCATCATCAG

CAACGCCACCTACAAAGAGATCGGCCTGCTGACCTGTGAAGCCACCGTGAATGGCC

ACCTGTACAAGACCAACTACCTGACACACAGACAGACCAACACCATCATCGACGTG

GTGCTGAGCCCTAGCCACGGCATTGAACTGTCTGTGGGCGAGAAGCTGGTGCTGAA

CTGTACCGCCAGAACCGAGCTGAACGTGGGCATCGACTTCAACTGGGAGTACCCCA

GCAGCAAGCACCAGCACAAGAAACTGGTCAACCGGGACCTGAAAACCCAGAGCGG

CAGCGAGATGAAGAAATTCCTGAGCACCCTGACCATCGACGGCGTGACCAGAAGTG

ACCAGGGCCTGTACACATGTGCCGCCAGCTCTGGCCTGATGACCAAGAAAAACAGC

ACCTTCGTGCGGGTGCACGAGAAGGACAAGACCCACACCTGTCCTCCATGTCCTGCT

CCAGAACTGCTCGGCGGACCTTCCGTGTTCCTGTTTCCTCCAAAGCCTAAGGACACC

CTGATGATCAGCAGAACCCCTGAAGTGACCTGCGTGGTGGTGGATGTGTCCCACGA

GGATCCCGAAGTGAAGTTCAATTGGTACGTGGACGGCGTGGAAGTGCACAACGCCA

AGACCAAGCCTAGAGAGGAACAGTACAATAGCACCTACAGAGTGGTGTCCGTGCTG

ACCGTGCTGCACCAGGATTGGCTGAACGGCAAAGAGTACAAGTGCAAGGTGTCCAA

CAAGGCCCTGCCTGCTCCTATCGAGAAAACCATCTCCAAGGCCAAGGGCCAGCCTA

GGGAACCCCAGGTTTACACACTGCCTCCAAGCAGGGACGAGCTGACAAAGAACCAG

GTGTCCCTGACCTGCCTGGTCAAGGGCTTCTACCCTTCCGATATCGCCGTGGAATGG

GAGAGCAATGGCCAGCCTGAGAACAACTACAAGACAACCCCTCCTGTGCTGGACAG

CGACGGCTCATTCTTCCTGTACAGCAAGCTGACAGTGGACAAGAGCAGATGGCAGC

AGGGCAACGTGTTCAGCTGCTCCGTGATGCACGAGGCCCTGCACAACCACTACACC

CAGAAGTCCCTGAGCCTGTCTCCTGGCAAACGGAAGAGAAGAGGCAGCGGCGAAG

GCAGAGGATCCCTGCTTACATGTGGCGACGTGGAAGAGAACCCCGGACCTATGCAA
```

-continued

```
GCTCTGGTGCTGCTGCTGTGTATCGGAGCCCTGCTGGGCCACAGCTCCTGTCAAAAT

CCTGCCTCTCCACCTGAGGAAGGCAGCCCCGATCCAGATTCTACAGGCGCCCTGGTG

GAAGAAGAGGACCCATTCTTCAAGGTGCCCGTGAACAAACTGGCCGCTGCCGTGTC

CAACTTCGGCTACGACCTGTACAGAGTGCGGAGCAGCACAAGCCCCACCACCAATG

TTCTGCTGAGCCCTCTGTCTGTGGCCACCGCTCTTTCTGCTCTGTCTCTGGGAGCCGA

GCAGAGAACCGAGAGCATCATTCACAGAGCCCTGTACTACGATCTGATCAGCAGCC

CTGACATCCACGGCACCTACAAAGAACTGCTGGACACCGTGACAGCCCCTCAGAAG

AATCTGAAGTCCGCCAGCCGGATCGTGTTCGAGAAGAAGCTGCGGATCAAGAGCAG

CTTCGTGGCCCCTCTGGAAAAGAGCTACGGCACCAGACCTAGAGTGCTGACCGGCA

ATCCCAGACTGGACCTGCAAGAGATCAACAACTGGGTGCAAGCCCAGATGAAGGGC

AAGCTGGCCAGAAGCACCAAAGAGATCCCCGACGAGATCAGCATCCTGCTGCTGGG

CGTCGCCCACTTTAAAGGCCAGTGGGTCACCAAGTTCGACTCCAGAAAGACCAGCC

TCGAGGACTTCTACCTGGACGAGGAACGGACCGTCAGAGTGCCCATGATGAGCGAT

CCTAAGGCCGTGCTGAGATACGGCCTGGATAGCGACCTGAGCTGCAAGATTGCTCA

GCTGCCTCTGACCGGCTCTATGAGCATCATATTCTTTCTGCCCCTGAAAGTGACCCA

GAATCTGACCCTGATCGAGGAAAGCCTGACCAGCGAGTTCATCCACGACATCGACC

GCGAGCTGAAAACCGTGCAGGCTGTGCTGACTGTGCCCAAGCTGAAGCTGAGCTAC

GAGGGCGAAGTGACCAAGAGCCTGCAAGAAATGAAGCTGCAGAGCCTGTTCGACAG

CCCCGACTTCAGCAAGATCACCGGCAAGCCCATCAAGCTGACCCAGGTGGAACACA

GAGCCGGCTTCGAGTGGAATGAAGATGGCGCCGGAACCACACCTTCTCCAGGACTG

CAACCTGCTCACCTGACCTTTCCACTGGACTACCACCTGAACCAGCCTTTCATCTTCG

TGCTGCGGGACACAGATACTGGCGCCCTGCTGTTCATCGGCAAGATCCTGGATCCTA

GAGGCCCCTGAGCCACGCGTAACACGTGCATGCGAGAGATCTGCGGCCGCGAGCTC

GGGGATCCAGACATGATAAGATACATTGATGAGTTTGGACAAACCACAACTAGAAT

GCAGTGAAAAAAATGCTTTATTTGTGAAATTTGTGATGCTATTGCTTTATTTGTAACC

ATTATAAGCTGCAATAAACAAGTTAACAACAACAATTGCATTCATTTTATGTTTCAG

GTTCAGGGGGAGGTGTGGGAGGTTTTTTAAAGCAAGTAAAACCTCTACAAATGTGG

TATGGCTGATTATGATCAATGCATCCTAGCCGGAGGAACCCCTAGTGATGGAGTTGG

CCACTCCCTCTCTGCGCGCTCGCTCGCTCACTGAGGCCGCCCGGGCAAAGCCCGGGC

GTCGGGCGACCTTTGGTCGCCCGGCCTCAGTGAGCGAGCGAGCGCGCAGAGAGGGA
```

```
GTGGCCAA,
``` and its use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection.

In other aspects, the nucleic acid comprises a nucleotide sequence encoding aflibercept and a nucleotide sequence encoding a soluble fusion protein comprising one or more VEGF-binding portions from the extracellular domain of VEGFR-3. In particularly preferred embodiments, provided herein is an rAAV vector comprising a capsid protein of SEQ ID NO:48 and a nucleic acid comprising the following sequence (aflibercept+ OPT-302 dual construct) or a sequence at least 80%, at least 85%, at least 90%, at least 95%; at least 98% or at least 99% identical thereto:

(SEQ ID NO: 65)
```
TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTATCGATTGAATTCCAGGCGCGCCAT

CCTGCAGGTATTGACGTCAATAATGACGTATGTTCCCATAGTAACGCCAATAGGGAC

TTTCCATTGACGTCAATGGGTGGAGTATTTACGGTAAACTGCCCACTTGGCAGTACA

TCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACAT

CTACGTATTAGTCATCGCTATTACCATGGTCGAGGTGAGCCCCACCTTCTGCTTCACT

CTCCCCATCTCCCCCCCCTCCCCACCCCCAATTTTGTATTTATTTATTTTTTAATTATT

TTGTGCAGCGATGGGGGGGGGGGGGGGGGGGGGGCGCGCCAGGCGGGGGGGG

CGGGGCGAGGGGCGGGGGGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTAT

AAAAAGCGAAGCGCGCGGCGGGGGGGAGTCGCTGCGCGCTGCCTTCGCCCCGTGCC

CCGCTCCGCCGCCGCCTCGCGCCGCCCCCCCCCGGCTCTGACTGACCGCGTTACTCCC

ACAGGTGAGCGGGCGGGACGGCCCTTCTCCTCCGGGCTGTAATTAGCGCTTGGTTTA

ATGACGGCTTGTTTCTTTTCTGTGGCTGCGTGAAAGCCTTGAGGGGCTCCGGGAGGG

CCCTTTGTGCGGGGGGAGCGGCTCGGGGCTGTCCGCGGGGGGACGGCTGCCTTCGG

GGGGGACGGGGCAGGGGGGGGGTTCGGCTTCTGGCGTGTGACCGGCGGCTCTAGAGC

CTCTGCTAACCATGTTCATGCCTTCTTCTTTTTCCTACAGCTCCTGGGCAACGTGCTG

GTTATTGTGCTGTCTCATCATTTTGGCAAAGAATTGTACAGGATATCTTGCTAGCACG

CCACCATGGTTTCTTACTGGGACACCGGCGTGCTGCTGTGTGCCCTGCTTTCTTGTCT

GCTGCTGACCGGCTCTAGCAGCGGCTCTGATACCGGCAGACCCTTCGTGGAAATGTA

CAGCGAGATCCCCGAGATCATCCACATGACCGAGGGCAGAGAGCTGGTCATCCCTT

GCAGAGTGACAAGCCCCAACATCACCGTGACTCTGAAGAAGTTCCCTCTGGACACA

CTGATCCCCGACGGCAAGAGAATCATCTGGGACAGCCGGAAGGGCTTCATCATCAG

CAACGCCACCTACAAAGAGATCGGCCTGCTGACCTGTGAAGCCACCGTGAATGGCC

ACCTGTACAAGACCAACTACCTGACACACAGACAGACCAACACCATCATCGACGTG

GTGCTGAGCCCTAGCCACGGCATTGAACTGTCTGTGGGCGAGAAGCTGGTGCTGAA

CTGTACCGCCAGAACCGAGCTGAACGTGGGCATCGACTTCAACTGGGAGTACCCCA

GCAGCAAGCACCAGCACAAGAAACTGGTCAACCGGGACCTGAAAACCCAGAGCGG

CAGCGAGATGAAGAAATTCCTGAGCACCCTGACCATCGACGGCGTGACCAGAAGTG

ACCAGGGCCTGTACACATGTGCCGCCAGCTCTGGCCTGATGACCAAGAAAAACAGC

ACCTTCGTGCGGGTGCACGAGAAGGACAAGACCCACACCTGTCCTCCATGTCCTGCT

CCAGAACTGCTCGGCGGACCTTCCGTGTTCCTGTTTCCTCCAAAGCCTAAGGACACC

CTGATGATCAGCAGAACCCCTGAAGTGACCTGCGTGGTGGTGGATGTGTCCCACGA

GGATCCCGAAGTGAAGTTCAATTGGTACGTGGACGGCGTGGAAGTGCACAACGCCA

AGACCAAGCCTAGAGAGGAACAGTACAATAGCACCTACAGAGTGGTGTCCGTGCTG

ACCGTGCTGCACCAGGATTGGCTGAACGGCAAAGAGTACAAGTGCAAGGTGTCCAA

CAAGGCCCTGCCTGCTCCTATCGAGAAAACCATCTCCAAGGCCAAGGGCCAGCCTA

GGGAACCCCAGGTTTACACACTGCCTCCAAGCAGGGACGAGCTGACAAAGAACCAG
```

```
GTGTCCCTGACCTGCCTGGTCAAGGGCTTCTACCCTTCCGATATCGCCGTGGAATGG

GAGAGCAATGGCCAGCCTGAGAACAACTACAAGACAACCCCTCCTGTGCTGGACAG

CGACGGCTCATTCTTCCTGTACAGCAAGCTGACAGTGGACAAGAGCAGATGGCAGC

AGGGCAACGTGTTCAGCTGCTCCGTGATGCACGAGGCCCTGCACAACCACTACACC

CAGAAGTCCCTGAGCCTGTCTCCTGGCAAACGGAAGAGAAGAGGCAGCGGCGAAG

GCAGAGGATCCCTGCTTACATGTGGCGACGTGGAAGAGAACCCCGGACCTATGCAA

AGAGGCGCCGCTCTCTGTCTGAGACTGTGGCTGTGTCTGGGCCTGCTGGATGGACTG

GTGTCTGGCTACAGCATGACCCCTCCAACACTGAACATCACCGAGGAATCCCACGTG

ATCGACACCGGCGATAGCCTGAGCATCAGCTGCAGAGGACAGCACCCTCTGGAATG

GGCTTGGCCTGGTGCTCAAGAAGCTCCTGCCACAGGCGACAAGGACAGCGAGGATA

CAGGCGTTGTGCGGGATTGCGAGGGCACAGATGCCAGACCTTACTGCAAGGTGCTG

CTGCTGCACGAAGTGCACGCCCAGGATACCGGCAGCTACGTGTGCTACTACAAGTA

CATCAAGGCCCGGATCGAGGGCACCACAGCCGCTAGCTCTTATGTGTTCGTGCGGG

ACTTCGAGCAGCCCTTCATCAACAAGCCCGACACACTGCTGGTCAACCGGAAGGAC

GCTATGTGGGTGCCCTGTCTGGTGTCTATCCCCGGCCTGAATGTGACCCTGAGAAGC

CAGAGTTCCGTGCTGTGGCCTGATGGCCAAGAGGTCGTGTGGGACGATAGAAGGGG

CATGCTGGTGTCCACACCTCTGCTGCATGATGCCCTGTACCTGCAGTGCGAGACAAC

CTGGGGCGACCAGGACTTCCTGAGCAACCCTTTCCTGGTGCACATCACCGGCAACGA

GCTGTACGACATCCAGCTGCTGCCTCGCAAGAGCCTGGAACTGCTCGTGGGAGAGA

ACCTGGTGCTGAACTGTACCGTGTGGGCCGAGTTCAATAGCGGCGTGACCTTCGACT

GGGACTACCCTGGAAAGCAGGCCGAGCGTGGAAAATGGGTGCCCGAGAGAAGAAG

CCAGCAGACCCACACAGAGCTGAGCAGCATCCTGACCATCCACAACGTGTCCCAGC

ACGATCTGGGCTCTTACGTGTGCAAGGCCAACAACGGCATCCAGCGGTTCCGGGAA

AGCACCGAAGTGATCGTGCATGAGGAACCCAAGAGCTGCGACAAGACACACACCTG

TCCTCCATGTCCTGCTCCAGAGCTTCTCGGCGGACCTTCCGTGTTCCTGTTTCCTCCA

AAGCCTAAGGACACCCTGATGATCAGCAGAACCCCTGAAGTGACCTGCGTGGTGGT

GGATGTGTCCCACGAGGATCCCGAAGTGAAGTTCAATTGGTACGTGGACGGCGTGG

AAGTGCACAATGCCAAGACCAAGCCTAGAGAGGAACAGTACAACAGCACCTACAG

AGTGGTGTCCGTGCTGACCGTGCTGCATCAGGATTGGCTGAACGGCAAAGAGTACA

AGTGCAAGGTGTCCAACAAGGCCCTGCCTGCTCCTATCGAGAAAACCATCTCCAAG

GCCAAGGGCCAGCCTCGGGAACCTCAAGTGTATACCCTGCCTCCTAGCCGCGACGA

ACTCACCAAGAATCAAGTGTCTCTGACATGTCTCGTGAAGGGGTTTTACCCCAGCGA

CATTGCCGTCGAGTGGGAGTCCAATGGACAACCCGAGAACAATTATAAGACCACGC

CACCAGTCCTGGACTCCGACGGCTCATTTTTTCTCTACTCCAAACTGACCGTGGATA

AGTCCCGGTGGCAGCAAGGGAATGTGTTTTCCTGTAGCGTGATGCATGAAGCTCTCC

ACAATCATTACACCCAAAAATCTCTGTCTCTGAGCCCCGGCAAATGAGCCACGCGTA

ACACGTGCATGCGAGAGATCTGCGGCCGCGAGCTCGGGGATCCAGACATGATAAGA

TACATTGATGAGTTTGGACAAACCACAACTAGAATGCAGTGAAAAAAATGCTTTATT

TGTGAAATTTGTGATGCTATTGCTTTATTTGTAACCATTATAAGCTGCAATAAACAA

GTTAACAACAACAATTGCATTCATTTTATGTTTCAGGTTCAGGGGGAGGTGTGGGAG

GTTTTTTAAAGCAAGTAAAACCTCTACAAATGTGGTATGGCTGATTATGATCAATGC
```

-continued

```
ATCCTAGCCGGAGGAACCCCTAGTGATGGAGTTGGCCACTCCCTCTCTGCGCGCTCG

CTCGCTCACTGAGGCCGCCCGGGCAAAGCCCGGGCGTCGGGCGACCTTTGGTCGCC

CGGCCTCAGTGAGCGAGCGAGCGCGCAGAGAGGGAGTGGCCAA
``` and its use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection.

In other aspects, the nucleic acid comprises a nucleotide sequence encoding aflibercept and a nucleotide sequence encoding an antibody or antigen-binding fragment thereof that binds to and inhibits the activity of a pro-angiogenic protein. In preferred embodiments, the antibody or antigen-binding fragment thereof binds to human ang-1 or human ang-2. In particularly preferred embodiments, provided herein is an rAAV vector comprising a capsid protein of SEQ ID NO:48 and a nucleic acid comprising the following sequence (aflibercept+anti-Ang-2 HL construct) or a sequence at least 80%, at least 85%, at least 90%, at least 95%; at least 98% or at least 99% identical thereto:

(SEQ ID NO: 66)

```
TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTATCGATTGAATTGCAGGCGCGCCAT

CCTGCAGGTATTGACGTCAATAATGACGTATGTTCCCATAGTAACGCCAATAGGGAC

TTTCCATTGACGTCAATGGGTGGAGTATTTACGGTAAACTGCCCACTTGGCAGTACA

TCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACT

CTCCCCATCTCCCCCCCCTCCCCACCCCCAATTTTGTATTTATTTATTTTTTAATTATT

TTGTGCAGCGATGGGGGGGGGGGGGGGGGGGGGGGGGCGCGCCAGGCGGGGGGGG

CGGGGCGAGGGGGGGGGGGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTAT

AAAAAGCGAAGCGCGCGGGGGGCGGGAGTCGCTGCGCGCTGCCTTCGCCCCGTGCC

CCGCTCCGCCGCCGCCTCGCGCCGCCCGCCCCGGCTCTGACTGACCGCGTTACTCCC

ACAGGTGAGCGGGCGGGACGGCCCTTCTCCTCCGGGCTGTAATTAGCGCTTGGTTTA

ATGACGGCTTGTTTCTTTTCTGTGGCTGCGTGAAAGCCTTGAGGGGCTCCGGGAGGG

CCCTTTGTGCGGGGGGAGCGGCTCGGGGCTGTCCGCGGGGGGACGGCTGCCTTCGG

GGGGGACGGGGCAGGGGGGGGTTCGGCTTCTGGCGTGTGACCGGCGGCTCTAGAGC

CTCTGCTAACCATGTTCATGCCTTCTTCTTTTTCCTACAGCTCCTGGGCAACGTGCTG

GTTATTGTGCTGTCTCATCATTTTGGCAAAGAATTGTACAGGATATCTTGCTAGCACG

CCACCATGGTTTCTTACTGGGACACCGGCGTGCTGCTGTGTGCCCTGCTTTCTTGTCT

GCTGCTGACCGGCTCTAGCAGCGGCTCTGATACCGGCAGACCCTTCGTGGAAATGTA

CAGCGAGATCCCCGAGATCATCCACATGACCGAGGGCAGAGAGCTGGTCATCCCTT

GCAGAGTGACAAGCCCCAACATCACCGTGACTCTGAAGAAGTTCCCTCTGGACACA

CTGATCCCCGACGGCAAGAGAATCATCTGGGACAGCCGGAAGGGCTTCATCATCAG

CAACGCCACCTACAAAGAGATCGGCCTGCTGACCTGTGAAGCCACCGTGAATGGCC

ACCTGTACAAGACCAACTACCTGACACACAGACAGACCAACACCATCATCGACGTG

GTGCTGAGCCCTAGCCACGGCATTGAACTGTCTGTGGGCGAGAAGCTGGTGCTGAA
```

-continued

```
CTGTACCGCCAGAACCGAGCTGAACGTGGGCATCGACTTCAACTGGGAGTACCCCA

GCAGCAAGCACCAGCACAAGAAACTGGTCAACCGGGACCTGAAAACCCAGAGCGG

CAGCGAGATGAAGAAATTCCTGAGCACCCTGACCATCGACGGCGTGACCAGAAGTG

ACCAGGGCCTGTACACATGTGCCGCCAGCTCTGGCCTGATGACCAAGAAAAACAGC

ACCTTCGTGCGGGTGCACGAGAAGGACAAGACCCACACCTGTCCTCCATGTCCTGCT

CCAGAACTGCTCGGCGGACCTTCCGTGTTCCTGTTTCCTCCAAAGCCTAAGGACACC

CTGATGATCAGCAGAACCCCTGAAGTGACCTGCGTGGTGGTGGATGTGTCCCACGA

GGATCCCGAAGTGAAGTTCAATTGGTACGTGGACGGCGTGGAAGTGCACAACGCCA

AGACCAAGCCTAGAGAGGAACAGTACAATAGCACCTACAGAGTGGTGTCCGTGCTG

ACCGTGCTGCACCAGGATTGGCTGAACGGCAAAGAGTACAAGTGCAAGGTGTCCAA

CAAGGCCCTGCCTGCTCCTATCGAGAAAACCATCTCCAAGGCCAAGGGCCAGCCTA

GGGAACCCCAGGTTTACACACTGCCTCCAAGCAGGGACGAGCTGACAAAGAACCAG

GTGTCCCTGACCTGCCTGGTCAAGGGCTTCTACCCTTCCGATATCGCCGTGGAATGG

GAGAGCAATGGCCAGCCTGAGAACAACTACAAGACAACCCCTCCTGTGCTGGACAG

CGACGGCTCATTCTTCCTGTACAGCAAGCTGACAGTGGACAAGAGCAGATGGCAGC

AGGGCAACGTGTTCAGCTGCTCCGTGATGCACGAGGCCCTGCACAACCACTACACC

CAGAAGTCCCTGAGCCTGTCTCCTGGCAAACGGAAGAGAAGAGGCAGCGGCGAAG

GCAGAGGATCCCTGCTTACATGTGGCGACGTGGAAGAGAACCCCGGACCTATGGAT

TGGACCTGGTCCATCCTGTTTCTGGTGGCCGCTGCCACAGGCACATACTCTCAGGTT

CAGCTGGTGCAGTCTGGCGCCGAAGTGAAAAAACCTGGCGCCTCCGTGAAGGTGTC

CTGCAAGGCTAGCGGCTACACCTTTACCGGCTACTACATGCACTGGGTCCGACAGGC

TCCAGGACAGGGACTTGAATGGATGGGCTGGATCAACCCCAATAGCGGCGGCACCA

ATTACGCCCAGAAATTCCAGGGCAGAGTGACCATGACCAGAGACACCAGCATCAGC

ACCGCCTACATGGAACTGAGCCGGCTGAGATCCGATGACACCGCCGTGTACTACTG

CGCCAGATCTCCCAATCCTTACTACTACGACAGCAGCGGGTACTACTACCCAGGCGC

CTTTGATATCTGGGGCCAGGGCACAATGGTCACCGTGTCATCTGCATCTGTGGCCGC

TCCTAGCGTGTTCATCTTCCCACCTTCCGACGAACAGCTGAAGTCTGGCACAGCCAG

CGTCGTGTGCCTGCTGAACAACTTCTACCCCAGAGAAGCCAAGGTGCAGTGGAAGG

TGGACAACGCTCTGCAGTCCGGCAACAGCCAAGAGAGCGTGACAGAGCAGGACAG

CAAGGACTCCACCTACAGCCTGAGCAGCACCCTGACACTGAGCAAGGCCGACTACG

AGAAGCACAAAGTGTACGCCTGCGAAGTGACCCACCAGGGCCTTTCTAGCCCTGTG

ACCAAGAGCTTCAACCGGGGCGAGTGCGATAAGACACACACAGGCGGAAGCAGCG

GCAGCGGATCTGGATCTACCGGCACATCTAGCTCTGGCACCGGAACATCTGCCGGC

ACAACTGGCACAAGCGCCTCTACATCTGGAAGCGGTTCTGGCGGAGGCGGAGGATC

TGGTGGTGGTGGATCTGCTGGCGGAACAGCTACAGCTGGCGCTTCTAGCGGCAGCA

GCTATGTGCTGACACAGCCTCCATCCGTGTCTGTGGCACCTGGACAGACCGCCAGAA

TTACCTGTGGCGGCAACAACATCGGCAGCAAGAGCGTGCACTGGTATCAGCAGAAG

CCTGGACAGGCACCAGTGCTGGTGGTGTACGACGACAGCGATAGACCTAGCGGCAT

CCCCGAGAGATTCAGCGGCTCTAACAGCGGCAATACCGCCACACTGACCATCAGCA

GAGTGGAAGCTGGCGACGAGGCCGATTACTACTGCCAAGTGTGGGACAGCAGCAGC

CACCACTGGGTTTTCGGCGGAGGCACCAAACTGACAGTGCTGTCTAGCGCCAGCAC
```

-continued

```
AAAGGGCCCATCTGTGTTCCCTCTGGCTCCCAGCAGCAAGTCTACAAGCGGAGGAA

CAGCCGCTCTGGGCTGCCTCGTGAAGGATTACTTTCCCGAGCCTGTGACCGTGTCCT

GGAATAGCGGAGCACTGACAAGCGGCGTGCACACCTTTCCAGCTGTGCTGCAAAGC

TCCGGCCTGTACTCTCTGAGCAGCGTGGTCACAGTGCCTAGCTCTAGCCTGGGCACC

CAGACCTACATCTGCAATGTGAACCACAAGCCTAGCAACACCAAGGTCGACAAGAA

GGTGGAACCCAAGAGCTGCTGAGCCACGCGTAACACGTGCATGCGAGAGATCTGCG

GCCGCGAGCTCGGGGATCCAGACATGATAAGATACATTGATGAGTTTGGACAAACC

ACAACTAGAATGCAGTGAAAAAAATGCTTTATTTGTGAAATTTGTGATGCTATTGCT

TTATTTGTAACCATTATAAGCTGCAATAAACAAGTTAACAACAACAATTGCATTCAT

TTTATGTTTCAGGTTCAGGGGGAGGTGTGGGAGGTTTTTTAAAGCAAGTAAAACCTC

TACAAATGTGGTATGGCTGATTATGATCAATGCATCCTAGCCGGAGGAACCCCTAGT

GATGGAGTTGGCCACTCCCTCTCTGCGCGCTCGCTCGCTCACTGAGGCCGCCCGGGC

AAAGCCCGGGCGTCGGGCGACCTTTGGTCGCCCGGCCTCAGTGAGCGAGCGAGCGC

GCAGAGAGGGAGTGGCCAA
```

<sup>25</sup>and an rAAV vector comprising a capsid protein of SEQ ID NO:48 and a nucleic acid comprising the following sequence (aflibercept+anti-Ang-2 LH construct) or a sequence at least 80%, at least 85%, at least 90%, at least 95%; at least 98% or at least 99% identical thereto:

```
                                        (SEQ ID NO: 67)
TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTATCGATTGAATTCCAGGCGCGCCAT

CCTGCAGGTATTGACGTCAATAATGACGTATGTTCCCATAGTAACGCCAATAGGGAC

TTTCCATTGACGTCAATGGGTGGAGTATTTACGGTAAACTGCCCACTTGGCAGTACA

TCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACAT

CTACGTATTAGTCATCGCTATTACCATGGTCGAGGTGAGCCCCACGTTCTGCTTCACT

CTCCCCATCTCCCCCCCCTCCCCACCCCCAATTTTGTATTTATTTATTTTTTAATTATT

TTGTGCAGCGATGGGGGGGGGGGGGGGGGGGGGGGCGCGCCAGGCGGGGGGGGG

CGGGGCGAGGGCGGGGGGGGGCGAGGCGGAGAGGTGCGGCGGCAGCCAATCAGA

GCGGCGCGCTCCGAAAGTTTCCTTTTATGGCGAGGCGGCGGCGGCGGCGGCCCTAT

AAAAAGCGAAGCGCGCGGCGGGCGGGAGTCGCTGCGCGCTGCCTTCGCCCCGTGCC

CCGCTCCGCCGCCGCCTCGCGCCGCCCGCCCCGGCTCTGACTGACCGCGTTACTCCC

ACAGGTGAGCGGGCGGGACGGCCCTTCTCCTCCGGGCTGTAATTAGCGCTTGGTTTA

ATGACGGCTTGTTTCTTTTCTGTGGCTGCGTGAAAGCCTTGAGGGGCTCCGGGAGGG

CCCTTTGTGGGGGGGGAGCGGCTCGGGGCTGTCCGCGGGGGGACGGCTGCCTTCGG

GGGGGACGGGGCAGGGGGGGGGTTCGGCTTCTGGCGTGTGACCGGCGGCTCTAGAGC

CTCTGCTAACCATGTTCATGCCTTCTTCTTTTTCCTACAGCTCCTGGGCAACGTGCTG

GTTATTGTGCTGTCTCATCATTTTGGCAAAGAATTGTACAGGATATCTTGCTAGCACG

CCACCATGGTTTCTTACTGGGACACCGGCGTGCTGCTGTGTGCCCTGCTTTCTTGTCT
```

-continued

```
GCTGCTGACCGGCTCTAGCAGCGGCTCTGATACCGGCAGACCCTTCGTGGAAATGTA

CAGCGAGATCCCCGAGATCATCCACATGACCGAGGGCAGAGAGCTGGTCATCCCTT

GCAGAGTGACAAGCCCCAACATCACCGTGACTCTGAAGAAGTTCCCTCTGGACACA

CTGATCCCCGACGGCAAGAGAATCATCTGGGACAGCCGGAAGGGCTTCATCATCAG

CAACGCCACCTACAAAGAGATCGGCCTGCTGACCTGTGAAGCCACCGTGAATGGCC

ACCTGTACAAGACCAACTACCTGACACACAGACAGACCAACACCATCATCGACGTG

GTGCTGAGCCCTAGCCACGGCATTGAACTGTCTGTGGGCGAGAAGCTGGTGCTGAA

CTGTACCGCCAGAACCGAGCTGAACGTGGGCATCGACTTCAACTGGGAGTACCCCA

GCAGCAAGCACCAGCACAAGAAACTGGTCAACCGGGACCTGAAAACCCAGAGCGG

CAGCGAGATGAAGAAATTCCTGAGCACCCTGACCATCGACGGCGTGACCAGAAGTG

ACCAGGGCCTGTACACATGTGCCGCCAGCTCTGGCCTGATGACCAAGAAAAACAGC

ACCTTCGTGCGGGTGCACGAGAAGGACAAGACCCACACCTGTCCTCCATGTCCTGCT

CCAGAACTGCTCGGCGGACCTTCCGTGTTCCTGTTTCCTCCAAAGCCTAAGGACACC

CTGATGATCAGCAGAACCCCTGAAGTGACCTGCGTGGTGGTGGATGTGTCCCACGA

GGATCCCGAAGTGAAGTTCAATTGGTACGTGGACGGCGTGGAAGTGCACAACGCCA

AGACCAAGCCTAGAGAGGAACAGTACAATAGCACCTACAGAGTGGTGTCCGTGCTG

ACCGTGCTGCACCAGGATTGGCTGAACGGCAAAGAGTACAAGTGCAAGGTGTCCAA

CAAGGCCCTGCCTGCTCCTATCGAGAAAACCATCTCCAAGGCCAAGGGCCAGCCTA

GGGAACCCCAGGTTTACACACTGCCTCCAAGCAGGGACGAGCTGACAAAGAACCAG

GTGTCCCTGACCTGCCTGGTCAAGGGCTTCTACCCTTCCGATATCGCCGTGGAATGG

GAGAGCAATGGCCAGCCTGAGAACAACTACAAGACAACCCCTCCTGTGCTGGACAG

CGACGGCTCATTCTTCCTGTACAGCAAGCTGACAGTGGACAAGAGCAGATGGCAGC

AGGGCAACGTGTTCAGCTGCTCCGTGATGCACGAGGCCCTGCACAACCACTACACC

CAGAAGTCCCTGAGCCTGTCTCCTGGCAAACGGAAGAGAAGAGGCAGCGGCGAAG

GCAGAGGATCCCTGCTTACATGTGGCGACGTGGAAGAGAACCCCGGACCTATGGTT

CTGCAGACCCAGGTGTTCATCAGCCTGCTGCTGTGGATCTCTGGCGCCTACGGCAGC

TATGTGCTGACACAGCCTCCATCCGTGTCTGTGGCTCCAGGACAGACCGCCAGAATT

ACCTGCGGCGGCAACAACATCGGCAGCAAGAGCGTGCACTGGTATCAGCAGAAGCC

TGGACAGGCTCCAGTGCTGGTGGTGTACGACGACAGCGATAGACCTAGCGGCATCC

CCGAGAGATTCAGCGGCAGCAATTCCGGCAATACCGCCACACTGACCATCAGCAGA

GTGGAAGCTGGCGACGAGGCCGACTACTACTGCCAAGTGTGGGATAGCAGCAGCGA

CCACTGGGTTTTCGGCGGAGGCACCAAACTGACAGTGCTGAGCAGCGCCTCTACAA

AGGGCCCTAGTGTGTTCCCTCTGGCTCCCAGCAGCAAGTCTACATCTGGCGGAACAG

CCGCTCTGGGCTGCCTCGTGAAGGATTACTTTCCCGAGCCTGTGACCGTGTCCTGGA

ATAGCGGAGCACTGACAAGCGGCGTGCACACCTTTCCAGCTGTGCTGCAAAGCAGC

GGCCTGTACTCTCTGTCCAGCGTGGTCACAGTGCCAAGCTCTAGCCTGGGCACCCAG

ACCTACATCTGCAATGTGAACCACAAGCCTAGCAACACCAAGGTCGACAAGAAGGT

GGAACCCAAGAGCTGTGGCGGCAGCTCTGGTTCTGGATCTGGCAGCACAGGCACAT

CTAGCTCTGGCACCGGAACAAGCGCTGGCACAACTGGCACATCTGCCAGCACAAGC

GGATCTGGAAGTGGCGGAGGCGGAGGATCTGGTGGCGGTGGATCTGCAGGCGGAAC

TGCTACAGCTGGCGCTTCTAGTGGAAGCCAGGTGCAGCTGGTTCAGTCTGGCGCCGA
```

-continued

```
AGTGAAAAAGCCTGGCGCCTCTGTGAAGGTGTCCTGCAAGGCCAGCGGCTACACCT

TTACCGGCTACTACATGCACTGGGTCCGACAGGCACCAGGACAGGGACTTGAATGG

ATGGGCTGGATCAACCCCAATAGCGGCGGCACCAATTACGCCCAGAAATTCCAGGG

CAGAGTGACCATGACCAGAGACACCAGCATCAGCACCGCCTACATGGAACTGAGCC

GGCTGAGATCCGATGACACCGCCGTGTACTACTGCGCCAGATCTCCCAATCCTTACT

ACTACGACAGCAGCGGGTACTACTACCCAGGCGCCTTTGATATCTGGGGCCAGGGC

ACCATGGTCACCGTGTCATCTGCATCTGTGGCCGCTCCTAGCGTGTTCATCTTCCCAC

CTTCCGACGAACAGCTGAAGTCCGGCACAGCCTCTGTCGTGTGCCTGCTGAACAACT

TCTACCCCAGAGAAGCCAAAGTGCAGTGGAAGGTGGACAACGCCCTGCAGAGCGGC

AATAGCCAAGAGAGCGTGACCGAGCAGGACAGCAAGGACTCTACCTACAGCCTGAG

CAGCACCCTGACACTGAGCAAGGCCGATTACGAGAAGCACAAGGTGTACGCCTGCG

AAGTGACACACCAGGGCCTGTCTAGCCCTGTGACCAAGAGCTTCAATCGGGGCGAG

TGCGACAAGACCCACACCTAAGCCACGCGTAACACGTGCATGCGAGAGATCTGCGG

CCGCGAGCTCGGGGATCCAGACATGATAAGATACATTGATGAGTTTGGACAAACCA

CAACTAGAATGCAGTGAAAAAAATGCTTTATTTGTGAAATTTGTGATGCTATTGCTT

TATTTGTAACCATTATAAGCTGCAATAAACAAGTTAACAACAACAATTGCATTCATT

TTATGTTTCAGGTTCAGGGGGAGGTGTGGGAGGTTTTTTAAAGCAAGTAAAACCTCT

ACAAATGTGGTATGGCTGATTATGATCAATGCATCCTAGCCGGAGGAACCCCTAGTG

ATGGAGTTGGCCACTCCCTCTCTGCGCGCTCGCTCGCTCACTGAGGCCGCCCGGGCA

AAGCCCGGGCGTCGGGCGACCTTTGGTCGCCCGGCCTCAGTGAGCGAGCGAGCGCG

CAGAGAGGGAGTGGCCAA
``` and their use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection.

In some aspects, the nucleic acid comprises a nucleotide sequence encoding aflibercept and a nucleotide sequence encoding an interfering RNA that reduces expression of a pro-angiogenic protein. In preferred embodiments, the nucleotide sequence encoding an interfering RNA encodes a natural or artificial miRNA comprising a sense strand and antisense strand that reduces expression of a pro-angiogenic protein.

In related aspects, the interfering RNA reduces expression of human ang-1 and/or human ang-2. In particularly preferred embodiments, an rAAV vector is provided comprising a capsid protein of SEQ ID NO:48 and a nucleic acid comprising the following sequence (aflibercept+ human Ang-2 interfering RNA (SEQ ID NO:13) construct)) or a sequence at least 80%, at least 90%, at least 95%, at least 98% or at least 99% identical thereto:

(SEQ ID NO: 68)
```
TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGAGA

GGGAGTGGCCAACTCCATCACTAGGGGTTCCTATCGATTGAATTCCCCGGGGATCCA

CTAGTTATTAATAGTAATCAATTACGGGGTCATTAGTTCATAGCCCATATATGGAGT

TCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAG

TGTATCATATGCCAAGTACGCCCCCTATTGACGTCAATGACGGTAAATGGCCCGCCT

GGCATTATGCCCAGTACATGACCTTATGGGACTTTCCTACTTGGCAGTACATCTACG
```

-continued

```
TATTAGTCATCGCTATTACCATGGTCGAGGTGAGCCCCACGTTCTGCTTCACTCTCCC

CATCTCCCCCCCCTCCCCACCCCCAATTTTGTATTTATTTATTTTTTAATTATTTTGTG

CAGCGATGGGGGGGGGGGGGGGGGGGGGGGCGCGCCAGGCGGGGGGGGGGGGG

GCGAGGGGCGGGGCGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCAAGCGCGCGGCGGGCGGGGAGTCGCTGCGACGCTGCCTTCGCCCCGTGCCCC

GCTCCGCCGCCGCCTCGCGCCGCCCGCCCCGGCTCTGACTGACCGCGTTACTCCCAC

AGGTGAGCGGGCGGGACGGCCCTTCTCCTCCGGGCTGTAATTAGCGCTTGGTTTAAT

GACGGCTTGTTTCTTTTCTGTGGCTGCGTGAAAGCCTTGAGGGGCTCCGGGAGGGCC

CTTTGTGCGGGGGGAGCGGCTCGGGGGGTGCGTGCGTGTGTGTGCGTGGGGAGC

GCCGCGTGCGGCTCCGCGCTGCCCGGCGGCTGTGAGCGCTGCGGGCGCGGCGCGGG

GCTTTGTGCGCTCCGCAGTGTGCGCGAGGGGAGCGCGGCCGGGGGCGGTGCCCCGC

GGTGCGGGGGGGGCTGCGAGGGGAACAAAGGCTGCGTGCGGGGTGTGTGCGTGGG

GGGGTGAGCAGGGGGTGTGGGCGCGTCGGTCGGGCTGCAACCCCCCCTGCACCCCC

CTCCCCGAGTTGCTGAGCACGGCCCGGCTTCGGGTGCGGGGCTCCGTACGGGGCGT

GGCGCGGGGCTCGCCGTGCCGGGGGGGGGGGGCGGCAGGTGGGGGTGCCGGGCG

GGGGGGGGCCGCCTGGGGCCGGGGAGGGCTCGGGGGAGGGGGGGGGGGGCCCCG

GAGCGCCGGCGCGACTTCTTAACCCAACAGAAGGCTCGAGAAGGTATATTGCTGTT

GACAGTGAGCGGCTTACTCATTGTATGAACATTTAGTGAAGCCACAGATGTAAATGT

TCATACAATGAGTAAGCTGCCTACTGCCTCGGACTTCAAGGGGCTAGAATTCGCGGC

TGTCGAGGCGCGGCGAGCCGCAGCCATTGCCTTTTATGGTAATCGTGCGAGAGGGC

GCAGGGACTTCCTTTGTCCCAAATCTGTGCGGAGCCGAAATCTGGGAGGCGCCGCC

GCACCCCCTCTAGCGGGCGCGGGGCGAAGCGGTGCGGCGCCGGCAGGAAGGAAAT

GGGGGGGGAGGGCCTTCGTGCGTCGCCGCGCCGCCGTCCCCTTCTCCCTCTCCAGCC

TCGGGGCTGTCCGCGGGGGGACGGCTGCCTTCGGGGGGGGACGGGGCAGGGGGGGGT

TCGGCTTCTGGCGTGTGACCGGCGGCTCTAGAGCCTCTGCTAACCATGTTCATGCCTT

CTTCTTTTTCCTACAGTCTAGAGTCGACCTGCAGGTGGATATCTTGGCTAGCACGCCA

CCATGGTTTCTTACTGGGACACCGGCGTGCTGCTGTGTGCCCTGCTTTCTTGTCTGCT

GCTGACCGGCTCTAGCAGCGGCTCTGATACCGGCAGACCCTTCGTGGAAATGTACA

GCGAGATCCCCGAGATCATCCACATGACCGAGGGCAGAGAGCTGGTCATCCCTTGC

AGAGTGACAAGCCCCAACATCACCGTGACTCTGAAGAAGTTCCCTCTGGACACACT

GATCCCCGACGGCAAGAGAATCATCTGGGACAGCCGGAAGGGCTTCATCATCAGCA

ACGCCACCTACAAAGAGATCGGCCTGCTGACCTGTGAAGCCACCGTGAATGGCCAC

CTGTACAAGACCAACTACCTGACACACAGACAGACCAACACCATCATCGACGTGGT

GCTGAGCCCTAGCCACGGCATTGAACTGTCTGTGGGCGAGAAGCTGGTGCTGAACT

GTACCGCCAGAACCGAGCTGAACGTGGGCATCGACTTCAACTGGGAGTACCCCAGC

AGCAAGCACCAGCACAAGAAACTGGTCAACCGGGACCTGAAAACCCAGAGCGGCA

GCGAGATGAAGAAATTCCTGAGCACCCTGACCATCGACGGCGTGACCAGAAGTGAC

CAGGGCCTGTACACATGTGCCGCCAGCTCTGGCCTGATGACCAAGAAAAACAGCAC

CTTCGTGCGGGTGCACGAGAAGGACAAGACCCACACCTGTCCTCCATGTCCTGCTCC

AGAACTGCTCGGCGGACCTTCCGTGTTCCTGTTTCCTCCAAAGCCTAAGGACACCCT
```

-continued

```
GATGATCAGCAGAACCCCTGAAGTGACCTGCGTGGTGGTGGATGTGTCCCACGAGG

ATCCCGAAGTGAAGTTCAATTGGTACGTGGACGGCGTGGAAGTGCACAACGCCAAG

ACCAAGCCTAGAGAGGAACAGTACAATAGCACCTACAGAGTGGTGTCCGTGCTGAC

CGTGCTGCACCAGGATTGGCTGAACGGCAAAGAGTACAAGTGCAAGGTGTCCAACA

AGGCCCTGCCTGCTCCTATCGAGAAAACCATCTCCAAGGCCAAGGGCCAGCCTAGG

GAACCCCAGGTTTACACACTGCCTCCAAGCAGGGACGAGCTGACAAAGAACCAGGT

GTCCCTGACCTGCCTGGTCAAGGGCTTCTACCCTTCCGATATCGCCGTGGAATGGGA

GAGCAATGGCCAGCCTGAGAACAACTACAAGACAACCCCTCCTGTGCTGGACAGCG

ACGGCTCATTCTTCCTGTACAGCAAGCTGACAGTGGACAAGAGCAGATGGCAGCAG

GGCAACGTGTTCAGCTGCTCCGTGATGCACGAGGCCCTGCACAACCACTACACCCA

GAAGTCCCTGAGCCTGTCTCCTGGCAAATGAGCCACGCGTAACACGTGGGGGATCC

AGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAG

CTGCAATAAACAAGTTAACAACAACAATTGCATTCATTTTATGTTTCAGGTTCAGGG

GGAGGTGTGGGAGGTTTTTTAAAGCAAGTAAAACCTCTACAAATGTGGTATGGCTG

ATTATGATCAATGCATGGCCGGCCGGAGGAACCCCTAGTGATGGAGTTGGCCACTCC

CTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCA

A
``` and its use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection.

In related aspects, the interfering RNA reduces expression of human VEGF-C. In particularly preferred embodiments, an rAAV vector is provided comprising a capsid protein of SEQ ID NO:48 and a nucleic acid comprising the following sequence (aflibercept+ human VEGF-C interfering RNA (SEQ ID NOs:19/20) construct) or a sequence at least 80%, at least 90%, at least 95%, at least 98% or at least 99% identical thereto:

(SEQ ID NO: 69)
```
TTGGCCACTCCCTCTCTGCGCGCTCGCTCGCTCACTGAGGCCGGGCGACCAAAGGTC

GCCCGACGCCCGGGCTTTGCCCGGGGGGCCTCAGTGAGCGAGCGAGCGCGCAGAGA

GGGAGTGGCCAACTCCATCACTAGGGGTTCCTATCGATTGAATTCCCCGGGGATCCA

CTAGTTATTAATAGTAATCAATTACGGGGTCATTAGTTCATAGCCCATATATGGAGT

TCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAG

TGTATCATATGCCAAGTACGCCCCCTATTGACGTCAATGACGGTAAATGGCCCGCCT

GGCATTATGCCCAGTACATGACCTTATGGGACTTTCCTACTTGGCAGTACATCTACG

TATTAGTCATCGCTATTACCATGGTCGAGGTGAGCCCCACGTTCTGCTTCACTCTCCC

CATCTCCCCCCCCTCCCCACCCCCAATTTTGTATTTATTTATTTTTTAATTATTTTGTG

CAGCGATGGGGGGGGGGGGGGGGGGGGGGGCGCGCCAGGCGGGGGGGGGCGGG

GCGAGGGGCGGGGGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA
```

```
AGCGAAGCGCGCGGCGGGGGGGGAGTCGCTGCGACGCTGCCTTCGCCCCGTGCCCC

GCTCCGCCGCCGCCTCGCGCCGCCCGCCCCGGCTCTGACTGACCGCGTTACTGCCAC

AGGTGAGCGGGGGGGACGGCCCTTCTCCTCCGGGCTGTAATTAGCGCTTGGTTTAAT

GACGGCTTGTTTCTTTTCTGTGGCTGCGTGAAAGCCTTGAGGGGCTCCGGGAGGGCC

CTTTGTGCGGGGGGAGCGGCTCGGGGGGTGCGTGCGTGTGTGTGCGTGGGGAGC

GCCGCGTGCGGCTCCGCGCTGCCCGGCGGCTGTGAGCGCTGCGGGCGCGGCGCGGG

GCTTTGTGCGCTCCGCAGTGTGCGCGAGGGGAGCGCGGCCGGGGGGGGTGCCCCGC

GGTGCGGGGGGGGCTGCGAGGGGAACAAAGGCTGCGTGCGGGGTGTGTGCGTGGG

GGGGTGAGCAGGGGGTGTGGGCGCGTCGGTCGGGCTGCAACCCCCCCTGCACCCCC

CTCCCCGAGTTGCTGAGCACGGCCCGGCTTCGGGTGCGGGGCTCCGTACGGGGCGT

GGCGCGGGGCTCGCCGTGCCGGGCGGGGGGTGGCGGCAGGTGGGGGTGCCGGGCG

GGGCGGGGCCGCCTCGGGCCGGGGAGGGCTCGGGGGAGGGGCGCGGCGGCCCCCG

GAGCGCCGGCGCGACTTCTTAACCCAACAGAAGGCTCGAGAAGGTATATTGCTGTT

GACAGTGAGCGGCTACCTCAGCAAGACGTTATTTAGTGAAGCCACAGATGTAAATA

ACGTCTTGCTGAGGTAGCTGCCTACTGCCTCGGACTTCAAGGGGCTAGAATTCGCGG

CTGTCGAGGCGCGGCGAGCCGCAGCCATTGCCTTTTATGGTAATCGTGCGAGAGGGC

GCAGGGACTTCCTTTGTCCCAAATCTGTGCGGAGCCGAAATCTGGGAGGCGCCGCC

GCACCCCTCTAGCGGGCGCGGGGCGAAGCGGTGCGGCGCCGGCAGGAAGGAAAT

GGGCGGGGAGGGCCTTCGTGCGTCGCCGCGCCGCCGTCCCCTTCTCCCTCTCCAGCC

TCGGGGCTGTCCGCGGGGGGACGGCTGCCTTCGGGGGGGGACGGGGCAGGGGGGGGT

TCGGCTTCTGGCGTGTGACCGGCGGCTCTAGAGCCTCTGCTAACCATGTTCATGCCTT

CTTCTTTTTCCTACAGTCTAGAGTCGACCTGCAGGTGGATATCTTGGCTAGCACGCCA

CCATGGTTTCTTACTGGGACACCGGCGTGCTGCTGTGTGCCCTGCTTTCTTGTCTGCT

GCTGACCGGCTCTAGCAGCGGCTCTGATACCGGCAGACCCTTCGTGGAAATGTACA

GCGAGATCCCCGAGATCATCCACATGACCGAGGGCAGAGAGCTGGTCATCCCTTGC

AGAGTGACAAGCCCCAACATCACCGTGACTCTGAAGAAGTTCCCTCTGGACACACT

GATCCCCGACGGCAAGAGAATCATCTGGGACAGCCGGAAGGGCTTCATCATCAGCA

ACGCCACCTACAAAGAGATCGGCCTGCTGACCTGTGAAGCCACCGTGAATGGCCAC

CTGTACAAGACCAACTACCTGACACACAGACAGACCAACACCATCATCGACGTGGT

GCTGAGCCCTAGCCACGGCATTGAACTGTCTGTGGGCGAGAAGCTGGTGCTGAACT

GTACCGCCAGAACCGAGCTGAACGTGGGCATCGACTTCAACTGGGAGTACCCCAGC

AGCAAGCACCAGCACAAGAAACTGGTCAACCGGGACCTGAAAACCCAGAGCGGCA

GCGAGATGAAGAAATTCCTGAGCACCCTGACCATCGACGGCGTGACCAGAAGTGAC

CAGGGCCTGTACACATGTGCCGCCAGCTCTGGCCTGATGACCAAGAAAAACAGCAC

CTTCGTGCGGGTGCACGAGAAGGACAAGACCCACACCTGTCCTCCATGTCCTGCTGC

AGAACTGCTCGGCGGACCTTCCGTGTTCCTGTTTCCTCCAAAGCCTAAGGACACCCT

GATGATCAGCAGAACCCCTGAAGTGACCTGCGTGGTGGTGGATGTGTCCCACGAGG

ATCCCGAAGTGAAGTTCAATTGGTACGTGGACGGCGTGGAAGTGCACAACGCCAAG

ACCAAGCCTAGAGAGGAACAGTACAATAGCACCTACAGAGTGGTGTCCGTGCTGAC

CGTGCTGCACCAGGATTGGCTGAACGGCAAAGAGTACAAGTGCAAGGTGTCCAACA
```

-continued

AGGCCCTGCCTGCTCCTATCGAGAAAACCATCTCCAAGGCCAAGGGCCAGCCTAGG

GAACCCCAGGTTTACACACTGCCTCCAAGCAGGGACGAGCTGACAAAGAACCAGGT

GTCCCTGACCTGCCTGGTCAAGGGCTTCTACCCTTCCGATATCGCCGTGGAATGGGA

GAGCAATGGCCAGCCTGAGAACAACTACAAGACAACCCCTCCTGTGCTGGACAGCG

ACGGCTCATTCTTCCTGTACAGCAAGCTGACAGTGGACAAGAGCAGATGGCAGCAG

GGCAACGTGTTCAGCTGCTCCGTGATGCACGAGGCCCTGCACAACCACTACACCCA

GAAGTCCCTGAGCCTGTCTCCTGGCAAATGAGCCACGCGTAACACGTGGGGGATCC

AGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAG

CTGCAATAAACAAGTTAACAACAACAATTGCATTCATTTTATGTTTCAGGTTCAGGG

GGAGGTGTGGGAGGTTTTTTAAAGCAAGTAAAACCTCTACAAATGTGGTATGGCTG

ATTATGATCAATGCATGGCCGGCCGGAGGAACCCCTAGTGATGGAGTTGGCCACTCC

CTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCA

A and its use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection.

In related aspects, the interfering RNA reduces expression of human VEGFR-3. In particularly preferred embodiments, an rAAV vector is provided comprising a capsid protein of SEQ ID NO:48 and a nucleic acid comprising the following sequence (aflibercept+ human VEGFR-3 interfering RNA (SEQ ID NO:37) construct) or a sequence at least 80%, at least 90%, at least 95%, at least 98% or at least 99% identical thereto:

(SEQ ID NO: 70)

TTGGCCACTCCCTCTCTGCGCGCTCGCTCGCTCACTGAGGCCGGGCGACCAAAGGTC

CCCCGACGCCCGGGCTTTGCCCGGGCGGCCTCAGTGAGCGAGCGAGCGCGCAGAGA

GGGAGTGGCCAACTCCATCACTAGGGGTTCCTATCGATTGAATTCCCCGGGGATCCA

CTAGTTATTAATAGTAATCAATTACGGGGTCATTAGTTCATAGCCCATATATGGAGT

TCCGCGTTACATAACTTACGGTAAATGGCCCGCCTGGCTGACCGCCCAACGACCCCC

GCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAG

TGTATCATATGCCAAGTACGCCCCCTATTGACGTCAATGACGGTAAATGGCCCGGCT

GGCATTATGCCCAGTACATGACCTTATGGGACTTTCCTACTTGGCAGTACATCTACG

TATTAGTCATCGCTATTACCATGGTCGAGGTGAGCCCCACGTTCTGCTTCACTCTCCC

CATCTCCCCCCCCTCCCCACCCCCAATTTTGTATTTATTTATTTTTTAATTATTTTGTG

CAGCGATGGGGGGGGGGGGGGGGGGGGGGGGCGCGCCAGGCGGGGGGGGGGGGG

GCGAGGGGGGGGGGGGGCGAGGCGGAGAGGTGCGGCGGCAGCCAATCAGAGCGG

CGCGCTCCGAAAGTTTCCTTTTATGGCGAGGCGGCGGCGGCGGCGGCCCTATAAAA

AGCGAAGCGCGCGGCGGGGGGGGAGTCGCTGCGACGCTGCCTTCGCCCCGTGCCCC

GCTCCGCCGCCGCCTCGCGCCGCCCGCCCCGGCTCTGACTGACCGCGTTACTCCCAC

AGGTGAGCGGGCGGGACGGCCCTTCTCCTCCGGGCTGTAATTAGCGCTTGGTTTAAT

GACGGCTTGTTTCTTTTCTGTGGCTGCGTGAAAGCCTTGAGGGGCTCCGGGAGGGCC

```
CTTTGTGCGGGGGGAGCGGCTCGGGGGGTGCGTGCGTGTGTGTGCGTGGGGAGC

GCCGCGTGCGGCTCCGCGCTGCCCGGCGGCTGTGAGCGCTGCGGGCGCGGCGCGGG

GCTTTGTGCGCTCCGCAGTGTGCGCGAGGGGAGCGCGGCCGGGGGGGGTGCCCCGC

GGTGCGGGGGGGCTGCGAGGGGAACAAAGGCTGCGTGCGGGGTGTGTGCGTGGG

GGGGTGAGCAGGGGGTGTGGGCGCGTCGGTCGGGCTGCAACCCCCCCTGCACCCCC

CTCCCCGAGTTGCTGAGCACGGCCCGGCTTCGGGTGCGGGGCTCCGTACGGGGCGT

GGCGCGGGGCTCGCCGTGCCGGGGGGGGGGGGGCGGCAGGTGGGGGTGCCGGGCG

GGGGGGGGCCGCCTCGGGCCGGGGAGGGCTCGGGGGAGGGGCGCGGGGGCCCCCG

GAGCGCCGGCGCGACTTCTTAACCCAACAGAAGGCTCGAGAAGGTATATTGCTGTT

GACAGTGAGCGCACCGTGTGGGCTGAGTTTAACTAGTGAAGCCACAGATGTAGTTA

AACTCAGCCCACACGGTGTGCCTACTGCCTCGGACTTCAAGGGGCTAGAATTCGCGG

CTGTCGAGGCGCGGCGAGCCGCAGCCATTGCCTTTTATGGTAATCGTGCGAGAGGGC

GCAGGGACTTCCTTTGTGCCAAATCTGTGCGGAGCCGAAATCTGGGAGGCGCCGCC

GCACCCCCTCTAGCGGGCGCGGGGCGAAGCGGTGCGGCGCCGGCAGGAAGGAAAT

GGGCGGGGAGGGCCTTCGTGCGTCGCCGCGCCGCCGTCCCCTTCTCCCTCTCCAGCC

TCGGGGCTGTCCGCGGGGGGACGGCTGCCTTCGGGGGGGGACGGGGCAGGGGGGGGT

TCGGCTTCTGGCGTGTGACCGGCGGCTCTAGAGCCTCTGCTAACCATGTTCATGCCTT

CTTCTTTTTCCTACAGTCTAGAGTCGACCTGCAGGTGGATATCTTGGCTAGCACGCCA

CCATGGTTTCTTACTGGGACACCGGCGTGCTGCTGTGTGCCCTGCTTTCTTGTCTGCT

GCTGACCGGCTCTAGCAGCGGCTCTGATACCGGCAGACCCTTCGTGGAAATGTACA

GCGAGATCCCCGAGATCATCCACATGACCGAGGGCAGAGAGCTGGTCATCCCTTGC

AGAGTGACAAGCCCCAACATCACCGTGACTCTGAAGAAGTTCCCTCTGGACACACT

GATCCCCGACGGCAAGAGAATCATCTGGGACAGCCGGAAGGGCTTCATCATCAGCA

ACGCCACCTACAAAGAGATCGGCCTGCTGACCTGTGAAGCCACCGTGAATGGCCAC

CTGTACAAGACCAACTACCTGACACACAGACAGACCAACACCATCATCGACGTGGT

GCTGAGCCCTAGCCACGGCATTGAACTGTCTGTGGGCGAGAAGCTGGTGCTGAACT

GTACCGCCAGAACCGAGCTGAACGTGGGCATCGACTTCAACTGGGAGTACCCCAGC

AGCAAGCACCAGCACAAGAAACTGGTCAACCGGGACCTGAAAACCCAGAGCGGCA

GCGAGATGAAGAAATTCCTGAGCACCCTGACCATCGACGGCGTGACCAGAAGTGAC

CAGGGCCTGTACACATGTGCCGCCAGCTCTGGCCTGATGACCAAGAAAAACAGCAC

CTTCGTGCGGGTGCACGAGAAGGACAAGACCCACACCTGTCCTCCATGTCCTGCTGC

AGAACTGCTCGGCGGACCTTCCGTGTTCCTGTTTCCTCCAAAGCCTAAGGACACCCT

GATGATCAGCAGAACCCCTGAAGTGACCTGCGTGGTGGTGGATGTGTCCCACGAGG

ATCCCGAAGTGAAGTTCAATTGGTACGTGGACGGCGTGGAAGTGCACAACGCCAAG

ACCAAGCCTAGAGAGGAACAGTACAATAGCACCTACAGAGTGGTGTCCGTGCTGAC

CGTGCTGCACCAGGATTGGCTGAACGGCAAAGAGTACAAGTGCAAGGTGTCCAACA

AGGCCCTGCCTGCTCCTATCGAGAAAACCATCTCCAAGGCCAAGGGCCAGCCTAGG

GAACCCCAGGTTTACACACTGCCTGCAAGCAGGGACGAGCTGACAAAGAACCAGGT

GTCCCTGACCTGCCTGGTCAAGGGCTTCTACCCTTCCGATATCGCCGTGGAATGGGA

GAGCAATGGCCAGCCTGAGAACAACTACAAGACAACCCCTCCTGTGCTGGACAGCG

ACGGCTCATTCTTCCTGTACAGCAAGCTGACAGTGGACAAGAGCAGATGGCAGCAG
```

-continued

```
GGCAACGTGTTCAGCTGCTCCGTGATGCACGAGGCCCTGCACAACCACTACACCCA

GAAGTCCCTGAGCCTGTCTCCTGGCAAATGAGCCACGCGTAACACGTGGGGGATCC

AGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAG

CTGCAATAAACAAGTTAACAACAACAATTGCATTCATTTTATGTTTCAGGTTCAGGG

GGAGGTGTGGGAGGTTTTTTAAAGCAAGTAAAACCTCTACAAATGTGGTATGGCTG

ATTATGATCAATGCATGGCCGGCCGGAGGAACCCCTAGTGATGGAGTTGGCCACTCC

CTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCA
```

A and its use in treating wet (neovascular, exudative) age-related macular degeneration; diabetic macular edema; macular edema following retinal vein occlusion; diabetic retinopathy; or myopic choroidal neovascularization, preferably wherein the vector is intraocularly administered to a human subject, preferably wherein intraocular administration comprises intravitreal injection (e.g., a single intravitreal injection), subretinal injection or suprachoroidal injection is administered to a subject, preferably by intravitreal injection (e.g., a single intravitreal injection), to treat wet (neovascular, exudative) age-related macular degeneration; diabetic macular edema; macular edema following retinal vein occlusion; diabetic retinopathy; or myopic choroidal neovascularization.

Also provided herein are pharmaceutical compositions comprising: a) a nucleic acid as herein described, preferably encapsidated within an rAAV (preferably an rAAV comprising a capsid protein of SEQ ID NO:48) and; and b) a pharmaceutically acceptable carrier, diluent, excipient, or buffer. In some preferred embodiments, the nucleic acid comprises a nucleotide sequence selected from SEQ ID Nos:64-70. In some embodiments, the pharmaceutically acceptable carrier, diluent, excipient, or buffer is suitable for use in a human or non-human patient. Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, surfactants, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

In some preferred embodiments, the pharmaceutical composition comprises Dulbecco's Phosphate Buffered Saline (DPBS) and a non-ionic surfactant (e.g., Pluronic F68, preferably at about 0.005%).

In some embodiments, the pharmaceutical composition comprises $1 \times 10^8$ to $1 \times 10^{15}$ vector particles or vector genomes, $1 \times 10^{10}$ to $1 \times 10^{13}$ vector particles or vector genomes, or about $1 \times 10^{10}$, about $2 \times 10^{10}$, $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, about $1 \times 10^{11}$, about $2 \times 10^{11}$, about $3 \times 10^{11}$, about $4 \times 10^{11}$, about $5 \times 10^{11}$, about $6 \times 10^{11}$, about $7 \times 10^{11}$, about $8 \times 10^{11}$, about $9 \times 10^{11}$, about $1 \times 10^{12}$, about $2 \times 10^{12}$, about $3 \times 10^{12}$, about $4 \times 10^{12}$, about $5 \times 10^{12}$, about $6 \times 10^{12}$, about $7 \times 10^{12}$, about $8 \times 10^{12}$, about $9 \times 10^{12}$ or about $1 \times 10^{13}$ vector particles or vector genomes. In some aspects, the pharmaceutical composition comprises about $1 \times 10^{11}$ to about $1 \times 10^{12}$ vector particles or vector genomes.

In some preferred embodiments, the pharmaceutical composition is administered intraocularly to a human with a VEGF-related ocular disorder, preferably wherein the pharmaceutical composition is administered via intravitreal, subretinal and/or suprachoroidal injection, more preferably via a single intravitreal injection.

EXAMPLES

The following examples illustrate preferred embodiments of the present invention and are not intended to limit the scope of the invention in any way. While this invention has been described in relation to its preferred embodiments, various modifications thereof will be apparent to one skilled in the art from reading this application.

Example 1

The following examples describe multi-mechanistic approaches to anti-angiogenic gene therapy with recombinant adeno-associated virus (rAAV) comprising a genetically modified capsid protein that confers improved transduction of a panoply of retinal cells. The rAAV constructs described below provide sustained delivery of anti-angiogenic agents from a single intravitreal dose, limiting the burden of repeated injections, maintaining consistent levels of therapeutic gene products in pertinent retinal cells and improving therapeutic response compared to delivery of single anti-angiogenic agents. Each of the representative constructs described below comprises a nucleic acid encoding aflibercept (targeting VEGF-A, VEGF-B and PIGF) and at least one other anti-angiogenic agent to enhance efficacy beyond delivery of aflibercept alone.

Figures 1A, 1B:
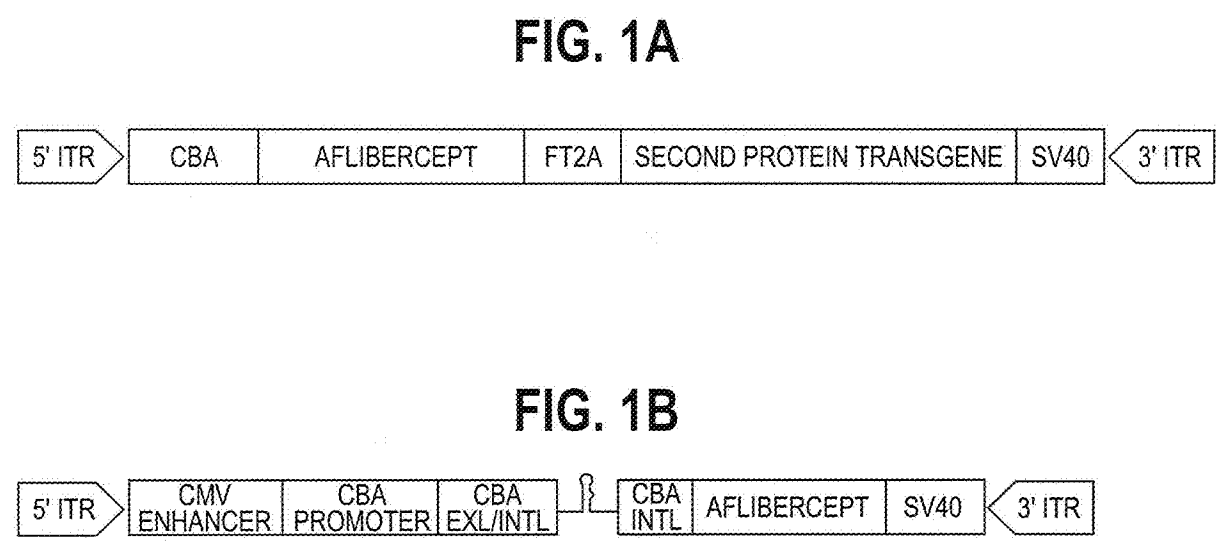

Representative construct designs (AAV vector backbones) are illustrated at FIGS. 1A-B. In the first approach

(FIG. 1A), nucleotide sequence encoding aflibercept and a second anti-angiogenic polypeptide, separated by an FT2A (ribosomal-skipping peptide) sequence, are controlled by a ubiquitous CBA promoter (it is a bicistronic construct). Second anti-angiogenic polypeptides exemplified herein include PEDF, VEGFR-3-Fe fusion protein and Anti-Ang-2 scFab fragments, selected on the basis of their function in reducing angiogenesis and/or vascular permeability. In each case, the encoding gene was codon-optimized for human expression. In the second approach (FIG. 1B), nucleotide sequence encoding aflibercept is driven by a CAG promoter with nucleotide sequence encoding an interfering RNA that targets a pro-angiogenic protein. In each case, the RNAi sequence was embedded in the well-characterized miR-E backbone (as described e.g., in US Patent Application Publication No. 2015-0018539, the contents of which are incorporated herein by reference and Fellmann et al., Cell Reports, 5(6):1704-1713 (2013)) and placed within the hybrid chicken b-actin/rabbit b-globin intron (See FIG. 1B). The CBA promoter is a well-characterized ubiquitous promoter capable of driving sustained, high levels of expression. The CBA promoter is a hybrid of the human cytomegalovirus (CMV) upstream enhancer with the chicken β-actin (CBA) promoter and also contains chicken b-actin exon 1, a hybrid chicken b-actin and rabbit b-globin intron and a rabbit b-globin exon 3 fragment (creating an artificial splice site). Use of the miR-E backbone and placement within the intron of the CAG promoter was validated using a model antigen (data not shown).

Construction of dual protein constructs—Codon-optimized genes for Pigment Epithelium Derived Factor (PEDF), VEGF Receptor 3 (VEGFR3)-Fc fusion protein, and anti-Angiopoietin-2 (ANG2) single-chain Fab (scFab) fragments were excised from shuttle vectors and inserted into the AAV vector backbone between the CBA promoter and the SV40 late polyA (SV40 pA) sequence on NheI-MluI fragments. For co-expression with Aflibercept, the synthetic DNA included sequences encoding the C-terminal portion of Aflibercept (AFLB), a Furin cleavage site, and a T2A ribosomal-skipping peptide upstream of the PEDF, VEGFR3-Fe, or anti-ANG2 scFab sequences. These synthetic DNAs were excised from the shuttle vectors and inserted into pAAV-CAG-AFLB-SV40 pA on AvrII-MluI fragments. Plasmids were propagated in E. coli and purified plasmid DNA was verified by restriction digest and sequencing.

Construction Details for Protein+ RNAi Constructs
Construction of pAAV-CAG-miR-E—("Target Sequence")-AFLB-SV40

The pAAV-CAG-AFLB-SV40 construct expressing human codon optimized Aflibercept was synthesized as described previously. The miR-E-(target) miRNA transgene, encoding for hairpin targeting ANGPT2, VEGF-C, or VEGFR3, containing the region of the CAG beta-actin intron encoded between the SgrAI and NheI restriction cloning sites was synthesized and cloned into pUC57 by Genscript (Genscript, Picataway, NJ). pUC57 μlasmid and the pAAV-CAG-AFLB-SV40-Kan-Stuffer plasmid were cut with various restriction enzymes (New England Biolabs) as indicated, backbone DNA was also treated with recombinant shrimp alkaline phosphatase (rSAP, M0371L, New England Biolabs) during digest to remove free phosphates on cut DNA ends. DNA fragments were added at a 7:1 molar ratio insert:backbone and ligated with Quick Ligase per manufacturer's instructions (#M2200L, New England Biolabs). Ligated plasmid was transformed into NEB Stable bacterial competent cells (#C3040H, New England Biolabs) per manufacturer's instructions and the cells were spread on Kanamycin 50 mg/ml plates (#L1025, Teknova, Hollister, CA) and grown at 30 C.

Preparation of pAAV-CAG-miR-E-AFLB-SV40

Miniprep cultures were grown from the resulting colonies, DNA was prepared with the GeneJET Plasmid Miniprep kit (Cat. #0503, ThermoFisher, Waltham, MA) and restriction digested to identify positive clones. A 50-ml culture in Terrific Broth was grown from one positive clone of each construct and DNA was prepared with the Qiagen EndoFree Plasmid Maxi Kit (Cat. #12362, Qiagen, Hilden, Germany).

Restriction Digest and Sequencing of pAAV-CAG-RFP657-miRNA Plasmid Variants

Maxiprep plasmid DNA (0.5 mg) was digested with various restriction enzymes (New England BioLabs) according to the manufacturer's instructions and analyzed by agarose gel electrophoresis. Sanger DNA sequencing was performed by ELIM using primers.

A summary of the constructs designed and tested in the examples herein is provided below:

TABLE 5

| Name | Promoter | Additional Transgene(s)* | RNAi location | Size (bp) |
|---|---|---|---|---|
| | CBA | PEDF (SEQ ID NO: 60) | N/A | 4297 |
| | CBA | anti-Ang-2 scFab LH | N/A | 4645 |
| | CBA | anti-Ang-2 scFab HL | N/A | 4642 |
| pP141.001 | CAG | Ang2-targeting RNAi (SEQ ID NOs: 13 and 14) | Promoter intron | 3863 |
| | CAG | VEGFR3-targeting RNAi (SEQ ID NOs: 37 and 38) | Promoter intron | 3863 |
| pP145.001 | CAG | VEGF-C-targeting RNAi (SE ID NOs: 19 and 20) | Promoter intron | 3830 |
| pP151.001 | CAG | VEGF-C-targeting RNAi (SEQ ID NOs: 19 and 20) | Promoter intron | 4136 |
| | | Ang-2-targeting RNAi (SEQ ID NOs: 13 and 14) | 3' UTR (AFLB) | |
| pP152.001 | CAG | VEGF-C-targeting RNAi (SEQ ID NOs: 19 and 20) | Promoter intron | 4138 |
| | | Ang-2-targeting RNAi (SEQ ID Nos: 13 and 14) | AFLB coding sequence | |
| pP153.001 | CAG | VEGF-C-targeting RNAi (SEQ ID Nos: 19 and 20) | Promoter intron | 3987 |
| | | Ang-2-targeting RNAi (SEQ ID Nos: 13 and 14) | Promoter intron | |

*each construct comprises nucleotide sequence encoding aflibercept (AFLB)

Aflibercept is expressed in human RPE and RGC cells at therapeutic levels following delivery in rAAV virions comprising a capsid protein of SEQ ID NO:48, resulting in efficient blockade of VEGF-A, VEGF-B and PIGF-mediated activity in these cells. See US Patent Application Publication No. 2020/0282077A1, the contents of which are incorporated herein by reference.

Studies were conducted to assess the effect of including a second transgene (encoding a protein or an RNAi) in AAV expression plasmids on expression of aflibercept following transfection of HEK293T cells.

Briefly, HEK293T cells were seeded in 12-well plates at 2.0× $10^5$ cells/well in 1.0 ml DMEM/10% FBS media. The next day, 1.0 mg plasmid DNA (comprising nucleotide sequence encoding aflibercept and a second transgene under the control of the same promoter) complexed with 3.0 ml FuGeneHD (Cat. #E2691, Promega, Madison, WI) was added to the cells in triplicate wells. 48 hrs post-transfection, cell supernatant was harvested and spun @2000 g to remove cellular debris. Media was then assayed for the presence of aflibercept (ALFB) via ELISA.

For Western Blot analysis, media from transduced HEK293T cells were pooled from 3 replicates and mixed with 4× LDS (B0007, Thermo), 10× Reducing Agent (B0009, Thermo) and denatured at 70° C. for 10 minutes. Samples were loaded on a 10-well Bolt 4-12% Bis-Tris Plus polyacrylamide gel (Invitrogen, NW04120BOX) and ran in 1× MOPS buffer (NP000102, Thermo) at 200V for 32 minutes. Separated proteins were transferred to a nitrocellulose filter (1704158, BioRad) with the BioRad TransBlot Turbo device (BioRad) for 7 minutes and probed anti-Human IgG Fc Cross-Adsorbed Secondary Antibody, HRP (ThermoFisher, 31413) at 1:500 in iBind Flex solution (SLF2020, Thermo). Proteins were visualized with Super-Signal West Dura Chemiluminescent Substrate (ThermoFisher 34076) and imaged on a ChemiDoc MP (BioRad, Hercules, CA).

Cell lysates for ELISA (secreted free-AFLB, ANGPT2, and VEGF-A Levels) were prepared in M-PER lysis buffer (#78501, Thermo) supplemented with 1× Halt Protease and Phosphatase Inhibitor Cocktail (78440, Thermo) as per manufacturer's instructions. Cell media and lysate were diluted appropriately for each sample and were used to evaluate secreted analyte levels using the Aflibercept ELISA kit (to measure free AFLB levels) (Cat. #IG-AA 115, Eagle Biosciences, Nashua, NH), the Quantikine human VEGF-A ELISA kit (DVE00, R&D Systems) and the Quantikine human ANGPT2 ELISA kit (DANG20, R&D Systems) following the provider's instructions. The optical density (OD) was measured with a Cytation 3 (BioTek, Winooski, VT) photometer at 450 nm (reference at OD 620 nm) within 15 min after pipetting the Stop Solution. Media concentrations were defined based on the generated standard curve.

Figure 3A:
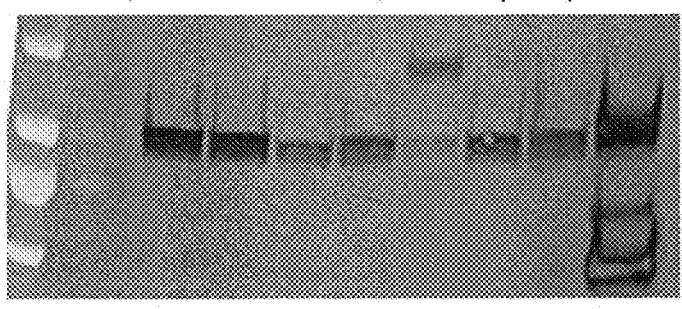
FIGS. 3A-B FIG. 3A is a Western blot using anti-Human IgG Fe to detect aflibercept in HEK293T media following transfection with AAV plasmid comprising nucleotide sequence encoding aflibercept along with a second polypeptide (PEDF, VEGFR3, anti-Ang2 scFab (LH and HL)) with both sequences under control of a CBA promoter.

FIG. 3A demonstrates the results of Western Blot analysis of AFLB from media of HEK293T cells following transfection with AAV plasmids encoding AFLB and a second transgene (PEDF, VEGFR3, Anti-Ang HL, or Anti-AngLH) under the control of a CAG promoter. Results are normalized to AFLB level in media of HEK293T cells transfected with AAV plasmid encoding only AFLB under the control of CBA promoter. Elyea (commercial preparation) is provided as a positive control for aflibercept. Addition of a second transgene encoding a polypeptide product significantly reduces expression of aflibercept by ~50-60%.

Figure 3B:
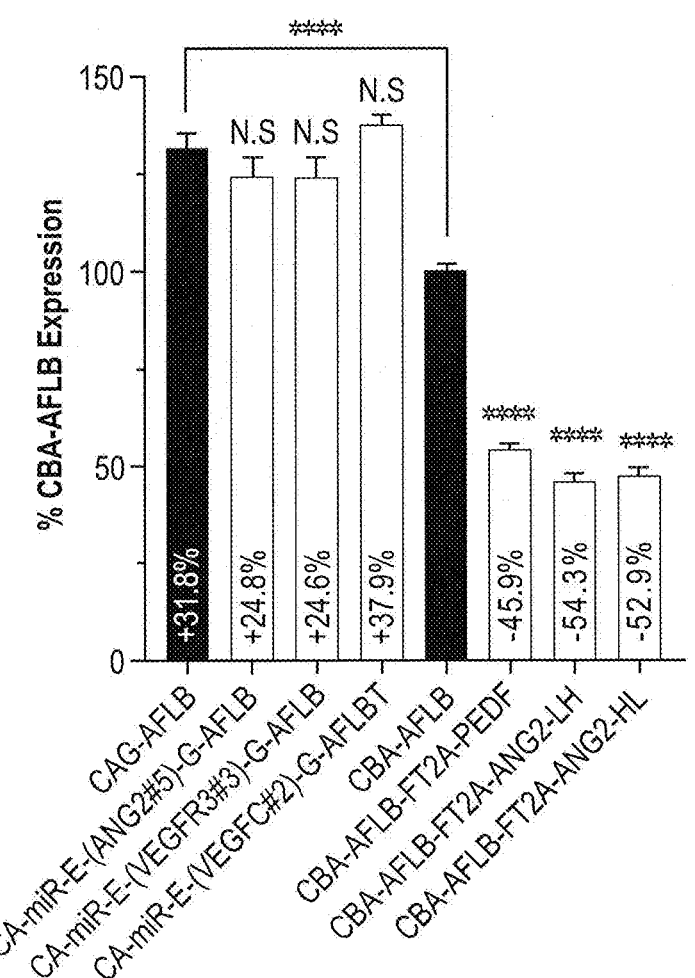

FIG. 3B demonstrates expression of aflibercept from various constructs encoding either a second polypeptide (PEDF, anti-Ang2 LH, anti-Ang2 HL) or interfering RNA (targeting Ang2, FEGR3 or VEGF-C) normalized to AFLB level in media of HEK293T cells transfected with AAV plasmid encoding only AFLB under the control of CBA promoter. Notably, no significant reduction in aflibercept expression occurs with plasmids encoding AFLB and an interfering RNA. Expression from the CAG promoter was observed to be 25% greater than expression from the CBA promoter.

Next, studies were conducted to assess the effect of including a second transgene (encoding a protein or an RNAi) in AAV expression plasmids on expression of aflibercept following transduction of human retinal pigment epithelium (RPE) cells with recombinant AAV virus comprising a capsid protein of SEQ ID NO:48.

For RPE transduction, human stem cell derived retinal pigment epithelial cells (RPE) were differentiated from embryonic stem cells (ESI-017) following published protocols (Buchholz D 2013, Leach L 2015). RPE cells were grown on Matrigel (Corning) for 30 days in XVIVO-10 media (Lonza), in a 96 well plate format. Prior to transduction, three wells were harvested and counted for an accurate calculation of multiplicity of infection (MOI). Virus was added to the cells for 48 hours in XVIVO-10 media based on each viral titer in a total volume of 100 μL per well. Media was collected on day 3, 7, 11, 15 and 19 and replaced with 200 μL of media per well. Media samples were stored at 4° C. until processed.

Cell lysates for ELISA (to assess secreted free-AFLB, ANGPT2, and VEGF-A levels) were prepared in M-PER lysis buffer (#78501, Thermo) supplemented with 1× Halt Protease and Phosphatase Inhibitor Cocktail (78440, Thermo) as per manufacturer's instructions. Cell media and lysate were diluted appropriately for each sample and were used to evaluate secreted analyte levels using the Aflibercept ELISA kit (to measure free AFLB levels) (Cat. #IG-AA115, Eagle Biosciences, Nashua, NH), the Quantikine human VEGF-A ELISA kit (DVE00, R&D Systems) and the Quantikine human ANGPT2 ELISA kit (DANG20, R&D Systems) following the provider's instructions. The optical density (OD) was measured with a Cytation 3 (BioTek, Winooski, VT) photometer at 450 nm (reference at OD 620 nm) within 15 min after pipetting the Stop Solution. Media concentrations were defined based on the generated standard curve.

Figure 4:
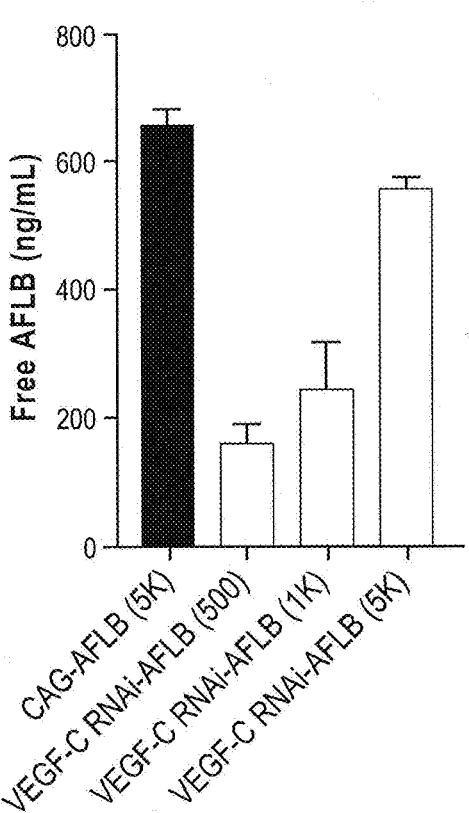
FIG. 4 illustrates free and active aflibercept (AFLB) in the media eight days after transduction of RPE cells with rAAV comprising a capsid of SEQ ID NO:48 and heterologous nucleic acid encoding the indicated transgenes at the specified MOI (N=3 biological replicates per conditions; statistics only calculated for matched MOIs).

As can be seen from FIG. 4, a dose-dependent increase in aflibercept expression is seen (day 8 is shown) with rAAV expressing aflibercept and an RNAi targeting VEGF-C, with the high multiplicity of infection (MOI) near that of the control (rAAV expressing aflibercept alone operably linked to CAG promoter). All constructs expressing aflibercept are able to completely neutralize endogenous VEGF-A at all multiplicities of infection (MOIs) tested. The amounts shown in FIG. 4 are free and active aflibercept in the media of RPE cells following transduction.

Figure 5A:
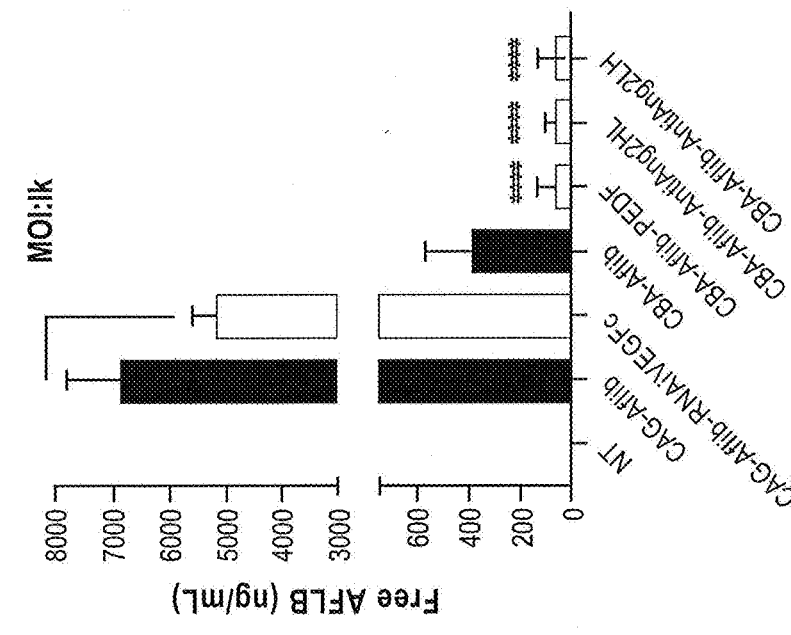
Figure 5C:
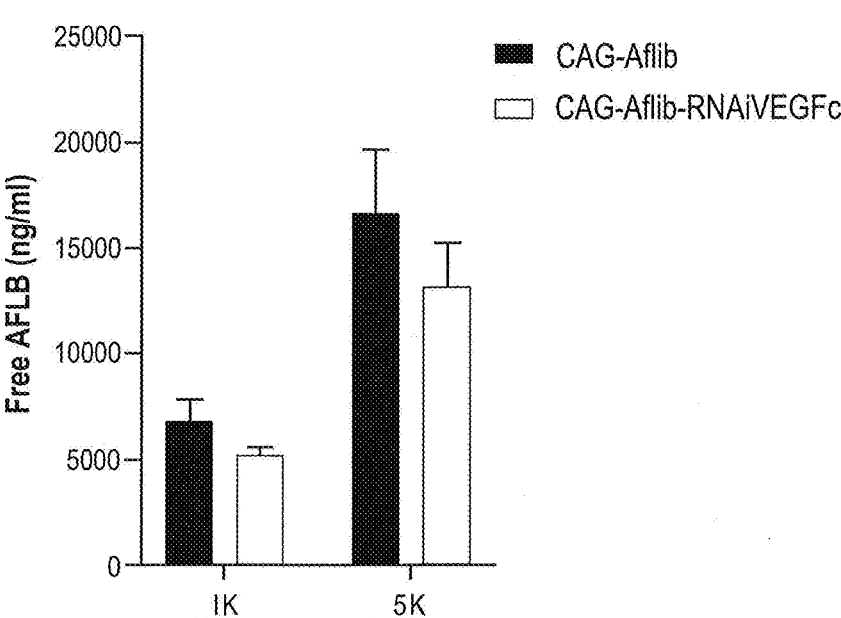
Figure 6A:
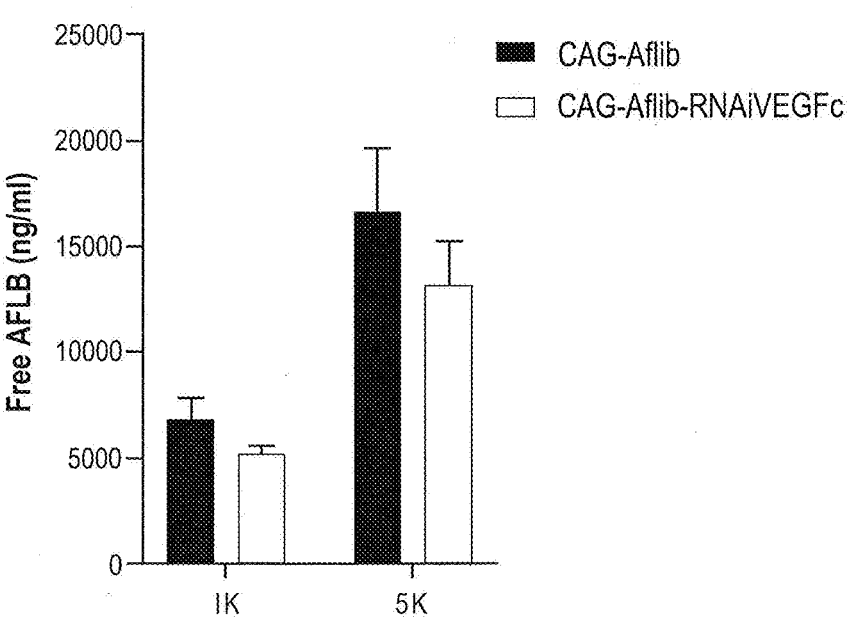

FIGS. 5A and 5B illustrate analysis of free aflibercept in RPE supernatant on days 7 (FIG. 5A) and 11 (FIG. 5B) following transduction with rAAV carrying the indicated expression cassettes (and a capsid protein of SEQ ID NO:48). As in HEK293T cells, expression of a second protein dramatically reduces the level of aflibercept expression in transduced RPE cells. In contrast, while some reduction in aflibercept expression was observed with co-expression of interfering RNA, aflibercept expression remained robust at both MOIs. The CBA promoter was surprisingly determined to be much weaker than the CAG promoter at driving expression in RPE cells. See also FIGS. 6A-B illustrating some decrease in aflibercept expression at the higher MOI with co-expression of interfering RNA but much less pronounced than with co-expression of a second polypeptide.

Figure 7A:
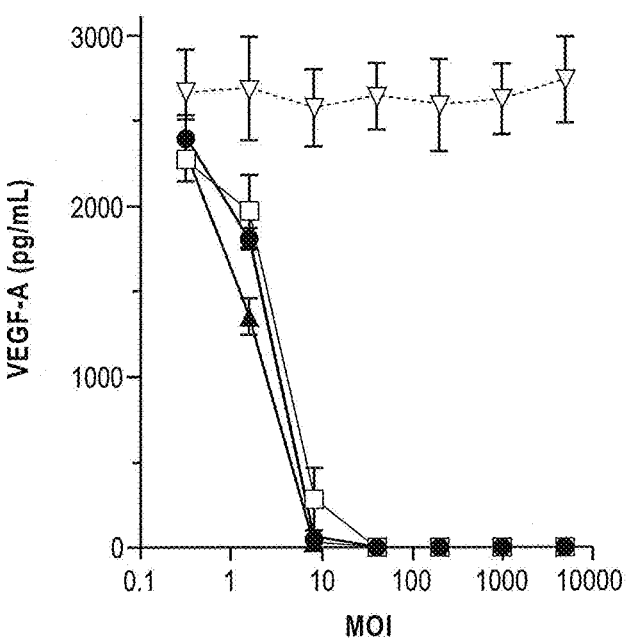
FIGS. 7A-B illustrate a comparison of VEGF-A neutralization (assessed by ELISA) in RPE supernatant at day 7 (FIG. 7A) and day 11 (FIG. 7B) following transduction at the specified MOIs with rAAV comprising a capsid protein of SEQ ID NO:48 and the indicated constructs.
Figure 7B:
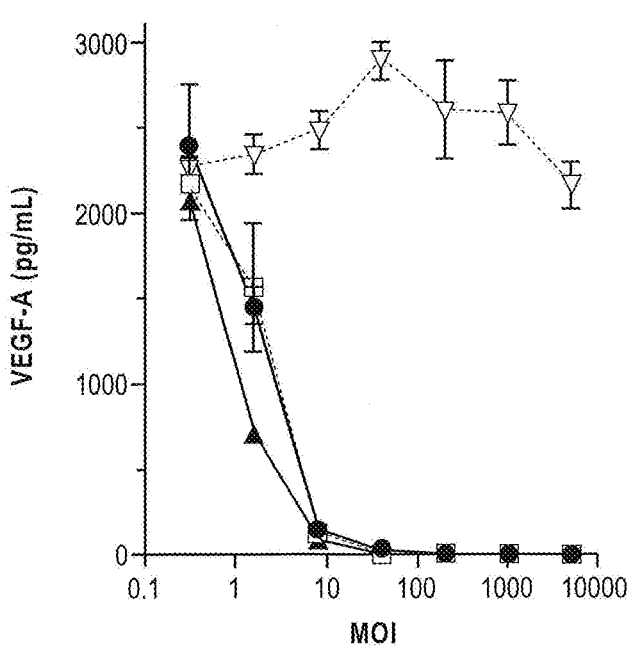

Importantly, aflibercept co-expressed with interfering RNA was functional and able to bind VEGF-A produced by RPE cells (see FIGS. 7A-B illustrating neutralization of VEGF-A at MOIs above 40 for AFLB+ VEGFC-RNAi and AFLB+ANG2 RNAi constructs).

CONCLUSIONS

In HEK293T cells, aflibercept expression is reduced ~20% when driven by the CBA promoter compared to the CAG promoter; expression of aflibercept was ~-13× weaker when driven by the CBA promoter compared to the than the CAG promoter in RPE cells.

In HEK293T cells, RNAi has no significant effect on transgene expression compared to control (aflibercept alone under the control of the same promoter), whereas all dual protein constructs exhibited a ~50% reduction in aflibercept compared to control (aflibercept alone under the control of the same promoter) in HEK293T cells. In RPE cells, under most conditions a slight, but insignificant, reduction in free aflibercept levels was observed compared to control in RPE cells for constructs containing RNAi, whereas all dual protein constructs expressed ~5-10× less aflibercept than their control counterpart.

Example 2—Characterization of Dual Protein Constructs

Characterization of Constructs Expressing Aflibercept+Anti-Ang-2 scFab

HEK293T cells were transfected with AAV plasmid comprising nucleotide sequence encoding aflibercept and nucleotide sequence expressing anti-Ang-2 scFab in a bicistronic configuration driven by the CAG promoter (see FIG. 1A). Briefly, HEK293T cells were seeded in 12-well plates at 2.0× 10' cells/well in 1.0 ml DMEM/10% FBS media. The next day, 1.0 mg plasmid DNA complexed with 3.0 ml FuGeneHD (Cat. #E2691, Promega, Madison, WI) was added to the cells in triplicate wells. 48 hrs post-transfection, cell supernatant was harvested and spun @2000 g to remove cellular debris. Media was then assayed for the presence of ALFB via ELISA.

Western Blot—media from transfected HEK293T cells (6.25 µl) was mixed with 12.5 µl 4× LDS, 5 µl 10× Reducing Agent, and 26.25 1× PBS (final volume=50 µl) and denatured at 70° C. for 10 minutes. 40 µl of the samples were loaded on a 10-well Bolt 4-12% Bis-Tris Plus polyacrylamide gel (Invitrogen, NW04120BOX) and ran in 1× MOPS buffer at 200V for 32 minutes. Separated proteins were transferred to a nitrocellulose filter with the iBlot 2 device (ThermoFisher) for 7 minutes and probed with anti-Human IgG F(ab')2 Secondary Antibody (ThermoFisher 31482 1:1000) using the iBind Flex device (ThermoFisher). Proteins were visualized with SuperSignal West Dura Chemiluminescent Substrate (ThermoFisher 34076) and imaged on a ChemiDoc MP (BioRad, Hercules, CA).

Functional anti-ANG2 ELISA with ANG2 coated plates—Nunc MaxiSorp flat-bottom plates (Invitrogen, 44-2404-21) were coated with 100 µl of 1.0 µg/µl Recombinant Human Angiopoietin-2 (R&D, 623-AN/CF) in PBS, sealed with an adhesive sheet, and placed at 4° C. overnight. The next day, the coating solution was aspirated, and the plates were washed 3 times with 300 µl PBST (PBS/0.05% Tween 20). The plates were blocked with 200 µl PBS/2.0% BSA at room temperature for 2 hours. After the 2-hour incubation, the blocking solution was aspirated, and the plate was washed 3 times with 300 µl PBST. Media from transfected HEK293T cells was diluted in PBS/0.2% BSA, and 100 µl of the diluted media was added to the plate and incubated at room temperature for 2 hours with gentle shaking. The plate was washed again 3 times with 300 µl PBST. 100 µl of anti-Human IgG F(ab')2 Secondary Antibody (ThermoFisher 31482, 1:20,000) was added to the plate and incubated at room temperature for 1 hour with gentle shaking. The plate was washed again 3 times with 300 µl PBST. The plates were developed with 100 µl TMB ELISA Substrate (Abcam, ab171522) at room temperature for 5-15 minutes. The TMB reaction was stopped with 100 µl 450 nm Stop Solution for TMB Substrate (Abcam, ab171529). The plates were read at 450 nm and 540 nm (as a reference blank for the plate) using the Cytation 5 device (BioTek).

ANG2 Competition ELISA—media from transfected HEK293T cells was diluted in PBS/0.2% BSA, mixed with an equal volume of 2.0 ng/ml Recombinant Human Angiopoietin-2 (R&D, 623-AN/CF), and incubated overnight at room temperature (final ANG2 concentration=1,000 µg/ml). The next day, the concentration of free ANG2 was determined with the Angiopoietin-2 Human ELISA Kit (Invitrogen, KHC1641) as interpolated from a freshly made Recombinant Human Angiopoietin-2 (R&D, 623/AN-CF) standard.

ANG2 Receptor Competition Assay—nunc MaxiSorp flat-bottom plates (Invitrogen, 44-2404-21) were coated with 100 µl of 1.0 µg/ml Recombinant Human Tie-2 Fc Chimera Protein (R&D, 313-TI/CF) in PBS, sealed with an adhesive sheet, and placed at 4° C. overnight. The competition mix was prepared using dilutions of media from transfected HEK293T cells with an equal volume of 80 ng/ml Human Angiopoietin-2 with an N-terminal FLAG-tag (Adipogen, AG-40B-0114-C010) (final ANG2-Flag concentration=80 ng/ml). The next day, the coating solution was aspirated, and the plates were washed 3 times with 300 µl PBST. The plates were blocked with 200 µl PBS/2.0% BSA at room temperature for 2 hours. After the 2-hour incubation, the blocking solution was aspirated, and the plate was washed 3 times with 300 µl PBST. 100 µl of the competition mix samples along with a freshly made ANG2-Flag standard were added to the plate and incubated at room temperature for 2 hours with gentle shaking. The samples in the plate were aspirated and washed 3 times with 300 µl PBST. 100 µl of DYKDDDDK (SEQ ID NO:71) Epitope Tag Horseradish Peroxidase-conjugated antibody (R&D HAM85291 1:10000) was added to the plate and incubated at room temperature for 1 hour with gentle shaking. The plate was washed 3 times with 300 µl PBST and developed with 100 µl TMB ELISA Substrate (Abcam, ab171522) at room temperature for 5-15 minutes. The TMB reaction was stopped with 100 µl 450 nm Stop Solution for TMB Substrate (Abcam, ab171529). The plates were read at 450 nm and 540 nm (as a reference blank for the plate) using the Cytation 5 device (BioTek) and the concentration of ANG2-Flag was interpolated from the ANG2-Flag standard.

Figure 8A:
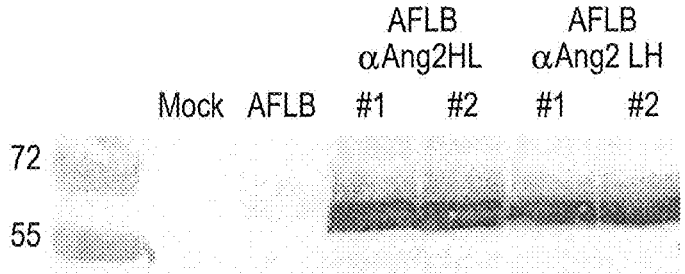
Figure 8B:
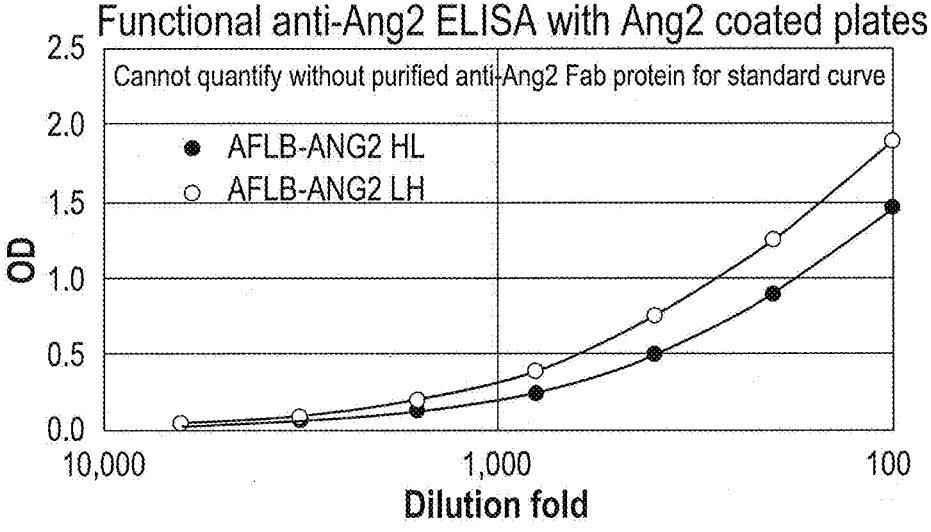

FIG. 8A illustrates expression of protein products of the expected size for anti-Ang-2 HL and HL Fab. FIG. 8B illustrates that expressed anti-Ang-2 Fab is functional (binding of expressed protein to Ang-2-coated plates is shown). FIG. 8C illustrates that expressed anti-Ang-2 Fab blocks binding of Ang-2 to antibody-coated plates (competition ELISA). FIG. 8D illustrates that expressed anti-Ang-2 Fab blocks binding of Ang-2 to Tie-2 (receptor competition assay).

Dose-dependent expression of anti-Ang-2 Fab (LH and HL formats) from dual protein construct was shown from transfected HEK cells. The expressed anti-Ang-2 Fab proteins were the correct size and functional at binding Ang2 and blocking Ang2-binding to its receptor.

Next, studies were conducted to characterize expression of aflibercept and anti-Ang-2 Fab following transduction of human retinal pigment epithelium (RPE) cells with recombinant AAV virus comprising a capsid protein of SEQ ID NO:48 and a nucleic acid encoding aflibercept and anti-Ang-2 Fab (LH or HL).

FIG. 9 illustrates expression of a single protein of the correct size (53 kD) for Anti-Ang-2 scFab (LH and HL), with similar expression levels of LH and HL conformations. Briefly, RPE cells were transduced with rAAV comprising a capsid protein of SEQ ID NO:48 and a nucleic acid encoding aflibercept and anti-Ang-2 scFab at MOI 5,000 and 1,000 in 96 well plates. Media (0.2 ml) was changed at day 3 post-transduction and collected on day 7. 25 ml media of the MOI 5,000 samples was run on 4-12% SDS-PAGE, transferred to nitrocellulose with iBlot and probed on the iBind Flex with HRP-conjugated anti-Hu-Fab antibody to detect the anti-Ang-2 scFab and anti-Hu-Fe antibody to detect Aflibercept.

FIG. 10A illustrates dose-dependent expression of functional Anti-Ang-2 scFab in transduced RPE cells at MOI of 1,000 and 5000. Briefly, dilutions of media from transduced RPE cells (day 11) were incubated on Ang-2-coated plates. Anti-Ang-2 scFab bound to Ang-2 was detected with HRP-conjugated anti-Hu-Fab antibody. The LH format was slightly more effective at binding Ang2 than the HL format, especially at lower MOL FIG. 10B illustrates the results of competition ELISA with day 11 samples in transduced RPE. Briefly, 1000 μg/ml Ang2 protein was incubated overnight with a dilution series of media from transduced RPE cells. Competition mixtures were assayed by Ang-2 ELISA (Invitrogen KHC1641).

Next, binding affinities of anti-Ang-2 scFab LH and HL were compared via SPR by Biacore assay performed at Genscript.

Immobilization of Angiopoietin-2 onto CM5 sensor chip. The immobilization of Angiopoietin-2 was performed under 25 degrees Celsius while HBS-EP+ was used as the running buffer. The sensor chip surface of flow cells 1, 2 were activated by freshly mixed 50 mmol/L N-Hydroxysuccinimide (NHS) and 200 mmol/L 1-ethyl-3-(3-dimethylamino-propyl) carbodiimide hydrochloride (EDC) for 420s (10 μL/min). Afterwards, Angiopoietin-2 diluted in 10 mmol/L NaAC (pH 4.5) were injected into the flow cell 2 to achieve conjugation of 243.1 Response Unit. After the amine coupling reaction, the remaining active coupling sites on chip surface were blocked with 420 s injection of 1 mol/L ethanolamine hydrochloride. For affinity measurement, the assay was performed at 25° C. and the running buffer was HBS-EP+. Diluted V2.2/V2.3 were injected over the surface of flow cell 1, 2 as association phase, followed by injecting running buffer as dissociation phase. Running configuration was listed below (Sample concentrations (nM)=1.5625, 3.125, 6.25, 12.5, 25, 50, 100)

| Immobilization | Ligand = Angiopoietin 2 | Immobilization level (RU) 234.1 | Flow rate (ml/min) = 10 |
|---|---|---|---|
| Association & Dissociation | Association contact time = 180 | Dissociation contact time = 600 | Flow rate (ml/min) = 30 |

Figure 11:
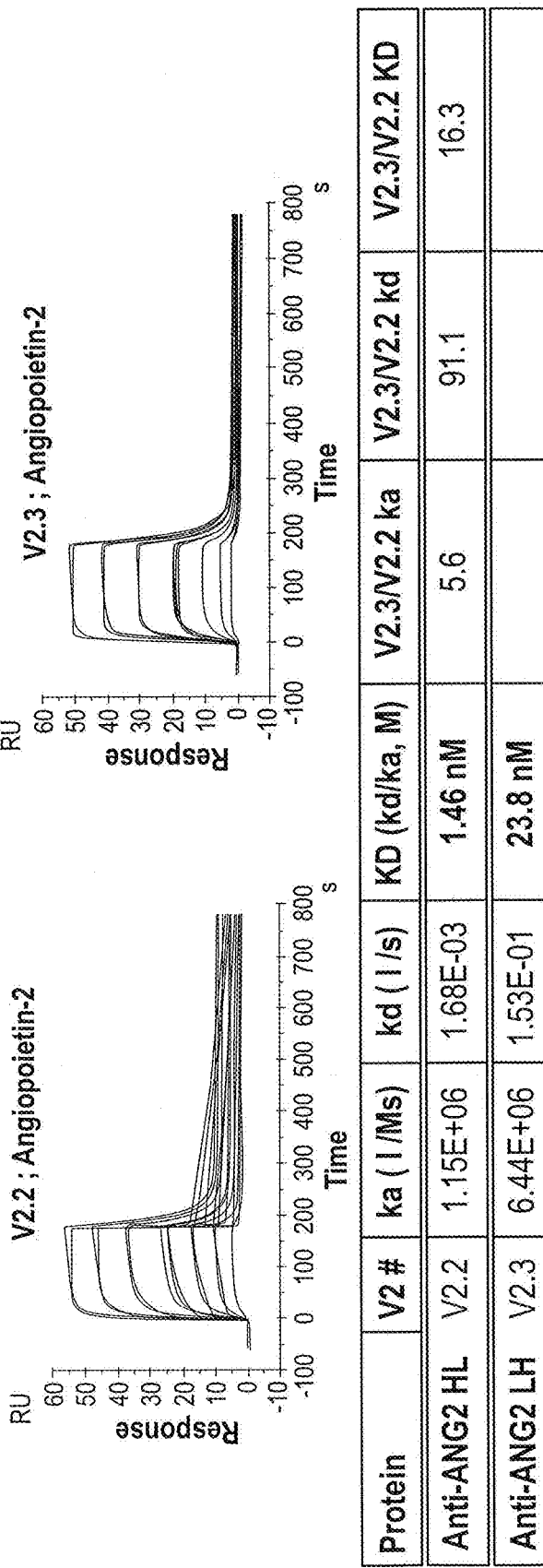
FIG. 11 illustrates binding affinities of anti-Ang2 scFab (assessed by Biacore) encoded by the rAAV as described in FIG. 9.

The results are provided at FIG. 11. The LH configuration (V2.3) has a 5.6-fold faster association (higher ka value) than the HL configuration (V2.2) suggesting stronger binding. The LH configuration has a 91-fold faster dissociation (higher kd value) than HL suggesting weaker binding. The HL configuration has an overall binding affinity of 1.46 nM and the LH has a binding affinity of 23.8 nM. Thus, LH configuration has about 16-fold higher Ang-2-binding affinity than the HL configuration. These values are consistent with the published affinity for the anti-Ang2 arm of faricimab.

Next, PEDF expression in HEK293T cells was assessed following transfection with AAV plasmid dual protein construct encoding aflibercept and PEDF. Briefly, HEK293T cells were seeded in 12-well plates at 2.0× 10^5 cells/well in 1.0 ml DMEM/10% FBS media. HEK293T cells were used due to their high transfectability and protein expression. The next day, 1.0 mg plasmid DNA complexed with 3.0 ml FuGene6 (Cat. #E2691, Promega, Madison, WI) was added to the cells in duplicate wells. Two days after transfection, the supernatants were collected. Cell debris were pelleted by centrifugation in a microcentrifuge at 12,000 g for 10 minutes at 4° C. The supernatant was collected and stored at 4° C. A no plasmid condition was included in the transfection as negative control.

For SDS-PAGE and Western Blot, PEDF samples were diluted 1:10, prior to running the SDS-PAGE/Western blot assay. Aflibercept samples were diluted 1:50. Diluted media was combined with 4× sample buffer and 10× reducing buffer according to the ThermoFisher iBlot system. Samples were then boiled at 90° C. for 5 minutes. A 4-12% Bis/Tris reducing gel was run in 1× MOPS buffer at 125V for 1.5 hours. The proteins were transferred onto nitrocellulose using the BioRad Trans Blot Turbo System using the preset MIXED protocol for 7 minutes. Membranes were blocked for 1-2 minutes in iBind Flex Buffer prior to loading the iBind Flex Western Device according to manufacturer's instructions. Primary antibodies (anti-PEDF EMD Millipore, 1:1000, anti-Human FC HRP ThermoFisher 1:2000) with species specific secondary antibodies conjugated to HRP (1:10000) were used and detected with Femto ECL Substrate and imaged on a BioRad ChemiDoc system.

ELISA (R&D, Human serpin F1/PEDF ELISA Cat. No. DY1177) was carried out according to manufacturer's instructions. Media was diluted 1:1000 or 1:10000 prior to running the assay.

Figure 12A:
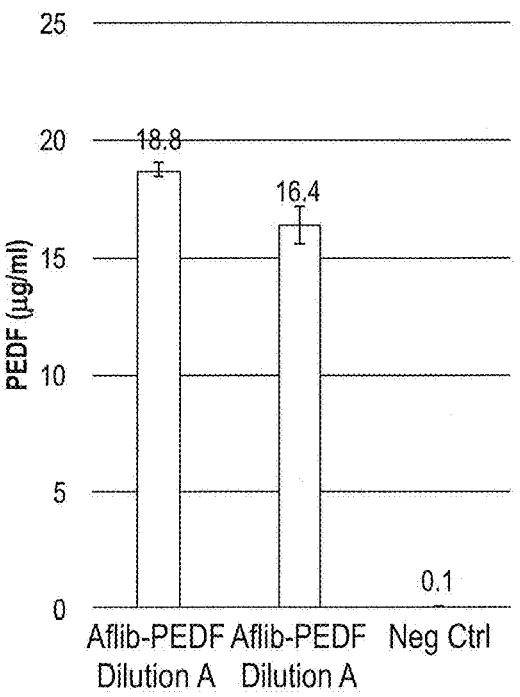
FIGS. 12A-B illustrate PEDF expression from dual protein constructs (encoding AFLB+ PEDF) following plasmid transfection of HEK293T cells
Figure 12B:
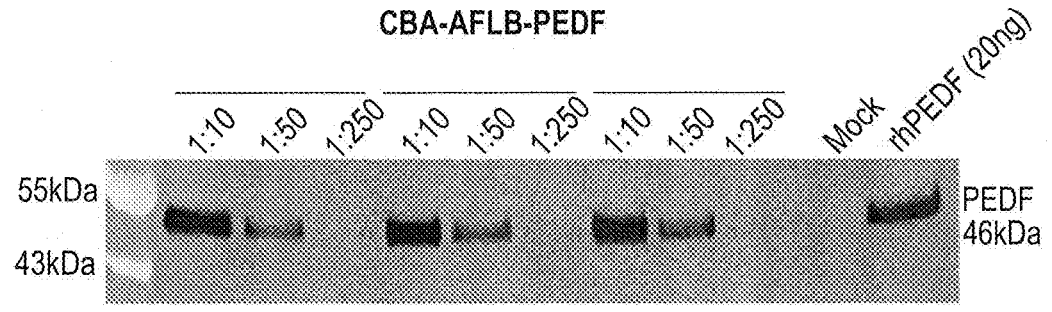

FIGS. 12A-B illustrate expression of a single protein product of the expected size for PEDF from transfected HEK293T cells, with production of ~17 mg/ml PEDF.

VEGFR3-Fc expression in HEK293T cells was assessed following transfection. with AAV plasmid dual protein construct encoding aflibercept and VEGFR3-Fc. Briefly, HEK293T cells were seeded in 12-well plates at 2.0× 10^5 cells/well in 1.0 ml DMEM/10% FBS media. HEK293T cells were used due to their high transfectability and protein expression. The next day, 1.0 mg plasmid DNA complexed with 3.0 ml FuGene6 (Cat. #E2691, Promega, Madison, WI) was added to the cells in duplicate wells. Two days after transfection, the supernatants were collected. Cell debris were pelleted by centrifugation in a microcentrifuge at 12,000 g for 10 minutes at 4° C. The supernatant was collected and stored at 4° C. A no plasmid condition was included in the transfection as negative control.

For reducing Western Blotting, cell soups (20 ml) was mixed with 10 ml 4× LDS, 4 ml 10× Reducing Agent, and 6 ml water (final volume=40 ml) and denatured at 70° C. for 10 minutes. Samples were loaded on a 12-well Bolt 4-12% Bis-Tris Plus polyacrylamide gel (Invitrogen, NW04122BOX) and ran in 1× MOPS buffer at 100 V for 75 minutes. Separated proteins were transferred to a nitrocellulose filter with the iBlot 2 device (ThermoFisher) for 10 minutes and probed with HRP-conjugated goat anti-Human IgG Fe (ThermoFisher Scientific, Cat. #31413, 1:2000) using the iBind Flex device (ThermoFisher). Proteins were visualized with SuperSignal West Dura Chemiluminescent Substrate (ThermoFisher 34076) and imaged on a Chemi-Doc MP (BioRad, Hercules, CA).

For non-reducing Western Blotting, cell supernatant (30 ml) was mixed with 10 ml 4× LDS (final volume=40 ml) and denatured at 70° C. for 10 minutes. Samples were loaded on a 12-well Bolt 4-12% Bis-Tris Plus polyacrylamide gel (Invitrogen, NW04122BOX) and ran in 1× MOPS buffer at 100 V for 120 minutes. Separated proteins were transferred to a nitrocellulose filter with the iBlot 2 device (ThermoFisher) for 10 minutes and probed with HRP-conjugated goat anti-Human IgG Fc (ThermoFisher Scientific, Cat. #31413, 1:2000) using the iBind Flex device (ThermoFisher). Proteins were visualized with SuperSignal West Dura Chemiluminescent Substrate (ThermoFisher 34076) and imaged on a ChemiDoc MP (BioRad, Hercules, CA).

Figure 13A:
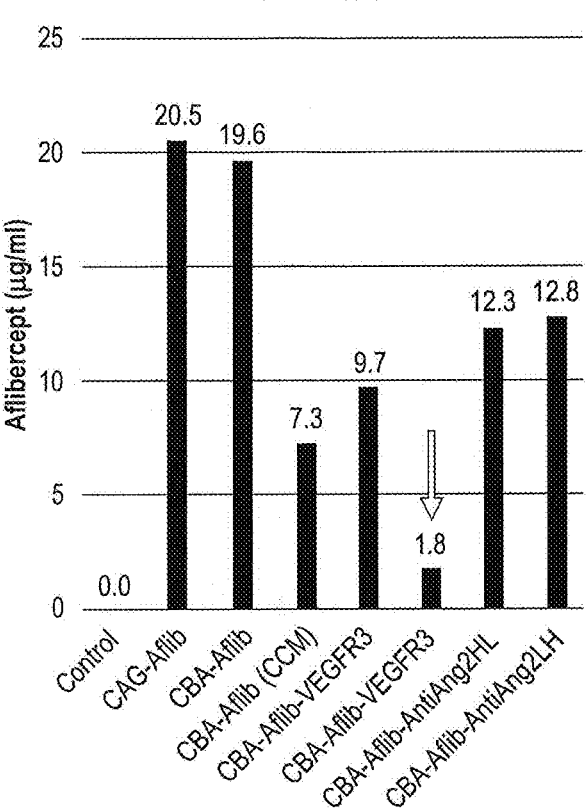
FIGS. 13A-B illustrate VEGFR3-Fc expression from dual protein constructs (encoding AFLB+ VEGFR3-Fc) following plasmid transfection of HEK293T cells. Dramatic loss of aflibercept is shown by ELISA, resulting from heterodimerization.
Figure 13B:
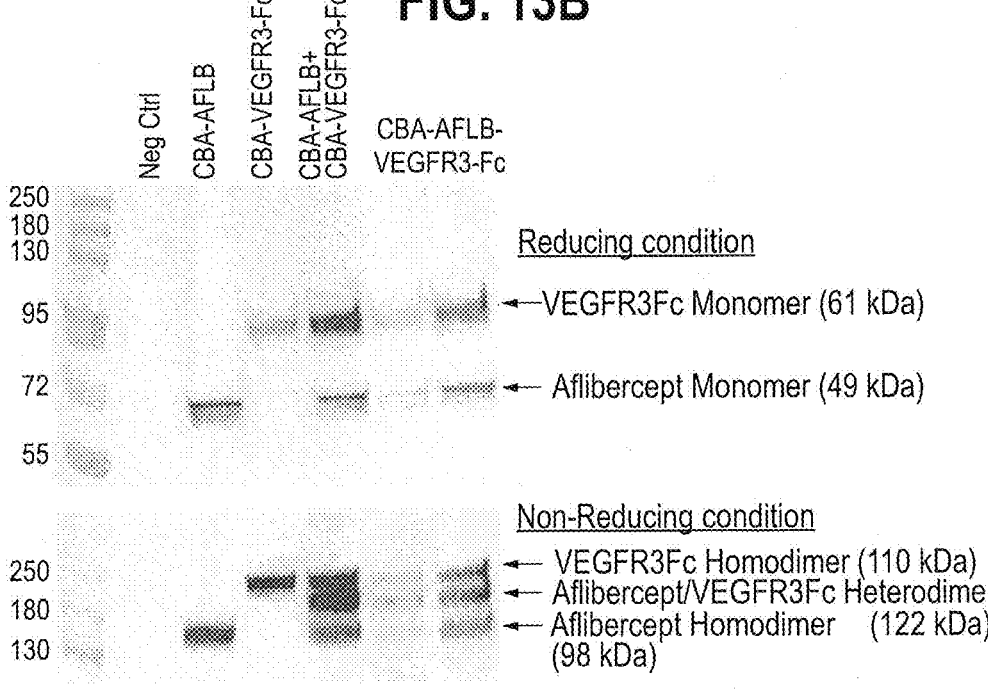

FIG. 13A compares expression of aflibercept following transfection of HEK293T cells with dual protein AAV constructs also encoding PEDF, VEGFR3-Fe, Anti-Ang-2 HL or Anti-Ang-2 LH. FIG. 13B illustrates a dramatic reduction in aflibercept when co-expressed with VEGFR3-Fc due to formation of VEGFR3-Fc/Aflibercept heterodimers

Example 3—Characterization of Constructs Encoding Aflibercept+ RNAi

The general strategy employed was to (i) design shRNA against human targets (ii) select shRNA sequence based on (a) knockdown of endogenous expression of target using lentivirus and (b) homology to NHP sequences (iii) embed miR-E containing sequences from selected shRNA within intron of CAG in anti-VEGF-expressing plasmids or in combination with RFP to assess RNAi function alone.

Ang2 and VEGFR3 are both expressed by endothelial cells—transduction of endothelial cells by rAAV comprising a capsid protein of SEQ ID NO:48 was confirmed. Characterization of constructs comprising RNAi targeting Ang-2

Figure 14:
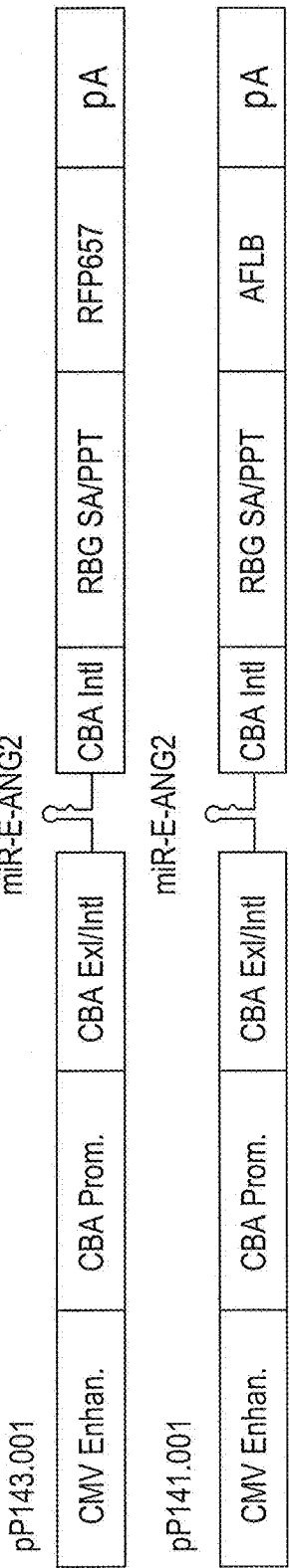
FIG. 14 illustrates constructs pP143.001 (miRNA-only efficacy control) and pP141.001, encoding Ang2 miR-E (RNAi sense and antisense strands embedded within miR-E backbone) and RPF657 (pP143.001) or AFLB (pP141.001).

Construction of pAAV-CAG-miR-E (Ang-2)-AFLB-SV40 (see FIG. 14; constructs pP143.001 encodes RFP675 and pP141.001 encodes aflibercept but are otherwise identical; pP143.001 is an miRNA only efficacy control for in vitro studies). The pAAV-CAG-AFLB-SV40 construct expressing human codon optimized Aflibercept, VEGF-A/B Trap was synthesized. The miR-E-(ANG-2) miRNA transgene containing the region of the CAG beta-actin intron encoded between the SgrAI and NheI restriction cloning sites was synthesized and cloned into pUC57 by Genscript (Genscript, Picataway, NJ). pUC57 μlasmid and the pAAV-CAG-AFLB-SV40-Kan-Stuffer plasmid were cut with various restriction enzymes (New England Biolabs) as indicated, backbone DNA was also treated with recombinant shrimp alkaline phosphatase (rSAP, M0371L, New England Biolabs) during digest to remove free phosphates on cut DNA ends. DNA fragments were added at a 7:1 molar ratio insert:backbone and ligated with Quick Ligase per manufacturer's instructions (#M2200L, New England Biolabs). Ligated plasmid was transformed into NEB Stable bacterial competent cells (#C3040H, New England Biolabs) per manufacturer's instructions and the cells were spread on Kanamycin 50 mg/ml plates (#L1025, Teknova, Hollister, CA) and grown at 30 C.

Miniprep cultures were grown from the resulting colonies (7.1), DNA was prepared with the GeneJET Plasmid Miniprep kit (Cat. #0503, ThermoFisher, Waltham, MA) and restriction digested to identify positive clones. A 50-ml culture in Terrific Broth was grown from one positive clone and DNA was prepared with the Qiagen EndoFree Plasmid Maxi Kit (Cat. #12362, Qiagen, Hilden, Germany). Maxiprep plasmid DNA (0.5 mg) was digested with various restriction enzymes (New England BioLabs) according to the manufacturer's instructions and analyzed by agarose gel electrophoresis. Sanger DNA sequencing was performed by ELIM using primers.

Several shRNA sequences targeting Ang-2 (the five sequences listed in Table 1) were evaluated for their ability to reduce expression of Ang-2 in HUVEC cells. Briefly, pooled Human umbilical vein endothelial cells were sourced from Lonza (Catalog #C2519A) and cultured in Lonza Endothelial Cell Growth medium (EGM-2, Catalog #: CC-3162) according to manufacturer instructions. HUVECs were passaged using PBS (without Ca and Mg), Trypsin 0.05% and Defined trypsin inhibitor. HUVECs were seeded into plastic (uncoated) cell cultureware at a density of 2,500 cells per $cm^2$. Assays were typically performed in 24-well cell culture plates with a 0.5 mL volume of EGM-2, refreshed every other day. HUVECs were typically used only before passage 8, upon which a new culture would be initiated.

HUVEC Transduction—HUVECs were seeded into assay plates at 2,500 cells per $cm^2$. After two days, cells were confluent and a single well was dissociated and counted. Multiplicity of infection was calculated using qPCR-derived viral titer and the cell count. The appropriate volume of AAV was applied to the cells in 0.5 mL EGM-2 media. This was incubated for 48 hours and final assay takedown was performed at one week post-transduction.

Generation of ANG2 shRNA Lentiviral Lines—pLKO.1-shANG2 plasmids were generated by ligation of annealed phosphorylated oligos, corresponding to 5 unique target sequences in human ANG2 identified from the Broad RNAi consortium (Table 1), into the pLKO.1 vector (Sigma Aldrich, Cat #: SCH001) via EcoRI and AgeI (New England Biolabs) restriction cloning. Plasmid was confirmed by sequencing as with AAV vectors. Maxi prep DNA was generated as with AAV vectors. HEK293T cells were seeded in 6-well plates at $5.0 \times 10^5$ cells/well in 2.0 ml DMEM/10% FBS media. The next day, 0.5 ug pSF-GFP plasmid DNA, 4.6 uL of MISSION Lentiviral Packaging Mix (Sigma Aldrich, Cat #: SHP001) complexed with 2.7 ul FuGene6 (Cat. #E2691, Promega, Madison, WI) was added to the cells. The next day, the media was replaced with 2 mL of fresh media. On the two subsequent days, media containing lentivirus was collected and replaced on the cells with fresh media. Supernatant was collected and filtered with a 0.45 um syringe filter (Millipore Sigma, Cat #SLHVM33RS), aliquoted and stored at −80 C. Lentivirus was titered using the Lenti-X™ qRT-PCR Titration Kit via qPCR manufacturer's instructions (Takara, Cat #631235). Human umbilical vein endothelial cells (HUVECs) (#PCS-100-O13, ATCC) were seeded at $2.0 \times 10^5$ cells/well in 6 well plates in 2 ml complete EGM-2 media (CC-3162, Lonza). Immediately after plating, cells were transduced with lentivirus at a multiplicity of infection (MOI) of 25 viral genomes per cell. After 48 hrs, media containing lentivirus was removed and replaced with fresh media containing 1.5 ug/mL puromycin (10 mg/ml stock solution, Sigma Aldrich, Cat #: P9620-10 ml). After 72 hrs of selection with puromycin, media containing dead-uninfected cells was removed. Cells expressing shRNA were continually cultured in 1.0 ug/mL puromycin in all experiments to retain shRNA expression. Media and lysate of infected HUVECs was analyzed by ELISA for ANGPT2

Figure 15A:
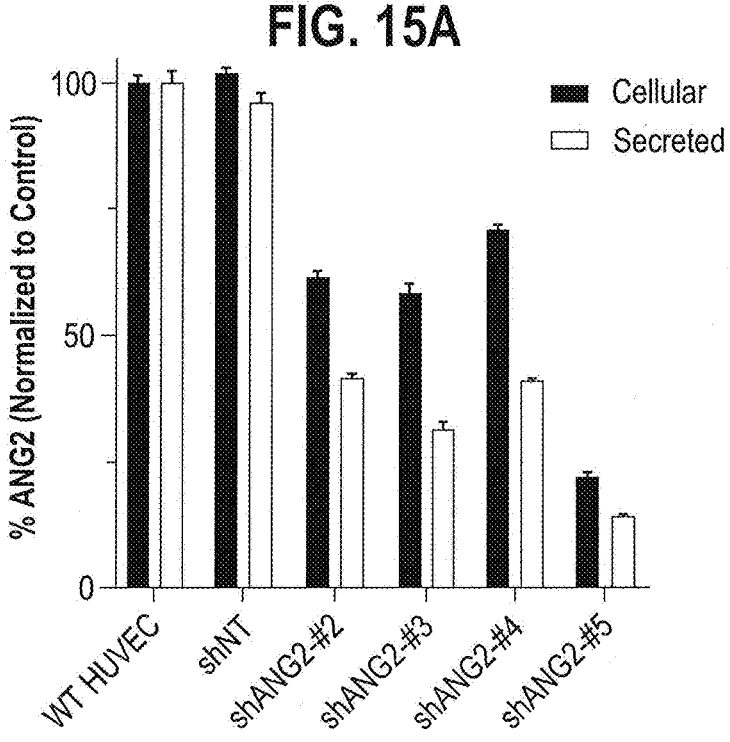
FIGS. 15A-B illustrate kD of Ang2 by ELISA (secreted and cellular) following transduction of HUVECs with the indicated shAng2 constructs, normalized to control (FIG. 15A) or non-normalized (FIG. 15B)
Figure 15B:
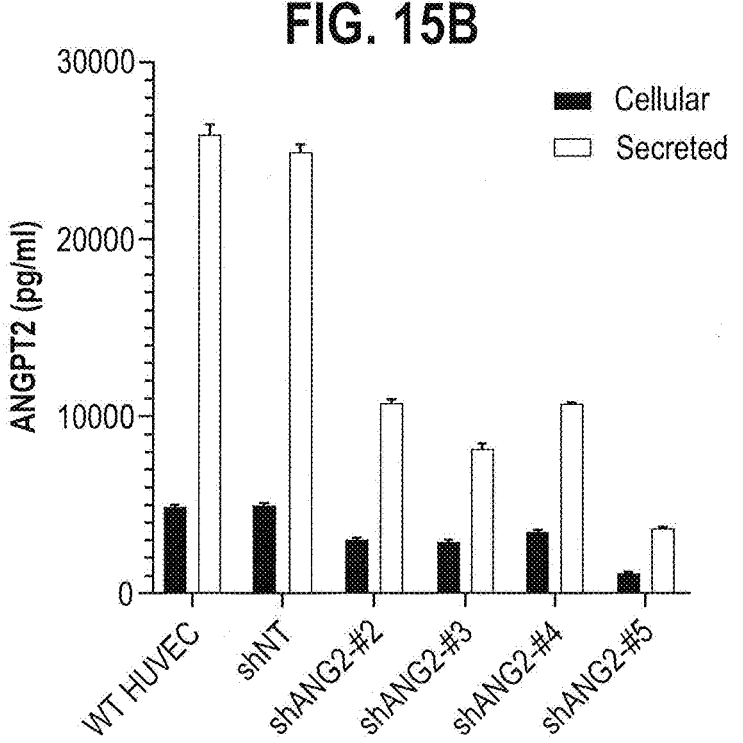

FIGS. 15A-B illustrate the percent of Ang-2 (secreted and cellular) in HUVEC cells following transduction with lentivirus containing each of the candidate shRNAs. All constructs worked well (>50% KD in secreted Ang-2), with shRNA #5 exhibiting the greatest reduction of Ang-2 protein from HUVECs. Notably, shRNAs #1, #4, and #5 are perfect matches in non-human primates. shRNA #5 was selected for inclusion into AAV plasmid constructs encoding aflibercept and miRNA targeting Ang-2. Ang-2 shRNAs #1-5 comprise the following sense and antisense strand sequences:

| shRNA Sequence # | Sense Strand Sequence | Antisense Strand Sequence |
|---|---|---|
| 1 | GCCGCAGCCTATAACAACTTT (SEQ ID NO: 1) | AAAGTTGTTATAGGCTGCGGC (SEQ ID NO: 2) |
| 2 | CCCTAATTCTACAGAAGAGAT (SEQ ID NO: 4) | ATCTCTTCTGTAGAATTAGGG (SEQ ID NO: 5) |
| 3 | GATGATAGAAATAGGGACAAA (SEQ ID NO: 7) | TTTGTCCCTATTTCTATCATC (SEQ ID NO: 8) |
| 4 | GCCACGGTGAATAATTCAGTT (SEQ ID NO: 10) | AACTGAATTATTCACCGTGGC (SEQ ID NO: 11) |
| 5 | GCTTACTCATTGTATGAACAT (SEQ ID NO: 13) | ATGTTCATACAATGAGTAAGC (SEQ ID NO: 14) |

Next, human retinal microvascular endothelial cells were transduced with rAAV comprising a capsid protein of SEQ ID NO:48 and a nucleic acid encoding miRNA comprising the sense and antisense strands of shRNA #5 (the sense and antisense strands of shRNA #5 were embedded within mir-E and the miRNA was placed within the hybrid intron of the CAG promoter). rAAV comprising a capsid protein of SEQ ID NO:48 and a nucleic acid encoding GFP under the control of CAG promoter was used as a control.

Briefly, human retinal microvascular endothelial cells were purchased from Cell Systems (Catalog number ACBRI 181) along with "The System" (catalog number CSS-A101), which contains media, coating matrix, and passaging reagents. All passaging, cryopreservation, and cell thawing were performed according to manufacturer's instructions. Cultures are vialed by Cell Systems at passage 3 and, upon receipt, this vial was expanded and cryopreserved as a bank. Experiments were performed on cultures only before passage 9. Experiments were typically performed in 24-well plates, passaged at a 1:3 ratio (1E+ 4 cells per cm²). The media volume was 1 mL per well and media replenished every other day until passage.

For RMVEC transduction, RMVEC were seeded at a density of 1E+ 4 cells/cm² in attachment factor coated 24-well cell culture plates. This density is sufficient for confluence at 3 days post-seeding. AAV carrying a CAG-GFP payload was added to the cell for 48 hours at MOIs calculated by a cell count at the time of transduction and qPCR-derived viral titer. The transduction volume was the same as the standard culture volume (1 ml per well of a 24-well plate). After transduction, media was replenished and every other day thereafter until final readout at seven days post-transduction.

ELISAs for secreted free-AFLB, ANGPT2, and VEGF-A Levels—Cell lysates for ELISA were prepared in M-PER lysis buffer (#78501, Thermo) supplemented with 1× Halt Protease and Phosphatase Inhibitor Cocktail (78440, Thermo) as per manufacturer's instructions. Cell media and lysate were diluted appropriately for each sample and were used to evaluate secreted analyte levels using the Aflibercept ELISA kit (to measure free AFLB levels) (Cat. #IG-AA115, Eagle Biosciences, Nashua, NH), the Quantikine human VEGF-A ELISA kit (DVE00, R&D Systems) and the Quantikine human ANGPT2 ELISA kit (DANG20, R&D Systems) following the provider's instructions. The optical density (OD) was measured with a Cytation 3 (BioTek, Winooski, VT) photometer at 450 nm (reference at OD 620 nm) within 15 min after pipetting the Stop Solution. Media concentrations were defined based on the generated standard curve.

RT-qPCR of Mature miRNAs and Targets from Transduced Cells—cells were lysed on the plate in RLT and total RNA containing miRNAs was purified using the Qiagen RNeasy kit per manufacturer's instructions (#74104, Qiagen), with the modifications for isolating miRNA suggested in the manufacturers supplemental protocol. Briefly, RLT lysate was filtered through a gDNA elimination column, followed by addition of 1.5 volumes of 100% Ethanol to lysate. After running through RNeasy mini column, Wash step with RW1 was skipped and proceeded directly to washing with buffer RPE. Total cDNA was produced using the Maxima RT with dsDNA kit (#M1681, Thermo-Fisher) as per manufacturer's instructions from 100 ng of total RNA. qPCR was performed using TaqMan Fast Advanced Mastermix (#4444963, Thermo-Fisher) and predesigned Taqman probe sets targeting ANGPT2 (Hs00169867_m1, Thermo), a custom Tagman assay against our human optimized AFLB (AR7DTHZ, Thermo) and RPL32 (Hs07291819_s1, Thermo) as a housekeeping control for normalization. Measured levels of VEGF-C and AFLB were normalized to RPL32 expression and expressed as a function of percent reduction from an untreated or vehicle treated control. miRNA specific cDNA was produced using the TaqMan miRNA RT Kit (#4366596, Thermo) as per manufacturer's instructions using 10 ng total RNA and the custom RT primers provided with the ANG2 custom miRNA Taqman Assay (CTU6249, Thermo) targeting the FL mature miRNA guide sequence: 5'—AAUGUUCAUACAAUG-AGUAAGC-3' (SEQ ID NO:72). qPCR was performed using TaqMan Fast Advanced Mastermix (#4444963, Thermo-Fisher) and custom Taqman probe sets targeting ANG2 (CTU6249, Thermo). A standard curve was generated from the custom miRvana miRNA mimic of ANG2 (AKS063L, Thermo) with input ranging from 1e9 to 1e2 copies of the miRNA mimic RT product per reaction, miRNA concentrations were calculated from the generated standard curve.

Figure 16A:
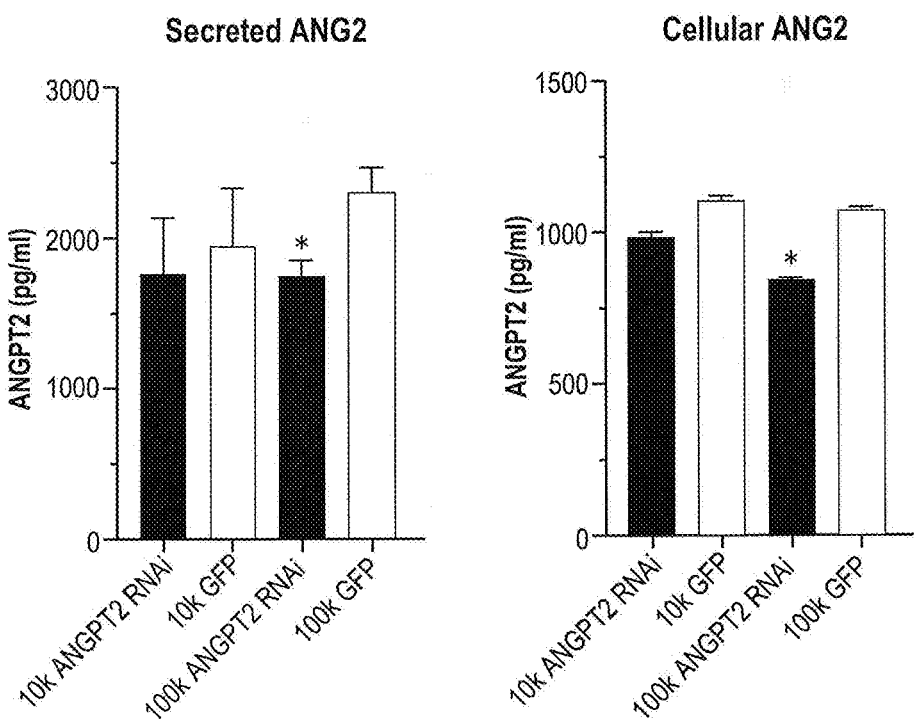
FIGS. 16A-B FIG. 16A illustrates results of Ang2 ELISA (secreted and cellular) following transduction of human RMVEC cells with rAAV comprising a capsid protein of SEQ ID NO:48 and a nucleic acid encoding miRNA comprising the sense and antisense strands of shRNA #5 (as described in FIGS. 15A-B) embedded within an miR-E backbone.
Figure 16B:
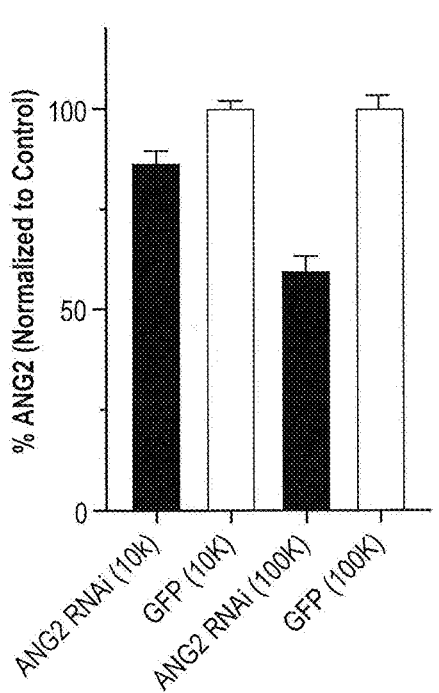
Figure 17A:
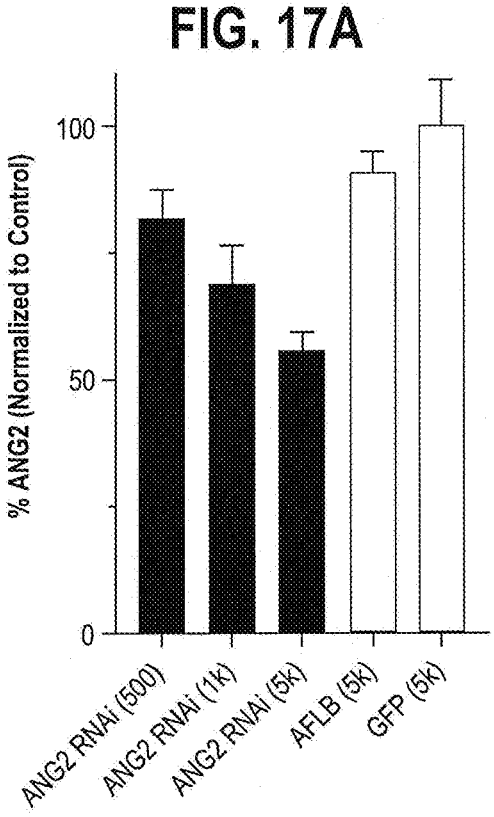
FIGS. 17A-B illustrate Ang2 RNA levels (RT-qPCR.
Figure 17B:
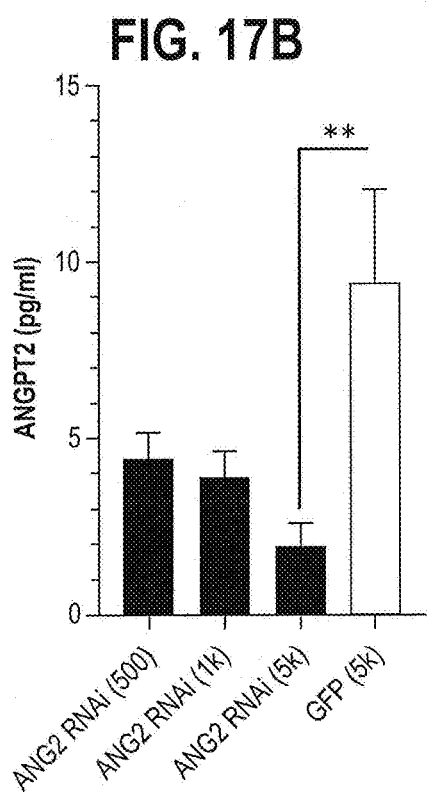

FIG. 16A illustrates results of Ang-2 ELISA showing a reduction of secreted and cellular Ang-2 protein (endogenously made by RMVEC cells) by expression of miRNA targeting Ang-2 in transduced RMVEC cells. A significant decrease in Ang-2 secretion is observed at MOI of 100K; a trend for decreased secretion is also observed at MOI 10 k. A marked decrease in Ang-2 was observed in cellular samples. FIG. 16B illustrates a significant decrease in expression of Ang-2 mRNA at 100 k MOI in transduced RMVEC cells by Ang-2 qPCR Next, Ang-2 levels were assessed in human RPE cells following transduction with rAAV (the same as described above for RMVEC cells). FIGS. 17A-B illustrate Ang-2 levels at day 8 (post-transduction) in RPE cells by RT-qPCR (FIG. 17A—mRNA levels) and ELISA (FIG. 17B—protein levels). A strong decrease in Ang-2 RNA levels is observed, with KD increasing with increasing MOL Notably, Ang-2 protein levels in RPE are quite low; however, a trend is observed toward increased KD of Ang-2 protein compared to GFP control-transduced cells at all MOI, trending towards more KD with increased MOI. Significance is observed in matched MOIs.

Next, the effect of including RNAi targeting Ang-2 or VEGF-C on aflibercept expression in dual constructs was assessed in RMVEC cells. Briefly, RMVEC cells were transduced with rAAV comprising a capsid protein of SEQ ID NO:48 and a nucleic acid encoding (i) AFLB only (CAG-AFLB) (ii) encoding AFLB and miRNA targeting Ang-2 (CAG-AFLB-ANG2-RNAi) or (iii) encoding AFLB and miRNA targeting VEGF-C(CAG-AFLB-VEGFC-RNAi).

RMVEC were seeded at a density of $1E+4$ cells/cm$^2$ in attachment factor coated 24-well cell culture plates. This density is sufficient for confluence at 3 days post-seeding. AAV carrying a CAG-GFP payload was added to the cell for 48 hours at MOIs calculated by a cell count at the time of transduction and qPCR-derived viral titer. The transduction volume was the same as the standard culture volume (1 ml per well of a 24-well plate). After transduction, media was replenished and every other day thereafter until final readout at seven days post-transduction.

RT-qPCR of Mature miRNAs and Targets from Transduced Cells—cells were lysed on the plate in RLT and total RNA containing miRNAs was purified using the Qiagen RNeasy kit per manufacturer's instructions (#74104, Qiagen), with the modifications for isolating miRNA suggested in the manufacturers supplemental protocol. Briefly, RLT lysate was filtered through a gDNA elimination column, followed by addition of 1.5 volumes of 100% Ethanol to lysate. After running through RNeasy mini column, Wash step with RW1 was skipped and proceeded directly to washing with buffer RPE. Total cDNA was produced using the Maxima RT with dsDNA kit (#M1681, Thermo-Fisher) as per manufacturer's instructions from 100 ng of total RNA. qPCR was performed using TaqMan Fast Advanced Mastermix (#4444963, Thermo-Fisher) and predesigned Taqman probe sets targeting ANGPT2 (Hs00169867_m1, Thermo), a custom Taqman assay against our human optimized AFLB (AR7DTHZ, Thermo) and RPL32 (Hs07291819_s1, Thermo) as a housekeeping control for normalization. Measured levels of VEGF-C and AFLB were normalized to RPL32 expression and expressed as a function of percent reduction from an untreated or vehicle treated control. miRNA specific cDNA was produced using the TaqMan miRNA RT Kit (#4366596, Thermo) as per manufacturer's instructions using 10 ng total RNA and the custom RT primers provided with the ANG2 custom miRNA Taqman Assay (CTU6249, Thermo) targeting the FL mature miRNA guide sequence: 5'—AAUGUUCAUACAAUG-AGUAAGC-3' (SEQ ID NO:72). qPCR was performed using TaqMan Fast Advanced Mastermix (#4444963, Thermo-Fisher) and custom Taqman probe sets targeting ANG2 (CTU6249, Thermo). A standard curve was generated from the custom miRvana miRNA mimic of ANG2 (AKS063L, Thermo) with input ranging from 1e9 to 1e2 copies of the miRNA mimic RT product per reaction. miRNA concentrations were calculated from the generated standard curve.

ELISAs for secreted free-AFLB, ANGPT2, and VEGF-A Levels—cell lysates for ELISA were prepared in M-PER lysis buffer (#78501, Thermo) supplemented with 1× Halt Protease and Phosphatase Inhibitor Cocktail (78440, Thermo) as per manufacturer's instructions. Cell media and lysate were diluted appropriately for each sample and were used to evaluate secreted analyte levels using the Aflibercept ELISA kit (to measure free AFLB levels) (Cat. #IG-AA 115, Eagle Biosciences, Nashua, NH), the Quantikine human VEGF-A ELISA kit (DVE00, R&D Systems) and the Quantikine human ANGPT2 ELISA kit (DANG20, R&D Systems) following the provider's instructions. The optical density (OD) was measured with a Cytation 3 (BioTek, Winooski, VT) photometer at 450 nm (reference at OD 620 nm) within 15 min after pipetting the Stop Solution. Media concentrations were defined based on the generated standard curve.

Figure 18A:
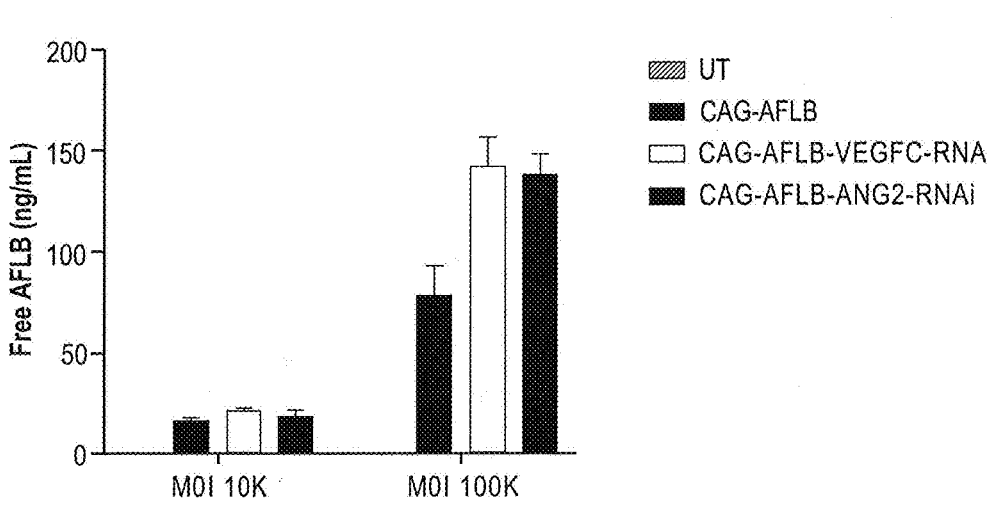
FIGS. 18A-B illustrate free AFLB protein levels (FIG. 18A) and AFLB mRNA levels (FIG. 18B) in RMVEC cells eight days after transduction at the specified MOIs with rAAV comprising a capsid protein of SEQ ID NO:48 and the specified nucleic acid constructs.
Figure 18B:
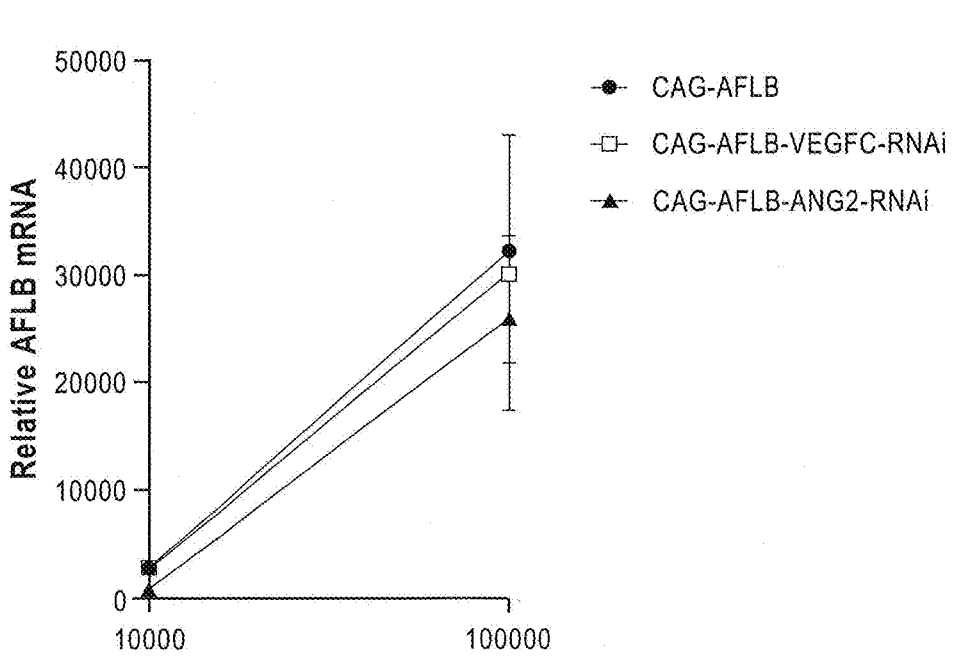
Figure 19A:
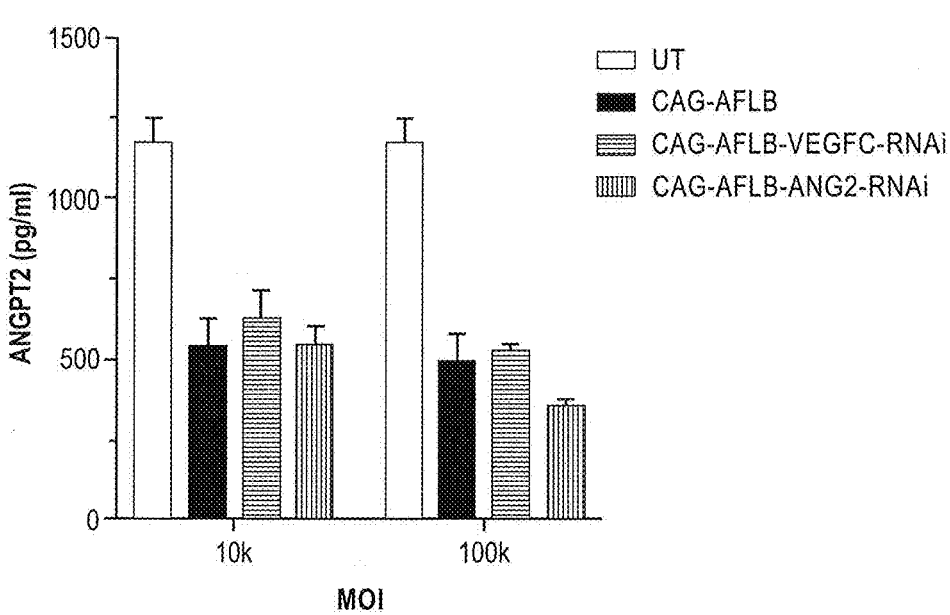
FIGS. 19A-C illustrate Ang2 secretion (FIG. 19A) and Ang2 RNA levels (FIGS. 19B and 19C) in RMVEC cells eight days after transduction with rAAV comprising a capsid protein of SEQ ID NO:48 and the specified nucleic acid constructs.
Figure 19B:
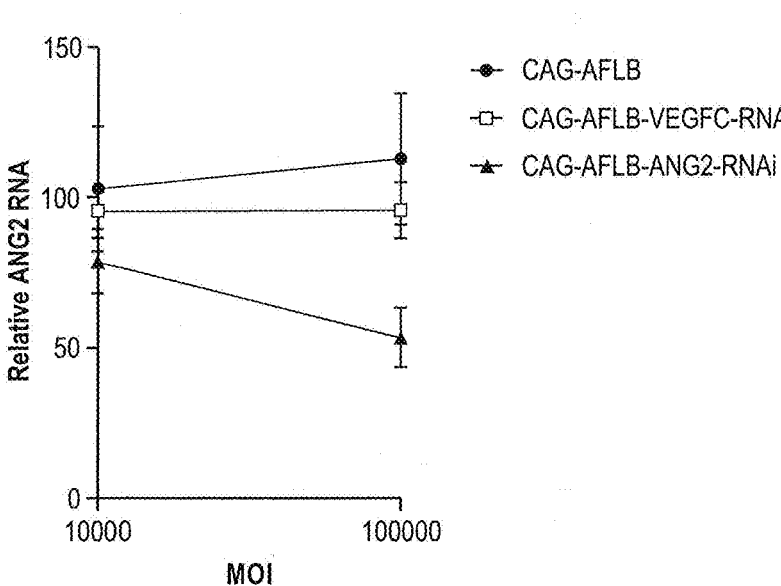

Aflibercept expression was assessed on day 8. FIG. 18A illustrates an increase in free aflibercept levels following transduction with the miRNA constructs compared to transduction with the CAG-AFLB control in both the ANG2 and the VEGF-C.RNAi. FIG. 19B illustrates a corresponding dose-dependent increase in aflibercept miRNA.

Figure 19C:
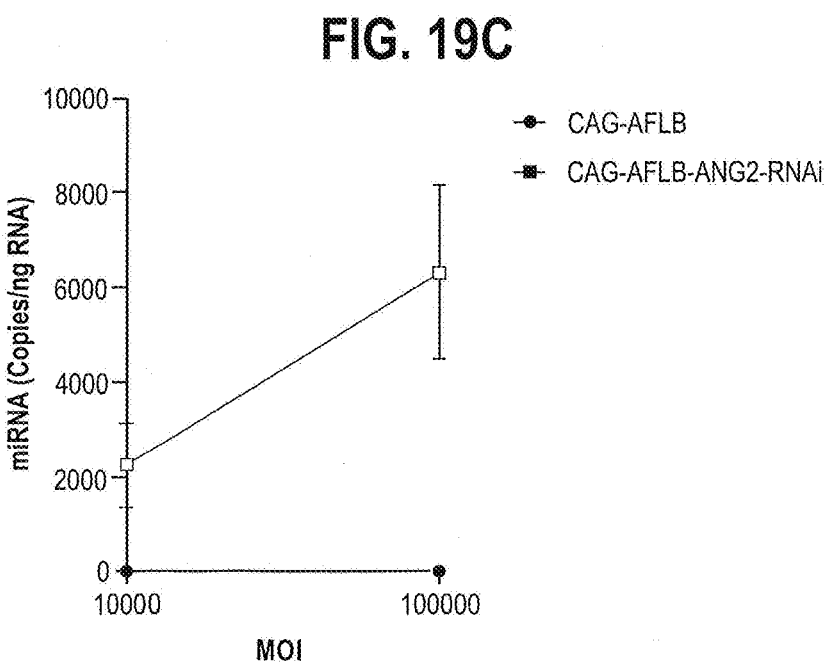

Ang-2 expression was assessed on day 8. FIG. 19A illustrates a significant decrease in Ang-2 protein levels in all constructs encoding aflibercept, with a further reduction in Ang-2 observed with miRNA targeting Ang-2 compared to other constructs at 100 k MOL. FIG. 19B illustrates a dose response in terms of decrease in Ang-2 transcripts with RNAi targeting Ang-2. Aflibercept alone doesn't appear to affect Ang-2 transcriptionally but may be preventing secretion stimulated by VEGF-A, leading to the decrease observed in supernatants (FIG. 19A). A dose-dependent increase in anti-Ang-2 miRNA (as a function of MOI) is observed (FIG. 19C).

Characterization of VEGF miRNA-Containing Vectors

AAV plasmid pP145.001 (pAAV-CAG-miR-E-(VEGFC)-AFLB-SV40) (see FIG. 2) was constructed as follows.

The pAAV-CAG-AFLB-SV40 construct expressing human codon optimized Aflibercept, VEGF-A/B Trap was synthesized. The miR-E-(VEGF-C) miRNA transgene containing the region of the CAG beta-actin intron encoded between the SgrAI and NheI restriction cloning sites was synthesized and cloned into pUC57 by Genscript (Genscript, Picataway, NJ). pUC57 μlasmid and the pAAV-CAG-AFLB-SV40-Kan-Stuffer plasmid were cut with various restriction enzymes (New England Biolabs) as indicated, backbone DNA was also treated with recombinant shrimp alkaline phosphatase (rSAP, M0371L, New England Biolabs) during digest to remove free phosphates on cut DNA ends. DNA fragments were added at a 7:1 molar ratio insert:backbone and ligated with Quick Ligase per manufacturer's instructions (#M2200L, New England Biolabs). Ligated plasmid was transformed into NEB Stable bacterial competent cells (#C3040H, New England Biolabs) per manufacturer's instructions and the cells were spread on Kanamycin 50 mg/ml plates (#L1025, Teknova, Hollister, CA) and grown at 30 C.

Miniprep cultures were grown from the resulting colonies (7.1), DNA was prepared with the GeneJET Plasmid Miniprep kit (Cat. #0503, ThermoFisher, Waltham, MA) and restriction digested to identify positive clones. A 50-ml culture in Terrific Broth was grown from one positive clone and DNA was prepared with the Qiagen EndoFree Plasmid Maxi Kit (Cat. #12362, Qiagen, Hilden, Germany).

Maxiprep plasmid DNA (0.5 mg) was digested with various restriction enzymes (New England BioLabs) according to the manufacturer's instructions and analyzed by agarose gel electrophoresis. Sanger DNA sequencing was performed by ELIM using primers.

Several shRNA sequences targeting VEGF-C were evaluated for their ability to reduce expression of VEGF-C in HEK293T cells.

Generation of VEGF-C shRNA Lentiviral Lines—pLKO.1-shVEGFC plasmids were generated by ligation of annealed phosphorylated oligos, corresponding to 5 unique target sequences in human VEGF-C identified from the Broad RNAi consortium (Table 1), into the pLKO.1 vector (Sigma Aldrich, Cat #: SCHOOl) via EcoRI and AgeI (New England Biolabs) restriction cloning. Plasmid was confirmed by sequencing as with AAV vectors. Maxi prep DNA was generated as with AAV vectors. HEK293T cells were seeded in 6-well plates at 5.0× 10^5 cells/well in 2.0 ml DMEM/10% FBS media. The next day, 0.5 ug pSF-GFP plasmid DNA, 4.6 uL of MISSION Lentiviral Packaging Mix (Sigma Aldrich, Cat #: SHP001) complexed with 2.7 ul FuGene6 (Cat. #E2691, Promega, Madison, WI) was added to the cells. The next day, the media was replaced with 2 mL of fresh media. On the two subsequent days, media containing lentivirus was collected and replaced on the cells with fresh media. Supernatant was collected and filtered with a 0.45 um syringe filter (Millipore Sigma, Cat #SLHVM33RS), aliquoted and stored at –80 C. Lentivirus was titered using the *Lenti*-X™ qRT-PCR Titration Kit via qPCR manufacturer's instructions (Takara, Cat #631235). MCF7 cells (#HTB-22, ATCC) were seeded at 5.0× 10^5 cells/well in 6 well plates in 2 ml EMEM/10% FBS media supplemented with 0.01 mg/mL human recombinant insulin (#19278-5ML, Sigma Aldrich). Immediately after plating, cells were transduced with lentivirus at a multiplicity of infection (MOI) of 25 viral genomes per cell. After 48 hrs, media containing lentivirus was removed and replaced with fresh media containing 0.75 ug/mL puromycin (10 mg/ml stock solution, Sigma Aldrich, Cat #: P9620-10 ml). After 72 hrs of selection with puromycin, media containing dead-uninfected cells was removed. Cells expressing shRNA were continually cultured in 0.5 ug/mL puromycin in all experiments to retain shRNA expression. Cells cultured with puromycin were lysed in RLT and total RNA was purified using the Qiagen RNEasy kit per manufacturer's instructions.

qPCR Analysis of MCF7 VEGF-C Knockdown—cells cultured with puromycin were lysed on the plate in RLT and total RNA was purified using the Qiagen RNeasy kit per manufacturer's instructions (#74104, Qiagen). Total cDNA was produced using the Maxima RT with dsDNA kit (#M1681, Thermo-Fisher) as per manufacturer's instructions from 5 ug of total RNA. qPCR was performed using TaqMan Fast Advanced Mastermix (#4444963, Thermo-Fisher) and predesigned Taqman probe sets targeting VEGF-C(Hs01099203_m1, Thermo) and RPL32 (Hs07291819_s1, Thermo) as a housekeeping control for normalization. Measured levels of VEGF-C were normalized to RPL32 expression and expressed as a function of percent reduction from a non-targeting shRNA.

RT-qPCR of Mature miRNAs and Targets from Transduced Cells—cells were lysed on the plate in RLT and total RNA containing miRNAs was purified using the Qiagen RNeasy kit per manufacturer's instructions (#74104, Qiagen), with the modifications for isolating miRNA suggested in the manufacturers supplemental protocol. Briefly, RLT lysate was filtered through a gDNA elimination column, followed by addition of 1.5 volumes of 100% Ethanol to lysate. After running through RNeasy mini column, Wash step with RW1 was skipped and proceeded directly to washing with buffer RPE. Total cDNA was produced using the Maxima RT with dsDNA kit (#M1681, Thermo-Fisher) as per manufacturer's instructions from 100 ng of total RNA. qPCR was performed using TaqMan Fast Advanced Mastermix (#4444963, Thermo-Fisher) and predesigned Taqman probe sets targeting VEGF-C (HsO1099203_m1, Thermo), a custom Taqman assay against our human optimized AFLB (AR7DTHZ, Thermo) and RPL32 (Hs07291819_s1, Thermo) as a housekeeping control for normalization. Measured levels of VEGF-C and AFLB were normalized to RPL32 expression and expressed as a function of percent reduction from an untreated or vehicle treated control. miRNA specific cDNA was produced using the TaqMan miRNA RT Kit (#4366596, Thermo) as per manufacturer's instructions using 10 ng total RNA and the custom RT primers provided with the VEGF-C custom miRNA Tagman Assay (CTTZ9KC, Thermo) targeting the FL mature miRNA guide sequence: 5'-AAUAACGUC-UUGCUGAGGUAGC-3' (SEQ ID NO:73). qPCR was performed using TaqMan Fast Advanced Mastermix (#4444963, Thermo-Fisher) and custom Taqman probe sets targeting VEGF-C(CTTZ9KC, Thermo). A standard curve was generated from the custom miRvana miRNA mimic of VEGF-C(AKT949T, Thermo) with input ranging from 1e9 to 1e2 copies of the miRNA mimic RT product per reaction. miRNA concentrations were calculated from the generated standard curve.

Figures 20, 21A:
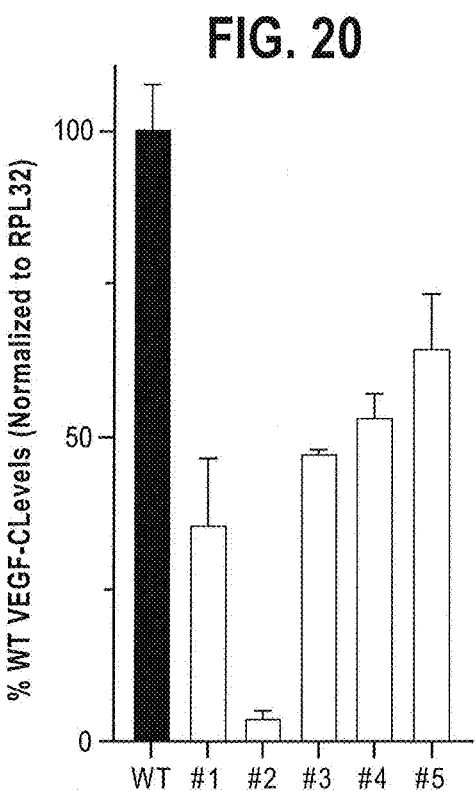
FIG. 20 illustrates the percentage of VEGF-C RNA levels (normalized to RPL32; RNA analysis by qPCR) in HEK293T cells following transduction with the indicated shVEGF-C constructs.
FIGS. 21A-C illustrate VEGF-C protein (by ELISA.

FIG. 20 illustrates the percentage of VEGF-C RNA levels (normalized to RPL32) in HEK293T cells following transduction with the shRNAs. Potent KD of VEGF-C in all constructs was observed, with shRNA #2 resulting in >90% knockdown of VEGF-C. shRNA #2 was selected for inclusion into AAV plasmid constructs encoding aflibercept and miRNA targeting VEGF-C. VEGF-C shRNAs #1-5 comprise the following sense and antisense strand sequences:

| shRNA Sequence # | Sense Strand Sequence | Antisense Strand Sequence |
|---|---|---|
| 1 | CGCGACAAACACCTTCTTTAA (SEQ ID NO: 16) | TTAAAGAAGGTGTTTGTCGCG (SEQ ID NO: 17) |
| 2 | CTACCTCAGCAAGACGTTATT (SEQ ID NO: 19) | AATAACGTCTTGCTGAGGTAG (SEQ ID NO: 20) |
| 3 | ACCAATTACATGTGGAATAAT (SEQ ID NO: 22) | ATTATTCCACATGTAATTGG (SEQ ID NO: 23) |
| 4 | ATGACCAAACAGCCAAGATTT (SEQ ID NO: 25) | AAATCTTGGCTGTTTGGTCA (SEQ ID NO: 26) |
| 5 | GTCGTTGTGTCCCTTCATATT (SEQ ID NO: 28) | AATATGAAGGGACACAACGAC (SEQ ID NO: 29) |

Next, human RPE cells were transduced with rAAV comprising a capsid protein of SEQ ID NO:48 and a nucleic acid encoding miRNA comprising the sense and antisense strands of shRNA #2 (the sense and antisense strands of shRNA #2 were embedded within mir-E and the miRNA was placed within the hybrid intron of the CAG promoter). rAAV comprising a capsid protein of SEQ ID NO:48 and a nucleic acid encoding GFP under the control of CAG promoter was used as a control.

RPE Transduction—human stem cell derived retinal pigment epithelial cells (RPE) were differentiated from embryonic stem cells (ESI-017) following published protocols (Buchholz D 2013, Leach L 2015). RPE cells were grown on Matrigel (Corning) for 30 days in XVIVO-10 media (Lonza), in a 96 well plate format. Prior to transduction, three wells were harvested and counted for an accurate calculation of multiplicity of infection (MOI). Virus was added to the cells for 48 hours in XVIVO10 media based on each viral titer in a total volume of 100 μL per well. Media was collected on day 3, 7, 11, 15 and 19 and replaced with 200 μL of media per well. Media samples were stored at 4° C. until processed.

ELISAs for secreted free-AFLB, ANGPT2, and VEGF-A Levels—cell lysates for ELISA were prepared in M-PER lysis buffer (#78501, Thermo) supplemented with 1× Halt Protease and Phosphatase Inhibitor Cocktail (78440, Thermo) as per manufacturer's instructions. Cell media and lysate were diluted appropriately for each sample and were used to evaluate secreted analyte levels using the Aflibercept ELISA kit (to measure free AFLB levels) (Cat. #IG-AA115, Eagle Biosciences, Nashua, NH), the Quantikine human VEGF-A ELISA kit (DVE00, R&D Systems) and the Quantikine human ANGPT2 ELISA kit (DANG20, R&D Systems) following the provider's instructions. The optical density (OD) was measured with a Cytation 3 (BioTek, Winooski, VT) photometer at 450 nm (reference at OD 620 nm) within 15 min after pipetting the Stop Solution. Media concentrations were defined based on the generated standard curve.

FIG. 21A illustrates VEGF-C levels (by ELISA) in RPE cells following transduction with rAAV carrying the indicated constructs. A dose-dependent decrease in VEGF-C in supernatants of RPE cells (which make VEGF-C endogenously) is observed that is specific to the VEGF-C miRNA construct. A slight decrease in VEGF-C in other constructs is observed at the highest MOI. The miRNA targeting VEGF-C is functional.

Figure 21B:
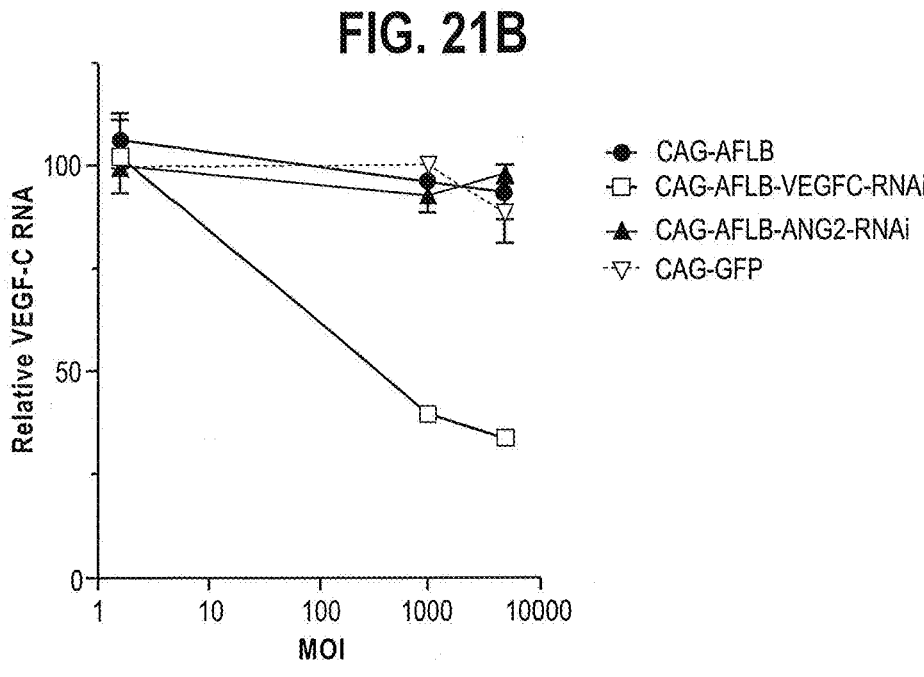

FIG. 21B illustrates a corresponding dose-dependent decrease (MOIs of 1.6, 1000 and 5000) in VEGF-C mRNA that is specific to the VEGF-C construct.

Figure 21C:
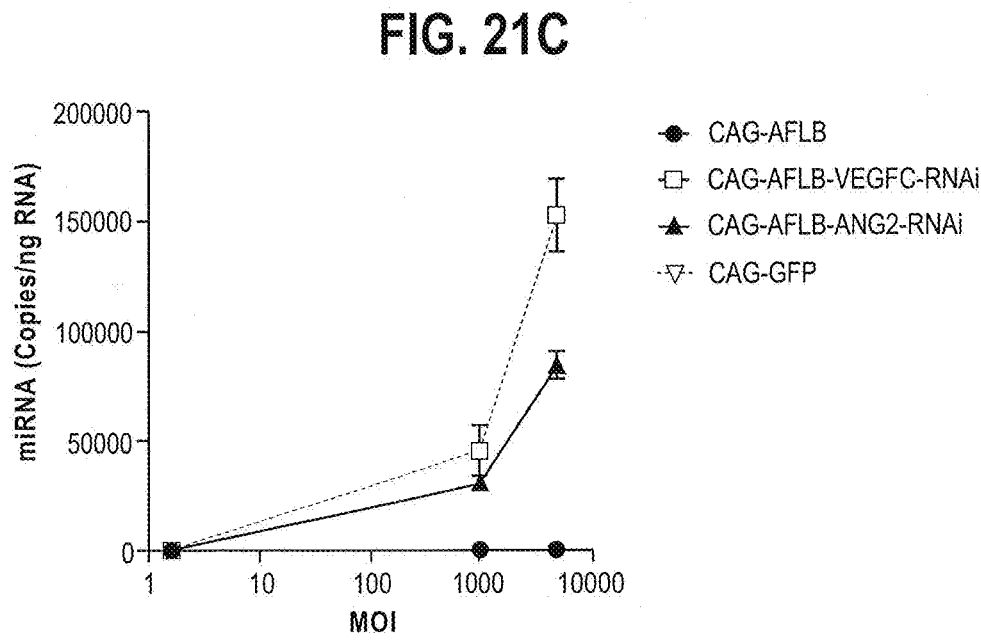

FIG. 21C illustrates a dose-dependent increase in expression of miRNA targeting VEGF-C in RPE cells.

Figure 22A:
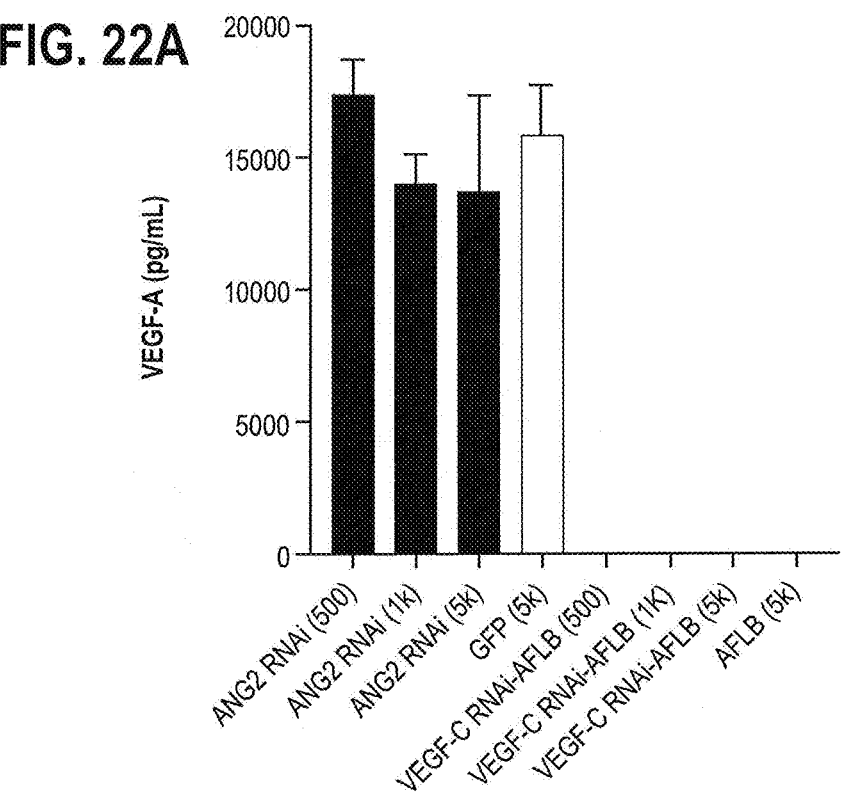
FIGS. 22A-C illustrate endogenous VEGF-A neutralization (FIG. 22A) and VEGF-C protein (FIG. 22B) and mRNA levels (FIG. 22C) in RPE cells eight days after transduction at the specified MOIs with rAAV comprising a capsid protein of SEQ ID NO:48 and the specified nucleic acid constructs
Figure 22B:
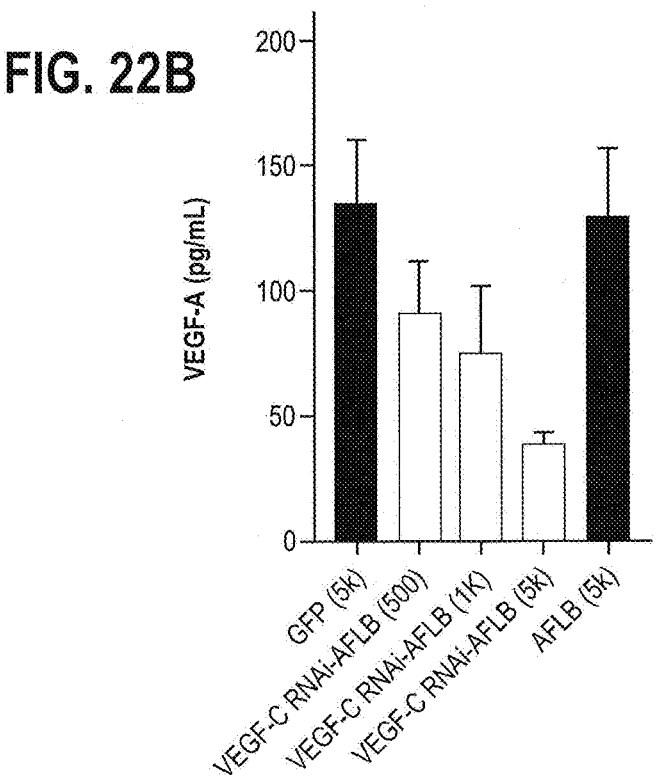
Figure 22C:
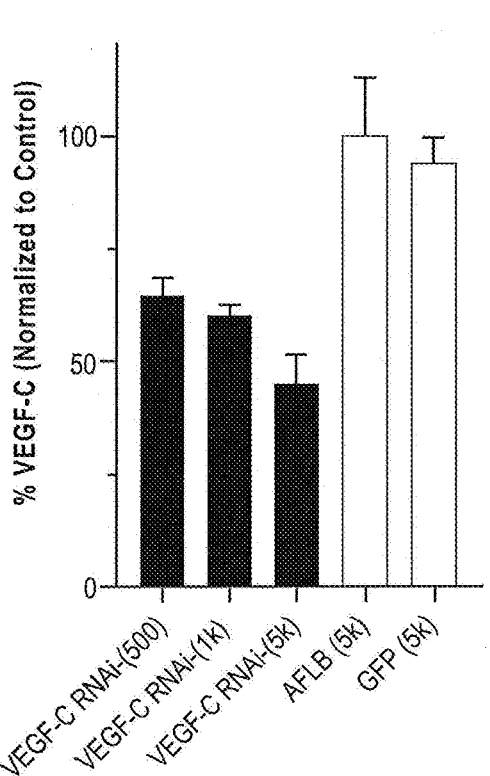

The ability of the dual constructs (encoding aflibercept+miRNA targeting VEGF-C or Ang-2) to neutralize VEGF-A in RPE cells was assessed at day 8 post-transduction with rAAV vectors comprising a capsid protein of SEQ ID NO:48 and nucleic acid comprising the dual construct ("VEGF-C RNAi-AFLB", "Ang-2 RNAi-AFLB" "AFLB"). FIG. 22A illustrates that all constructs expressing AFLB are able to completely neutralize endogenous VEGF-A at all MOI tested, Notably, constructs not expressing AFLB ("GFP", "Ang2 RNAi") do not have any significant effect on VEGF-A levels in the media. FIGS. 21B-C illustrate that VEGF-C protein (FIG. 22B; ELISA) and mRNA levels (FIG. 22C; RT-qPCR) are reduced in dose dependent manner in RPE levels following transduction with rAAV encoding miRNA targeting VEGF-C.

Example 4—Dual RNAi Vectors

A dual RNAi approach (targeting VEGF-C and Ang-2) was investigated. Representative embodiments included pP151.001, pP152.001 and pP153.001 (see FIG. 2).

pP151 comprises an miRNA targeting Ang-2 placed within an artificial intron located in the 3' UTR of the aflibercept coding region and an miRNA targeting VEGF-C placed within the hybrid intron of the CAG promoter. pP152 comprises an miRNA targeting Ang-2 placed within an artificial intron located within the aflibercept coding region and an miRNA targeting VEGF-C placed within the hybrid intron of the CAG promoter. pP153 comprises miRNA targeting Ang-2 and miRNA targeting VEGF-C, each placed at different locations within the hybrid intron of the CAG promoter.

rAAV comprising a capsid comprising SEQ ID NO:48 have been shown to transduce CD31+ endothelial cells following intravitreal administration to non-human primates ($1\times10^{12}$ vg/eye) with a transduction efficiency of ≤25% of total CD31+ cells (see FIG. 23A— rAAV comprised nucleic acid encoding GFP reporter gene).

Example 5—NHP Model of Angiogenesis

A pilot pharmacology study was performed in non-human primates (NHPs) to (i) assess acute ocular safety (ii) measure expression of aflibercept and intracellular miR targeting VEGF-C and (iii) confirm the dominant miRNA species in vivo following intravitreal administration of an rAAV comprising a capsid protein of SEQ ID NO:48 and a nucleic acid comprising nucleotide sequence encoding aflibercept and miR targeting VEGF-C. The nucleic acid comprises sense and antisense strands corresponding to SEQ ID Nos: 19 and 20 and the full construct corresponds to SEQ ID NO:69.

As shown in FIG. 24, aqueous and vitreous aflibercept (AFLB) levels were well within/above the range reported for efficacy. Robust retinal AFLB levels were detected. There was no evidence of uveitis or retinal abnormalities during the study.

As shown in FIG. 25, a high number of miRNA copies were detected across all retinas of all eyes of NHPs in the study. Inter-animal expression levels parallel what is observed with AFLB ELISA. MiSeq data confirms full-length 22-bp targeting VEGF-C as predominant miRNA species as shown in transfected HEK293T and transduced RPE cells.

Next, a proof-of-concept study was initiated to investigate the efficacy of the rAAV in an NHP model of angiogenesis. See e.g., Goody et al., Experimental Eye Research, 92(6): 464-472 (2011). Briefly, African Green NHPs, n=7 per group, were intravitreally administered the rAAV (comprising a capsid protein of SEQ ID NO:48 and a nucleic acid comprising nucleotide sequence encoding aflibercept and miR targeting VEGF-C) or vehicle at three doses (bilaterally at $1\times10^{11}$ vg/eye, $3\times10^{11}$ vg/eye or $1\times10^{2}$ vg/eye). Steroids (40 mg methylprednisolone IM weekly starting on D-1 and 2 mg triamcinolone acetonide sub-tenon post-injection) were discontinued after 4 weeks (post-administration). Laser was administered 42 days after dosing to induce choroidal neovascularization (CNV) and lesions were scored 2 and 4 weeks after CNV laser.

As illustrated in FIG. 26, evaluation of Grade IV lesion incidence revealed that treatment with all doses of the rAAV significantly blocked CNV as demonstrated by complete absence of clinically relevant Grade IV lesions in all treated groups (i.e., at all tested doses of the rAAV). See FIG. 26, compared to vehicle control. No dose-response was observed suggesting complete efficacy of the rAAV at all doses administered.

Figure 28:
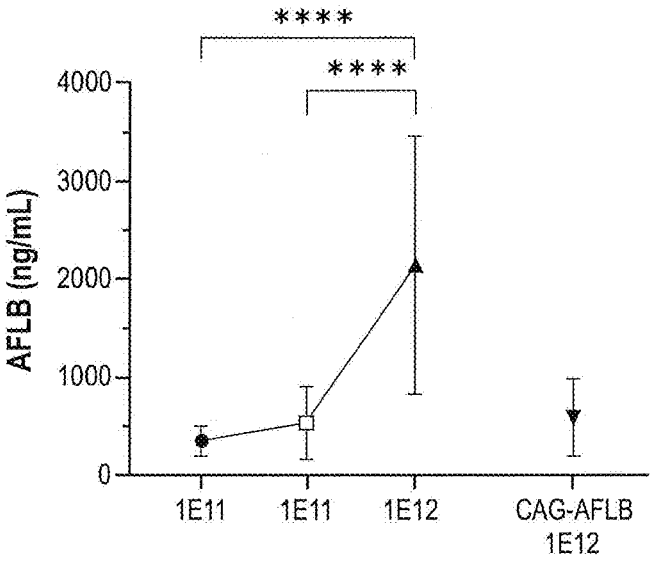
FIG. 28 illustrates aflibercept concentration (ng/ml) in aqueous humor of NHPs following a single intravitreal administration at the specified dose of (i) rAAV comprising a capsid protein of SEQ ID NO:48 and a nucleic acid encoding aflibercept and miR targeting VEGF-C(comprising the sense and antisense strands corresponding to SEQ ID Nos: 19 and 20 and the full construct corresponding to SEQ ID NO:69) or (ii) rAAV comprising capsid protein of SEQ ID NO:48 and a nucleic acid encoding aflibercept only.

Aqueous humor samples collected from the NHPs at 21 days after intravitreal administration of an rAAV comprising a capsid protein of SEQ ID NO:48 and a nucleic acid encoding aflibercept and miR targeting VEGF-C(comprising the sense and antisense strands corresponding to SEQ ID Nos: 19 and 20 and the full construct corresponding to SEQ ID NO:69), hereinafter referred to as rAAV SEQ ID NO. 48 CAG-AFLB-VEGFC-RNAi, were analyzed for aflibercept protein expression. As shown in FIG. 28, aqueous levels of aflibercept are dose dependent. Additionally, at the $1\times10^{12}$ vg/eye dose, aflibercept expression from the eyes dosed with the rAAV SEQ ID NO. 48 CAG-AFLB-VEGFC-RNAi was not inferior to rAAV comprising the capsid protein of SEQ ID NO:48 and a nucleic acid encoding aflibercept only, hereinafter referred to as rAAV SEQ ID NO. 48 CAG-AFLB.

Intraocular inflammation in the NHPs was examined with slit lamp biomicroscopy at designated time points. Scoring was applied to qualitative clinical ophthalmic findings using a nonhuman primate ophthalmic exam scoring system with a summary score derived from exam components. At designated time points, intraocular pressure (IOP) measurements were collected using a TonoVet (iCare, Finland)

tonometer set to the dog (d) calibration setting. Three measures were taken from each eye at each time point and the mean IOP defined.

Figure 29:
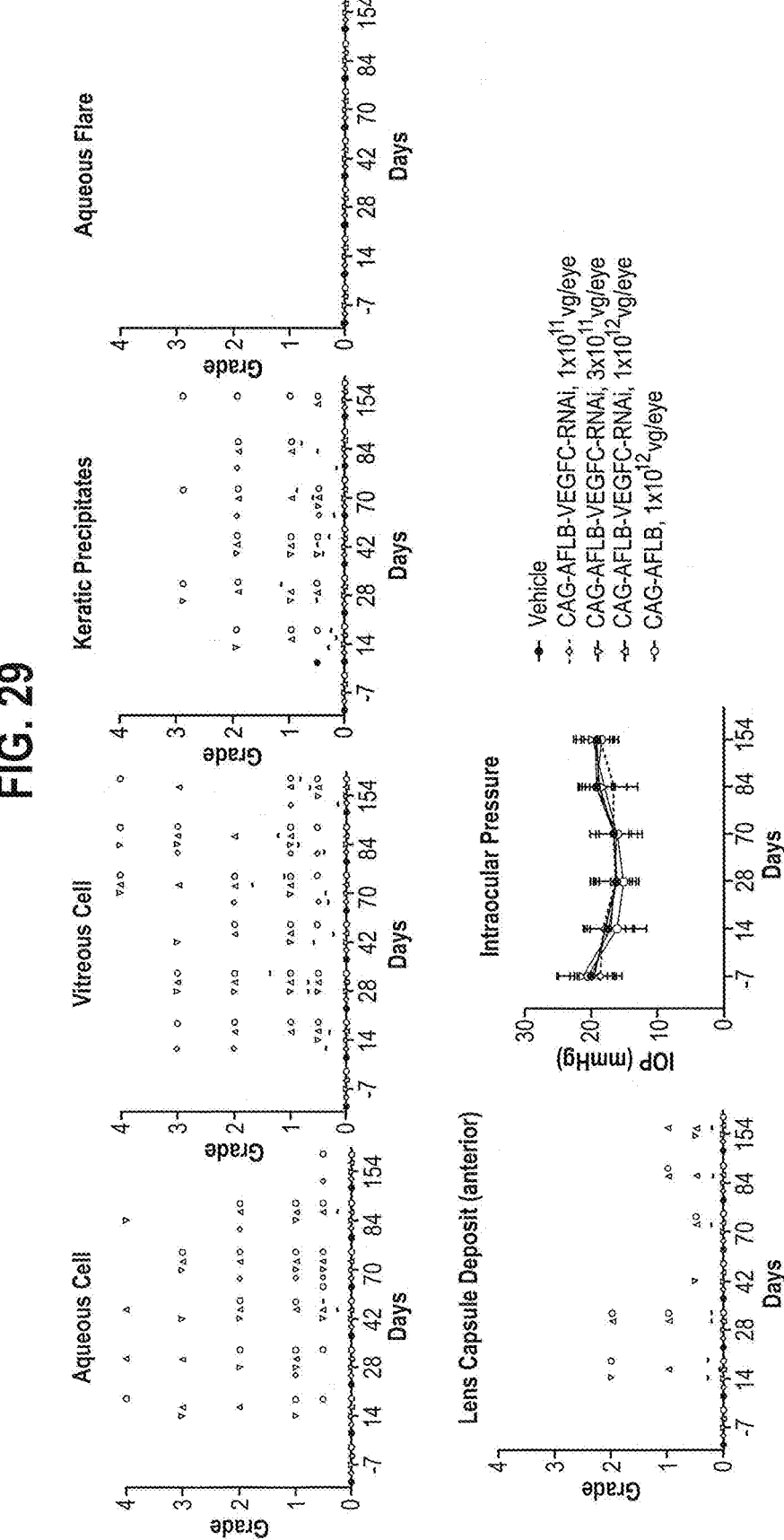
FIG. 29 illustrates intraocular inflammation in NHPs following a single intravitreal administration at the specified dose of (i) rAAV comprising a capsid protein of SEQ ID NO:48 and a nucleic acid encoding aflibercept and miR targeting VEGF-C (comprising the sense and antisense strands corresponding to SEQ ID Nos: 19 and 20 and the full construct corresponding to SEQ ID NO:69) or (ii) rAAV comprising a capsid protein of SEQ ID NO:48 and a nucleic acid encoding aflibercept only, at the specified timepoints as assessed by slit lamp biomicroscopy compared to vehicle-treated control eyes.

In comparison to vehicle-treated eyes that exhibited consistently low integrated clinical score, the eyes receiving rAAV SEQ ID NO. 48 CAG-AFLB at 1× $10^2$ vg/eye or rAAV SEQ ID NO. 48 CAG-AFLB-VEGFC-RNAi at 1×$10^{12}$ vg/eye exhibited mild to moderate intraocular inflammation, peaking around 28 days post IVT injection (see FIG. 29).

At Week 22, there was no or only mild intraocular inflammation in eyes treated with vehicle, rAAV SEQ ID NO. 48 CAG-AFLB-VEGFC-RNAi at 1×$10^{11}$ vg/eye or 3× $10^1$ vg/eye, while half or more of the eyes treated with rAAV SEQ ID NO.48 CAG-AFLB at 1× $10^{12}$ vg/eye or rAAV SEQ ID NO. 48 CAG-AFLB-VEGFC-RNAi at 1× $10^{12}$ vg/eye exhibited mild to moderate intraocular inflammation. See FIG. 29. The inflammatory responses mainly included mild aqueous cells, keratic precipitates, vitreous cell findings, and deposits on the anterior capsular membrane of the lens. Intraocular pressure (IOP) remained normal in all groups.

Retinal volume and central retinal thickness were assessed in the NHPs. Briefly, at designated time points, Optical Coherence Tomography (OCT) was performed using a Heidelberg Spectralis OCT Plus with eye tracking and HEYEX image capture and analysis software. An over-all volume scan of encompassing the posterior retina was performed. At examinations prior to laser, the retinal thickness map and cross-sectional display image were obtained.

Figure 30:
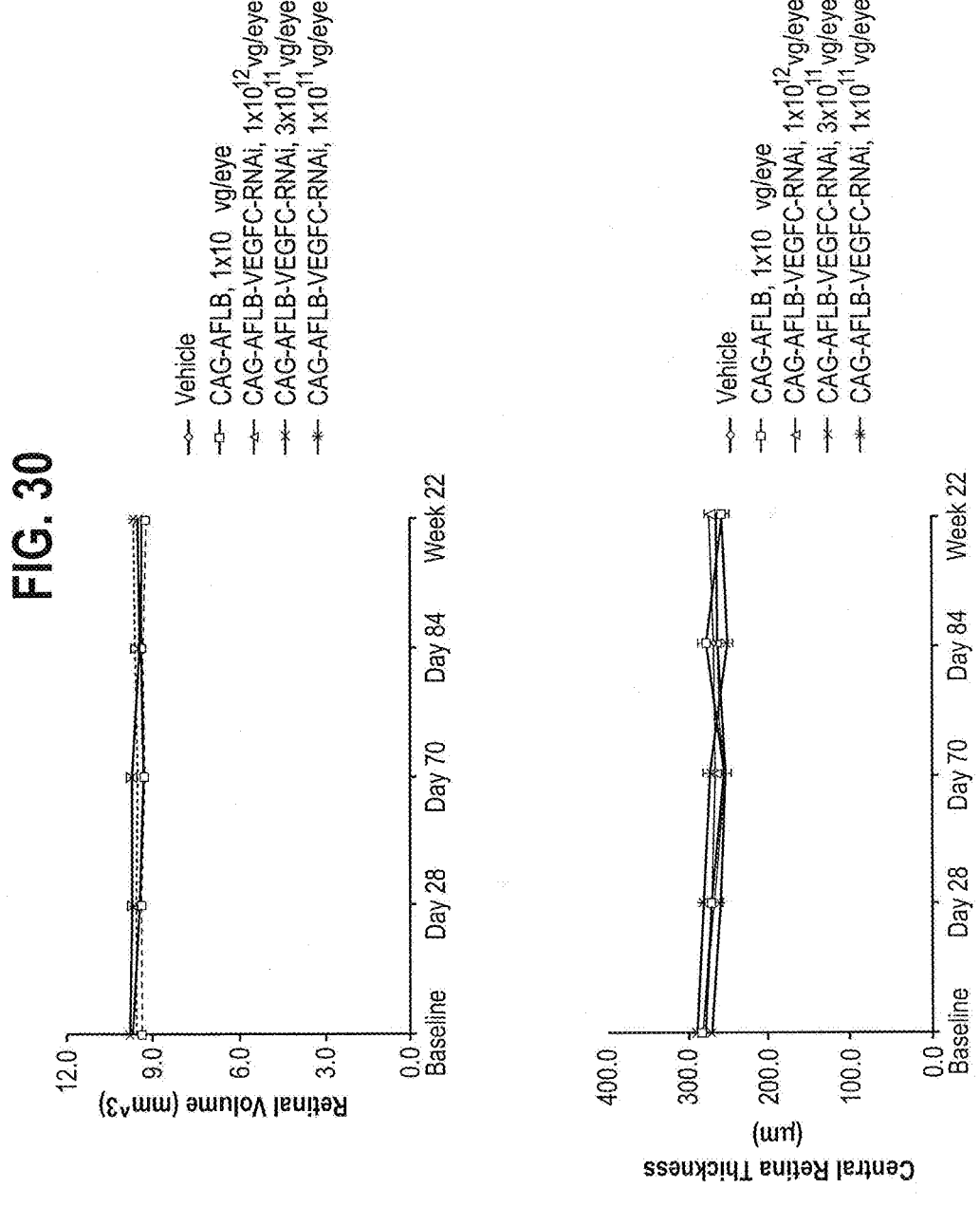
FIG. 30 illustrates mean values of the sum of retinal volume and average central retinal thickness in NHPs from baseline to 22 weeks following a single intravitreal administration at the specified dose of (i) rAAV comprising a capsid protein of SEQ ID NO:48 and a nucleic acid encoding aflibercept and miR targeting VEGF-C(comprising the sense and antisense strands corresponding to SEQ ID Nos: 19 and 20 and the full construct corresponding to SEQ ID NO:69) or (ii) rAAV comprising a capsid protein of SEQ ID NO:48 and a nucleic acid encoding aflibercept only.

OCT derived retinal volume and retinal thickness exhibited a stable comprehensive retinal thickness from baseline to 22 weeks, indicating no retinal edema or degeneration-related thinning occurred during the observation period after any treatment. Mean values of the sum of retinal volume and average central retinal thickness within an applied ETDRS grid remained stable throughout the study (see FIG. 30).

Full Field Electroretinography (ffERG) was conducted at Day 84 and Week 22 to compare the change of retinal function in the NHPs. Briefly, a minimum 25-minute period of dark-adaptation preceded scotopic ffERG recording. Dark adaptation was achieved by retaining the monkey under sedation in a transfer cage situated in a dark room accessed with a scotopic red light. Pupils were dilated with phe-nylephrine (10%), augmented with cyclopentolate (1%), at the beginning of dark adaptation and potentially again before stimulus exposure to ensure that animals had maxi-mum pupil dilation at the point of stimulus induction.

A minimum 10-minute period of light-adaptation pre-ceded photopic ffERG recording with the eyes kept open and DTL electrodes kept in place. Pupils were dilated with phenylephrine (10%), augmented with cyclopentolate (1%), at the beginning of light adaptation and potentially again before stimulus exposure to ensure that monkeys had maxi-mum pupil dilation at the point of stimulus induction.

The following procedures were performed using the Veris platform to the ISCEV standards for a toxicology study and included the following stimulus exposures:

Scotopic 0.16 cd-s m2 stimulus (rod-driven response of on bipolar cells measured, b wave)

Scotopic 2.51 cd-s m2 stimulus (rod and cone-driven response of both photoreceptors, a wave, and on bipolar cells, b wave)

Photopic 2.51 cd-s m2 stimulus (cone driven response of both photoreceptors, a wave, and on and off bipolar cells, b wave)

Photopic 30 Hz flicker stimulus at 2.51 cd-s m2 stimulus (cone driven response)

NHPs underwent scotopic exams before photopic exams and always underwent stimulus exposure order of increasing stimulus strength for a given adaptation. Single stimulus exposures always preceded flicker stimulus exposure to avoid bleaching and impacting retinal adaptation.

To validate consistency as well as establish the range of variability inherent in ffERGs, each stimulus at each time point was captured by two independent runs. Each run was a composite of 3 separate, sequential stimulus inductions. Data recording followed the format guided by the ISCEV standards.

Stimulus induction was denoted by a marker

Figure 31:
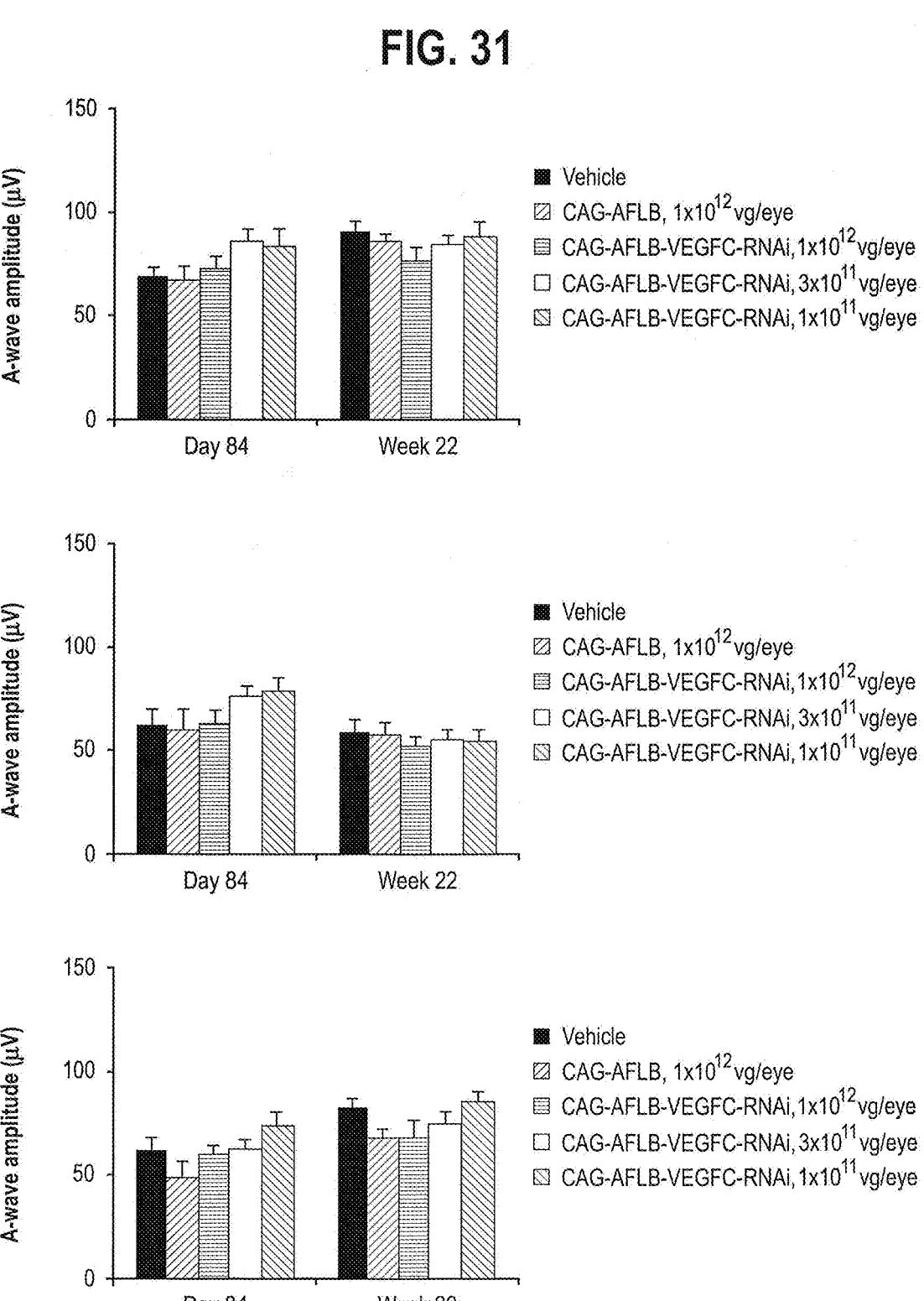
FIG. 31 illustrates the results of full field electroretinography (ffERG) at day 84 and week 22 in NHPs following a single intravitreal administration at the specified dose of (i) rAAV comprising a capsid protein of SEQ ID NO:48 and a nucleic acid encoding aflibercept and miR targeting VEGF-C(comprising the sense and antisense strands corresponding to SEQ ID Nos: 19 and 20 and the full construct corresponding to SEQ ID NO:69) or (ii) rAAV comprising a capsid protein of SEQ ID NO:48 and a nucleic acid encoding aflibercept only.

The time integrated luminance of not only the stimulus, but also the background was recorded in absolute values Time and date of stimulus induction Pupil diameter Type and position of corneal electrodes No statistically significant difference of scotopic A wave, scotopic B wave and photopic flicker was observed between treatment groups at the same time point or between different time points of the same treatment group (all p>0.05, Two-way ANOVA followed by Tukey-Krammer HSD). The mean amplitude of scotopic A wave, scotopic B wave and photopic flicker are presented in FIG. 31.

CONCLUSION—rAAV comprising a capsid protein of SEQ ID NO:48 and a nucleic acid encoding aflibercept+ miR targeting VEGF-C completely abolished grade IV lesion development compared to vehicle-treated controls and significantly attenuated CNV development, supporting the safety and efficacy of the rAAV in the treatment of a variety of diseases associated with ocular angiogenesis such as wet AMD.

Example 6—HUVEC Proliferation & Migration Assays

In vitro angiogenesis assays were performed to assess effects of plasmids encoding (i) aflibercept+ miRNA target-ing VEGF-C(CAG-AFLB-VEGFC-RNAi) (ii) aflibercept only (CAG-AFLB) or (iii) GFP (CAG-GFP) on proliferation and migration of human umbilical vein endothelial cells (HUVECs) following electroporation. Briefly, HUVECs were lifted using 0.05% Trypsin EDTA and electroporated according to Thermo Fisher Neon Electroporator kit instruc-tions. Two million cells per condition were resuspended in R buffer with the appropriate amount of plasmid. One microgram of total DNA was transfected per condition (CAG-AFLB-VEGFC-RNAi, CAG-AFLB, or CAG-GFP). Equimolar concentrations of CAG-AFLB-VEGFC-RNAi plasmid and CAG-AFLB plasmids were transfected. Because the length of CAG-AFLB plasmid (6,660 bp; 1.4×$10^{11}$ copies/pg) was less that CAG-AFLB-VEGFC-RNAi plasmid (10,711 bp: 8.6× $10^{10}$ copies/pg), extra CAG-GFP plasmid was added to the CAG-AFLB condition to equalize the total DNA. A mock transfection "Shock" was also performed as a control. Cells were electroporated by a single pulse at 1350 V for 30 milliseconds. Media was changed four hours post-electroporation to remove residual R buffer. Following electroporation cells were plated for proliferation or migration assays.

HUVEC Cell Counts for Proliferation Assay

Four days post-electroporation, cells were lifted with 0.05% Trypsin-EDTA. Trypsin was quenched with an equal volume of complete media. Cells were centrifuged at 400×g for five minutes and resuspended in 50 μl complete media. Cell suspension was counted using a BD countess cell counter. Six replicates per condition were counted. The total experiment was run three distinct times.

HUVEC Cell Counts for Migration Assay

Four days post-electroporation, cells were lifted with 0.05% Trypsin-EDTA. Trypsin was quenched with an equal volume of complete media. Cells were centrifuged at 400×g for five minutes and counted. 25,000 cells were seeded in starvation EGM-2 medium (without VEGF) into the upper compartment of an 8 µm pore transwell insert coated with 0.1% gelatin, according to Nareshkumar et al. Scientific reports. 8.1 (2018): 1-16. The bottom compartment contained complete EGM-2 media, creating a growth factor gradient. Four hours post-seeding, cultures were fixed and washed with PBS. Nuclei were counterstained with DAPI for 5 minutes at room temperature. The upper compartment was then scraped thoroughly with a rubber scraper. Images were taken at 50× magnification using a Zeiss AxioVert.A1 fluorescent microscope. Four images per insert were taken in a non-biased grid pattern, three replicates per transfection condition. The total experiment was run three distinct times. Quantification of DAPI was done using FIJI software. Schindelin, et al. Nature methods. 9.7 (2012): 676-682. Briefly, a threshold was applied to each image and converted to binary mask. DAPI points were then quantified using the "analyze particles" function. Thresholds were the same within each experiment, but different between experimental replicates because of variability in DAPI staining intensity.

Figure 27:
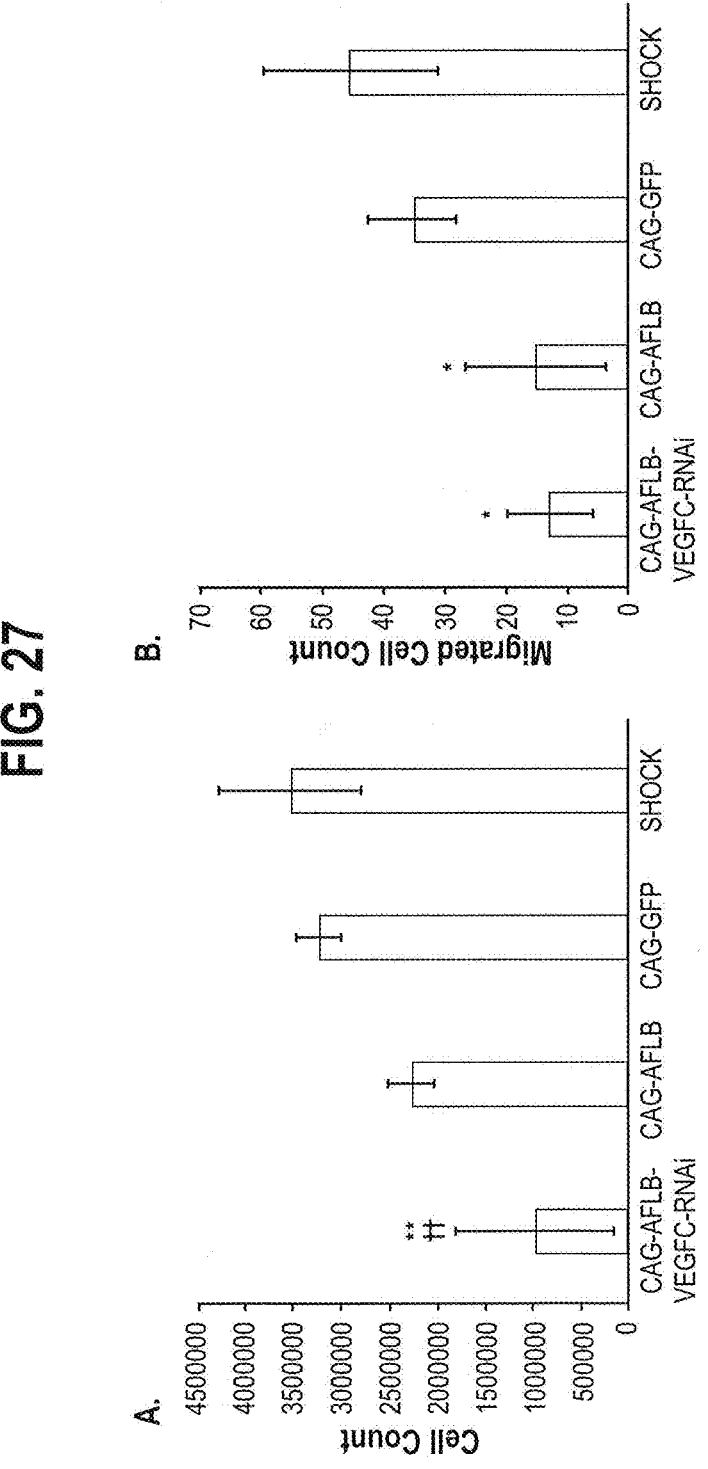
FIG. 27 illustrates cell proliferation (left) and migration (right) of HUVEC cells following electroporation with plasmids encoding (i) aflibercept and an miRNA targeting VEGF-C(ii) aflibercept only or (iii) GFP only.

As shown in FIG. 27, HUVEC cells transfected with plasmid DNA comprising a nucleic acid encoding aflibercept and miR targeting VEGF-C led to a decrease in number of cells present in the culture system compared to plasmid containing GFP under the control of CAG promoter or Shock conditions controls (FIG. 27A). The nucleic acid encoding aflibercept and miR targeting VEGF-C comprises sense and antisense strands corresponding to SEQ ID Nos: 19 and 20 and the full construct corresponds to SEQ ID NO:69. In addition, fewer cells migrated through the transwell membrane after transfection with plasmid DNA comprising the nucleic acid encoding aflibercept and miR targeting VEGF-C compared to the Shock condition (FIG. 27B). Importantly, in both assays, the plasmid containing the nucleic acid encoding aflibercept and miR targeting VEGF-C was not inferior to cells transfected with plasmid containing aflibercept under control of the CAG promoter only. These data demonstrate robust inhibition of endothelial cell proliferation and migration by nucleic acid encoding aflibercept and miR targeting VEGF-C in HUVEC cells.

While the materials and methods of this invention have been described in terms of preferred embodiments, it will be apparent to those of skill in the art that variations may be applied to the method described herein without departing from the concept, spirit and scope of the invention. All such similar substitutes and modifications apparent to those skilled in the art are deemed to be within the spirit, scope and concept of the invention.

---

The invention claimed is:

1. A synthetic ribonucleic acid (RNA) molecule, wherein the synthetic RNA molecule comprises a sense strand comprising a nucleotide sequence set forth as SEQ ID NO:19 and an antisense strand comprising a nucleotide sequence set forth as SEQ ID NO:20.

2. The synthetic RNA molecule according to claim 1, wherein the RNA is a small hairpin RNA (shRNA) or an artificial microRNA (miRNA).

3. A nucleic acid comprising a nucleotide sequence to be transcribed to an RNA, wherein the RNA comprises a synthetic RNA molecule according to claim 1.

4. The nucleic acid of claim 3 wherein the nucleic acid comprises (i) a nucleotide sequence to be transcribed to an artificial miRNA comprising a sense sequence comprising the nucleotide sequence set forth as SEQ ID No: 19 and an antisense sequence comprising the nucleotide sequence set forth as SEQ ID No: 20 and further comprises (ii) a nucleotide sequence encoding a first anti-angiogenic polypeptide that inhibits the activity of VEGF-A, wherein the nucleotide sequence of (i) and (ii) are operably linked to an expression control sequence.

5. The nucleic acid according to claim 4, wherein the first anti-angiogenic polypeptide is aflibercept.

6. The nucleic acid according to claim 5, wherein the nucleotide sequence encoding aflibercept comprises the nucleotide sequence of SEQ ID NO:50 or a sequence at least 90% identical thereto.

7. The nucleic acid according to claim 6, wherein the nucleotide sequence encoding the first anti-angiogenic polypeptide and the nucleotide sequence encoding said artificial miRNA are under the control of the same ubiquitous promoter.

8. The nucleic acid according to claim 7, wherein the promoter is a CAG or CBA promoter.

9. The nucleic acid according to claim 8, wherein the promoter is a CAG promoter and wherein the nucleotide sequence encoding the artificial miRNA is located within the hybrid chicken β-actin and rabbit β-globin intron of the CAG promoter.

10. The nucleic acid according to claim 9, wherein the nucleic acid comprises the nucleotide sequence set forth in SEQ ID No: 69 or a sequence at least 90% identical thereto.

11. The nucleic acid according to claim 10, wherein the nucleic acid comprises the nucleotide sequence set forth as SEQ ID NO:69.

12. A vector comprising the nucleic acid according to claim 5.

13. A vector comprising the nucleic acid according to claim 11.

14. The vector according to claim 13, wherein the vector is a recombinant adeno-associated virus (rAAV) vector.

15. The vector according to claim 14, wherein the rAAV comprises a capsid protein comprising an amino acid sequence at least 90% identical to SEQ ID NO:48.

16. The vector according to claim 15, wherein the rAAV comprises a capsid comprising a capsid protein comprising an amino acid sequence at least 95% identical to SEQ ID NO:48 and a heterologous nucleic acid comprising the sequence set forth as SEQ ID No: 69 or a sequence at least 95% identical thereto.

17. The vector according to claim 16, wherein the rAAV comprises a capsid protein comprising the amino acid sequence set forth as SEQ ID NO:48 and a heterologous nucleic acid sequence comprising the sequence set forth as SEQ ID NO:69.

18. A host cell comprising the vector according to claim 17.

19. A pharmaceutical composition comprising the vector according to claim 17 and a pharmaceutically acceptable carrier.

20. A method for the treatment of an ocular disease associated with VEGF-A in a subject in need of such treatment, the method comprising intraocularly administering to the subject a pharmaceutical composition according to claim 19.

21. The method according to claim 20, wherein the pharmaceutical composition is administered by intravitreal injection.

22. The method according to claim 21, wherein the pharmaceutical composition comprises $1 \times 10^8$ to $1 \times 10^{15}$ vector particles or $1 \times 10^{10}$ to $5 \times 10^{13}$ vector particles.

23. The method according to claim 22, wherein the disease associated with VEGF-A is selected from the group consisting of wet age-related macular degeneration; macular edema following retinal vein occlusion; retinal neovascularization resulting from retinal vein occlusion; diabetic macular edema, diabetic retinopathy, myopic macular degeneration, branch retinal vein occlusion, hemi-retinal vein occlusion, and central retinal vein occlusion; retinopathy of prematurity; idiopathic choroidal neovascularization; myopia macular degeneration and secondary retinal and choroidal neovascularization; retinal telangiectasia; neovascular glaucoma; vitreous hemorrhage; retinal and choroidal neovascularization secondary to retinal diseases, including but not limited to uveitis, trauma, retinal degenerative disorders, genetic retinal and/or choroidal disease, tumors of the eye, corneal and iris neovascularization.

24. The method according to claim 23, wherein the disease associated with VEGF-A is selected from wet age-related macular degeneration; diabetic macular edema; macular edema following retinal vein occlusion; diabetic retinopathy; and myopic choroidal neovascularization.

* * * * *